(12) United States Patent
Macdonald et al.

(10) Patent No.: US 11,583,529 B2
(45) Date of Patent: *Feb. 21, 2023

(54) TREATMENT OF INFLAMMATORY DISORDERS

(71) Applicant: Aldeyra Therapeutics, Inc., Lexington, MA (US)

(72) Inventors: Susan Macdonald, Danvers, MA (US); Adna Halilovic, Arlington, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/328,772

(22) Filed: May 24, 2021

(65) Prior Publication Data

US 2021/0353628 A1 Nov. 18, 2021

Related U.S. Application Data

(63) Continuation of application No. 16/157,069, filed on Oct. 10, 2018, now Pat. No. 11,040,039.

(60) Provisional application No. 62/644,263, filed on Mar. 16, 2018, provisional application No. 62/570,389, filed on Oct. 10, 2017.

(51) Int. Cl.
| | |
|---|---|
| *A61K 31/47* | (2006.01) |
| *A61K 31/517* | (2006.01) |
| *A61K 31/423* | (2006.01) |
| *A61K 31/428* | (2006.01) |
| *A61K 31/136* | (2006.01) |
| *A61P 27/04* | (2006.01) |
| *A61P 1/00* | (2006.01) |
| *A61P 9/10* | (2006.01) |
| *A61P 9/12* | (2006.01) |
| *A61P 13/12* | (2006.01) |
| *A61P 25/08* | (2006.01) |
| *A61P 25/28* | (2006.01) |
| *A61P 15/08* | (2006.01) |
| *A61P 27/14* | (2006.01) |

(52) U.S. Cl.
CPC .......... *A61K 31/517* (2013.01); *A61K 31/136* (2013.01); *A61K 31/423* (2013.01); *A61K 31/428* (2013.01); *A61K 31/47* (2013.01); *A61P 1/00* (2018.01); *A61P 9/10* (2018.01); *A61P 9/12* (2018.01); *A61P 13/12* (2018.01); *A61P 15/08* (2018.01); *A61P 25/08* (2018.01); *A61P 25/28* (2018.01); *A61P 27/04* (2018.01); *A61P 27/14* (2018.01)

(58) Field of Classification Search
CPC .............................. C07D 215/38; A61K 31/47
See application file for complete search history.

(56) References Cited

U.S. PATENT DOCUMENTS

| | | |
|---|---|---|
| 2,086,186 A | 7/1937 | Messer |
| 3,912,748 A | 10/1975 | Evans et al. |
| 4,668,626 A | 5/1987 | Kobayashi et al. |
| 4,956,351 A | 9/1990 | Mesens et al. |
| 5,024,998 A | 6/1991 | Bodor |
| 5,364,637 A | 11/1994 | De et al. |
| 5,376,645 A | 12/1994 | Stella et al. |
| 5,419,898 A | 5/1995 | Ikejiri et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |
| 5,767,109 A | 6/1998 | Sanchez et al. |
| 5,998,488 A | 12/1999 | Shinohara et al. |
| 6,107,300 A | 8/2000 | Bakthavatchalam et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,492,520 B1 | 12/2002 | Chen |
| 6,498,154 B1 | 12/2002 | Grubb et al. |
| 6,515,010 B1 | 2/2003 | Franchini et al. |
| 6,525,056 B2 | 2/2003 | Arvanitis et al. |
| 6,569,879 B2 | 5/2003 | Liu et al. |
| 7,083,803 B2 | 8/2006 | Peyman |
| 7,297,709 B2 | 11/2007 | Dai et al. |
| 7,531,564 B2 | 5/2009 | Malamas et al. |
| 7,842,312 B2 | 11/2010 | Burgermeister et al. |
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,575,221 B2 | 11/2013 | Masse et al. |
| 8,722,669 B2 | 5/2014 | Palczewski et al. |
| 8,791,154 B2 | 7/2014 | Gamache et al. |

(Continued)

FOREIGN PATENT DOCUMENTS

| | | |
|---|---|---|
| CA | 3032609 A1 | 3/2018 |
| EP | 0186367 A2 | 7/1986 |

(Continued)

OTHER PUBLICATIONS

Chao et al., Co-existence of non-alcoholic fatty liver disease and inflammatory bowel disease: A review article, World Journal of Gastroenterology, 22(34), pp. 7727-7734 (2016).*
Brandt et al., Abstract 966: The prevalence of non-alcoholic fatty liver disease in patients with inflammatory bowel disease, The American Journal of Gastroenterogy, vol. 112, Supplement 1 (2017).*
"Malondialdehyde," Wikipedia, retrieved from Internet URL: "https://en.wikipedia.org/w/index.php?title=Malondialdehyde&oldid=993228459" on Aug. 4, 2021. Page last edited Dec. 9, 2020. (4 pages).
International Search Report and Written Opinion issued by the United States Patent and Trademark Office as International Searching Authority for International Patent Application No. PCT/US2021/023884, dated Jul. 28, 2021 (11 pages).

(Continued)

*Primary Examiner* — Deepak R Rao

(74) *Attorney, Agent, or Firm* — Dechert LLP; Andrea L. C. Reid; Joseph W. Arico

(57) ABSTRACT

The present disclosure provides compounds and methods of use thereof for treating inflammatory diseases or disorders.

6 Claims, 24 Drawing Sheets

(56) References Cited

U.S. PATENT DOCUMENTS

| | | |
|---|---|---|
| 8,940,721 B2 | 1/2015 | Jordan et al. |
| 8,940,764 B2 | 1/2015 | Jordan et al. |
| 9,067,963 B2 | 6/2015 | Thompson et al. |
| 9,265,759 B2 | 2/2016 | Jordan et al. |
| 9,364,471 B2 | 6/2016 | Jordan et al. |
| 9,375,408 B2 | 6/2016 | Singh |
| 9,604,997 B2 | 3/2017 | Jordan et al. |
| 9,650,342 B2 | 5/2017 | Jordan et al. |
| 9,687,481 B2 | 6/2017 | Brady et al. |
| 9,814,701 B2 | 11/2017 | Jordan et al. |
| 9,896,419 B2 | 2/2018 | Jordan et al. |
| 10,058,095 B2 | 8/2018 | Czarnik |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,543,181 B2 | 1/2020 | Brady et al. |
| 10,550,085 B2 | 2/2020 | Brady et al. |
| 10,588,874 B2 | 3/2020 | Brady et al. |
| 11,040,039 B2 * | 6/2021 | Macdonald ............ A61P 29/00 |
| 11,046,650 B2 | 6/2021 | Brady et al. |
| 11,129,823 B2 | 9/2021 | Brady et al. |
| 11,197,821 B2 | 12/2021 | Clark et al. |
| 11,312,692 B1 | 4/2022 | Machatha et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2006/0257488 A1 | 11/2006 | Hubbard |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2008/0108818 A1 | 5/2008 | Chen et al. |
| 2008/0241256 A1 | 10/2008 | Kuhn |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2014/0235722 A1 | 8/2014 | Jordine et al. |
| 2015/0209333 A1 | 7/2015 | Jordan et al. |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0009698 A1 | 1/2016 | Julia Jane et al. |
| 2016/0030449 A1 | 2/2016 | Persicaner et al. |
| 2016/0052930 A1 | 2/2016 | Fensome et al. |
| 2016/0136231 A1 | 5/2016 | Gadek |
| 2016/0151381 A1 | 6/2016 | Blackburn et al. |
| 2017/0029354 A1 | 2/2017 | Singh |
| 2017/0095449 A1 | 4/2017 | Winters et al. |
| 2017/0143627 A1 | 5/2017 | Misra |
| 2017/0239196 A1 | 8/2017 | Brady et al. |
| 2017/0266220 A1 | 9/2017 | Young et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0125729 A1 | 5/2019 | Chabala et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0246345 A1 | 8/2020 | Brady et al. |
| 2021/0269402 A1 | 9/2021 | Jordan et al. |
| 2021/0275469 A1 | 9/2021 | Brady et al. |
| 2021/0347735 A1 | 11/2021 | Brady et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |
| 2022/0184057 A1 | 6/2022 | Brady et al. |
| 2022/0202745 A1 | 6/2022 | Brady et al. |
| 2022/0211691 A1 | 7/2022 | Brady et al. |

FOREIGN PATENT DOCUMENTS

| | | |
|---|---|---|
| EP | 0245054 A1 | 11/1987 |
| EP | 0483881 A1 | 5/1992 |
| EP | 1621199 A1 | 2/2006 |
| EP | 2301549 A1 | 3/2011 |
| EP | 1888548 B1 | 8/2012 |
| GB | 2327672 A | 2/1999 |
| JP | 2002003364 A | 1/2002 |
| JP | 2005-132834 A | 5/2005 |
| JP | 3736916 B2 | 1/2006 |
| JP | 2007532648 A | 11/2007 |
| JP | 2008542291 A | 11/2008 |
| JP | 4466875 B2 | 5/2010 |
| JP | 2012506449 A | 3/2012 |
| JP | 5194218 B2 | 5/2013 |
| SU | 50906 A1 | 11/1936 |
| WO | WO-1996022992 A1 | 8/1996 |
| WO | WO-1998005645 A1 | 2/1998 |
| WO | WO-1999046237 A1 | 9/1999 |
| WO | WO-2001041757 A1 | 6/2001 |
| WO | WO-2004082622 A2 | 9/2004 |
| WO | WO-2004091630 A1 | 10/2004 |
| WO | WO-2005035506 A1 | 4/2005 |
| WO | WO-2005040151 A1 | 5/2005 |
| WO | WO-2005051328 A2 | 6/2005 |
| WO | WO-2005079774 A2 | 9/2005 |
| WO | WO-2005105067 A2 | 11/2005 |
| WO | WO-2006000421 A2 | 1/2006 |
| WO | WO-2006002473 A1 | 1/2006 |
| WO | WO-2006049968 A1 | 5/2006 |
| WO | WO-2006077821 A1 | 7/2006 |
| WO | WO-2006127945 A1 | 11/2006 |
| WO | WO-2007118276 A1 | 10/2007 |
| WO | WO-2008014602 A1 | 2/2008 |
| WO | WO-2009045479 A1 | 4/2009 |
| WO | WO-2009102418 A1 | 8/2009 |
| WO | WO-2010048332 A2 | 4/2010 |
| WO | WO-2010133672 A1 | 11/2010 |
| WO | WO-2011008202 A1 | 1/2011 |
| WO | WO-2011071995 A2 | 6/2011 |
| WO | WO-2011072141 A1 | 6/2011 |
| WO | WO-2011078204 A1 | 6/2011 |
| WO | WO-2012097173 A2 | 7/2012 |
| WO | WO-2012105887 A1 | 8/2012 |
| WO | WO-2014100425 A1 | 6/2014 |
| WO | WO-2014116593 A1 | 7/2014 |

(56) References Cited

FOREIGN PATENT DOCUMENTS

| WO | WO-2014116836 A2 | 7/2014 |
|---|---|---|
| WO | WO-2015002893 A1 | 1/2015 |
| WO | WO-2015187942 A1 | 12/2015 |
| WO | WO-2016085939 A2 | 6/2016 |
| WO | WO-2016165626 A1 | 10/2016 |
| WO | WO-2017035077 A1 | 3/2017 |
| WO | WO-2017035082 A1 | 3/2017 |
| WO | WO-2017147617 A1 | 8/2017 |
| WO | WO-2017196881 A1 | 11/2017 |
| WO | WO-2017214201 A1 | 12/2017 |
| WO | WO-2018039192 A1 | 3/2018 |
| WO | WO-2018039197 A1 | 3/2018 |
| WO | WO-2018064354 A1 | 4/2018 |
| WO | WO-2018067860 A1 | 4/2018 |
| WO | WO-2018170476 A1 | 9/2018 |
| WO | WO-2020018498 A1 | 1/2020 |
| WO | WO-2020028820 A1 | 2/2020 |
| WO | WO-2020033344 A1 | 2/2020 |
| WO | WO-2020072621 A1 | 4/2020 |
| WO | WO-2020118045 A1 | 6/2020 |
| WO | WO-2020198064 A1 | 10/2020 |
| WO | WO-2021195211 A1 | 9/2021 |
| WO | WO-2021211625 A1 | 10/2021 |
| WO | WO-2021248031 A1 | 12/2021 |
| WO | 2022150580 A1 | 7/2022 |

OTHER PUBLICATIONS

International Search Report and Written Opinion issued by the United States Patent and Trademark Office as International Searching Authority for International Patent Application No. PCT/US2021/027148, dated Jun. 28, 2021 (9 pages).
International Search Report and Written Opinion issued by the United States Patent and Trademark Office as International Searching Authority for International Patent Application No. PCT/US2021/032335, dated Jul. 27, 2021 (11 pages).
International Search Report and Written Opinion issued by the United States Patent and Trademark Office as International Searching Authority for International Patent Application No. PCT/US2021/035948, dated Oct. 26, 2021 (12 pages).
Mathew et al., "Updates in the management of diabetic macular edema," J Diabetes Res. 2015; 2015:794036.
Roumen et al. "Serum lipofuscin as a prognostic indicator of adult respiratory distress syndrome and multiple organ failure," Br J Surg. 1994; 81(9):1300-5.
Weaver et al., "The Th17 pathway and inflammatory diseases of the intestines, lungs, and skin," Annu. Rev. Pathol., 8:477-512 (2013).
Abelson et al., "Combined analysis of two studies using the conjunctival allergen challenge model to evaluate olopatadine hydrochloride, a new ophthalmic antiallergic agent with dual activity," American Journal of Ophthalmology, 125(6):797-804 (Jun. 1998).
Abelson et al., "Conjunctival allergen challenge. A clinical approach to studying allergic conjunctivitis," Archives of Ophthalmology, 108(1):84-88 (1990).
Abelson et al., "Conjunctival allergen challenge: models in the investigation of ocular allergy," Current Allergy and Asthma Reports, 3(4):363-368 (2003).
Abelson et al., The conjunctival provocation test model of ocular allergy: utility for assessment of an ocular corticosteroid, loteprednol etabonate, J Ocul Pharmacol Ther, 14(6):533-42 (Dec. 1998).
Abramovitz, M. et al., "The utilization of recombinant prostanoid receptors to determine the affinities and selectivities of prostaglandins and related analogs," Biochem. Biophys. Acta., 1483(2):285-293 (2000).
Ackerman et al., "Ocular itch associated with allergic conjunctivitis: latest evidence and clinical management," Ther. Adv. Chronic Dis., 2016; 7(1):52-67.
Acland et al., "Gene Therapy Restores Vision in a Canine Model of Childhood Blindness," Nature Genetics, 28(1):92-95 (2001).

Aharony, D. et al., "Pharmacological characterization of cloned human NK-2 (neurokinin A) receptor expressed in a baculovirus/Sf-21 insect cell system," Molecular Pharmacology, 44(2):356-363 (1993).
Akturk, S. et al., "Nitric oxide and malondialdehyde levels in plasma and tissue of psoriasis patients," Journal of the European Academy of Dermatology and Venereology, 26(7):833-837 (2012).
Al-Bari, "Chloroquine analogues in drug discovery: new directions of uses, mechanisms of actions and toxic manifestations from malaria to multifarious diseases," J Antimicrob Chemother. 2015;70(6):1608-21.
Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev., 22(2):127-31 (2000).
Al-Hasani, H. et al., "Phosphoryl exchange is involved in the mechanism of the insulin receptor kinase," FEBS Lett., 349:17-22 (1994).
Albano et al., "Immune response towards lipid peroxidation products as a predictor of progression of non-alcoholic fatty liver disease to advanced fibrosis," Gut 54:987-93 (2005).
Aldeyra Press Release—Aldeyra Therapeutics Abstract Accepted at 2015 American Academy of Allergy Asthma & Immunology Annual Meeting, Dec. 16, 2014 (2 pages).
Aldeyra Press Release—Aldeyra Therapeutics Abstract Accepted for Presentation at the 2015 Multinational Association of Supportive Care in Cancer—International Society of Oral Oncology (MASCCISOO) Annual Meeting, Apr. 23, 2015 (2 pages).
Aldeyra Press Release—Aldeyra Therapeutics Abstracts Accepted for Presentation at the 2015 Annual Meeting of the Association for Research in Vision and Ophthalmology, Feb. 2, 2015 (2 pages).
Aldeyra Press Release—Aldeyra Therapeutics Announces Agreement with Johnson & Johnson Innovation to Advance Novel Immune-Modulating Drugs for Systemic Inflammatory Diseases, Feb. 27, 2018 (2 pages).
Aldeyra Press Release—Aldeyra Therapeutics Announces Clinical Development Update for Phase 3 Programs, Jan. 25, 2017 (2 pages).
Aldeyra Press Release—Aldeyra Therapeutics Announces Collaboration With the National Organization for Rare Disorders to Enhance Awareness for Sjogren-Larsson Syndrome Patients, Dec. 4, 2014 (2 pages).
Aldeyra Press Release—Aldeyra Therapeutics Announces Development Programs at 2018 Research Day, Jun. 26, 2018 (2 pages).
Aldeyra Press Release—Aldeyra Therapeutics Announces First Patient Enrolled in Allergic Conjunctivitis Phase 2b Clinical Trial, Feb. 7, 2017 (2 pages).
Aldeyra Press Release—Aldeyra Therapeutics Announces First Patient Enrolled in Allergic Conjunctivitis Phase 3 Clinical Trial, Apr. 24, 2018 (2 pages).
Aldeyra Press Release—Aldeyra Therapeutics Announces First Patient Enrolled in Allergic Conjunctivitis Phase IIa Clinical Trial, Sep. 29, 2015 (2 pages).
Aldeyra Press Release—Aldeyra Therapeutics Announces First Patient Enrolled in Dry Eye Disease Phase 2a Clinical Trial, Jun. 6, 2017 (2 pages).
Aldeyra Press Release—Aldeyra Therapeutics Announces First Patient Enrolled in Dry Eye Disease Phase 2b Clinical Trial, Jan. 30, 2018 (2 pages).
Aldeyra Press Release—Aldeyra Therapeutics Announces First Patient Enrolled in Noninfectious Anterior Uveitis Phase 3 Clinical Trial, Apr. 27, 2017 (2 pages).
Aldeyra Press Release—Aldeyra Therapeutics Announces First Patient Enrolled in Noninfectious Anterior Uveitis Phase II Clinical Trial, Apr. 16, 2015 (2 pages).
Aldeyra Press Release—Aldeyra Therapeutics Announces First Patient Enrolled in Sjogren-Larsson Syndrome Phase II Clinical Trial, Mar. 24, 2015 (2 pages).
Aldeyra Press Release—Aldeyra Therapeutics Announces First Patient Enrolled in Sjögren-Larsson Syndrome Pivotal Phase 3 Clinical Trial, Jul. 24, 2018 (2 pages).

(56) References Cited

OTHER PUBLICATIONS

Aldeyra Press Release—Aldeyra Therapeutics Announces Last Patient Dosed in Dry Eye Disease Phase 2a Clinical Trial, Jul. 18, 2017 (2 pages).
Aldeyra Press Release—Aldeyra Therapeutics Announces Last Patient Dosed in Dry Eye Disease Phase 2b Clinical Trial, Jul. 12, 2018 (2 pages).
Aldeyra Press Release—Aldeyra Therapeutics Announces Last Patient Dosed in Phase II Trial of NS2 in Patients with Allergic Conjunctivitis, Dec. 16, 2015 (2 pages).
Aldeyra Press Release—Aldeyra Therapeutics Announces Last Patient Dosed in the ALLEVIATE Phase 3 Clinical Trial, Dec. 20, 2018 (2 pages).
Aldeyra Press Release—Aldeyra Therapeutics Announces Positive Mesothelioma Investigator-Sponsored Clinical Trial Results Presented at the International Association for the Study of Lung Cancer 19th World Conference on Lung Cancer, Sep. 25, 2018 (2 pages).
Aldeyra Press Release—Aldeyra Therapeutics Announces Positive Results from Dry Eye Disease Phase 2a Clinical Trial, Sep. 12, 2017 (3 pages).
Aldeyra Press Release—Aldeyra Therapeutics Announces Positive Results from Phase 2b Dry Eye Disease Clinical Trial, Sep. 26, 2018 (2 pages).
Aldeyra Press Release—Aldeyra Therapeutics Announces Positive Top-Line Results from the Phase 3 ALLEVIATE Trial in Patients with Allergic Conjunctivitis, Mar. 26, 2019 (2 pages).
Aldeyra Press Release—Aldeyra Therapeutics Announces Presentation of Novel Data on the Efficacy of ADX-102 in a Model of Succinic Semialdehyde Dehydrogenase Activity at the 2017 American Society of Human Genetics Annual Meeting, Oct. 5, 2017 (2 pages).
Aldeyra Press Release—Aldeyra Therapeutics Announces Presentation of Phase 2 Allergic Conjunctivitis Results at the 2016 American College of Allergy, Asthma and Immunology Annual Scientific Meeting, Nov. 7, 2016 (2 pages).
Aldeyra Press Release—Aldeyra Therapeutics Announces Presentation of Results on the Efficacy of ADX-102 in Noninfectious Anterior Uveitis at the American Uveitis Society Held at the American Academy of Ophthalmology 2017 Annual Meeting, Oct. 25, 2017 (2 pages).
Aldeyra Press Release—Aldeyra Therapeutics Announces Results from Allergic Conjunctivitis Phase 2b Clinical Trial and Plans for Phase 3 Clinical Testing, Jun. 14, 2017 (3 pages).
Aldeyra Press Release—Aldeyra Therapeutics Announces Third Quarter 2017 Financial Results, Nov. 9, 2017 (4 pages).
Aldeyra Press Release—Aldeyra Therapeutics Launches the Aldeyra Registry for Patients with Sjögren-Larsson Syndrome, Feb. 22, 2017 (2 pages).
Aldeyra Press Release—Aldeyra Therapeutics Opens Enrollment in Noninfectious Anterior Uveitis Phase II Clinical Trial, Mar. 26, 2015 (2 pages).
Aldeyra Press Release—Aldeyra Therapeutics Opens Enrollment in Sjogren-Larsson Syndrome Clinical Trial and Finalizes Noninfectious Anterior Uveitis Clinical Trial Protocol, Mar. 17, 2015 (2 pages).
Aldeyra Press Release—Aldeyra Therapeutics Presents Dry Eye Disease Phase 2a Clinical Trial Results at the Association for Research in Vision and Ophthalmology 2018 Annual Meeting, May 1, 2018 (2 pages).
Aldeyra Press Release—Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting, Oct. 24, 2017 (2 pages).
Aldeyra Press Release—Aldeyra Therapeutics Presents Noninfectious Anterior Uveitis Phase 2 Clinical Trial Data at the Association for Research in Vision and Ophthalmology 2017 Annual Meeting, May 17, 2017 (3 pages).
Aldeyra Press Release—Aldeyra Therapeutics Presents Noninfectious Anterior Uveitis Phase 2 Clinical Trial Data to the American Uveitis Society Held at the American Academy of Ophthalmology 2017 Annual Meeting, Nov. 29, 2017 (2 pages).
Aldeyra Press Release—Aldeyra Therapeutics Provides Update on Late-Stage Clinical Trials at 2016 Research and Development Day, Sep. 26, 2016 (2 pages).
Aldeyra Press Release—Aldeyra Therapeutics Provides Update on NS2 Clinical Program, Mar. 2, 2015 (2 pages).
Aldeyra Press Release—Aldeyra Therapeutics Provides Update on Ophthalmic Programs at 2019 Research & Development Day, Feb. 28, 2019 (2 pages).
Aldeyra Press Release—Aldeyra Therapeutics Schedules Conference Call and Webcast to Announce Results from Allergic Conjunctivitis Phase 2b Clinical Trial, Jun. 13, 2017 (1 page).
Aldeyra Press Release—Aldeyra Therapeutics Schedules Conference Call to Present Results of a Randomized, Double-Blind, Vehicle-Controlled Clinical Trial in Sjogren-Larsson Syndrome, Aug. 8, 2016 (2 pages).
Aldeyra Press Release—Aldeyra Therapeutics Schedules Webcast and Conference Call to Announce Results from Dry Eye Disease Phase 2a Clinical Trial, Sep. 11, 2017 (1 page).
Aldeyra Press Release—Aldeyra Therapeutics Selected for Podium Presentation of Phase 2a Dry Eye Disease Results at the 2018 Association for Research in Vision and Ophthalmology (ARVO) Annual Meeting, Feb. 21, 2018 (3 pages).
Aldeyra Press Release—Aldeyra Therapeutics Submits FDA IND Filing for Noninfectious Anterior Uveitis, Dec. 18, 2014 (2 pages).
Aldeyra Press Release—Aldeyra Therapeutics Submits IND Filing to FDA for Clinical Testing of NS2 in Patients With Sjogren-Larsson Syndrome, Jan. 5, 2015 (2 pages).
Aldeyra Press Release—Aldeyra Therapeutics to Host 2019 Research & Development Day, Feb. 12, 2019 (1 page).
Aldeyra Press Release—Aldeyra Therapeutics to Present at the 2016 SSADH Symposium, Mar. 24, 2016 (1 page).
Aldeyra Press Release—Aldeyra Therapeutics to Present Novel Data on a Potential Treatment for Sjogren-Larsson Syndrome at the 2015 Society for Inherited Metabolic Disorders Annual Meeting, Jan. 29, 2015 (2 pages).
Aldeyra Press Release—Aldeyra Therapeutics to Present Novel Data on a Potential Treatment for Succinic Semi-Aldehyde Dehydrogenase Deficiency at the 2015 American Society of Human Genetics (ASHG) Annual Meeting, Sep. 9, 2015 (2 pages).
Aldeyra Press Release—Aldeyra Therapeutics' Data on Lead Candidate NS2 to be Presented at Society for Investigative Dermatology 2014 Annual Meeting, May 8, 2014 (2 pages).
Aldeyra Press Release—Aldeyra Therapeutics, Inc. Announces Last Patient Dosed in Allergic Conjunctivitis Phase 2b Clinical Trial, Apr. 18, 2017 (2 pages).
Aldeyra Press Release—Aldeyra Therapeutics, Inc. Announces Last Patient Dosed in Phase II Clinical Trial of Topical Dermatologic NS2 in Patients With Sjögren-Larsson Syndrome Jun. 7, 2016 (2 pages).
Aldeyra Press Release—Aldeyra Therapeutics, Inc. Receives Orphan Drug Designation from the U.S. Food and Drug Administration for ADX-102 in Sjögren-Larsson Syndrome, Apr. 20, 2017 (2 pages).
Aldeyra Press Release—Positive Results From Phase II Clinical Trial in Subjects With Noninfectious Anterior Uveitis, May 9, 2016 (4 pages).
Aldeyra Press Release—Phase II Allergic Conjunctivitis, Feb. 29, 2016 (3 pages).
Aldini et al., "Lipoxidation-Derived Reactive Carbonyl Species as Potential Drug Targets in Preventing Protein Carbonylation and Related Cellular Dysfunction," ChemMedChem, 1(10):1045-1058 (2006).
Aldini et al., "The carbonyl scavenger carnosine ameliorates dyslipidaemia and renal function in Zucker obese rats," The Journal of Cellular and Molecular Medicine, 15(6):1339-1354 (2011).
Amara et al., "Autoantibodies to malondialdehyde-modified epitope in connective tissue disease and vasculitides," Clinical and Experimental Immunology, 101(2):233-238 (1995).
Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 39(6):1029-1034 (2016).

(56) References Cited

OTHER PUBLICATIONS

Apparsundaram, S. et al., "Molecular cloning of a human, hemicholinium-3-sensitive choline transporter," Biochem. Biophys. Res. Commun., 276(3):862-867 (2000).

Ardati, A. et al., "Interaction of [3H]orphanin FQ and 125I-Tyr14-orphanin FQ with the orphanin FQ receptor: kinetics and modulation by cations and guanine nucleotides," Mol. Pharmacol., 51:816-824 (1997).

Ashton et al., "Location of penetration and metabolic barriers to levobunolol in the corneal epithelium of the pigmented rabbit," The Journal of Pharmacology and Experimental Therapeutics, 259(2):719-724 (1991).

Atkinson et al., "Triazaphenanthrenes. Part VI.* Further Observations on the Widman-Stoermer and Brosche Reactions," J. Chem. Soc. (C) pp. 2053-2060 (1966).

Augustin et al., "Oxidative reactions in the tear fluid of patients suffering from dry eyes," Graefe's Archive for Clinical and Experimental Ophthalmology, 233(11):694-698 (1995).

Axelsson et al., "Experimental colitis induced by dextran sulphate sodium in mice: beneficial effects of sulphasalazine and olsalazine," Aliment Pharmacol Ther, 12:925-934 (1998).

Bachman, G.B. et al., "Quinoline derivatives from 3-nitro-4-hydroxyquinoline," Am. Chem. Soc., 69:365-371 (1947).

Bacsi et al., "Effect of pollen-mediated oxidative stress on immediate hypersensitivity reactions and late-phase inflammation in allergic conjunctivitis," J. Allergy Clin. Immunol., 2005; 116(4):836-843.

Badii, "Allergic Conjunctivitis," https://www.healthline.com/health/allergic-conjunctivitis, Apr. 28, 2016 (12 pages) [retrieved on Nov. 22, 2019].

Balci et al., "Effects of computer monitor-emitted radiation on oxidant/antioxidant balance in cornea and lens from rats," Molec Vis, 15:2521-2525 (2009).

Balci et al., "Investigation of oxidative stress in pterygium tissue," Molecular Vision, 17:443-447 (Feb. 2011).

Ballard, S.A. et al., "Effects of sildenafil on the relaxation of human corpus cavernosum tissue in vitro and on the activities of cyclic nucleotide phosphodiesterase isozymes," J. Urol., 159(6):2164-2171 (1998).

Baltatzis et al., "Mycophenolate mofetil as an immunomodulatory agent in the treatment of chronic ocular inflammatory disorders," Ophthalmology, 110(5):1061-5 (May 2003).

Bardwell, A.J. et al., "Docking sites on mitogen-activated protein kinase (MAPK) kinases, MAPK phosphatases and the Elk-1 transcription factor compete for MAPK binding and are crucial for enzymic activity," Biochem. J., 370:1077-1085 (2003).

Baron, B.M. et al., "[3H]MDL 105,519, a high-affinity radioligand for the N-methyl-D-aspartate receptor-associated glycine recognition site," J. Pharmacol. Exp. Ther., 279:62-68 (1996).

Bartoli et al., "Malondialdehyde in Exhaled Breath Condensate as a Marker of Oxidative Stress in Different Pulmonary Diseases," Mediators of Inflammation, vol. 2011, Article ID 891752 (2011) (7 pages).

Batista et al., "Age-dependent changes in rat lacrimal gland antioxidant and vesicular related protein expression profiles," Molecular Vision, 18:194-202 (2012).

Batista et al., "Short-term treatment with bisphenol-A leads to metabolic abnormalities in adult male mice," PLOS One, vol. 7, No. 3, (2012).

Baum et al, "Omega 3 fatty acid inhibition of inflammatory cytokine-mediated Connexin43 regulation in the heart," Front. Physiol. 3:272 doi: 10.3389/fphys.2012.00272. eCollection 2012 (2012).

Baz et al., "Plasma reactive oxygen species activity and antioxidant potential levels in rosacea patients: correlation with seropositivity to Helicobacter pylori," International Journal of Dermatology, 43(7):494-497 (2004).

Berge et al., "Pharmaceutical salts," The Journal of Pharmaceuticals Sciences, 66(1):1-19 (1977).

Berkhout, T.A. et al., "Cloning, in vitro expression, and functional characterization of a novel human CC chemokine of the monocyte chemotactic protein (MCP) family (MCP-4) that binds and signals through the CC chemokine receptor 2B,", J. Biol. Chem., 272:16404-16413 (1997).

Bermudez et al., "Thermosensitive poloxamer-based injectables as controlled drug release platforms for veterinary use: Development and in-vitro evaluation," Intl Res J Pharmacy Pharmacol, 1(6):109-118 (Sep. 2011).

Bernstein et al., "Mechanism of Action of Aromatic Amines that Short-Circuit the Visual Cycle," Biochemistry, 25(11):3370-3377 (1986).

Bernstein et al., "Retinal Toxicity Associated with Occupational Exposure to the Fish Anesthetic MS-222," Am J Ophthalmol, 124(6):843-844 (1997).

Bernstein et al., "Short-Circuiting the Visual Cycle with Retinotoxic Aromatic Amines," Proc Natl Acad Sci USA, 83(6):1632-1635 (1986).

Bernstein et al., The Specific Inhibition of 11-cis-retinyl Palmitate Formation in the Frog Eye by Diaminophenoxypentane, an Inhibitor of Rhodopsin Regeneration, Vision Research, 25(6):741-748 (1985).

Bickett, D.A. et al., "A high throughput fluorogenic substrate for interstitial collagenase (MMP-1) and gelatinase (MMP-9)," Anal. Biochem., 212:58-64 (1993).

Bignon, E. et al., "SR146131: a new potent, orally active, and selective nonpeptide cholecystokinin subtype 1 receptor agonist. I. In vitro studies," J. Pharmacol. Exp. Ther. 289:742-751 (1999).

Boldogh et al., "ROS generated by pollen NADPH oxidase provide a signal that augments antigen-induced allergic airway inflammation," J. Clin. Invest., 2005; 115(8):2169-2179.

Bousquet et al., "How to Design and Evaluate Randomized Controlled Trials in Immunotherapy for Allergic Rhinitis: An ARIA-GA2 LEN Statement," Allergy, 66(6):765-774 (2011).

Boyer et al., "Lipofuscin and N-Retinylidene-N-Retinylethanolamine (A2E) Accumulate in Retinal Pigment Epithelium in Absence of Light Exposure," J Biol Chem, 287(26):22276-22286 (Jun. 2012).

Bozkir et al., "Effect of hydroxypropyl-beta-cyclodextrin on the solubility, stability and in-vitro release of ciprofloxacin for ocular drug delivery," Acta Poloniae Pharmaceutica, 69(4):719-24 (2012).

Bragagni et al., "Cyclodextrin complexation highly enhances efficacy of arylsulfonylureido benzenesulfonamide carbonic anhydrase inhibitors as a topical antiglaucoma agents," Bioorganic & Medicinal Chemistry, 23(18):6223-6227) (2015).

Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy, Jun. 28-Jun. 3, 2014 (p. 73).

Brenneman et al., "Small Molecule Anticonvulsant Agents with Potent In Vitro Neuroprotection," Journal of Molecular Neuroscience, 47(2):368-379 (2012).

Brewitt et al., "Dry Eye Disease—The Scale of the Problem," Survey of Ophthalmol, 45(Suppl 2):S199-S2 (Mar. 2001).

Bridion® (sugammadex) Injection Prescribing Information, for intravenous use, Initial U.S. Approval: 2015, Last Revised Dec. 2015 (19 pages).

Brockhaus, M. et al., "Identification of two types of tumor necrosis factor receptors on human cell lines by monoclonal antibodies," Proc. Natl. Acad. Sci. U.S.A., 87:3127-3131 (1990).

Brown, G.B., "3H-batrachotoxinin-A benzoate binding to voltage-sensitive sodium channels: inhibition by the channel blockers tetrodotoxin and saxitoxin," J. Neurosci., 6:2064-2070 (1986).

Brozek et al., "Grading quality of evidence and strength of recommendations in clinical practice guidelines: Part 2 of 3. The GRADE approach to grading quality of evidence about diagonstic tests and strategies," Allergy, 64(8):1109-1116 (2009).

Bryant, H.U. et al., "A novel class of 5-HT2A receptor antagonists: aryl aminoguanidines," Life Sci., 59(15):1259-1268 (1996).

Bucciantini et al., "Inherent Toxicity of Aggregates Implies a Common Mechanism for Protein Misfolding Diseases," Nature, 416(6880):507-511 (2002).

Buchan, K.W. et al., "Characterization of three non-peptide endothelin receptor ligands using human cloned ETA and ETB receptors," Brit. J. Pharmacol., 112:1251-1257 (1994).

(56) References Cited

OTHER PUBLICATIONS

Buddi et al., "Evidence of oxidative stress in human corneal diseases," The Journal of Histochemistry and Cytochemistry: official journal of the Histochemistry Society, 50(3):341-351 (2002).
Bundgaard et al., "Glycolamide esters as biolabile prodrugs of carboxylic acid agents: Synthesis, Stability, bioconversion, and physicochemical properties," Journal of Pharmaceutical Sciences, 77(4):285-298 (1988).
Bundgaard, "Means to enhance penetration: (1) Prodrugs as a means to improve the delivery of peptide drugs," Advanced Drug Delivery Reviews, 8(1):1-38 (1992).
Burcham et al., "Aldehyde-Sequestering Drugs: Tools for Studying Protein Damage by Lipid Peroxidation Products," Toxicology, 181-182:229-236 (2002).
Burstein, "Preservative cytotoxic threshold for benzalkonium chloride and chlorhexidine digluconate in cat and rabbit corneas," Investigative Ophthalmology and Visual Science, 19(3):308-313 (1980).
Burstein, "The effects of topical drugs and preservatives on the tears and corneal epithelium in dry eye," Transactions of the Ophthalmological Societies of the United Kingdom, 104:402-409 (1985).
Canonica et al., "Recommendations for standardization of clinical trials with Allergen Specific Immunotherapy for respiratory allergy. A statement of a World Allergy Organization (WAO) taskforce," Allergy, 62(3):317-324 (2007).
Canonica et al., "Sub-lingual immunotherapy: World Allergy Organization Position Paper 2009," Allergy, 64(Suppl 91:1-59 (2009).
Casanaro et al., "A convenient solvent system for cellulose dissolution and derivatization: Mechanistic aspects of the acylation of the biopolymer in tetraallylammonium fluoride/dimethyl sulfoxide," Carbohydrate Polymers, 8(3):1395-1402 (2011).
Casanaro et al., "Efficacy of vigabatrin intervention in a mild phenotypic expression of succinic semialdehyde dehydrogenase deficiency," JIMD Rep. 2:119-23 (2011).
Cejkova et al., "The role of conjunctival epithelial cell xanthine oxidoreductase/xanthine oxidase in oxidative reactions on the ocular surface of dry eye patients with Sjögren's syndrome," Histol Histopathol 22(9):997-1003 (Sep. 2007).
Cesura et al., "Characterization of the binding of [3H]Ro 41-1049 to the active site of human monoamine oxidase-A," Mol. Pharmacol., 37:358-366 (1990).
Chapple et al., "Unfolding Retinal Dystrophies: a Role for Molecular Chaperones?" Trends Mol Med, 7(9):414-421 (2001).
Chen et al., "Methazolamide Calcium Phosphate Nanoparticles in an Ocular Delivery System," Pharm Soc Japan, 130(3):419-24 (2010).
Cheng et al., "A synthetic peptide derived from p34cdc2 is a specific and efficient substrate of src-family tyrosine kinases," J. Biol. Chem., 267:9248-9256 (1992).
Chiarpotto et al., "Role of 4-hydroxy-2,3-nonenal in the pathogenesis of fibrosis," Biofactors, 24(1-4):229-36 (2005).
Chicchi et al., "Alterations in receptor activation and divalent cation activation of agonist binding by deletion of intracellular domains of the glucagon receptor," J. Biol. Chem., 272:7765-7769 (1997).
Choi et al., "Expression of Lipid Peroxidation Markers in the Tear Film and Ocular Surface of Patients with Non-Sjogren Syndrome: Potential Biomarkers for Dry Eye Disease," Curr Eye Res, 41(9):1143-11 (2016).
Choi et al., "The human serotonin 5-HT2B receptor: pharmacological link between 5-HT2 and 5-HT1D receptors," FEBS Lett., 352:393-399 (1994).
Ciolino et al., "Effect of alcaftadine 0.25% on ocular itch associated with seasonal or perennial allergic conjunctivitis: a pooled analysis of two multicenter randomized clinical trials," Clin Ophthalmol, 9:765-72 (May 2015).
Clark et al., "Inhibition of dexamethasone-induced cytoskeletal changes in cultured human trabecular meshwork cells by tetrahydrocortisol," Invest. Ophtalmol. Vis. Sci., 37:805-813 (1996).
Clinical Trials Results for Outcome Measures of Ocular Itching and Ocular Tearing (1 page) (2016).
Clinical Trials Results of Treatment with Aldehyde Trapping Compound NS2 (1 page) (2015).
Clinical Trials Results of Treatment with NS2 Topical Formulation (1 page) (2015).
ClinicalTrials.gov identifier NCT02402309, "A Study of Topical NS2 Cream to Treat Ichthyosis in Sjogren-Larsson Syndrome (SLS)," https://clinicaltrials.gov/ct2/show/NCT02402309 (3 pages) (2015).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
ClinicalTrials.gov identifier NCT02578914, "A Safety and Activity Study of NS2 in Subjects with Allergic Conjunctivitis," https://clinicaltrials.gov/ct2/show/NCT02578914 (6 pages) (2015).
ClinicalTrials.gov identifier NCT03162783, "A Randomized, Double Masked, Clinical Study of Subjects with Dry Eye Syndrome," (7 pages) (2017).
Conover et al., "Thiazole Analogs of Pyridoxine," Journal of the American Chemical Society, 72(11):5221-5225 (1950).
Cooper et al., "Clinicopathologic study of dextran sulfate sodium experimental murine colitis," Lab Invest, 69(2):238-49 (Aug. 1993).
Couvineau et al., "Molecular identification and structural requirement of vasoactive intestinal peptide (VIP) receptors in the human colon adenocarcinoma cell line, HT-29," Biochem. J., 231:139-143 (1985).
Cullen et al, "Administration of the small molecule aldehyde trap NS2 in a hamster model of radiation-induced oral mucositis," ISOO 2015 Annual Meeting Abstract, Support Care Cancer, 23 (Suppl 1):S107 (Jun. 2015).
Cullen et al., "The small molecule aldehyde trap NS2 exhibits potent anti-inflammatory activity in three murine models of inflammation," AAAAI Annual Meeting Abstract, 1 page (Feb. 2015).
Davies, "Biopharmaceutical considerations in topical ocular drug delivery," Clin Exp Pharmacol Physiol, 27(7):558-62 (Jul. 2000).
De Jong, "Age-Related Macular Degeneration," N Engl J Med, 355(14):1474-1485 (2006).
Del Valle, "Cyclodextrins and their uses: a review," Process Biochemistry, 39(9):1033-1046 (2004).
Demir et al., "Oxidative stress of intracameral lidocaine and levobupivacaine on ocular tissues," Br J Ophthalmol, 94(8):1083-7 (Aug. 2010).
Demir et al., "The protective effect of alpha-lipoic acid against oxidative damage in rabbit conjunctiva and cornea exposed to ultraviolet radiation," Ophthalmologica, 219(1):49-53 (Jan.-Feb. 2005).
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [3H]RX821002 binding and definition of additional selective drugs," Eur. J. Pharmacol., 252:43-49 (1994).
Devillier et al., "The allergen challenge chamber: A valuable tool for optimizing the clinical development of pollen immunotherapy," Allergy, 2011; 66(2):163-9.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, 33 pages. (Nov. 2014).
Dolmotova et al, "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46(6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).

(56) References Cited

OTHER PUBLICATIONS

Egger, et al., "Keratinocyte growth factor ameliorates dextran sodium sulfate colitis in mice," Dig Dis Sci, 44(4): 836-44 (Apr. 1999).
Ellman et al., "A new and rapid colorimetric determination of acetylcholinesterase activity," Biochem. Pharmacol., 7: 88-95 (1961).
Erdos et al, "Neutral endopeptidase 24.11 (enkephalinase) and related regulators of peptide hormones," FASEB J. 3:145 (1989).
Ermolieff et al., "Proteolytic activation of recombinant pro-memapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2):128-32 (2010).
Esterbauer et al., "Chemistry and Biochemistry of 4-Hydroxynonenal, Malonaldehyde and Related Aldehydes," Free Radic Biol Med, 11:81-128 (1991).
European Supplementary Partial Search Report issued by the European Patent Office for European Patent Application No. 13865015.5 dated Mar. 31, 2016 (9 pages).
European Supplementary Partial Search Report issued by the European Patent Office for European Patent Application No. 14743711.5 dated Jul. 20, 2016 (14 pages).
Everest-Todd, "Topical Application of Cyclodextrin Ethers in the Control of Pain," Proceedings of the Eighth International Symposium on Cyclodextrins, pp. 495-498 (1998).
FDA, "BAM R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPAR?: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alpha1A-adrenoceptor: implications for alpha1-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).

Full 1H NMR assignment for RAL-NS2 in CDCIJ, submitted to Japanese Patent Office Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HP?CD) reduces age-related lipofuscin accumulation through a cholesterol-associated pathway," Scientific Reports, 7(2197):1-7 (2017).
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Godard et al., "Sur les orthoamino formyl quinoleines, nouveaux synthons heterocycliques," J Heterocyclic Chem, 17(3):465-473 (1980).
Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 41(3):145-55 (May 2015).
Gomez, "Dimethyltin(IV) 2,6-disubstituted pyridine complexes," J. Organometallic Chemistry, 672(2):115-122 (2003).
Good, "Measuring field loss in children administered vigabatrin: a problem in search of a solution," J AAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Characterization of [(3)H]-CGP54626A binding to heterodimeric GABA(B) receptors stably expressed in mammalian cells," Brit. J. Pharmacol., 131:1766-1774 (2000).
Green et al., "Influence of Various Agents on Corneal Permeability," American Journal of Ophthalmology, 72(5):897-905 (1971).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950) [Machine Translation].
Gromachevskaya et al., "4H-3,1-benzoxazines. 2. Synthesis of 2,4-substituted 1,2-dihydro-4H-3,1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 32(1):169-174 (2009).
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Hampson et al., "Cannabidiol and (-)Delta9-tetrahydrocannabinol are neuroprotective antioxidants," Proc. Nat. Acad. Sci 95:8268-8273 (1998).
Hassan et al., "Oxidative stress in systemic lupus erythematosus and rheumatoid arthritis patients: relationship to disease manifestations and activity," International Journal of Rheumatic Diseases, 14(1):325-331 (2011).
Herbort et al., "Endotoxin-induced uveitis in the rat," Graefe's Arch Clin Exp Ophthalmol, 226:553-8 (1988).
Hessen et al., "Dry Eye: an Inflammatory Ocular Disease," J Ophthalmic Vis Res, 9(2):240-250 (2014).
Heuillet et al., "Characterization of a Human NK1 Tachykinin Receptor in the Astrocytoma Cell Line U 373 MG," J. Neurochem., 60:868-876 (1993).

(56) References Cited

OTHER PUBLICATIONS

Hogema et al., "Pharmacologic rescue of lethal seizures in mice deficient in succinate semialdehyde dehydrogenase," Nat Genet. 29:212-16 (2001).
Hom et al., "Allergic conjunctivitis and dry eye syndrome," Ann Allergy Asthma Immunol, 108(3):163-6 (Mar. 2012).
Hope et al., "Characterization of a human 5-hydroxytryptamine3 receptor type A (h5-HT3R-AS) subunit stably expressed in HEK 293 cells," Brit. J. Pharmacol., 118:1237-1245 (1996).
Horner et al., "Analogs of 3-Amino-7-chloro-1,2,4-benzotriazine 1-Oxide as Antimalarial Agents," J. Med. Chem., 11(5):946-949 (1968).
Hoyer et al., "Characterization of the 5-HT1B recognition site in rat brain: binding studies with (-)[125I]iodocyanopindolol," Eur. J. Pharmacol., 118:1-12 (1985).
Huang et al., "Characterization of Calcium Phosphate Nanoparticles Based on a PEGylated Chelator for Gene Delivery," ACS Appl Mater Interfaces, 9:10435?10445 (Mar. 2017).
Huang et al., "Identification of human Ether-à-go-go related gene modulators by three screening platforms in an academic drug-discovery setting," Assay Drug Dev Technol., 8(6):727-42 (2010).
Huang et al., "Novel peptide inhibitors of angiotensin-converting enzyme 2," J. Biol. Chem., 278:15532-15540 (2003).
Hubbard, "Geometrical Isomerization of Vitamin A, Retinene and Retinene Oxime," Journal of the American Chemical Society, 78(18):4662-4667 (1956).
Hugues et al., "Preparation of a pure monoiodo derivative of the bee venom neurotoxin apamin and its binding properties to rat brain synaptosomes," J. Biol. Chem., 257:2762-2769 (1982).
Hurd et al., "Reaction of Propiolactone with Aniline Derivatives," Journal of the American Chemical Society, 74(23):5889-5893 (1952).
Inoue et al., "Filter-binding assay procedure for thyroid hormone receptors," Anal Biochem. 134(1):176 (1983).
International Preliminary Report on Patentability issued by the European Patent Office as International Searching Authority for International Application PCT/US2006/020320 dated Nov. 30, 2007 (8 pages).
International Preliminary Report on Patentability issued by the Korean Intellectual Property Office as International Searching Authority for International Application No. PCT/US2013/076592 dated Jun. 23, 2015 (6 pages).
International Preliminary Report on Patentability issued by the Korean Intellectual Property Office as International Searching Authority for International Application No. PCT/US2014/012356 dated Jul. 28, 2015 (7 pages).
International Preliminary Report on Patentability issued by the United States Patent and Trademark Office as International Searching Authority for International Application No. PCT/US2014/012762 dated Jul. 28, 2015 (8 pages).
International Preliminary Report on Patentability issued in PCT/US2016/048054 dated Feb. 27, 2018 (5 pages).
International Preliminary Report on Patentability issued in PCT/US2016/048064 dated Feb. 27, 2018 (6 pages).
International Search Report and Written Opinion issued by the European Patent Office as International Searching Authority for International Patent Application No. PCT/US2019/044929 dated Nov. 20, 2019 (15 pages).
International Search Report and Written Opinion issued by the Korean Intellectual Property Office as International Searching Authority for International Application No. PCT/US2013/076592 dated Apr. 30, 2014 (10 pages).
International Search Report and Written Opinion issued by the Korean Intellectual Property Office as International Searching Authority for International Application No. PCT/US2014/012356 dated May 30, 2014 (11 pages).
International Search Report and Written Opinion issued by the United States Patent and Trademark Office as International Searching Authority for International Application No. PCT/US2010/059719 dated Feb. 8, 2011 (7 pages).
International Search Report and Written Opinion issued by the United States Patent and Trademark Office as International Searching Authority for International Application No. PCT/US2014/012762 dated Jul. 18, 2014 (11 pages).
International Search Report and Written Opinion issued by the United States Patent and Trademark Office as International Searching Authority for International Application No. PCT/US2017/047945 dated Oct. 20, 2017 (9 pages).
International Search Report and Written Opinion issued by the United States Patent and Trademark Office as International Searching Authority for International Patent Application No. PCT/US2017/020020 dated May 24, 2017 (12 pages).
International Search Report and Written Opinion issued by the United States Patent and Trademark Office as International Searching Authority for International Patent Application No. PCT/US2017/031808 dated Aug. 11, 2017 (10 pages).
International Search Report and Written Opinion issued by the United States Patent and Trademark Office as International Searching Authority for International Patent Application No. PCT/US2017/047958 dated Oct. 31, 2017 (10 pages).
International Search Report and Written Opinion issued by the United States Patent and Trademark Office as International Searching Authority for International Patent Application No. PCT/US2018/023000 dated Jun. 1, 2018 (8 pages).
International Search Report and Written Opinion issued by the United States Patent and Trademark Office as International Searching Authority for International Patent Application No. PCT/US2018/055310 dated Jan. 29, 2019 (9 pages).
International Search Report and Written Opinion issued by the United States Patent and Trademark Office as International Searching Authority for International Patent Application No. PCT/US2019/041942 dated Sep. 30, 2019 (18 pages).
International Search Report and Written Opinion issued by the United States Patent and Trademark Office as International Searching Authority for International Patent Application No. PCT/US2019/045206 dated Oct. 17, 2019 (13 pages).
International Search Report and Written Opinion issued by the United States Patent and Trademark Office as International Searching Authority for International Patent Application No. PCT/US2019/052961, dated Dec. 10, 2019 (11 pages).
International Search Report and Written Opinion issued by the United States Patent and Trademark Office as International Searching Authority for International Patent Application No. PCT/US2019/054263, dated Jan. 6, 2020 (13 pages).
International Search Report and Written Opinion issued by the United States Patent and Trademark Office as International Searching Authority for International Patent Application No. PCT/US2019/064669, dated Feb. 27, 2020 (12 pages).
International Search Report and Written Opinion issued by the United States Patent and Trademark Office as International Searching Authority for International Patent Application No. PCT/US2020/024022, dated Jun. 17, 2020 (11 pages).
International Search Report and Written Opinion issued by the United States Patent and Trademark Office as International Searching Authority for International Patent Application No. PCT/US2020/031138, dated Jul. 13, 2020 (7 pages).
International Search Report and Written Opinion issued by the United States Patent and Trademark Office as International Searching Authority for International Patent Application No. PCT/US2020/031219, dated Aug. 31, 2020 (14 pages).
International Search Report and Written Opinion issued in PCT/US2006/020320, dated Sep. 26, 2006 (10 pages).
International Search Report and Written Opinion issued in PCT/US2016/048054 dated Nov. 4, 2016 (7 pages).
International Search Report and Written Opinion issued in PCT/US2016/048064 dated Nov. 15, 2016 (8 pages).
Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.
Ishida et al., "Stabilization of calmodulin-dependent protein kinase II through the autoinhibitory domain," J. Biol. Chem., 270:2163-2170 (1995).

(56) References Cited

OTHER PUBLICATIONS

Ito et al., "A Medium-Term Rat Liver Bioassay for Rapid in vivo Detection of Carcinogenic Potential of Chemicals," Cancer Science, 94(1):3-8 (2003).
Itokawa et al., "Antiangiogenic effect by SU5416 is partly attributable to inhibition of Flt-1 receptor signaling," Mol. Cancer Ther., 1:295-302 (2002).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Jafari et al., "Evaluation of plasma, erythrocytes, and bronchoalveolar lavage fluid antioxidant defense system in sulfur mustard-injured patients," Clin Toxicol (Phila)., 48(3):184-92 (2010).
Janowski et al., "Structural requirements of ligands for the oxysterol liver X receptors LXRalpha and LXRbeta," Proc. Natl. Acad. Sci. USA, 96:266-271 (1999).
Jarrett et al., "Mitochondrial DNA damage and impaired base excision repair during epileptogenesis," Neurobiology of Disease, 30(1):130-138 (2008).
Jellinger et al., "American Association of Clinical Endocrinologists and American College of Endocrinology Guidelines for Management of Dyslipemia and Prevention of Cardiovascular Disease," Endocr Pract, 23(Suppl 2):1-87 (Apr. 2017).
Ji et al., "Exploration of diverse hinge-binding scaffolds for selective Aurora kinase inhibitors," Bioorg. & Med. Chem. Let. 22:4528 (2012).
Johannsdottir et al., "Development of a Cyclodextrin-Based Aqueous Cyclosporin A Eye Drop Formulations," International Journal of Pharmaceutics, 493(1-2):86-95 (2015).
Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, 26(3):245-248 (2010).
Joseph et al., "Binding of (-)-[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 135:59-66 (2015).
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).
Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).
Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).
Kenney et al., "The Cascade Hypothesis of Keratoconus," Contact Lens & Ant Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 19(2):181-192 (2003).
La Rosa et al., "Allergic conjunctivitis: a comprehensive review of the literature," Ital J Pediatr, 39:18 (2013).
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[3H]RX821002: a new tool for the identification of alpha 2A-adrenoceptors," Eur. J. Pharmacol., 167: 95-104 (1989).

Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268 : 8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 4:760-764 (1990).
Leonardi, "Allergy and allergic mediators in tears," Exp. Eye Res., 2013; 117:106-17.
Leurs et al., "Pharmacological characterization of the human histamine H2 receptor stably expressed in Chinese hamster ovary cells," Brit. J. Pharmacol., 112: 847-854 (1994).
Levey et al., "A new equation to estimate glomerular filtration rate," Ann Intern Med, 150(9):604-12 (May 2009).
Levin et al., "The myocardium-protective Gly-49 variant of the beta 1-adrenergic receptor exhibits constitutive activity and increased desensitization and down-regulation," J. Biol.Chem., 277:30429-30435 (2002).
Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).
Li et al., "Effect of Vitamin A Supplementation on Rhodopsin Mutants Threonine-17-> Methionine and Proline-347-> Serine in Transgenic Mice and in Cell Cultures," Proc Natl Acad Sci USA, 95(20):11933-11938 (1998).
Liang et al., "Ocular safety of cationic emulsion of cyclosporine in an in vitro corneal wound-healing model and an acute in vivo rabbit model," Mol Vis, 18:2195-204 (2012).
Liu et al., "Comparison of human, mouse, rat, and guinea pig histamine H4 receptors reveals substantial pharmacological species variation," J. Pharmacol. Exp. Ther., 299:121-130 (2001).
Loftsson et al., "Cyclodextrin Microparticles for Drug Delivery to the Posterior Segment of the Eye: Aqueous Dexamethasone Eye Drops," Journal of Pharmacy and Pharmacology, 59(5):629-635 (2007).
Loftsson et al., "Cyclodextrins in Eye Drop Formulations: Enhanced Topical Delivery of Corticosteroids to the Eye," Acta Ophthalmologica Scandinavica, 80(2):144-150 (2002).
Lopachin et al., "Molecular mechanisms of aldehyde toxicity: a chemical perspective," Chem Res Toxicol, 27(7):1081-91 (Jul. 2014).
Lovenberg et al., "Cloning and functional expression of the human histamine H3 receptor," Mol. Pharmacol., 55:1101-1107 (1999).
Lukas, R.J., "Characterization of curaremimetic neurotoxin binding sites on membrane fractions derived from the human medulloblastoma clonal line, TE671," J. Neurochem., 46:1936-1941 (1986).
Luthin et al., "Characterization of two affinity states of adenosine A2a receptors with a new radioligand, 2-[2-(4-amino-3-[125I]iodophenyl)ethylamino]adenosine," Mol. Pharmacol., 47:307-313 (1995).
Macdonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
Macdonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
Macdonald et al., "Molecular characterization of the melanin-concentrating hormone/receptor complex: identification of critical residues involved in binding and activation," Mol. Pharmacol., 58:217-225 (2000).

(56) References Cited

OTHER PUBLICATIONS

Macdonald et al., "Novel Small Molecule Aldehyde Sequestering Agents Demonstrate Broad Therapeutic Potential for Ocular Inflammation," ARVO Annual Meeting Abstract, 2 pages (Jul. 2018).
Macdonald et al., "The novel aldehyde trap, ADX-102, reduces inflammation-mediated lung infilrate in a mouse model of LPS-induced acute lung injury," 13th World Congress on Inflammation Abstract, p. 192 (Jul. 2017).
Mackenzie et al., "Characterization of the human dopamine D3 receptor expressed in transfected cell lines," Eur. J. Pharmacol., 266:79-85 (1994).
Maeda et al., "Involvement of All-trans-retinal in Acute Light-induced Retinopathy of Mice," J Biol Chem, 284(22):15173-83 (May 2009).
Maeda et al., "Primary amines protect against retinal degeneration in mouse models of retinopathies," Nat Chem Biol, 8(2):170-178 (Dec. 2011).
Maguire et al., "Orphan-receptor ligand human urotensin II: receptor localization in human tissues and comparison of vasoconstrictor responses with endothelin-1," Brit. J. Pharmacol., 131:441-446 (2000).
Mandell et al., "The Aldehyde Trap NS2 Reduces Ocular Inflammation in an Endotoxin-Induced Model in Rats," ARVO Annual Meeting Abstract, 2 pages (Jun. 2015).
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).
Marnett, "Oxy radicals, lipid peroxidation and DNA damage," Toxicology, 181-182:219-222 (2002).
Martin et al., "Molecular cloning and functional characterization of murine cysteinyl-leukotriene 1 (CysLT(1)) receptors.," Biochem. Pharmacol., 62:1193-1200 (2001).
Matern et al.,"Seizures in a boy with succinic semialdehyde dehydrogenase deficiency treated with vigabatrin (gamma-vinyl-GABA)," J Inherit Metab Dis., 19(3):313-8 (1996).
Maurice et al., "Advances in targeting cyclic nucleotide phosphodiesterases," Nat Rev Drug Discov., 13:290-314 (2014).
Mccord et al., "Superoxide dismutase. An enzymic function for erythrocuprein (hemocuprein).," J. Biol. Chem., 244: 6049-6055 (1969).
Mcginnity et al., "Evaluation of fresh and cryopreserved hepatocytes as in vitro drug metabolism tools for the prediction of metabolic clearance." Drug Metab. Dispos., 32(11):1247-1253 (2004).
Mclaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 34(10):1245-1251 (2015).
Medline Plus. Macular Degeneration—age-related. (6 pages) (2013).
Meijer et al., "Biochemical and cellular effects of roscovitine, a potent and selective inhibitor of the cyclin-dependent kinases cdc2, cdk2 and cdk5," Eur. J. Biochem., 243:527-536 (1997).
Meng et al., "Cloning and pharmacological characterization of a rat kappa opioid receptor," Proc. Natl. Acad. Sci. U.S.A., 90:9954-9958 (1993).
Mialet et al., "Isolation of the serotoninergic 5-HT4(e) receptor from human heart and comparative analysis of its pharmacological profile in C6-glial and CHO cell lines," Brit. J. Pharmacol., 129:771-781 (2000).
Miceli et al., "Efficacy of keratinocyte growth factor-2 in dextran sulfate sodium-induced murine colitis," J Pharmacol Exp Ther, 290(1):464-71 (Jul. 1999).
Mishra et al., "Recent Patents and Emerging Therapeutics in the Treatment of Allergic Conjunctivitis," Recent Pat. Inflamm. Allergy Drug Discov.; 2011; 5(1):26-36.
Mittl et al., "Structure of recombinant human CPP32 in complex with the tetrapeptide acetyl-Asp-Val-Ala-Asp fluoromethyl ketone," J. Biol. Chem., 272:6539-6547 (1997).

Monaghan et el., "The distribution of [3H]kainic acid binding sites in rat CNS as determined by autoradiography," Brain Res., 252:91-100 (1982).
Monsma et al., "Cloning and expression of a novel serotonin receptor with high affinity for tricyclic psychotropic drugs," Mol. Pharmacol., 43:320-327 (1993).
Mulheron et al., "Human 5-HT1A receptor expressed in insect cells activates endogenous G(o)-like G protein(s)," J. Biol. Chem., 269:12954-12962 (1994).
Muller-Enoch et al., "[6.7-Dihydroxycoumarin (Aesculetin) as a substrate for catechol-o-methyltransferase (author's transl)]," Z. Naturforsch., 31:280-284 (1976).
Munro et al., "Molecular characterization of a peripheral receptor for cannabinoids," Nature, 365:61-65 (1993).
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Na et al.,"Molecular profiling of a 6-hydroxydopamine model of Parkinson's disease," Neurochem Res, 35(5):761-72 (May 2010).
Nagai et al., Improved corneal toxicity and permeability of tranilast by the preparation of ophthalmic formulations containing its nanoparticles, J Oleo Sci, 63(2):177-86 (2014).
Nagase et al., "Design and characterization of a fluorogenic substrate selectively hydrolyzed by stromelysin 1 (matrix metalloproteinase-3)," J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 48(4):1552-1558 (2007).
Negre-Salvayre et al., "Advanced Lipid Peroxidation End Products in Oxidative Damage to Proteins. Potential Role in Diseases and Therapeutic Prospects for the Inhibitors," Br J Pharmacol, 153(1):6-20 (2008).
Nema et al., "Excipients and Their Use in injectable Products," PDA J Pharm Sci Technol, 51(4):166-171 (1997).
Nerurkar et al., "Beta-Arylglutaconic Acids. II. Imides of Certain Beta-Arylglutaconic and Glutaric Acids," J Org Chem, 24(12):2055-2056 (1959).
Niwa et al., "Protein oxidative damage in the stratum corneum: Evidence for a link between environmental oxidants and the changing prevalence and nature of atopic dermatitis in Japan," Br J Dermatol., 149:248 (2003).
Nociari et al., "Beta cyclodextrins bind, stabilize, and remove lipofuscin bisretinoids from retinal pigment epithelium," Proc Natl Acad Sci U.S.A E1402-E1408 (2014).
Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).
O'Brien et al., "Aldehyde Sources, Metabolism, Molecular Toxicity Mechanisms, and Possible Effects on Human Health," Grit Rev Toxicol, 35:609-662 (2005).
Obourn et al., "Hormone- and DNA-binding mechanisms of the recombinant human estrogen receptor," Biochemistry 32(24):6229 (1993).
Organisciak et al., "Susceptibility to Retinal Light Damage in Transgenic Rats with Rhodopsin Mutations," Invest Ophthalmol Vis Sci, 44(2):486-492 (2003).
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri—cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Park et al., "Homogeneous proximity tyrosine kinase assays: scintillation proximity assay versus homogeneous time-resolved fluorescence," Anal. Biochem., 269:94-104 (1999).

(56) References Cited

OTHER PUBLICATIONS

Parracho et al., "Differences between the gut microflora of children with autistic spectrum disorders and that of healthy children," Journal of Medical Microbiology, 54:987-991 (2005).
Patel C.Y., "Subtype selectivity of peptide analogs for all five cloned human somatostatin receptors (hsstr 1-5)," Endocrinology, 135:2814-2817 (1994).
PCT International Search Report from PCT/US2019/054263 dated Jan. 6, 2020 (13 pages).
Pearl et al., "Inherited disorders of gamma-aminobutyric acid metabolism and advances in ALDH5A1 mutation identification," Dev Med Child Neurol., 57(7):611-617 (2015).
Pellock, "Balancing clinical benefits of vigabatrin with its associated risk of vision loss," Acta Neurologica. Scandinavica. Supplementum., 124(s192):83-91 (2011).
Peralta et al., "Distinct primary structures, ligand-binding properties and tissue-specific expression of four human muscarinic acetylcholine receptors," EMBO. J., 6:3923-3929 (1987).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pfaar et al., "Perspectives in allergen immunotherapy: 2017 and beyond," Allergy, 2018; 73(Suppl 104):5-23.
Pickering, D.S., "Pharmacological characterization of melatonin binding sites in Syrian hamster hypothalamus," Eur. J. Pharmacol., 175:71-77 (1990).
Pontikis et al., "Cyclodextrin alleviates neuronal storage of cholesterol in Niemann-Pick C disease without evidence of detectable blood-brain barrier permeability," Journal of Inherited Metabolic Disease, 36(3):491-498 (2013).
Pozzi et al., "Modification of Collagen IV by Glucose or Methylglyoxal Alters Distinct Mesangial Cell Function," Journal of the American Society of Nephrology, 20:2119-2125 (2009).
Pred Forte Prescribing Information, Allergan, 5 pages (2017).
Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).
Pruneau et al., "LF 16.0335, a novel potent and selective nonpeptide antagonist of the human bradykinin B2 receptor," Brit. J. Pharmacol., 125:365-372 (1998).
Pubchem, 1824609-67-7, SID 333824451, Apr. 24, 2017 (6 pages).
Pubchem, 2-(3-Aminoquinolin-2-yl)propan-2-ol, CID 117758222, Feb. 23, 2016, modified Jun. 13, 2020 (11 pages).
Pubchem, SCHEMBL16316728, CID 117758222, Feb. 23, 2016, modified Sep. 30, 2017 (13 pages).
Pufahl et al., "Development of a fluorescence-based enzyme assay of human 5-lipoxygenase," Anal. Biochem., 364:204-212 (2007).
Radu et al., "Isotretinoin treatment inhibits lipofuscin accumulation in a mouse model of recessive Stargardt's macular degeneration," Novartis Foundation Symposium, 255(51-63):177-178 (2004).
Radu et al., "Treatment with Isotretinoin Inhibits Lipofuscin Accumulation in a Mouse Model of Recessive Stargardt's Macular Degeneration," Proc Natl Acad Sci USA, 100(8):4742-4747(2003).
Rajewski et al., "Pharmaceutical applications of cyclodextrins. 2. In vivo drug delivery," J Pharm Sci, 85(11):1142-69 (Nov. 1996).
Rapp et al., "The Effects of Local Anaesthetics on Retinal Function," Vision Res, 22(9):1097-1103 (1982).
Rauli et al., "Validation of Malondialdehyde and 4-Hydroxy-2-trans-Nonenal Measurement in Plasma by NICI-GC-MS1," J Biochem, 123:918-923 (1998).
Reed, "Lipid peroxidation and neurodegenerative disease," Free Radical Biology and Medicine, 51(7):1302-1319 (2011).
Rees et al., "Cloning and characterisation of the human 5-HT5A serotonin receptor," FEBS Lett., 355:242-246 (1994).
Restasis® Prescribing Information, Allergan, copyright 2016, revised 2017 (15 pages).
Reynolds et al., "(-)-[3H] desmethoxyverapamil labels multiple calcium channel modulator receptors in brain and skeletal muscle membranes: differentiation by temperature and dihydropyridines," J. Pharmacol. Exp. Ther., 237: 731-738 (1986).
Rinaldi-Carmona et al., "Characterization of two cloned human CB1 cannabinoid receptor isoforms," J. Pharmacol. Exp. Ther., 278:871-878 (1996).
Rivkees et al., "Identification of domains of the human A1 adenosine receptor that are important for binding receptor subtype-selective ligands using chimeric A1/A2a adenosine receptors," J. Biol. Chem., 270:20485-20490 (1995).
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo et al., "Endogenous antioxidants and radical scavengers," Advances in Experimental Medicine and Biology, 698:52-6 (2010).
Rizzo et al., "Ichthyosis in Sjögren-Larsson syndrome reflects defective barrier function due to abnormal lamellar body structure and secretion," Arch Dermatol Res, 302(6):443-451 (2010).
Rizzo et al., "Sjögren-Larsson syndrome: molecular genetics and biochemical pathogenesis of fatty aldehyde dehydrogenase deficiency," Mol Genet Metab. 90(1):1-9 (2007).
Rizzo, Fatty aldehyde and fatty alcohol metabolism: review and importance for epidermal structure and function, Biochim Biophys Acta, 1841(3):377-89 (Mar. 2014).
Rizzo, "The role of fatty aldehyde dehydrogenase in epidermal structure and function" Dermato-Endocrinol, 3(2):91-99 (2011).
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Roberts et al., "Basic Principles of Organic Chemistry," 2nd edition, copyright 1977 W. A. Benjamin, Inc., pp. 580-582.
Roberts et al., "Experimental Organic Chemistry—A Miniscale Approach," copyright 1994 by Saunders College Publishing, pp. 580-581 and 584-586.
Rohrer et al., "Cloning and characterization of a fourth human somatostatin receptor," Proc. Natl. Acad. Sci. U.S.A. , 90:4196-4200 (1993).
Rønborg et al., "Exposure chamber for allergen challenge. The development and validation of a new concept," Allergy, 1996; 51(2):82-8.
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sanchez et al., "Allergic Conjunctivitis," J Investig Allergol Clin Immunol, 21(2):1-19 (2011).
Sandikci et al., "Lipid Peroxidation and Antioxidant Defence System in Patients with Active or Inactive Behcet's Disease," Acta Derm Venereol, 83:342-346 (2003).
Sarafian et al., "Synergistic cytotoxicity of Delta(9)-tetrahydrocannabinol and butylated hydroxyanisole," Toxicology Letters, 133(2-3):171-179 (2002).
Sarup et al., "Resolution of high and low affinity progesterone receptors from human breast carcinoma T47D cells," J. Biol. Chem., 263:5624-5633 (1988).

(56) References Cited

OTHER PUBLICATIONS

Sasaki et al., "Retinal drug delivery using eyedrop preparations of poly-L-lysine-modified liposomes," Eur J Pharm Biopharm, 83(3):364-9 (2013).
Satici et al., "Malondialdehyde and antioxidant enzyme levels in the aqueous humor of rabbits in endotoxin-induced uveitis," Eur J Ophthalmol, 13(9-10):779-83 (Nov.-Dec. 2003).
Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 127(6):763-768 (Jun. 2009).
Schaumberg et al., "Prevalence of Dry Eye Syndrome Among US Women," Am J Ophthalmol, 136(2):318-326 (Aug. 2003).
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).
Schwartz et al., "Measurement and estimation of GFR in children and adolescents," Clin J Am Soc Nephrol, 4(11):1832-43 (Nov. 2009).
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201504859Y dated Aug. 1, 2016 (12 pages).
Search Report and Written Opinion issued by the Intellectual Property Office of Singapore for Singapore Patent Application No. 11201505587Y dated Jul. 12, 2016 (12 pages).
Search Report and Written Opinion issued by the Intellectual Property Office of Singapore for Singapore Patent Application No. 11201505599Y dated Sep. 26, 2016 (11 pages).
Serbecic et al., "Anti-oxidative vitamins prevent lipid-peroxidation and apoptosis in corneal endothelial cells," Cell Tissue Res, 320(3):465-75 (Jun. 2005).
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sheppard et al., Targeting Anterior Uveitis: A Focus on Iontophoresis and Other Advanced Technologies, Sep. 1, 2018 [Retrieved Nov. 11, 2019] Retrieved from Internet URL: https://www.nyee.edu/files/NYEE/Health%20Professionals/Continuing%20Medical%20Education/Enduring%20CME%20Activities/158_supplernent.smaU_v 1_FINAL %20082818.pdf (8 pages).
Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Shoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simeone et al., "Modification of the Pyridine Moiety of Nonpeptidyl Indole GnRH Receptor Antagonists," Bioorganic & Medicinal Chemistry Letters, 12(22):3329-3332 (2002).
Simonin et al., "The human delta-opioid receptor: genomic organization, cDNA cloning, functional expression, and distribution in human brain," Mol. Pharmacol., 46:1015-1021 (1994).
Singh et al., "The epidemiology of ocular and nasal allergy in the United States, 1988-1994," J. Allergy Clin. Immunol., 2010; 126(4):778-783.
Smit et al., "Regulation of the human histamine H1 receptor stably expressed in Chinese hamster ovary cells," Brit. J. Pharmacol., 117:1071-1080 (1996).
Smith et al., "Basic pathogenic mechanisms operating in experimental models of acute anterior uveitis," Immunol Cell Biol, 76:497-512 (1998).
Smith et al., "Oxidative stress and dopamine depletion in an intrastriatal 6-hydroxydopamine model of Parkinson's disease," Neuroscience. 144(3):1057-1066 (Feb. 2007).
Snead et al., "Gamma-hydroxybutyric acid," New England Journal of Medicine, 352(26):2721-2732 (2005).
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Spadea et al., "Corneal wound healing after laser vision correction," Br J Ophthalmol. 2016; 100:28-33.
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stefansson, et al., "Cyclodextrins in Eye Drop Formulations," Journal of Inclusion Phenomena. 2002; 44:23-27; Abstract only, printed from https://insights.ovid.com/jinpmr/200244010/00984572-200244010-00006#, 2 pages.
Stehle et al., "Molecular cloning and expression of the cDNA for a novel A2-adenosine receptor subtype," Mol. Endocrinol., 6:384-393 (1992).
Stevenson et al., "Dry eye disease: an immune-mediated ocular surface disorder," Arch Ophthalmol. 2012; 130(1): 90-100.
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals: further evidence for d-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V. Mitteilung1) Ubergange heterocyclischer 6-Ringe in heterocyclische 5-Ringe," Liebigs Ann. Chem. 583:150 (1953).
Tahara et al., "Pharmacological characterization of the human vasopressin receptor subtypes stably expressed in Chinese hamster ovary cells," Brit. J. Pharmacol., 125:1463-1470 (1998).
Tang-Liu et al., "Effects of four penetration enhancers on corneal permeability of drugs in vitro," Journal of Pharmaceutical Sciences, 83(1):85-90 (1994).
Tatsumi et al., "Pharmacological profile of neuroleptics at human monoamine transporters," Eur. J. Pharmacol., 368 : 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).

(56) References Cited

OTHER PUBLICATIONS

Tempest-Roe et al., "Local therapies for inflammatory eye disease in translation: past, present and future," BMC Ophthalmol, 13(1):39 (Aug. 2013).
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methyl-3-methylamino-[N-butanoicacid-3-(9-methyl-8-propen-7-one)-amide]-benzo[f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).
Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11(2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
U.S. Appl. No. 16/547,930 of Buist et al., filed Aug. 22, 2019.
U.S. Appl. No. 16/773,654 of Brady et al., filed Jan. 27, 2020.
U.S. Appl. No. 16/825,898 of Clark et al., filed Mar. 20, 2020 Published.
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al, "Thirty years beyond discovery—clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wakamatsu et al., "Evaluation of lipid oxidative stress status and inflammation in atopic ocular surface disease," Mol Vis, 16:2465-75 (Nov. 2010).
Wall et al., "Plant Antitumor Agents. 30. Synthesis and Structure Activity of Novel Camptothecin Analogs," J. Med. Chem., 36(18):2689-2700 (1993).

Walter et al., "Novel Complex N-Heterocycles via Intramolecular 1,5-Electrocyclizations: 1,2,3,4,4a,5,5a,10-Octahydropyrido-[4",3":2',3']cyclobuta[1',2':4,5]pyrrolo[2,3-b]pyridines," Heterocycles, 48(8):1581-1591 (1998).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Wang et al., "Human mu opiate receptor. cDNA and genomic clones, pharmacologic characterization and chromosomal assignment," FEBS Lett., 338:217-222 (1994).
Wang et al., "Markers of oxidative and nitrosative stress in systemic lupus erythematosus: correlation with disease activity," Arthritis and Rheumatism, 62(7):2064-2072 (2010).
Wang, X.K., "Pharmacological study on recombinant human GABA-A receptor complex containing alpha5 (leucine155 to valine) combined with beta3gamma2s subunits," Acta. Pharmacol. Sin., 22:521-523 (2001).
Waslidge et al., "A colorimetric method for the determination of lipoxygenase activity suitable for use in a high throughput assay format," Anal. Biochem., 231:354-358 (1995).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in abcr Knockout Mice," Cell, 98(1):13-23 (1999).
Westphal et al., "Reactions with Pryridinium Pyruvic Acid Esters," Pharmazie, 31(11):770-773 (1976).
Wieland et al., "Subtype selectivity and antagonistic profile of the nonpeptide Y1 receptor antagonist BIBP 3226," J. Pharmacol. Exp. Ther., 275:143-149 (1995).
Witt-Enderby et al., "Characterization and regulation of the human ML1A melatonin receptor stably expressed in Chinese hamster ovary cells," Mol. Pharmacol., 50:166-174 (1996).
Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).
Wood et al., "Aldehyde Load in Ischemia-Reperfusion Brain Injury: Neuroprotection by Neutralization of reactive Aldehydes with Phenelzine," Brain Res, 1122(1):184-190 (2006).
Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).
Wurch et al., "Sequence and functional analysis of cloned guinea pig and rat serotonin 5-HT1D receptors: common pharmacological features within the 5-HT1D receptor subfamily," J. Neurochem., 68:410-418 (1997).
Yadav et al., "Regulation of NF-kB-Induced Inflammatory Signaling by Lipid Peroxidation-Derived Aldehydes," Oxidative Med & Cell Longev, 2013, Art ID 690545, 11 pages (2013).
Yarnell, "Light Flips the Lipid Switch: Palmitoylation—the reversible attachment of palmitate to proteins—gets a new role in vision," C&EN, 82(29):22-23 (2004).
Yokomizo et al., "Hydroxyeicosanoids bind to and activate the low affinity leukotriene B4 receptor, BLT2," J. Biol. Chem., 276:12454-12459 (2001).
Yu et al., "Injectable Chemically Crosslinked Hydrogel for the Controlled Release of Bevacizumab in Vitreous: A 6-Month In Vivo Study," Transl Vis Sci Technol, 4(2,5):1-11 (2015).
Zagol-Ikapitte et al., "Characterization of scavengers of γ-ketoaldehydes that do not inhibit prostaglandin biosynthesis," Chem Res Toxicol, 23(1):240-250 (2010).
Zarkovic "4-hydroxynonenal and neurodegenerative diseases," Molecular Aspects of Medicine, 24(4-5):293-303 (2003).

(56) References Cited

OTHER PUBLICATIONS

Zava et al., "Androgen receptor assay with [3H]methyltrienolone (R1881) in the presence of progesterone receptors," Endocrinology, 104:1007-1012 (1979).

Zhang et al., "Potent nonsteroidal progesterone receptor agonists: synthesis and SAR study of 6-aryl benzoxazines," Bioorg Med Chem Lett, 12(5):787-90 (Mar. 2002).

Zhou et al, "Cloning and expression of human and rat D1 dopamine receptors," Nature, 347:76-80 (1990).

Zhou et al., "Chemical and biological evidence for base propenals as the major source of the endogenous M1dG adduct in cellular DNA," J Biol Chem., 280(27):25377-82 (2005).

Zhou et al., "Mechanisms for the induction of HNE- MDA- and AGE-adducts, RAGE and VEGF in retinal pigment epithelial cells," Exp Eye Res., 80(4):567-80 (2005).

International Search Report and Written Opinion from PCT/US2022/011604 dated Mar. 4, 2022.

Ousler et al., "Use of the Controlled Adverse Environment (CAE) in Clinical Research: A Review," Ophthalmol Ther. 2017;6(2):263-276.

Winfield and Richards, "Ophthalmic Products," Pharmaceutical Practice, Published by Churchill Livingstone, 2004; 265-268.

\* cited by examiner

TREATMENT OF INFLAMMATORY DISORDERS

CROSS-REFERENCE TO RELATED APPLICATIONS

This application is a continuation of U.S. patent application Ser. No. 16/157,069, filed Oct. 10, 2018; which claims the benefit of U.S. Provisional Patent Application Nos. 62/644,263, filed on Mar. 16, 2018, and 62/570,389, filed on Oct. 10, 2017. The entirety of each application is incorporated herein by reference thereto.

TECHNICAL FIELD

The present invention relates to aldehyde-trapping compounds such as I-5, or a pharmaceutically acceptable salt thereof, for treatment of inflammatory disorders and other diseases, disorders, and conditions such as those described herein.

BACKGROUND

Inflammatory disorders include a group of diseases and conditions in which the body's biological response to stimuli results in the immune system attacking the body's own cells or tissues, leading to abnormal inflammation and resulting in chronic pain, redness, swelling, stiffness, and damage to normal tissues. Inflammatory disorders can be acute or chronic.

Generally, the treatment of inflammatory disorders includes the use of immunosuppressants, such as steroids (e.g., prednisone, budesonide (Entocort EC), and prednisolone), anti-metabolites (e.g., methotrexate), and cytotoxic agents (e.g., cyclophosphamide), to reduce or inhibit the activity of immune system cells that participate in the inflammatory response. Some treatments are directed to inhibiting cytokine mediators of the inflammatory response, such as TNF-α and proinflammatory cytokines, including IL-1, IL 6, IL-8, IL-12, IFN-γ, and IL-18, and some therapeutic agents attack specific immune cells involved in the inflammatory response. Many of these treatments include therapeutic antibodies, such as abatacept, adalimumab, anakinra (Kineret), certolizumab, etanercept, golimumab, infliximab, ixekizumab, natalizumab, rituximab, secukinumab, tocilizumab, ustekinumab, and vedolizumab.

Other treatments for inflammatory disorders include calcineurin inhibitors (e.g., cyclosporine and tacrolimus), mTOR inhibitors (e.g., sirolimus and everolimus), and IMPDH inhibitors (e.g., azathioprine, leflunomide, and mycophenolate), all of which affect immune system cells.

While existing treatments may provide effective relief, they are not effective for a significant percentage of patients or have associated side effects because of adverse effects on the immune system or other physiological targets. Desirable are treatments directed to aspects of the inflammatory response not targeted by existing approved therapeutics.

SUMMARY OF THE INVENTION

The present disclosure provides compounds that are capable of reacting with aldehydes for the treatment of certain inflammatory disorders. In some embodiments, the inflammatory disorder can be systemic or localized to a particular tissue or organ. In some embodiments, the disease, disorder or disease for treatment with the compounds of the disclosure is non-alcoholic fatty liver disease (NAFLD), non-alcoholic steatohepatitis, inflammatory bowel disease, Crohn's disease, ulcerative colitis (UC), psoriasis, IBS (irritable bowel syndrome or spastic colon), including spastic colon, ankylosing spondylitis, osteoporosis, rheumatoid arthritis (RA), psoriatic arthritis, chronic obstructive pulmonary disease (COPD), atherosclerosis, pulmonary arterial hypertension, pyridoxine-dependent epilepsy, atopic dermatitis, rosacea, multiple sclerosis (MS), systemic lupus erythematosus (SLE), lupus nephritis, sepsis, eosinophilic esophagitis, chronic kidney disease (CKD), fibrotic renal disease, chronic eosinophilic pneumonia, extrinsic allergic alveolitis, pre-eclampsia, endometriosis, polycystic ovary syndrome (PCOS), reduced female fertility, reduced sperm viability and motility, or cyclophosphamide-induced hemorrhagic cystitis.

In some embodiments, the disease, disorder, or condition for treatment with the compounds of the disclosure is light chain deposition disease, IgA nephropathy, end stage renal disease, gout, pseudogout, diabetic nephrophathy, diabetic neuropathy, traumatic brain injury, noise-induced hearing loss, Alzheimer's Disease, Parkinson's Disease, Huntington Diesease, amyotrophic lateral sclerosis, primary biliary cirrhosis, primary sclerosing cholangitis, uterine leiomyoma, sarcoidosis, or chronic kidney disease.

In some embodiments, the disease, disorder, or condition for treatment with the compounds of the disclosure is an ocular inflammatory disorder. In some embodiments, the ocular inflammatory disorder is diabetic macular edema (DME), atopic keratoconjunctivitis (AKC), vernal keratoconjunctivitis (VKC), age-related macular degeneration (AMD), dry eye disease (DED), allergic conjunctivitis (AC), dry eye disease with allergic conjunctivitis, noninfectious anterior uveitis, posterior uveitis, pan-uveitis, post-surgical ocular pain and inflammation.

In some embodiments, the compound of the disclosure is administered in an effective amount for the prevention of corneal fibrosis after radial keratotomy, prevention of corneal fibrosis after trauma, or prevention of corneal fibrosis after infection.

In some embodiments, a method of treating an inflammatory disorder comprises administering to a subject in need thereof a therapeutically effective amount of a compound of formula (I):

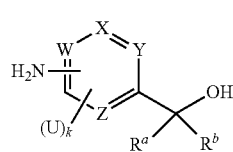

I or a pharmaceutically acceptable salt thereof, wherein W, X, Y, Z, U, $R^a$, $R^b$ and k are as described in the detailed description.

In some embodiments, the compound for use in the treatment of the disease, disorder, or condition is a compound of formula II:

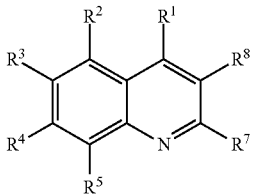

or a pharmaceutically acceptable salt thereof, wherein:
each of $R^1$, $R^7$, and $R^8$ is independently H, D, halogen, —$NH_2$, —CN, —OR, —SR, optionally substituted $C_{1-6}$ aliphatic, or

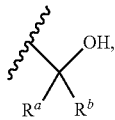

wherein one of $R^1$, $R^7$ and $R^8$ is —$NH_2$ and other one of $R^1$ $R^7$ and $R^8$ is

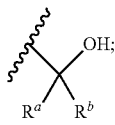

$R^2$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^3$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^4$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^5$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^a$ is $C_{1-4}$ aliphatic optionally substituted with 1, 2, or 3 deuterium or halogen atoms; $R^b$ is $C_{1-4}$ aliphatic optionally substituted with 1, 2, or 3 deuterium or halogen atoms; or $R^a$ and $R^b$, taken together with the carbon atom to which they are attached, form a 3- to 8-membered cycloalkyl or heterocyclyl ring containing 1-2 heteroatoms selected from nitrogen, oxygen, and sulfur; and each R is independently selected from hydrogen, deuterium, and an optionally substituted group selected from $C_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, and sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur.

In some embodiments, the compound for use in treatment of the disease, disorder, or condition is a compound of formula III:

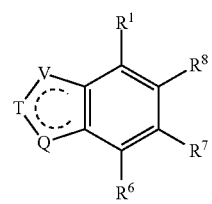

or a pharmaceutically acceptable salt thereof, wherein:
Q, T, and V are independently S, N, O, or —C—R;
each of $R^1$, $R^6$, $R^7$, and $R^8$ is independently H, D, halogen, —$NH_2$, —CN, —OR, —SR, optionally substituted $C_{1-6}$ aliphatic, or

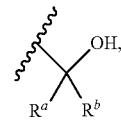

wherein one of $R^1$, $R^6$, $R^7$, and $R^8$ is —$NH_2$ and other one of $R^1$, $R^6$, $R^7$, and $R^8$ is

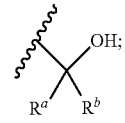

$R^a$ is $C_{1-4}$ aliphatic optionally substituted with 1, 2, or 3 deuterium or halogen atoms; and $R^b$ is $C_{1-4}$ aliphatic optionally substituted with 1, 2, or 3 deuterium or halogen atoms; or $R^a$ and $R^b$, taken together with the carbon atom to which they are attached, form a 3-8 membered cycloalkyl or heterocyclyl ring containing 1-2 heteroatoms selected from nitrogen, oxygen, and sulfur; and each R is independently selected from hydrogen, deuterium, and an optionally substituted group selected from: $C_{1-6}$ aliphatic, a 3- to 8-membered saturated or partially unsaturated monocyclic carbocyclic ring, phenyl, an 8- to 10-membered bicyclic aryl ring, a 3- to 8-membered saturated or partially unsaturated monocyclic heterocyclic ring having 1-4 heteroatoms independently selected from nitrogen, oxygen, and sulfur, a 5- to 6-membered monocyclic heteroaryl ring having 1-4 heteroatoms independently selected from nitrogen, oxygen, and sulfur, a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur.

In some embodiments, the compound for use in treating the disease, disorder, or condition is a compound of formula I-22:

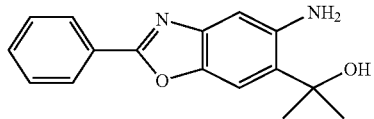

or a pharmaceutically acceptable salt thereof.

In some embodiments, the compound for use in treating the disease, disorder, or condition is a compound of formula I-5:

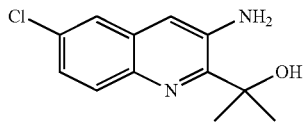

or a pharmaceutically acceptable salt thereof.

In some embodiments, the compound for use in treating the disease, disorder, or condition is a compound of formula I-6:

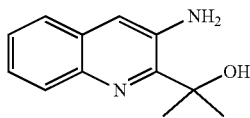

or a pharmaceutically acceptable salt thereof.

In various embodiments, the compounds can be administered systemically, such as intravenously or parenterally, or locally, such as topically or localized injection, to effect treatment of the disease, disorder or condition.

DETAILED DESCRIPTION

1. Detailed Description

Figure 1:
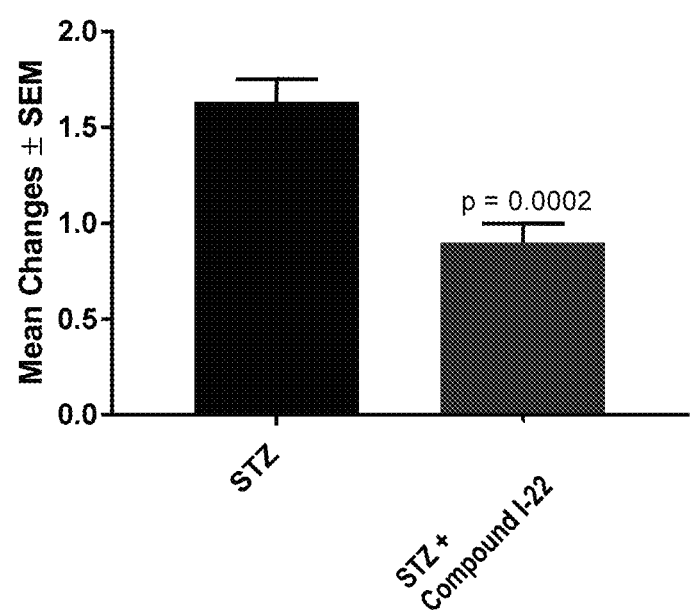
FIG. 1 shows results of administering compound I-22 to the eye of animals with chemically-induced diabetes. Retinas of animal treated with the Compound I-22 show reduced retinal thickness as compared to animals not treated with the compound.

The present disclosure provides compounds capable of reacting with aldehydes for use in methods of treating inflammatory disorders, including systemic inflammatory disorders and ocular inflammatory disorders. The compounds are amino carbinol-containing compounds that are capable of effectively reacting with and "trapping" aldehyde compounds, thus preventing their reaction with biological molecules and interfering with their normal function. The compounds and methods of treating inflammatory disorders with the compounds are described below.

1.1. Definitions

Compounds described herein include those described generally above, and are further illustrated by the classes, subclasses, and species disclosed herein. As used herein, the following definitions shall apply unless otherwise indicated. For purposes of the present disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In some embodiments, the term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. In certain embodiments of the compounds, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned for the compounds herein are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen, —$(CH_2)_{0-4}R^°$; —$(CH_2)_{0-4}OR^°$; —O$(CH_2)_{0-4}R^°$, —O—$(CH_2)_{0-4}C(O)OR^°$; —$(CH_2)_{0-4}CH(OR^°)_2$; —$(CH_2)_{0-4}SR^°$; —$(CH_2)_{0-4}Ph$, which may be substituted with $R^°$; —$(CH_2)_{0-4}O(CH_2)_{0-1}Ph$ which may be substituted with $R^°$; —CH=CHPh, which may be substituted with $R^°$; —$(CH_2)_{0-4}O(CH_2)_{0-1}$-pyridyl which may be substituted with $R^°$; —$NO_2$; —CN; —$N_3$; —$(CH_2)_{0-4}N(R^°)_2$; —$(CH_2)_{0-4}N(R^°)C(O)R^°$—$N(R^°)C(S)R^°$; —$(CH_2)_{0-4}N(R^°)C(O)NR^°_2$; —$N(R^°)C(S)NR^°_2$; —$(CH_2)_{0-4}N(R^°)C(O)OR^°$; —$N(R^°)N(R^°)C(O)R^°$; —$N(R^°)N(R^°)C(O)NR^°_2$; —$N(R^°)N(R^°)C(O)OR^°$; —$(CH_2)_{0-4}C(O)R^°$; —$C(S)R^°$; —$(CH_2)_{0-4}C(O)OR^°$; —$(CH_2)_{1-4}C(O)SR^°$; —$(CH_2)_{0-4}C(O)OSiR^°_3$; —$(CH_2)_{0-4}OC(O)R^°$; —OC(O)$(CH_2)_{0-4}SR$—, SC(S)SR^°$; —$(CH_2)_{0-4}SC(O)R^°$; —$(CH_2)_{0-4}C(O)NR^°_2$; —$C(S)NR^°_2$; —$C(S)SR^°$; —SC(S)SR^°$, —$(CH_2)_{0-4}OC(O)NR^°_2$)—$C(O)N(OR^°)R^°$; —$C(O)C(O)R^°$; —$C(O)CH_2C(O)R^°$; —$C(NOR^°)R^°$; —$(CH_2)_{0-4}SSR^°$; —$(CH_2)_{0-4}S(O)_2R^°$; —$(CH_2)_{0-4}S(O)_2OR^°$; —$(CH_2)_{0-4}OS(O)_2R^°$; —$S(O)_2NR^°_2$; —$(CH_2)_{0-4}S(O)R^°$; —$N(R^°)S(O)_2NR^°_2$; —$N(R^°)S(O)_2R^°$; —$N(OR^°)R^°$; —$C(NH)NR^°_2$; —$P(O)_2R_o$; —$P(O)R^°_2$; —$OP(O)R^°_2$; —$OP(O)(OR^°)_2$; $SiR^°_3$; —$(C_{1-4}$ straight or branched alkylene)O—$N(R^°)_2$; or —$(C_{1-4}$ straight or branched)alkylene)C(O)O—$N(R^°)_2$, wherein each $R^°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of $R^°$, taken together with their intervening atom(s), form a 3-12-membered saturated, partially unsaturated, or aryl mono- or bicyclic ring having 0-4 heteroatoms independently selected from nitrogen, oxygen, and sulfur, which may be substituted as defined below.

Suitable monovalent substituents on $R^°$ (or the ring formed by taking two independent occurrences of $R^°$ together with their intervening atoms), are independently halogen, —$(CH_2)_{0-2}R^•$, —(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each $R^•$ is unsubstituted or where preceded by "halo" is substituted only with one or more halogens, and is independently selected from $C_{1-4}$ aliphatic, —CH$_2$Ph, —O(CH$_2$)$_{0-1}$Ph, and a 5-6-membered saturated, partially unsaturated, or aryl ring having 0-4 heteroatoms independently selected from nitrogen, oxygen, and sulfur. Suitable divalent substituents on a saturated carbon atom of R$^o$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5- to 6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, and an unsubstituted 5 to 6-membered saturated, partially unsaturated, or aryl ring having 0-4 heteroatoms independently selected from nitrogen, oxygen, and sulfur.

Suitable substituents on the aliphatic group of R* include halogen, —R$^•$, —(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, and sulfur, or, notwithstanding the definition above, two independent occurrences of R$^†$, taken together with their intervening atom(s) form an unsubstituted 3- to 12-membered saturated, partially unsaturated, or aryl mono- or bicyclic ring having 0-4 heteroatoms independently selected from nitrogen, oxygen, and sulfur.

Suitable substituents on the aliphatic group of R$^†$ are independently halogen, —R$^•$, —(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present disclosure. Unless otherwise stated, all tautomeric forms of the compounds described herein are within the scope of the present disclosure.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In some embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

1.2. Description of Embodiments

As described above, compounds having amino-carbinol moiety can be used to react with and trap aldehydes. Such aldehydes may be generated as part of an inflammatory response, such that sequestering the aldehydes can ameliorate or attenuate the inflammatory response. Accordingly, in some embodiments, a method of inflammatory disease or disorder in a subject comprises administering to a subject in need thereof a therapeutically effective amount of an aldehyde trapping compound. In some embodiments, the compound is selected from the compounds recited in U.S. Pat. No. 7,973,025 and published international patent application nos. WO2014/116836, WO 2018/039192, WO 2018/039197, or WO2017/035077, the entireties of which are incorporated herein by reference. In some embodiments, the inflammatory disease or disorder is a systemic inflammatory disease or disorder. In some embodiments, the inflammatory disease or disorder is an ocular inflammatory disease or disorder.

In some embodiments, a method of treating an inflammatory disease or disorder in a subject comprises administering to a subject in need thereof a therapeutically effective amount of a compound of formula I:

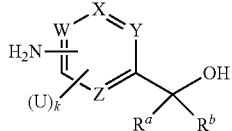

I or a pharmaceutically acceptable salt thereof, wherein:
  each W, X, Y, or Z is independently selected from N, O, S, CU, CH and C—NH$_2$, wherein one of W, X, Y, or Z is C—NH$_2$;
  R$^a$ is C$_{1-4}$ aliphatic optionally substituted with 1, 2, or 3 deuterium or halogen atoms;
  R$^b$ is C$_{1-4}$ aliphatic optionally substituted with 1, 2, or 3 deuterium or halogen atoms; or R$^a$ and R$^b$, taken together with the carbon atom to which they are attached, form a 3- to 8-membered cycloalkyl or heterocyclyl ring containing 1-2 heteroatoms selected from nitrogen, oxygen, and sulfur;
  k is 0, 1, 2, 3, or 4;
  each U is independently selected from halogen, cyano, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;
  two occurrences of U on adjacent carbon atoms can form an optionally substituted fused ring, selected from a fused phenyl ring; a fused 5- to 6-membered saturated or partially unsaturated heterocyclic ring containing 1-3 heteroatoms independently selected from nitrogen, oxygen, and sulfur; and a fused 5- to 6-membered heteroaryl ring containing 1-3 heteroatoms independently selected from nitrogen, oxygen, and sulfur; and
  each R is independently selected from hydrogen, deuterium, and an optionally substituted group selected from C$_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, and sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur.

As defined above and described herein, W is independently selected from N, O, S, CU, CH and C—NH$_2$. In some embodiments, W is N. In some embodiments, W is O. In some embodiments, W is S. In some embodiments, W is CU. In some embodiments, W is CH. In some embodiments, W is C—NH$_2$.

As defined above and described herein, X is independently selected from N, O, S, CU, CH and C—NH$_2$. In some embodiments, X is N. In some embodiments, X is O. In some embodiments, X is S. In some embodiments, X is CU. In some embodiments, X is CH. In some embodiments, X is C—NH$_2$.

As defined above and described herein, Y is independently selected from N, O, S, CU, CH and C—NH$_2$. In some embodiments, Y is N. In some embodiments, Y is O. In some embodiments, Y is S. In some embodiments, Y is CU. In some embodiments, Y is CH. In some embodiments, Y is C—NH$_2$.

As defined above and described herein, Z is independently selected from N, O, S, CU, CH and C—NH$_2$. In some embodiments, Z is N. In some embodiments, Z is O. In some embodiments, Z is S. In some embodiments, Z is CU. In some embodiments, Z is CH. In some embodiments, Z is C—NH$_2$.

As defined above and described herein, k is 0, 1, 2, 3, or 4. In some embodiments k is 0. In some embodiments, k is 1. In some embodiments, k is 2. In some embodiments, k is 3. In some embodiments, k is 4.

As defined above and described herein, each U is independently selected from halogen, cyano, —R, —OR, —SR, —N(R)$_2$, —N(R)C(O)R, —C(O)N(R)$_2$, —N(R)C(O)N(R)$_2$, —N(R)C(O)O R, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, U is halogen. In some embodiments, U is fluorine. In some embodiments, U is chlorine. In some embodiments, U is bromine.

In some embodiments, U is —R. In some embodiments, U is hydrogen. In some embodiments, U is deuterium. In some embodiments, U is optionally substituted C$_{1-6}$ aliphatic. In some embodiments, U is an optionally substituted 3- to 8-membered saturated or partially unsaturated monocyclic carbocyclic ring. In some embodiments, U is an optionally substituted 8- to 10-membered bicyclic aryl ring. In some embodiments, U is an optionally substituted 3- to 8-membered saturated or partially unsaturated monocyclic heterocyclic ring having 1-4 heteroatoms independently selected from nitrogen, oxygen, and sulfur. In some embodiments, U is an optionally substituted 5- to 6-membered monocyclic heteroaryl ring having 1-4 heteroatoms independently selected from nitrogen, oxygen, and sulfur. In some embodiments, U is an optionally substituted 6- to 10-membered bicyclic saturated or partially unsaturated heterocyclic ring having 1-5 heteroatoms independently selected from nitrogen, oxygen, and sulfur. In some embodiments, U is an optionally substituted 7- to 10-membered bicyclic heteroaryl ring having 1-5 heteroatoms independently selected from nitrogen, oxygen, and sulfur.

In some embodiments, U is —S(O)$_2$R. In some embodiments, U is —S(O)$_2$CH$_3$.

In some embodiments, U is an optionally substituted phenyl ring. In some embodiments, U is a phenyl ring, optionally substituted with halogen. In some embodiments, U is a phenyl ring, optionally substituted with fluorine. In some embodiments, U is a phenyl ring, optionally substituted with chlorine.

As defined above and described herein, two occurrences of U on adjacent carbon atoms can form an optionally substituted fused ring, selected from a fused phenyl ring; a fused 5- to 6-membered saturated or partially unsaturated heterocyclic ring containing 1-3 heteroatoms independently selected from nitrogen, oxygen, and sulfur; and a fused 5- to 6-membered heteroaryl ring containing 1-3 heteroatoms independently selected from nitrogen, oxygen, and sulfur.

In some embodiments, two occurrences of U on adjacent carbon atoms form a fused phenyl ring. In some embodiments, two occurrences of U on adjacent carbon atoms form an optionally substituted fused phenyl ring. In some embodiments, two occurrences of U on adjacent carbon atoms form a fused phenyl ring, optionally substituted with 1 or more halogen atoms. In some embodiments, two occurrences of U on adjacent carbon atoms form a fused phenyl ring, optionally substituted with one halogen atom. In some embodiments, two occurrences of U on adjacent carbon atoms form a fused phenyl ring, optionally substituted with fluorine. In some embodiments, two occurrences of U on adjacent carbon atoms form a fused phenyl ring, optionally substituted with chlorine. In some embodiments, two occurrences of U on adjacent carbon atoms form a fused phenyl ring, optionally substituted with 2 halogen atoms. In some embodiments, two occurrences of U on adjacent carbon atoms form a fused phenyl ring, optionally substituted with 2 fluorines. In some embodiments, two occurrences of U on adjacent carbon atoms form a fused phenyl ring, optionally substituted with 2 chlorines. In some embodiments, two occurrences of U on adjacent carbon atoms form a fused phenyl ring, optionally substituted with fluorine and chlorine.

In some embodiments, two occurrences of U on adjacent carbon atoms form a fused 5- to to 6-membered heteroaryl ring containing 1-3 heteroatoms independently selected from nitrogen, oxygen, and sulfur. In some embodiments, two occurrences of U on adjacent carbon atoms form an optionally substituted fused 5- to 6-membered heteroaryl ring containing 1-3 heteroatoms independently selected from nitrogen, oxygen, and sulfur.

In some embodiments, two occurrences of U on adjacent carbon atoms form a fused 5-membered heteroaryl ring containing 1-3 heteroatoms independently selected from nitrogen, oxygen, and sulfur. In some embodiments, two occurrences of U on adjacent carbon atoms form an optionally substituted fused 5-membered heteroaryl ring containing 1-3 heteroatoms independently selected from nitrogen, oxygen, and sulfur.

In some embodiments, two occurrences of U on adjacent carbon atoms form a fused 5-membered heteroaryl ring containing one nitrogen and one oxygen heteroatom. In some embodiments, two occurrences of U on adjacent carbon atoms form an optionally substituted fused 5-membered heteroaryl ring containing one nitrogen and one oxygen heteroatom. In some embodiments, two occurrences of U on adjacent carbon atoms form a fused 5-membered heteroaryl ring containing one nitrogen and one oxygen heteroatom, optionally substituted with phenyl. In some embodiments, two occurrences of U on adjacent carbon atoms form a fused 5-membered heteroaryl ring containing one nitrogen and one oxygen heteroatom, optionally substituted with tosyl. In some embodiments, two occurrences of U on adjacent carbon atoms form a fused 5-membered heteroaryl ring containing one nitrogen and one oxygen heteroatom, optionally substituted with $C_{1-6}$ aliphatic. In some embodiments, two occurrences of U on adjacent carbon atoms form a fused 5-membered heteroaryl ring containing one nitrogen and one oxygen heteroatom, optionally substituted with $C_{1-6}$ alkyl. In some embodiments, two occurrences of U on adjacent carbon atoms form a fused 5-membered heteroaryl ring containing one nitrogen and one oxygen heteroatom, optionally substituted with cyclopropyl.

In some embodiments, two occurrences of U on adjacent carbon atoms form a fused 5-membered heteroaryl ring containing one nitrogen and one sulfur heteroatom. In some embodiments, two occurrences of U on adjacent carbon atoms form an optionally substituted fused 5-membered heteroaryl ring containing one nitrogen and one sulfur heteroatom. In some embodiments, two occurrences of U on adjacent carbon atoms form a fused 5-membered heteroaryl ring containing one nitrogen and one sulfur heteroatom, optionally substituted with phenyl.

In some embodiments, two occurrences of U on adjacent carbon atoms form a fused 5-membered heteroaryl ring containing two nitrogen heteroatoms. In some embodiments, two occurrences of U on adjacent carbon atoms form an optionally substituted fused 5-membered heteroaryl ring containing two nitrogen heteroatoms. In some embodiments, two occurrences of U on adjacent carbon atoms form a fused 5-membered heteroaryl ring containing two nitrogen heteroatoms, optionally substituted with phenyl.

In some embodiments, two occurrences of U on adjacent carbon atoms form a fused 6-membered heteroaryl ring containing 1-3 heteroatoms independently selected from nitrogen, oxygen, and sulfur. In some embodiments, two occurrences of U on adjacent carbon atoms form an optionally substituted fused 6-membered heteroaryl ring containing 1-3 heteroatoms independently selected from nitrogen, oxygen, and sulfur.

In some embodiments, two occurrences of U on adjacent carbon atoms form a fused 6-membered heteroaryl ring containing one nitrogen heteroatom. In some embodiments, two occurrences of U on adjacent carbon atoms form an optionally substituted fused 6-membered heteroaryl ring containing one nitrogen heteroatom. In some embodiments, two occurrences of U on adjacent carbon atoms form a fused 6-membered heteroaryl ring containing two nitrogen heteroatoms. In some embodiments, two occurrences of U on adjacent carbon atoms form an optionally substituted fused 6-membered heteroaryl ring containing two nitrogen heteroatoms.

In some embodiments, the fused ring system formed by two occurrences of U on adjacent carbon atoms is quinazolinyl. In some embodiments, the fused ring system formed by two occurrences of U on adjacent carbon atoms is an optionally substituted quinazolinyl.

In some embodiments, the fused ring system formed by two occurrences of U on adjacent carbon atoms is quinolinyl. In some embodiments, the fused ring system formed by two occurrences of U on adjacent carbon atoms is optionally substituted quinolinyl. In some embodiments, the fused ring system formed by two occurrences of U on adjacent carbon atoms is quinolinyl, optionally substituted with 1-2 halogen atoms. In some embodiments, the fused ring system formed by two occurrences of U on adjacent carbon atoms is quinolinyl, optionally substituted with 1 halogen atom. In some embodiments, the fused ring system formed by two occurrences of U on adjacent carbon atoms is quinolinyl, optionally substituted with fluorine. In some embodiments, the fused ring system formed by two occurrences of U on adjacent carbon atoms quinolinyl, optionally substituted with chlorine.

In some embodiments, the fused ring system formed by two occurrences of U on adjacent carbon atoms is benzoxazolyl. In some embodiments, the fused ring system formed by two occurrences of U on adjacent carbon atoms is optionally substituted benzoxazolyl. In some embodiments, the fused ring system formed by two occurrences of U on adjacent carbon atoms is benzoxazolyl, optionally substituted with phenyl. In some embodiments, the fused ring system formed by two occurrences of U on adjacent carbon atoms is benzoxazolyl, optionally substituted with phenyl and a halogen atom. In some embodiments, the fused ring system formed by two occurrences of U on adjacent carbon atoms is benzoxazolyl, optionally substituted with phenyl and chlorine. In some embodiments, the fused ring system formed by two occurrences of U on adjacent carbon atoms is benzoxazolyl, optionally substituted with tosyl and chlorine.

In some embodiments, the fused ring system formed by two occurrences of U on adjacent carbon atoms is benzisoxazolyl. In some embodiments, the fused ring system formed by two occurrences of U on adjacent carbon atoms is optionally substituted benzisoxazolyl. In some embodiments, the fused ring system formed by two occurrences of U on adjacent carbon atoms is benzisoxazolyl, optionally substituted with phenyl. In some embodiments, the fused ring system formed by two occurrences of U on adjacent carbon atoms is benzisoxazolyl, optionally substituted with cyclopropyl and a halogen atom. In some embodiments, the fused ring system formed by two occurrences of U on adjacent carbon atoms is benzisoxazolyl, optionally substituted with cyclopropyl and chlorine.

In some embodiments, the fused ring system formed by two occurrences of U on adjacent carbon atoms is benzothiazolyl. In some embodiments, the fused ring system formed by two occurrences of U on adjacent carbon atoms is optionally substituted benzothiazolyl. In some embodiments, the fused ring system formed by two occurrences of U on adjacent carbon atoms is benzothiazolyl, optionally substituted with phenyl.

In some embodiments, the fused ring system formed by two occurrences of U on adjacent carbon atoms is benzisothiazolyl. In some embodiments, the fused ring system formed by two occurrences of U on adjacent carbon atoms is optionally substituted benzisothiazolyl. In some embodiments, the fused ring system formed by two occurrences of U on adjacent carbon atoms is benzisothiazolyl, optionally substituted with phenyl.

In some embodiments, the fused ring system formed by two occurrences of U on adjacent carbon atoms is benzimidazolyl. In some embodiments, the fused ring system formed by two occurrences of U on adjacent carbon atoms is optionally substituted benzimidazolyl. In some embodiments, the fused ring system formed by two occurrences of U on adjacent carbon atoms is benzimidazolyl, optionally substituted with phenyl.

In some embodiments, W, X, Y, and Z provide a phenyl ring. In some embodiments, W, X, Y, and Z provide a phenyl ring, substituted with k occurrences of U. In some embodiments where W, X, Y, and Z provide a phenyl ring, one of W, X, Y, and Z is —C—NH$_2$.

In some embodiments, W, X, Y, and Z provide a pyridinyl ring. In some embodiments, W, X, Y, and Z provide a pyridinyl ring, substituted with k occurrences of U. In some embodiments where W, X, Y, and Z provide a pyridinyl ring, one of W, X, Y, and Z is —C—NH$_2$.

In some embodiments, one of W, X, Y, and Z is —C—NH$_2$, one or more of the other of W, X, Y, and Z are CH; and k is 0. In some embodiments, one of W, X, and Y is —C—NH$_2$, one or more of the other of W, X, or Y are CH; Z is N; and k is 0.

In some embodiments, one of W, X, Y, and Z is —C—NH$_2$, one or more of the other of W, X, Y, and Z are CH; k is 1; and U is halogen. In some embodiments, one of W, X, Y, and Z is —C—NH$_2$, one or more of the other of W, X, Y, and Z are CH; k is 1; and U is chlorine. In some embodiments, one of W, X, Y, and Z is —C—NH$_2$, one or more of the other of W, X, Y, and Z are CH; k is 1; and U is fluorine. In some embodiments, one of W, X, Y, and Z is —C—NH$_2$, one or more of the other of W, X, Y, and Z are CH; k is 1; and U is bromine.

In some embodiments, one of W, X, and Y is —C—NH$_2$, one or more of the other of W, X, and Y are CH; Z is N; k is 1; and U optionally substituted phenyl. In some embodiments, one of W, X, and Y is —C—NH$_2$; one or more of the other of W, X, and Y are CH; Z is N; k is 1; and U is phenyl, optionally substituted with halogen. In some embodiments, one of W, X, and Y is —C—NH$_2$, one or more of the other of W, X, and Y are CH; Z is N; k is 1; and U is phenyl, optionally substituted with chlorine. In some embodiments, one of W, X, and Y is —C—NH$_2$, one or more of the other of W, X, and Y are CH; Z is N; k is 1; and U is phenyl, optionally substituted with fluorine.

In some embodiments, W is N; one of X, Y, and Z is —C—NH$_2$; the other of X, Y, and Z are CH; k is 1; and U is optionally substituted phenyl. In some embodiments, W is N; one of X, Y, and Z is —C—NH$_2$; the other of X, Y, and Z are CH; k is 1; and U is phenyl, optionally substituted with halogen. In some embodiments, W is N; one of X, Y, and Z is —C—NH$_2$; the other of X, Y, and Z are CH; k is 1; and U is phenyl, optionally substituted with chlorine. In some embodiments, W is N; one of X, Y, and Z is —C—NH$_2$; the other of X, Y, and Z are CH; k is 1; and U is phenyl, optionally substituted with fluorine.

In some embodiments, one of W, X, and Y is —C—NH$_2$; one or more of the other of W, X, and Y are CH; Z is N; k is 2; and the two occurrences of U on adjacent carbon atoms form a fused phenyl ring. In some embodiments, one of W, X, and Y is —C—NH$_2$; one or more of the other of W, X, and Y are CH; Z is N; k is 2; and the two occurrences of U on adjacent carbon atoms form an optionally substituted fused phenyl ring. In some embodiments, one of W, X, and Y is —C—NH$_2$; one or more of the other of W, X, and Y are CH; Z is N; k is 2; and the two occurrences of U on adjacent carbon atoms form a fused phenyl ring, optionally substituted with halogen. In some embodiments, one of W, X, and Y is —C—NH$_2$; one or more of the other of W, X, and Y are CH; Z is N; k is 2; and the two occurrences of U on adjacent carbon atoms form a fused phenyl ring, optionally substituted with chlorine. In some embodiments, one of W, X, and Y is —C—NH$_2$; one or more of the other of W, X, and Y are CH; Z is N; k is 2; and the two occurrences of U on adjacent carbon atoms form a fused phenyl ring, optionally substituted with fluorine.

In some embodiments, W is N; one of X, Y, and Z is —C—NH$_2$; the other of X, Y, and Z are CH; k is 2; and the two occurrences of U on adjacent carbon atoms form a fused phenyl ring. In some embodiments, W is N; one of X, Y, and Z is —C—NH$_2$; the other of X, Y, and Z are CH; k is 2; and the two occurrences of U on adjacent carbon atoms form an optionally substituted fused phenyl ring. In some embodiments, W is N; one of X, Y, and Z is —C—NH$_2$; the other of X, Y, and Z are CH; k is 2; and the two occurrences of U on adjacent carbon atoms form a fused phenyl ring, optionally substituted with halogen. In some embodiments, W is N; one of X, Y, and Z is —C—NH$_2$; the other of X, Y, and Z are CH; k is 2; and the two occurrences of U on adjacent carbon atoms form a fused phenyl ring, optionally substituted with fluorine. In some embodiments, W is N; one of X, Y, and Z is —C—NH$_2$; the other of X, Y, and Z are CH; k is 2; and the two occurrences of U on adjacent carbon atoms form a fused phenyl ring, optionally substituted with chlorine. In some embodiments, W is N; one of X, Y, and Z is —C—NH$_2$; the other of X, Y, and Z are CH; k is 2; and the two occurrences of U on adjacent carbon atoms form a fused phenyl ring, optionally substituted with chlorine and fluorine. In some embodiments, W is N; one of X, Y, and Z is —C—NH$_2$; the other of X, Y, and Z are CH; k is 2; and the two occurrences of U on adjacent carbon atoms form a fused phenyl ring, optionally substituted with chlorine at 2 positions.

In some embodiments, one of W, X, Y, and Z is —C—NH$_2$; one or more of the other of W, X, Y, and Z are CH; k is 2; and the two occurrences of U on adjacent carbon atoms form a fused 5- to 6-membered heteroaryl ring containing 1-3 heteroatoms independently selected from nitrogen, oxygen, and sulfur. In some embodiments, one of W, X, Y, and Z is —C—NH$_2$; one or more of the other of W, X, Y, and Z are CH; k is 2; and the two occurrences of U on adjacent carbon atoms form an optionally substituted fused 5- to 6-membered heteroaryl ring containing 1-3 heteroatoms independently selected from nitrogen, oxygen, and sulfur.

In some embodiments, one of W, X, Y, and Z is —C—NH$_2$; one or more of the other of W, X, Y, and Z are CH; k is 2; and the two occurrences of U on adjacent carbon atoms form an optionally substituted fused 6-membered heteroaryl ring containing one nitrogen heteroatom. In some embodiments, one of W, X, Y, and Z is —C—NH$_2$; one or more of the other of W, X, Y, and Z are CH; k is 2; and the two occurrences of U on adjacent carbon atoms form a fused pyridine ring. In some embodiments, one of W, X, Y, and Z is —C—NH$_2$; one or more of the other of W, X, Y, and Z are CH; k is 2; and the two occurrences of U on adjacent carbon atoms form an optionally substituted fused pyridine ring. In some embodiments, one of W, X, Y, and Z is —C—NH$_2$; one or more of the other of W, X, Y, and Z are CH; k is 2; and the two occurrences of U on adjacent carbon atoms form an optionally substituted fused 6-membered heteroaryl ring containing two nitrogen heteroatoms. In some embodiments, one of W, X, Y, and Z is —C—NH$_2$; one or more of the other of W, X, Y, and Z are CH; k is 2; and the two occurrences of U on adjacent carbon atoms form a fused pyrimidine ring. In some embodiments, one of W, X, Y, and Z is —C—NH$_2$; one or more of the other of W, X, Y, and Z are CH; k is 2; and the two occurrences of U on adjacent carbon atoms form an optionally substituted fused pyrimidine ring.

In some embodiments, one of W, X, Y, and Z is —C—NH$_2$; one or more of the other of W, X, Y, and Z are CH; k is 2; and the two occurrences of U on adjacent carbon atoms form fused aryl ring with 2 heteroatoms. In some embodiments, one of W, X, Y, and Z is —C—NH$_2$; one or more of the other of W, X, Y, and Z are CH; k is 2; and the two occurrences of U on adjacent carbon atoms form a 5-membered fused oxazole ring. In some embodiments, one of W, X, Y, and Z is —C—NH$_2$; one or more of the other of W, X, Y, and Z are CH; k is 2; and the two occurrences of U on adjacent carbon atoms form a 5-membered fused oxazole ring, optionally substituted with phenyl.

In some embodiments, one of W, X, Y, and Z is —C—NH$_2$; one or more of the other of W, X, Y, and Z is CH; k is 2; and the two occurrences of U on adjacent carbon atoms form an optionally substituted fused 5-membered heteroaryl ring containing one nitrogen and one oxygen heteroatom. In some embodiments, one of W, X, Y, and Z is —C—NH$_2$; one or more of the other of W, X, Y, and Z is CH; k is 2; and the two occurrences of U on adjacent carbon atoms form a fused 5-membered heteroaryl ring containing one nitrogen and one oxygen heteroatoms, optionally substituted with phenyl. In some embodiments, one of W, X, Y, and Z is —C—NH$_2$; one or more of the other of W, X, Y, and Z is CH; k is 2; and the two occurrences of U on adjacent carbon atoms form a fused 5-membered heteroaryl ring containing one nitrogen and one oxygen heteroatoms, optionally substituted with tosyl. In some embodiments, one of W, X, Y, and Z is —C—NH$_2$; one or more of the other of W, X, Y, and Z is CH; k is 2; and the two occurrences of U on adjacent carbon atoms form a fused 5-membered heteroaryl ring containing one nitrogen and one oxygen heteroatoms, optionally substituted with cyclopropyl.

In some embodiments, one of W, X, Y, and Z is —C—NH$_2$; one or more of the other of W, X, Y, and Z are CH; k is 2; and the two occurrences of U on adjacent carbon atoms form an optionally substituted fused oxazole ring. In some embodiments, one of W, X, Y, and Z is —C—NH$_2$; one or more of the other of W, X, Y, and Z are CH; k is 2; and the two occurrences of U on adjacent carbon atoms form a fused oxazole ring, optionally substituted with phenyl. In some embodiments, one of W, X, Y, and Z is —C—NH$_2$; one or more of the other of W, X, Y, and Z are CH; k is 2; and the two occurrences of U on adjacent carbon atoms form a fused oxazole ring, optionally substituted with tosyl.

In some embodiments, one of W, X, Y, and Z is —C—NH$_2$; one or more of the other of W, X, Y, and Z are CH; k is 2; and the two occurrences of U on adjacent carbon atoms form an optionally substituted fused isoxazole ring. In some embodiments, one of W, X, Y, and Z is —C—NH$_2$; one or more of the other of W, X, Y, and Z are CH; k is 2; and the two occurrences of U on adjacent carbon atoms form a fused isoxazole ring, optionally substituted with phenyl. In some embodiments, one of W, X, Y, and Z is —C—NH$_2$; one or more of the other of W, X, Y, and Z are CH; k is 2; and the two occurrences of U on adjacent carbon atoms form a fused isoxazole ring, optionally substituted with cyclopropyl.

In some embodiments, one of W, X, Y, and Z is —C—NH$_2$; one or more of the other of W, X, Y, and Z are CH; k is 2; and the two occurrences of U on adjacent carbon atoms form an optionally substituted fused 5-membered heteroaryl ring containing one nitrogen and one sulfur heteroatom. In some embodiments, one of W, X, Y, and Z is —C—NH$_2$; one or more of the other of W, X, Y, and Z is CH; k is 2; and the two occurrences of U on adjacent carbon atoms form a fused 5-membered heteroaryl ring containing one nitrogen and one sulfur heteroatom, optionally substituted by phenyl.

In some embodiments, one of W, X, Y, and Z is —C—NH$_2$; one or more of the other of W, X, Y, and Z are CH; k is 2; and the two occurrences of U on adjacent carbon atoms form an optionally substituted fused thiazole ring. In some embodiments, one of W, X, Y, and Z is —C—NH$_2$; one or more of the other of W, X, Y, and Z are CH; k is 2; and the two occurrences of U on adjacent carbon atoms form a fused thiazole ring, optionally substituted with phenyl.

In some embodiments, one of W, X, Y, and Z is —C—NH$_2$; one or more of the other of W, X, Y, and Z are CH; k is 2; and the two occurrences of U on adjacent carbon atoms form an optionally substituted fused 5 membered heteroaryl ring containing two nitrogen heteratoms. In some embodiments, one of W, X, Y, and Z is —C—NH$_2$; one or more of the other of W, X, Y, and Z are CH; k is 2; and the two occurrences of U on adjacent carbon atoms form an optionally substituted fused imidazole ring. In some embodiments, one of W, X, Y, and Z is —C—NH$_2$; one or more of the other of W, X, Y, and Z are CH; k is 2; and the two occurrences of U on adjacent carbon atoms form a fused imidazole ring, optionally substituted with phenyl.

In some embodiments, one of W, X, Y, and Z is —C—NH$_2$; one or more of the other of W, X, Y, and Z are CH; k is 3; U₁ is chlorine and U₃ on adjacent carbon atoms form an optionally substituted fused 5-membered heteroaryl ring containing one nitrogen and one oxygen heteroatom. In some embodiments, one of W, X, Y, and Z is —C—NH₂; one or more of the other of W, X, Y, and Z are CH; k is 3; U₁ is chlorine and U₂ and U₃ on adjacent carbon atoms form a fused 5-membered heteroaryl ring containing one nitrogen and one oxygen heteroatom, optionally substituted with phenyl. In some embodiments, one of W, X, Y, and Z is —C—NH₂; one or more of the other of W, X, Y, and Z are CH; k is 3; U₁ is chlorine and U₂ and U₃ on adjacent carbon atoms form a fused 5-membered heteroaryl ring containing one nitrogen and one oxygen heteroatom, optionally substituted with tosyl.

In some embodiments, one of W, X, Y, and Z is —C—NH₂; one or more of the other of W, X, Y, and Z are CH; k is 3; U₁ is chlorine and U₂ and U₃ on adjacent carbon atoms form an optionally substituted fused oxazole ring. In some embodiments, one of W, X, Y, and Z is —C—NH₂; one or more of the other of W, X, Y, and Z are CH; k is 3; U₁ is chlorine and U₂ and U₃ on adjacent carbon atoms form a fused oxazole ring, optionally substituted with phenyl. In some embodiments, one of W, X, Y, and Z is —C—NH₂; one or more of the other of W, X, Y, and Z are CH; k is 3; U₁ is chlorine and U₂ and U₃ on adjacent carbon atoms form a fused oxazole ring, optionally substituted with tosyl.

In some embodiments, one of W, X, Y, and Z is —C—NH₂; one or more of the other of W, X, Y, and Z are CH; k is 3; U₁ is chlorine and U₂ and U₃ on adjacent carbon atoms form an optionally substituted fused isoxazole ring. In some embodiments, one of W, X, Y, and Z is —C—NH₂; one or more of the other of W, X, Y, and Z are CH; k is 3; U₁ is chlorine and U₂ and U₃ adjacent carbon atoms form a fused isoxazole ring, optionally substituted with cyclopropyl.

As defined above and described herein, each R is independently selected from hydrogen, deuterium, and an optionally substituted group selected from $C_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, and sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur.

In some embodiments, R is hydrogen. In some embodiments, R is deuterium. In some embodiments, R is C1-6 aliphatic. In some embodiments R is methyl. In some embodiments, R is ethyl. In some embodiments, R is optionally substituted $C_{1-6}$ aliphatic. In some embodiments, R is optionally substituted methyl. In some embodiments, R is optionally substituted ethyl. In some embodiments, R is phenyl. In some embodiments, R is optionally substituted phenyl. In some embodiments, R is phenyl, optionally substituted with halogen. In some embodiments, R is phenyl, optionally substituted with fluorine.

As described generally above, $R^a$ is $C_{1-4}$ aliphatic optionally substituted with 1, 2, or 3 deuterium or halogen atoms.

In some embodiments, $R^a$ is $C_{1-4}$ aliphatic. In some embodiments, $R^a$ is $C_{1-4}$ aliphatic optionally substituted with 1, 2, or 3 deuterium atoms. In some embodiments, $R^a$ is $C_{1-4}$ aliphatic optionally substituted with 1, 2, or 3 halogen atoms.

In some embodiments, $R^a$ is $C_{1-4}$ alkyl. In some embodiments, $R^a$ is $C_{1-4}$ alkyl optionally substituted with 1, 2, or 3 deuterium or halogen atoms. In some embodiments, $R^a$ is $C_{1-4}$ alkyl optionally substituted with 1, 2, or 3 halogen atoms. In some embodiments, $R^a$ is methyl or ethyl optionally substituted with 1, 2, or 3 halogen atoms. In some embodiments, $R^a$ is methyl.

As defined generally above, $R^b$ is $C_{1-4}$ aliphatic optionally substituted with 1, 2, or 3 deuterium or halogen atoms.

In some embodiments, $R^b$ is $C_{1-4}$ aliphatic. In some embodiments, $R^b$ is $C_{1-4}$ aliphatic optionally substituted with 1, 2, or 3 deuterium atoms. In some embodiments, $R^b$ is $C_{1-4}$ aliphatic optionally substituted with 1, 2, or 3 halogen atoms.

In some embodiments, $R^b$ is $C_{1-4}$ alkyl. In some embodiments, $R^b$ is $C_{1-4}$ alkyl optionally substituted with 1, 2, or 3 deuterium or halogen atoms. In some embodiments, $R^b$ is $C_{1-4}$ alkyl optionally substituted with 1, 2, or 3 halogen atoms. In some embodiments, $R^b$ is methyl or ethyl optionally substituted with 1, 2, or 3 halogen atoms. In some embodiments, $R^b$ is methyl.

As defined generally above, in some embodiments, $R^a$ and $R^b$, taken together with the carbon atom to which they are attached, form a 3- to 8-membered cycloalkyl or heterocyclyl ring containing 1-2 heteroatoms selected from nitrogen, oxygen, and sulfur.

In some embodiments, $R^a$ and $R^b$, taken together with the carbon atom to which they are attached, form a 3- to 8-membered cycloalkyl. In some embodiments, $R^a$ and $R^b$, taken together with the carbon atom to which they are attached, form a 3- to 8-membered heterocyclyl ring containing 1-2 heteroatoms selected from nitrogen, oxygen, and sulfur.

In some embodiments, $R^a$ and $R^b$, taken together with the carbon atom to which they are attached, form a cyclopropyl, cyclobutyl, or cyclopentyl ring. In some embodiments, $R^a$ and $R^b$, taken together with the carbon atom to which they are attached, form an oxirane, oxetane, tetrahydrofuran, or aziridine.

In some embodiments, $R^a$ and $R^b$ are methyl.

In some embodiments, the compound for use in the treatment of an inflammatory disorder is a compound of formula II:

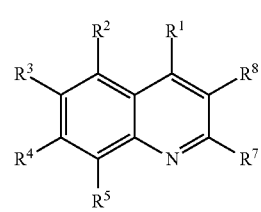

II or a pharmaceutically acceptable salt thereof, wherein:
each of $R^1$, $R^7$, and $R^8$ is independently H, D, halogen, —NH₂, —CN, —OR, —SR, optionally substituted $C_{1-6}$ aliphatic, or

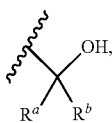

wherein one of $R^1$, $R^7$ and $R^8$ is —$NH_2$ and other one of $R^1$ $R^7$ and $R^8$ is

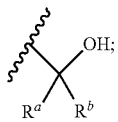

$R^2$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^3$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^4$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^5$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^a$ is $C_{1-4}$ aliphatic optionally substituted with 1, 2, or 3 deuterium or halogen atoms;

$R^b$ is $C_{1-4}$ aliphatic optionally substituted with 1, 2, or 3 deuterium or halogen atoms; or $R^a$ and $R^b$, taken together with the carbon atom to which they are attached, form a 3- to 8-membered cycloalkyl or heterocyclyl ring containing 1-2 heteroatoms selected from nitrogen, oxygen, and sulfur; and each R is independently selected from hydrogen, deuterium, and an optionally substituted group selected from $C_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, and sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; and a 7- to to 10-membered bicyclic heteroaryl ring having 1-5 heteroatoms independently selected from nitrogen, oxygen, and sulfur.

In some embodiments of formula II, $R^a$ is $C_{1-4}$ aliphatic. In some embodiments, $R^a$ is $C_{1-4}$ aliphatic optionally substituted with 1, 2, or 3 deuterium atoms. In some embodiments, $R^a$ is $C_{1-4}$ aliphatic optionally substituted with 1, 2, or 3 halogen atoms.

In some embodiments of formula II, $R^a$ is $C_{1-4}$ alkyl. In some embodiments, $R^a$ is $C_{1-4}$ alkyl optionally substituted with 1, 2, or 3 deuterium or halogen atoms. In some embodiments, $R^a$ is $C_{1-4}$ alkyl optionally substituted with 1, 2, or 3 halogen atoms. In some embodiments, $R^a$ is methyl or ethyl optionally substituted with 1, 2, or 3 halogen atoms. In some embodiments, $R^a$ is methyl.

As defined generally above, $R^b$ is $C_{1-4}$ aliphatic optionally substituted with 1, 2, or 3 deuterium or halogen atoms.

In some embodiments of formula II, $R^b$ is $C_{1-4}$ aliphatic. In some embodiments, $R^b$ is $C_{1-4}$ aliphatic optionally substituted with 1, 2, or 3 deuterium atoms. In some embodiments, $R^b$ is $C_{1-4}$ aliphatic optionally substituted with 1, 2, or 3 halogen atoms.

In some embodiments of formula II, $R^b$ is $C_{1-4}$ alkyl. In some embodiments, $R^b$ is $C_{1-4}$ alkyl optionally substituted with 1, 2, or 3 deuterium or halogen atoms. In some embodiments, $R^b$ is $C_{1-4}$ alkyl optionally substituted with 1, 2, or 3 halogen atoms. In some embodiments, $R^b$ is methyl or ethyl optionally substituted with 1, 2, or 3 halogen atoms. In some embodiments, $R^b$ is methyl.

As defined generally above, in some embodiments, $R^a$ and $R^b$, taken together with the carbon atom to which they are attached, form a 3- to 8-membered cycloalkyl or heterocyclyl ring containing 1-2 heteroatoms selected from nitrogen, oxygen, and sulfur.

In some embodiments of formula II, $R^a$ and $R^b$, taken together with the carbon atom to which they are attached, form a 3- to 8-membered cycloalkyl. In some embodiments, $R^a$ and $R^b$, taken together with the carbon atom to which they are attached, form a 3- to 8-membered heterocyclyl ring containing 1-2 heteroatoms selected from nitrogen, oxygen, and sulfur.

In some embodiments of formula II, $R^a$ and $R^b$, taken together with the carbon atom to which they are attached, form a cyclopropyl, cyclobutyl, or cyclopentyl ring. In some embodiments, $R^a$ and $R^b$, taken together with the carbon atom to which they are attached, form an oxirane, oxetane, tetrahydrofuran, or aziridine.

In some embodiments of formula II, the —$NH_2$ on one of $R^1$, $R^7$, and $R^8$ and the carbinol on the other of $R^1$, $R^7$, and $R^8$ are on adjacent carbon atoms of the pyridine moiety.

In some embodiments, the compound is a compound of formula II-a, II-b, or II-c:

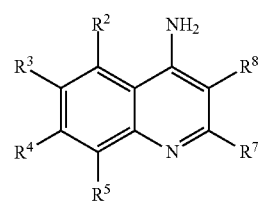

II-a

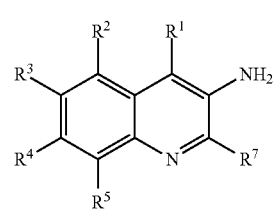

II-b

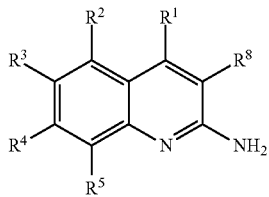
II-c or a pharmaceutically acceptable salt thereof, wherein:
each of $R^1$, $R^7$, and $R^8$ when present is independently H, D, halogen, —CN, —OR, —SR, optionally substituted $C_{1-6}$ aliphatic, or

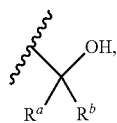

wherein one of $R^1$, $R^7$, and $R^8$ is

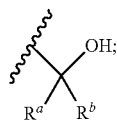

and
$R^2$, $R^3$, $R^4$, $R^5$, $R^a$, $R^b$ and R are as defined for formula II.

In some embodiments, the compound for use in the method is a compound of formula II-d, II-e, II-f or II-g:

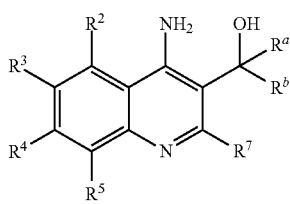
II-d

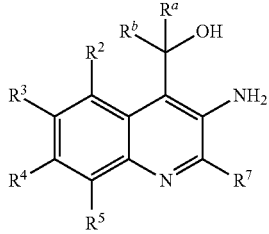
II-e

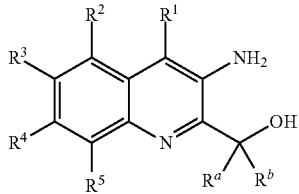
II-f

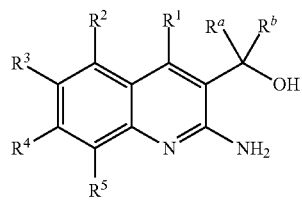
II-g or a pharmaceutically acceptable salt thereof, wherein;
$R^1$ and $R^7$ is independently H, D, halogen, —CN, —OR, —SR, optionally substituted $C_{1-6}$ aliphatic; and
$R^2$, $R^3$, $R^4$, $R^5$, $R^a$, $R^b$ and R are as defined for formula II.

In some embodiments, the compound for use in the method is a compound of formula III:

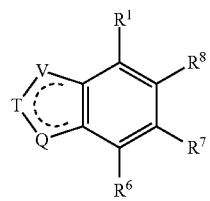
III or a pharmaceutically acceptable salt thereof, wherein:
Q, T and V are independently S, N, O, or —C—R;
each of $R^1$, $R^6$, $R^7$, and $R^8$ is independently H, D, halogen, —NH$_2$, —CN, —OR, —SR, optionally substituted $C_{1-6}$ aliphatic, or

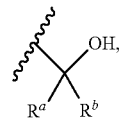

wherein one of $R^1$, $R^6$, $R^7$, and $R^8$ is —NH$_2$ and other one of $R_1$, $R^6$, $R^7$, and $R^8$ is

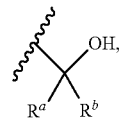

$R^a$ is $C_{1-4}$ aliphatic optionally substituted with 1, 2, or 3 deuterium or halogen atoms; and
$R^b$ is $C_{1-4}$ aliphatic optionally substituted with 1, 2, or 3 deuterium or halogen atoms; or $R^a$ and $R^b$, taken together with the carbon atom to which they are attached, form a 3-8 membered cycloalkyl or heterocyclyl ring containing 1-2 heteroatoms selected from nitrogen, oxygen, and sulfur; and
each R is independently selected from hydrogen, deuterium, and an optionally substituted group selected from: $C_{1-6}$ aliphatic, a 3- to 8-membered saturated or partially unsaturated monocyclic carbocyclic ring, phenyl, an 8- to 10-membered bicyclic aryl ring, a 3- to 8-membered saturated or partially unsaturated monocyclic heterocyclic ring having 1-4 heteroatoms independently selected from nitrogen, oxygen, and sulfur, a 5- to 6-membered monocyclic heteroaryl ring having 1-4 heteroatoms independently selected from nitrogen, oxygen, and sulfur, a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur.

In some embodiments of formula III, the —NH$_2$ on one of R$_1$, R$^6$, R$^7$, and R$^8$ and the carbinol on the other of R$_1$, R$^6$, R$^7$, and R$^8$ are on adjacent carbon atoms of the phenyl moiety.

In some embodiments of formula III, one of Q, T and V is N, and other of Q, T and V is 0. In some embodiments, Q is 0, V is N, and T is C—R. In some embodiments, Q is N, T is O and V is C—R.

In some embodiments of formula III, the compound is a compound of formula III-a or

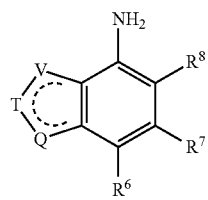

III-a

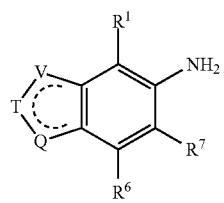

III-b or a pharmaceutically acceptable salt thereof, wherein:

each of R$^1$, R$^6$, R$^7$, and R$^8$ when present is independently H, D, halogen, —CN, —OR, —SR, optionally substituted C$_{1-6}$ aliphatic, or

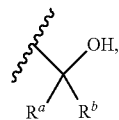

wherein one of R$_1$, R$^6$, R$^7$, and R$^8$ is

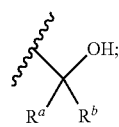

and

Q, T, V, R, R$^a$ and R$^b$ are as defined in formula III.

In some embodiments of formula III, the compound is a compound of formula III-c, III-d or III-e:

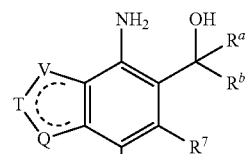

III-c

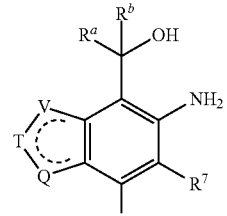

III-d

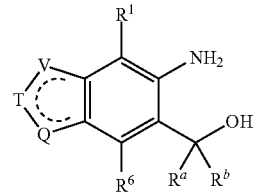

III-e or a pharmaceutically acceptable salt thereof, wherein:

each of R$_1$, R$^6$, and R$^7$ when present is independently H, D, halogen, —CN, —OR, —SR, optionally substituted C$_{1-6}$ aliphatic; and Q, T, V, R, R$^a$ and R$^b$ are as defined in formula III.

In some embodiments of formula III, the compound is a compound of formula III-f, III-h or III-i:

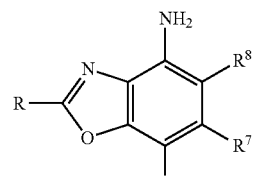

III-f

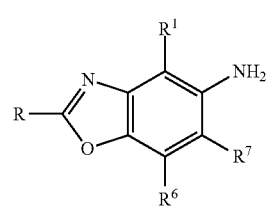

III-g

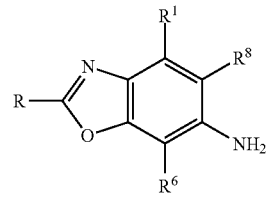

III-h

-continued

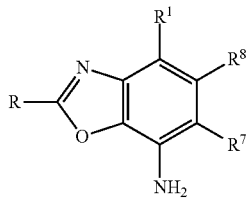

III-i or a pharmaceutically acceptable salt thereof, wherein:
each of $R^1$, $R^6$, $R^7$, and $R^8$ when present is independently H, D, halogen, —CN, —OR, —SR, optionally substituted $C_{1-6}$ aliphatic or

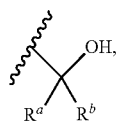

wherein one of $R^1$, $R^6$, $R^7$, and $R^8$ is

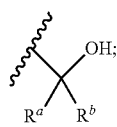

and

R, $R^a$ and $R^b$ are as defined in formula III.

In some embodiments of formula III, the compound is a compound of formula III-j, III-k, III-l or III-m:

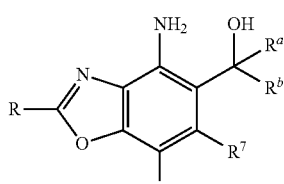

III-j

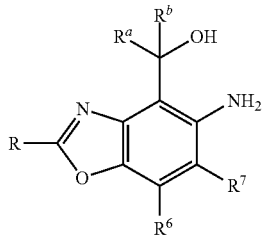

III-k

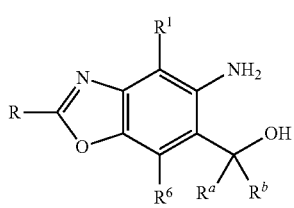

III-l

-continued

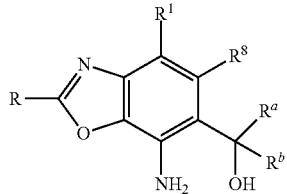

III-m or a pharmaceutically acceptable salt thereof, wherein:
each of $R^1$, $R^6$, $R^7$, and $R^8$ when present is independently H, D, halogen, —CN, —OR, —SR, optionally substituted $C_{1-6}$ aliphatic; and R, $R^a$ and $R^b$ are as defined in formula III.

In some embodiments of formula III, the compound is a compound of formula III-n:

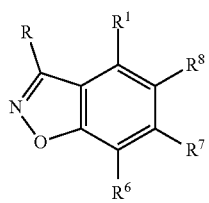

III-n or a pharmaceutically acceptable salt thereof, wherein:
each of $R^1$, $R^6$, $R^7$, and $R^8$ is independently H, D, halogen, —NH$_2$, —CN, —OR, —SR, optionally substituted $C_{1-6}$ aliphatic, or

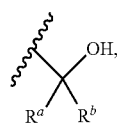

wherein one of $R^1$, $R^6$, $R^7$, and $R^8$ is —NH$_2$ and other one of $R^1$, $R^6$, $R^7$, and $R^8$ is

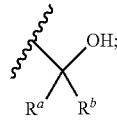

and

R, $R^a$, and $R^b$ are as defined in formula III

In some embodiments of formula III, the compound is a compound of formula III-o, III-q or III-r:

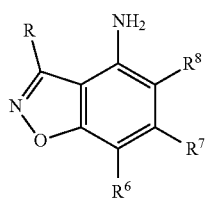

III-o

III-p
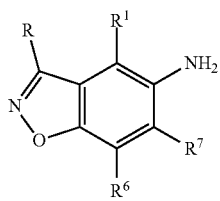

III-q
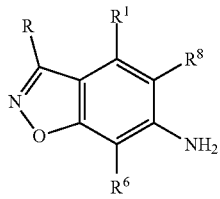

III-r
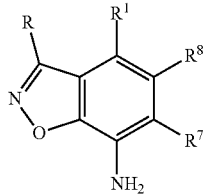

or a pharmaceutically acceptable salt thereof, wherein:

each of $R^1$, $R^6$, $R^7$, and $R^8$ when present is independently H, D, halogen, —CN, —OR, —SR, optionally substituted $C_{1-6}$ aliphatic, or

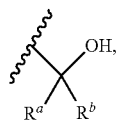

wherein one of $R^1$, $R^6$, $R^7$, and $R^8$ is

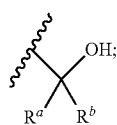

and

R, $R^a$, and $R^b$ are as defined in formula III

In some embodiments of formula III, the compound is a compound of formula III-s, III-w, or III-x:

III-s
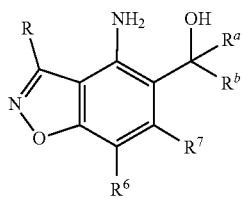

III-t
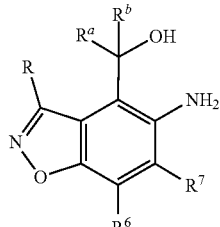

III-u
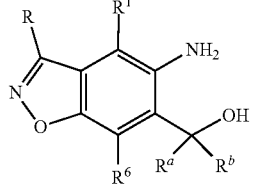

III-v
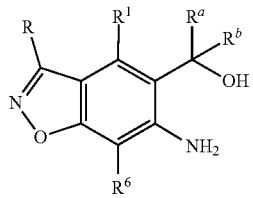

III-w
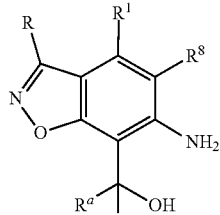

III-x
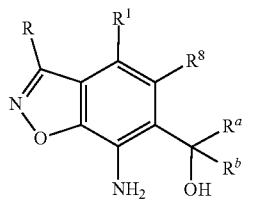

or a pharmaceutically acceptable salt thereof, wherein:

each of $R^6$, $R^7$, and $R^8$ when present is independently H, D, halogen, —CN, —OR, —SR, optionally substituted $C_{1-6}$ aliphatic; and R, $R^a$ and $R^b$ are as defined in formula III.

In some embodiments, the compound for use in the method is a compound of formula IV:

IV
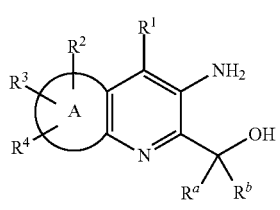

or a pharmaceutically acceptable salt thereof, wherein:
- Ring A is a 5-membered partially unsaturated heterocyclic or heteroaromatic ring containing 1-3 nitrogen atoms, 1 or 2 oxygen atoms, 1 sulfur atom, or 1 nitrogen and 1 sulfur atom; or a 6-membered partially unsaturated heterocyclic or heteroaromatic ring containing 1-3 heteroatoms independently selected from nitrogen, oxygen, and sulfur; or a 7-membered partially unsaturated heterocyclic or heteroaromatic ring containing 1-3 heteroatoms independently selected from nitrogen, oxygen, and sulfur;
- $R^1$ is H, D, halogen, —CN, —OR, —SR, or optionally substituted $C_{1-6}$ aliphatic; each R is independently selected from hydrogen, deuterium, and an optionally substituted group selected from: $C_{1-6}$ aliphatic, a 3- to 8-membered saturated or partially unsaturated monocyclic carbocyclic ring, phenyl, an 8- to 10-membered bicyclic aryl ring, a 3- to 8-membered saturated or partially unsaturated monocyclic heterocyclic ring having 1-4 heteroatoms independently selected from nitrogen, oxygen, and sulfur, a 5- to 6-membered monocyclic heteroaryl ring having 1-4 heteroatoms independently selected from nitrogen, oxygen, and sulfur, a 6- to 10-membered bicyclic heterocyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur;
- $R^2$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;
- $R^3$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;
- $R^4$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;
- $R^6$ is $C_{1-4}$ aliphatic optionally substituted with 1, 2, or 3 deuterium or halogen atoms; and
- $R^7$ is $C_{1-4}$ aliphatic optionally substituted with 1, 2, or 3 deuterium or halogen atoms; or $R^6$ and $R^7$, taken together with the carbon atom to which they are attached, form a 3- to 8-membered cycloalkyl or heterocyclyl ring containing 1-2 heteroatoms selected from nitrogen, oxygen, and sulfur.

As defined generally above, Ring A is a 5-membered partially unsaturated heterocyclic or heteroaromatic ring containing 1-3 nitrogen atoms, 1 or 2 oxygen atoms, 1 sulfur atom, or 1 nitrogen and 1 sulfur atom; or a 6-membered partially unsaturated heterocyclic or heteroaromatic ring containing 1-3 heteroatoms independently selected from nitrogen, oxygen, and sulfur; or a 7-membered partially unsaturated heterocyclic or heteroaromatic ring containing 1-3 heteroatoms independently selected from nitrogen, oxygen, and sulfur.

In some embodiments, Ring A is a 5-membered partially unsaturated heterocyclic or heteroaromatic ring containing 1-3 nitrogen atoms, 1 or 2 oxygen atoms, 1 sulfur atom, or 1 nitrogen and 1 sulfur atom. In some embodiments, Ring A is a 6-membered partially unsaturated heterocyclic or heteroaromatic ring containing 1-3 heteroatoms independently selected from nitrogen, oxygen, and sulfur. In some embodiments, Ring A is a 7-membered partially unsaturated heterocyclic or heteroaromatic ring containing 1-3 heteroatoms independently selected from nitrogen, oxygen, and sulfur.

In some embodiments, Ring A is imidazole or triazole. In some embodiments, Ring A is thiazole. In some embodiments, Ring A is thiophene or furan. In some embodiments, Ring A is pyridine, pyrimidine, pyrazine, pyridazine, or 1,2,4-triazine. In some embodiments, Ring A is pyridine.

As defined generally above, $R^1$ is H, D, halogen, —CN, —OR, —SR, or optionally substituted $C_{1-6}$ aliphatic.

In some embodiments, $R^1$ is H. In some embodiments, $R^1$ is D. In some embodiments, $R^1$ is halogen. In some embodiments, $R^1$ is —CN. In some embodiments, $R^1$ is —OR. In some embodiments, $R^1$ is —SR. In some embodiments, $R^1$ is optionally substituted $C_{1-6}$ aliphatic.

As described generally above, $R^2$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, $R^2$ is absent. In some embodiments, $R^2$ is —R. In some embodiments, $R^2$ is halogen. In some embodiments, $R^2$ is —CN. In some embodiments, $R^2$ is —OR. In some embodiments, $R^2$ is —SR. In some embodiments, $R^2$ is —N(R)$_2$. In some embodiments, $R^2$ is —N(R)C(O)R. In some embodiments, $R^2$ is —C(O)N(R)$_2$. In some embodiments, $R^2$ is —N(R)C(O)N(R)$_2$. In some embodiments, $R^2$ is —N(R)C(O)OR. In some embodiments, $R^2$ is —OC(O)N(R)$_2$. In some embodiments, $R^2$ is —N(R)S(O)$_2$R. In some embodiments, $R^2$ is —SO$_2$N(R)$_2$. In some embodiments, $R^2$ is —C(O)R. In some embodiments, $R^2$ is —C(O)OR. In some embodiments, $R^2$ is —OC(O)R. In some embodiments, $R^2$ is —S(O)R. In some embodiments, $R^2$ is —S(O)$_2$R.

In some embodiments, $R^2$ is hydrogen. In some embodiments, $R^2$ is deuterium. In some embodiments, $R^2$ is an optionally substituted $C_{1-6}$ aliphatic. In some embodiments, $R^2$ is an optionally substituted 3- to 8-membered saturated or partially unsaturated monocyclic carbocyclic ring. In some embodiments, $R^2$ is an optionally substituted phenyl. In some embodiments, $R^2$ is an optionally substituted 8- to 10-membered bicyclic aryl ring. In some embodiments, $R^2$ is an optionally substituted 3- to 8-membered saturated or partially unsaturated monocyclic heterocyclic ring having 1-4 heteroatoms independently selected from nitrogen, oxygen, and sulfur. In some embodiments, $R^2$ is an optionally substituted 5- to 6-membered monocyclic heteroaryl ring having 1-4 heteroatoms independently selected from nitrogen, oxygen, and sulfur. In some embodiments, $R^2$ is an optionally substituted 6- to 10-membered bicyclic saturated or partially unsaturated heterocyclic ring having 1-5 heteroatoms independently selected from nitrogen, oxygen, and sulfur. In some embodiments, $R^2$ is an optionally substituted 7- to 10-membered bicyclic heteroaryl ring having 1-5 heteroatoms independently selected from nitrogen, oxygen, and sulfur.

In some embodiments, $R^2$ is Cl or Br. In some embodiments, $R^2$ is Cl.

As defined generally above, $R^3$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, $R^3$ is absent. In some embodiments, $R^3$ is —R. In some embodiments, $R^3$ is halogen. In some embodiments, $R^3$ is —CN. In some embodiments, $R^3$ is —OR. In some embodiments, $R^3$ is —SR. In some embodiments, $R^3$ is —N(R)$_2$. In some embodiments, $R^3$ is —N(R)C(O)R. In some embodiments, $R^3$ is —C(O)N(R)$_2$. In some embodiments, $R^3$ is —N(R)C(O)N(R)$_2$. In some embodiments, $R^3$ is —N(R)C(O)OR. In some embodiments, $R^3$ is —OC(O)N(R)$_2$. In some embodiments, $R^3$ is —N(R)S(O)$_2$R. In some embodiments, $R^3$ is —SO$_2$N(R)$_2$. In some embodiments, $R^3$ is —C(O)R. In some embodiments, $R^3$ is —C(O)OR. In some embodiments, $R^3$ is —OC(O)R. In some embodiments, $R^3$ is —S(O)R. In some embodiments, $R^3$ is —S(O)$_2$R.

In some embodiments, $R^3$ is hydrogen. In some embodiments, $R^3$ is deuterium. In some embodiments, $R^3$ is an optionally substituted $C_{1-6}$ aliphatic. In some embodiments, $R^3$ is an optionally substituted 3- to 8-membered saturated or partially unsaturated monocyclic carbocyclic ring. In some embodiments, $R^3$ is an optionally substituted phenyl. In some embodiments, $R^3$ is an optionally substituted 8- to 10-membered bicyclic aryl ring. In some embodiments, $R^3$ is an optionally substituted 3- to 8-membered saturated or partially unsaturated monocyclic heterocyclic ring having 1-4 heteroatoms independently selected from nitrogen, oxygen, and sulfur. In some embodiments, $R^3$ is an optionally substituted 5- to 6-membered monocyclic heteroaryl ring having 1-4 heteroatoms independently selected from nitrogen, oxygen, and sulfur. In some embodiments, $R^3$ is an optionally substituted 6- to 10-membered bicyclic saturated or partially unsaturated heterocyclic ring having 1-5 heteroatoms independently selected from nitrogen, oxygen, and sulfur. In some embodiments, $R^3$ is an optionally substituted 7- to 10-membered bicyclic heteroaryl ring having 1-5 heteroatoms independently selected from nitrogen, oxygen, and sulfur.

In some embodiments, $R^3$ is Cl or Br. In some embodiments, $R^3$ is Cl.

As defined generally above, $R^4$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, $R^4$ is absent. In some embodiments, $R^4$ is —R. In some embodiments, $R^4$ is halogen. In some embodiments, $R^4$ is —CN. In some embodiments, $R^4$ is —OR. In some embodiments, $R^4$ is —SR. In some embodiments, $R^4$ is —N(R)$_2$. In some embodiments, $R^4$ is —N(R)C(O)R. In some embodiments, $R^4$ is —C(O)N(R)$_2$. In some embodiments, $R^4$ is —N(R)C(O)N(R)$_2$. In some embodiments, $R^4$ is —N(R)C(O)OR. In some embodiments, $R^4$ is —OC(O)N(R)$_2$. In some embodiments, $R^4$ is —N(R)S(O)$_2$R. In some embodiments, $R^4$ is —SO$_2$N(R)$_2$. In some embodiments, $R^4$ is —C(O)R. In some embodiments, $R^4$ is —C(O)OR. In some embodiments, $R^4$ is —OC(O)R. In some embodiments, $R^4$ is —S(O)R. In some embodiments, $R^4$ is —S(O)$_2$R.

In some embodiments, $R^4$ is hydrogen. In some embodiments, $R^4$ is deuterium. In some embodiments, $R^4$ is an optionally substituted $C_{1-6}$ aliphatic. In some embodiments, $R^4$ is an optionally substituted 3- to 8-membered saturated or partially unsaturated monocyclic carbocyclic ring. In some embodiments, $R^4$ is an optionally substituted phenyl. In some embodiments, $R^4$ is an optionally substituted 8- to 10-membered bicyclic aryl ring. In some embodiments, $R^4$ is an optionally substituted 3- to 8-membered saturated or partially unsaturated monocyclic heterocyclic ring having 1-4 heteroatoms independently selected from nitrogen, oxygen, and sulfur. In some embodiments, $R^4$ is an optionally substituted 5- to 6-membered monocyclic heteroaryl ring having 1-4 heteroatoms independently selected from nitrogen, oxygen, and sulfur. In some embodiments, $R^4$ is an optionally substituted 6- to 10-membered bicyclic saturated or partially unsaturated heterocyclic ring having 1-5 heteroatoms independently selected from nitrogen, oxygen, and sulfur. In some embodiments, $R^4$ is an optionally substituted 7- to 10-membered bicyclic heteroaryl ring having 1-5 heteroatoms independently selected from nitrogen, oxygen, and sulfur.

In some embodiments, $R^4$ is Cl or Br. In some embodiments, $R^4$ is Cl.

As described generally above, $R^a$ is $C_{1-4}$ aliphatic optionally substituted with 1, 2, or 3 deuterium or halogen atoms.

In some embodiments, $R^a$ is $C_{1-4}$ aliphatic. In some embodiments, $R^a$ is $C_{1-4}$ aliphatic optionally substituted with 1, 2, or 3 deuterium atoms. In some embodiments, $R^a$ is $C_{1-4}$ aliphatic optionally substituted with 1, 2, or 3 halogen atoms.

In some embodiments, $R^a$ is $C_{1-4}$ alkyl. In some embodiments, $R^a$ is $C_{1-4}$ alkyl optionally substituted with 1, 2, or 3 deuterium or halogen atoms. In some embodiments, $R^a$ is $C_{1-4}$ alkyl optionally substituted with 1, 2, or 3 halogen atoms. In some embodiments, $R^a$ is methyl or ethyl optionally substituted with 1, 2, or 3 halogen atoms. In some embodiments, $R^a$ is methyl.

As defined generally above, $R^b$ is $C_{1-4}$ aliphatic optionally substituted with 1, 2, or 3 deuterium or halogen atoms.

In some embodiments, $R^b$ is $C_{1-4}$ aliphatic. In some embodiments, $R^b$ is $C_{1-4}$ aliphatic optionally substituted with 1, 2, or 3 deuterium atoms. In some embodiments, $R^b$ is $C_{1-4}$ aliphatic optionally substituted with 1, 2, or 3 halogen atoms.

In some embodiments, $R^b$ is $C_{1-4}$ alkyl. In some embodiments, $R^b$ is $C_{1-4}$ alkyl optionally substituted with 1, 2, or 3 deuterium or halogen atoms. In some embodiments, $R^b$ is $C_{1-4}$ alkyl optionally substituted with 1, 2, or 3 halogen atoms. In some embodiments, $R^b$ is methyl or ethyl optionally substituted with 1, 2, or 3 halogen atoms. In some embodiments, $R^b$ is methyl.

As defined generally above, in some embodiments, $R^a$ and $R^b$, taken together with the carbon atom to which they are attached, form a 3- to 8-membered cycloalkyl or heterocyclyl ring containing 1-2 heteroatoms selected from nitrogen, oxygen, and sulfur.

In some embodiments, $R^a$ and $R^b$, taken together with the carbon atom to which they are attached, form a 3- to 8-membered cycloalkyl. In some embodiments, $R^a$ and $R^b$, taken together with the carbon atom to which they are attached, form a 3- to 8-membered heterocyclyl ring containing 1-2 heteroatoms selected from nitrogen, oxygen, and sulfur.

In some embodiments, $R^a$ and $R^b$, taken together with the carbon atom to which they are attached, form a cyclopropyl, cyclobutyl, or cyclopentyl ring. In some embodiments, $R^a$ and $R^b$, taken together with the carbon atom to which they are attached, form an oxirane, oxetane, tetrahydrofuran, or aziridine.

In some embodiments, $R^a$ and $R^b$ are methyl.

In some embodiments, the compound for use in the method is a compound of formula V:

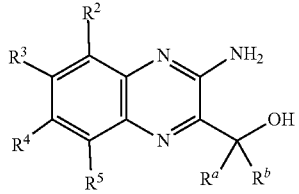

or a pharmaceutically acceptable salt thereof, wherein:
$R^2$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

each R is independently selected from hydrogen, deuterium, and an optionally substituted group selected from: $C_{1-6}$ aliphatic, a 3-to 8-membered saturated or partially unsaturated monocyclic carbocyclic ring, phenyl, an 8- to 10-membered bicyclic aryl ring, a 3- to 8-membered saturated or partially unsaturated monocyclic heterocyclic ring having 1-4 heteroatoms independently selected from nitrogen, oxygen, and sulfur, a 5- to 6-membered monocyclic heteroaryl ring having 1-4 heteroatoms independently selected from nitrogen, oxygen, and sulfur, a 6- to 10-membered bicyclic saturated or partially unsaturated heterocyclic ring having 1-5 heteroatoms independently selected from nitrogen, oxygen, and sulfur; or a 7- to 10-membered bicyclic heteroaryl ring having 1-5 heteroatoms independently selected from nitrogen, oxygen, and sulfur;

$R^3$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^4$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^5$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^a$ is $C_{1-4}$ aliphatic optionally substituted with 1, 2, or 3 deuterium or halogen atoms; and $R^b$ is $C_{1-4}$ aliphatic optionally substituted with 1, 2, or 3 deuterium or halogen atoms; or $R^a$ and $R^b$, taken together with the carbon atom to which they are attached, form a 3- to 8-membered cycloalkyl or heterocyclyl ring containing 1-2 heteroatoms selected from nitrogen, oxygen, and sulfur.

As described generally above, $R^2$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, $R^2$ is —R. In some embodiments, $R^2$ is halogen. In some embodiments, $R^2$ is —CN. In some embodiments, $R^1$ is —OR. In some embodiments, $R^2$ is —SR. In some embodiments, $R^2$ is —N(R)$_2$. In some embodiments, $R^2$ is —N(R)C(O)R. In some embodiments, $R^2$ is —C(O)N(R)$_2$. In some embodiments, $R^2$ is —N(R)C(O)N(R)$_2$. In some embodiments, $R^2$ is —N(R)C(O)OR. In some embodiments, $R^2$ is —OC(O)N(R)$_2$. In some embodiments, $R^2$ is —N(R)S(O)$_2$R. In some embodiments, $R^2$ is —SO$_2$N(R)$_2$. In some embodiments, $R^2$ is —C(O)R. In some embodiments, $R^2$ is —C(O)OR. In some embodiments, $R^2$ is —OC(O)R. In some embodiments, $R^2$ is —S(O)R. In some embodiments, $R^2$ is —S(O)$_2$R.

In some embodiments, $R^2$ is hydrogen. In some embodiments, $R^2$ is deuterium. In some embodiments, $R^2$ is an optionally substituted $C_{1-6}$ aliphatic. In some embodiments, $R^2$ is an optionally substituted 3- to 8-membered saturated or partially unsaturated monocyclic carbocyclic ring. In some embodiments, $R^2$ is an optionally substituted phenyl. In some embodiments, $R^2$ is an optionally substituted 8- to 10-membered bicyclic aryl ring. In some embodiments, $R^2$ is an optionally substituted 3- to 8-membered saturated or partially unsaturated monocyclic heterocyclic ring having 1-4 heteroatoms independently selected from nitrogen, oxygen, and sulfur. In some embodiments, $R^2$ is an optionally substituted 5- to 6-membered monocyclic heteroaryl ring having 1-4 heteroatoms independently selected from nitrogen, oxygen, and sulfur. In some embodiments, $R^2$ is an optionally substituted 6- to 10-membered bicyclic saturated or partially unsaturated heterocyclic ring having 1-5 heteroatoms independently selected from nitrogen, oxygen, and sulfur. In some embodiments, $R^2$ is an optionally substituted 7- to 10-membered bicyclic heteroaryl ring having 1-5 heteroatoms independently selected from nitrogen, oxygen, and sulfur.

In some embodiments, $R^2$ is Cl or Br. In some embodiments, $R^2$ is Cl.

As defined generally above, $R^3$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, $R^3$ is —R. In some embodiments, $R^3$ is halogen. In some embodiments, $R^3$ is —CN. In some embodiments, $R^3$ is —OR. In some embodiments, $R^3$ is —SR. In some embodiments, $R^3$ is —N(R)$_2$. In some embodiments, $R^3$ is —N(R)C(O)R. In some embodiments, $R^3$ is —C(O)N(R)$_2$. In some embodiments, $R^3$ is —N(R)C(O)N(R)$_2$. In some embodiments, $R^3$ is —N(R)C(O)OR. In some embodiments, $R^3$ is —OC(O)N(R)$_2$. In some embodiments, $R^3$ is —N(R)S(O)$_2$R. In some embodiments, $R^3$ is —SO$_2$N(R)$_2$. In some embodiments, $R^3$ is —C(O)R. In some embodiments, $R^3$ is —C(O)OR. In some embodiments, $R^3$ is —OC(O)R. In some embodiments, $R^3$ is —S(O)R. In some embodiments, $R^3$ is —S(O)$_2$R.

In some embodiments, $R^3$ is hydrogen. In some embodiments, $R^3$ is deuterium. In some embodiments, $R^3$ is an optionally substituted $C_{1-6}$ aliphatic. In some embodiments, $R^3$ is an optionally substituted 3- to 8-membered saturated or partially unsaturated monocyclic carbocyclic ring. In some embodiments, $R^3$ is an optionally substituted phenyl. In some embodiments, $R^3$ is an optionally substituted 8- to 10-membered bicyclic aryl ring. In some embodiments, $R^3$ is an optionally substituted 3- to 8-membered saturated or partially unsaturated monocyclic heterocyclic ring having 1-4 heteroatoms independently selected from nitrogen, oxygen, and sulfur. In some embodiments, $R^3$ is an optionally substituted 5- to 6-membered monocyclic heteroaryl ring having 1-4 heteroatoms independently selected from nitrogen, oxygen, and sulfur. In some embodiments, $R^3$ is an optionally substituted 6- to 10-membered bicyclic saturated or partially unsaturated heterocyclic ring having 1-5 heteroatoms independently selected from nitrogen, oxygen, or sulfur. In some embodiments, $R^3$ is an optionally substituted 7- to 10-membered bicyclic heteroaryl ring having 1-5 heteroatoms independently selected from nitrogen, oxygen, and sulfur.

In some embodiments, $R^3$ is Cl or Br. In some embodiments, $R^3$ is Cl.

As defined generally above, $R^4$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, $R^4$ is —R. In some embodiments, $R^4$ is halogen. In some embodiments, $R^4$ is —CN. In some embodiments, $R^4$ is —OR. In some embodiments, $R^4$ is —SR. In some embodiments, $R^4$ is —N(R)$_2$. In some embodiments, $R^4$ is —N(R)C(O)R. In some embodiments, $R^4$ is —C(O)N(R)$_2$. In some embodiments, $R^4$ is —N(R)C(O)N(R)$_2$. In some embodiments, $R^4$ is —N(R)C(O)OR. In some embodiments, $R^4$ is —OC(O)N(R)$_2$. In some embodiments, $R^4$ is —N(R)S(O)$_2$R. In some embodiments, $R^4$ is —SO$_2$N(R)$_2$. In some embodiments, $R^4$ is —C(O)R. In some embodiments, $R^4$ is —C(O)OR. In some embodiments, $R^4$ is —OC(O)R. In some embodiments, $R^4$ is —S(O)R. In some embodiments, $R^4$ is —S(O)$_2$R.

In some embodiments, $R^4$ is hydrogen. In some embodiments, $R^4$ is deuterium. In some embodiments, $R^4$ is an optionally substituted $C_{1-6}$ aliphatic. In some embodiments, $R^4$ is an optionally substituted 3- to 8-membered saturated or partially unsaturated monocyclic carbocyclic ring. In some embodiments, $R^4$ is an optionally substituted phenyl. In some embodiments, $R^4$ is an optionally substituted 8- to 10-membered bicyclic aryl ring. In some embodiments, $R^4$ is an optionally substituted 3- to 8-membered saturated or partially unsaturated monocyclic heterocyclic ring having 1-4 heteroatoms independently selected from nitrogen, oxygen, and sulfur. In some embodiments, $R^4$ is an optionally substituted 5- to 6-membered monocyclic heteroaryl ring having 1-4 heteroatoms independently selected from nitrogen, oxygen, and sulfur. In some embodiments, $R^4$ is an optionally substituted 6- to 10-membered bicyclic saturated or partially unsaturated heterocyclic ring having 1-5 heteroatoms independently selected from nitrogen, oxygen, and sulfur. In some embodiments, $R^4$ is an optionally substituted 7- to 10-membered bicyclic heteroaryl ring having 1-5 heteroatoms independently selected from nitrogen, oxygen, and sulfur.

In some embodiments, $R^4$ is Cl or Br. In some embodiments, $R^4$ is Cl.

As defined generally above, $R^5$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R.

In some embodiments, $R^5$ is —R. In some embodiments, $R^5$ is halogen. In some embodiments, $R^5$ is —CN. In some embodiments, $R^5$ is —OR. In some embodiments, $R^5$ is —SR. In some embodiments, $R^5$ is —N(R)$_2$. In some embodiments, $R^5$ is —N(R)C(O)R. In some embodiments, $R^5$ is —C(O)N(R)$_2$. In some embodiments, $R^5$ is —N(R)C(O)N(R)$_2$. In some embodiments, $R^5$ is —N(R)C(O)OR. In some embodiments, $R^5$ is —OC(O)N(R)$_2$. In some embodiments, $R^5$ is —N(R)S(O)$_2$R. In some embodiments, $R^5$ is —SO$_2$N(R)$_2$. In some embodiments, $R^5$ is —C(O)R. In some embodiments, $R^5$ is —C(O)OR. In some embodiments, $R^5$ is —OC(O)R. In some embodiments, $R^5$ is —S(O)R. In some embodiments, $R^5$ is —S(O)$_2$R.

In some embodiments, $R^5$ is hydrogen. In some embodiments, $R^5$ is deuterium. In some embodiments, $R^5$ is an optionally substituted $C_{1-6}$ aliphatic. In some embodiments, $R^5$ is an optionally substituted 3- to 8-membered saturated or partially unsaturated monocyclic carbocyclic ring. In some embodiments, $R^5$ is an optionally substituted phenyl. In some embodiments, $R^5$ is an optionally substituted 8- to 10-membered bicyclic aryl ring. In some embodiments, $R^5$ is an optionally substituted 3- to 8-membered saturated or partially unsaturated monocyclic heterocyclic ring having 1-4 heteroatoms independently selected from nitrogen, oxygen, and sulfur. In some embodiments, $R^5$ is an optionally substituted 5- to 6-membered monocyclic heteroaryl ring having 1-4 heteroatoms independently selected from nitrogen, oxygen, and sulfur. In some embodiments, $R^5$ is an optionally substituted 6- to 10-membered bicyclic saturated or partially unsaturated heterocyclic ring having 1-5 heteroatoms independently selected from nitrogen, oxygen, and sulfur. In some embodiments, $R^5$ is an optionally substituted 7- to 10-membered bicyclic heteroaryl ring having 1-5 heteroatoms independently selected from nitrogen, oxygen, and sulfur.

In some embodiments, $R^5$ is Cl or Br. In some embodiments, $R^5$ is Cl.

As described generally above, $R^a$ is $C_{1-4}$ aliphatic optionally substituted with 1, 2, or 3 deuterium or halogen atoms.

In some embodiments, $R^a$ is $C_{1-4}$ aliphatic. In some embodiments, $R^a$ is $C_{1-4}$ aliphatic optionally substituted with 1, 2, or 3 deuterium atoms. In some embodiments, $R^a$ is $C_{1-4}$ aliphatic optionally substituted with 1, 2, or 3 halogen atoms.

In some embodiments, $R^a$ is $C_{1-4}$ alkyl. In some embodiments, $R^a$ is $C_{1-4}$ alkyl optionally substituted with 1, 2, or 3 deuterium or halogen atoms. In some embodiments, $R^a$ is $C_{1-4}$ alkyl optionally substituted with 1, 2, or 3 halogen atoms. In some embodiments, $R^a$ is methyl or ethyl optionally substituted with 1, 2, or 3 halogen atoms. In some embodiments, $R^a$ is methyl.

As defined generally above, $R^b$ is $C_{1-4}$ aliphatic optionally substituted with 1, 2, or 3 deuterium or halogen atoms.

In some embodiments, $R^b$ is $C_{1-4}$ aliphatic. In some embodiments, $R^b$ is $C_{1-4}$ aliphatic optionally substituted with 1, 2, or 3 deuterium atoms. In some embodiments, $R^b$ is $C_{1-4}$ aliphatic optionally substituted with 1, 2, or 3 halogen atoms.

In some embodiments, $R^b$ is $C_{1-4}$ alkyl. In some embodiments, $R^b$ is $C_{1-4}$ alkyl optionally substituted with 1, 2, or 3 deuterium or halogen atoms. In some embodiments, $R^a$ is $C_{1-4}$ alkyl optionally substituted with 1, 2, or 3 halogen atoms. In some embodiments, $R^b$ is methyl or ethyl optionally substituted with 1, 2, or 3 halogen atoms. In some embodiments, $R^b$ is methyl.

As defined generally above, in some embodiments, $R^a$ and $R^b$, taken together with the carbon atom to which they are attached, form a 3- to 8-membered cycloalkyl or heterocyclyl ring containing 1-2 heteroatoms selected from nitrogen, oxygen, and sulfur.

In some embodiments, $R^a$ and $R^b$, taken together with the carbon atom to which they are attached, form a 3- to 8-membered cycloalkyl. In some embodiments, $R^a$ and $R^b$, taken together with the carbon atom to which they are attached, form a 3- to -membered heterocyclyl ring containing 1-2 heteroatoms selected from nitrogen, oxygen, and sulfur.

In some embodiments, $R^a$ and $R^b$, taken together with the carbon atom to which they are attached, form a cyclopropyl, cyclobutyl, or cyclopentyl ring. In some embodiments, $R^a$ and $R^b$, taken together with the carbon atom to which they are attached, form an oxirane, oxetane, tetrahydrofuran, or aziridine.

In some embodiments, $R^a$ and $R^b$ are methyl.

In some embodiments, the compound for use in treatment of an inflammatory disorder is a compound of formula VI-a, VI-b, VI-c, or VI-d:

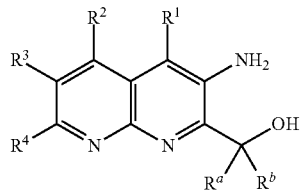

VI-a

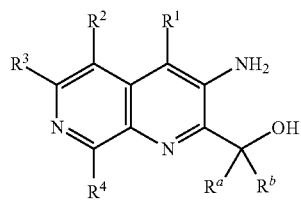

VI-b

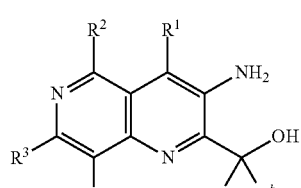

VI-c

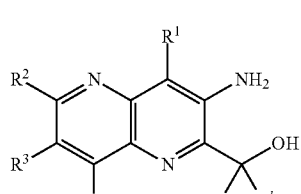

VI-d or a pharmaceutically acceptable salt thereof, wherein:

each of R, $R^1$, $R^2$, $R^3$, $R^4$, $R^a$, and $R^b$ is as defined is as defined above and described in embodiments herein, both singly and in combination.

In some embodiments, the compound is of formula VI-a above.

In some embodiments, $R^1$ and $R^4$ are H.

In some embodiments, $R^2$ is H.

In some embodiments, $R^a$ and $R^b$ are $C_{1-4}$ alkyl optionally substituted with 1, 2, or 3 deuterium or halogen atoms, or $R^a$ and $R^b$ are taken together with the carbon to which they are attached to form a 3-8 membered cycloalkyl ring.

In some embodiments, $R^3$ is H, $C_{1-4}$ alkyl, halogen, —NR, —OR, —SR, —$CO_2R$, or —C(O)R, wherein R is H, optionally substituted $C_{1-4}$ alkyl, or optionally substituted phenyl.

In another aspect, the compound for use in the method is a compound of formula VI-e, VI-f, VI-g, or VI-h:

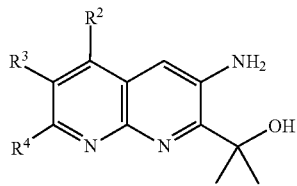

VI-e

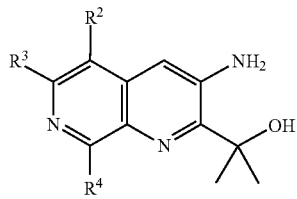

VI-f

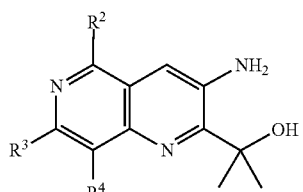

VI-g

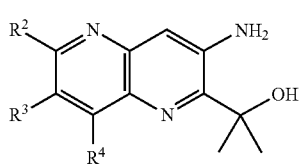

VI-h or a pharmaceutically acceptable salt thereof, wherein:

each of R, $R^1$, $R^2$, $R^3$, and $R^4$ is as defined is as defined above and described in embodiments herein, both singly and in combination.

In another aspect, the compound for use in the method is a compound of formula VI-i, VI-j, VI-k, VI-l, VI-m, or VI-n:

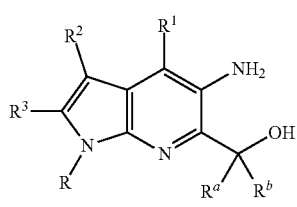

VI-i

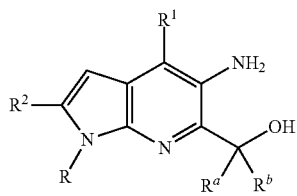

VI-j

-continued

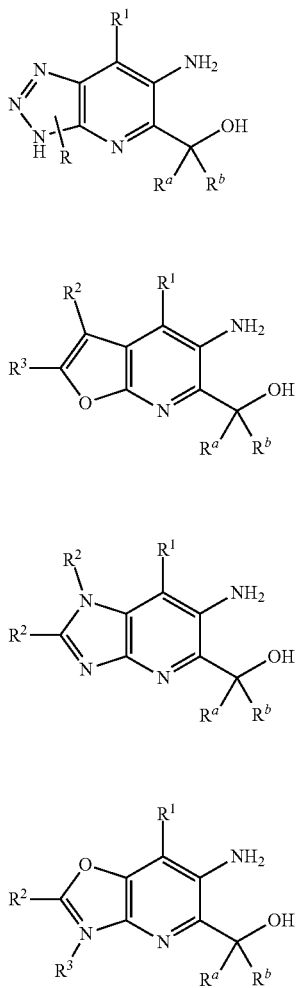

or a pharmaceutically acceptable salt thereof, wherein:

each of R, $R^1$, $R^2$, $R^3$, $R^4$, $R^a$, and $R^b$ is as defined is as defined above and described in embodiments herein, both singly and in combination.

In another aspect, the compound for use in the method is a compound of formula VII-a:

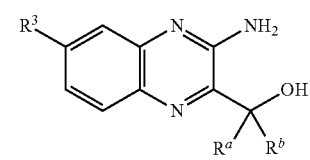

or a pharmaceutically acceptable salt thereof, wherein:

each of R, $R^3$, $R^a$, and $R^b$ is as defined is as defined above and described in embodiments herein, both singly and in combination.

In some embodiments, the compound for use in the method is a compound of formula I selected from those depicted in Table 1a, below:

TABLE 1a

Exemplary Compounds of Formula I

TABLE 1a-continued
Exemplary Compounds of Formula I
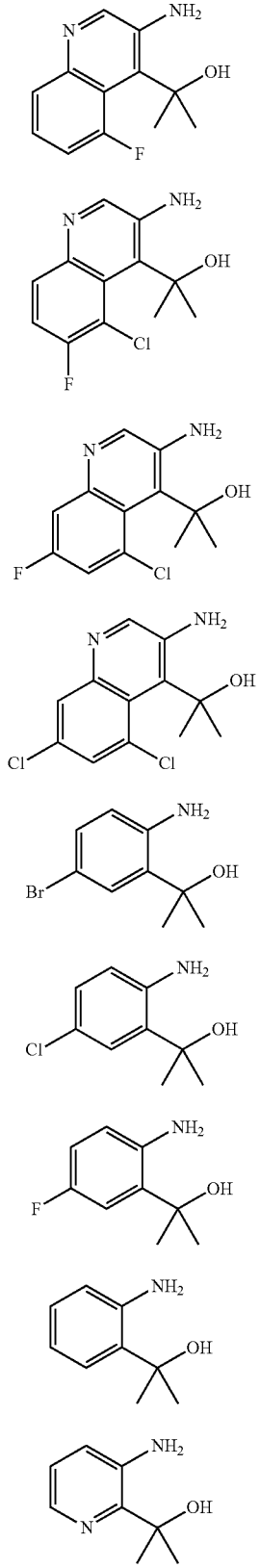
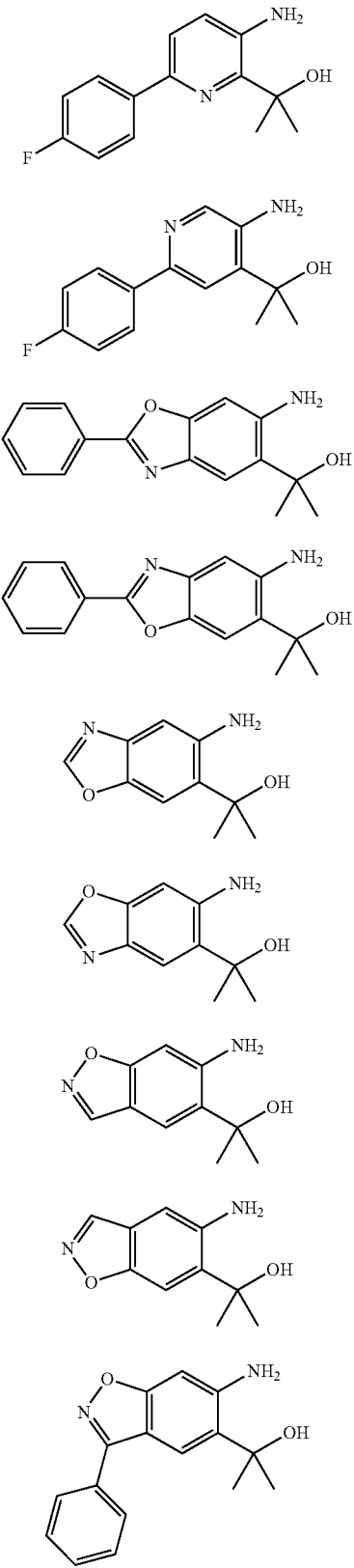

TABLE 1a-continued
Exemplary Compounds of Formula I
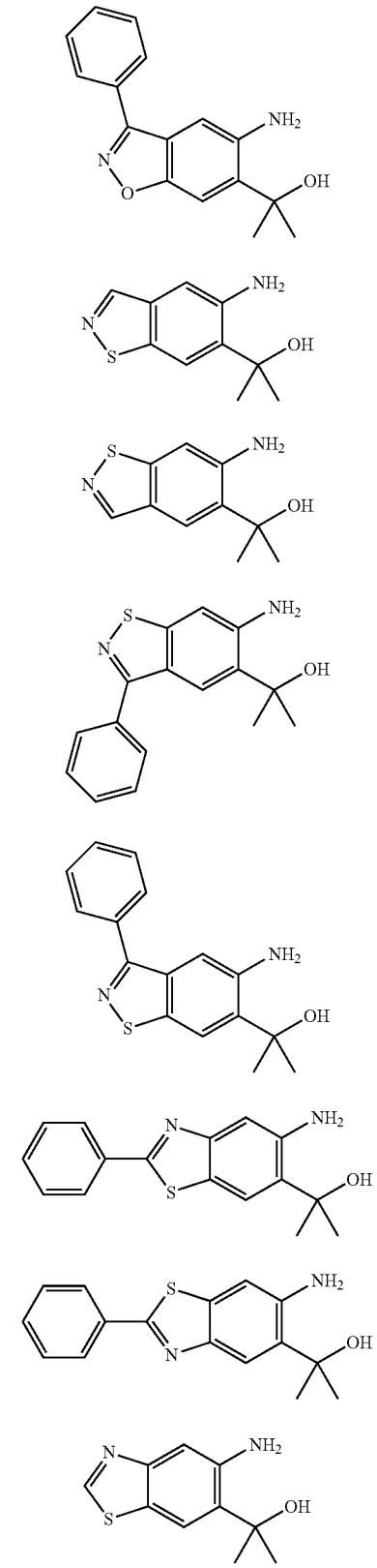
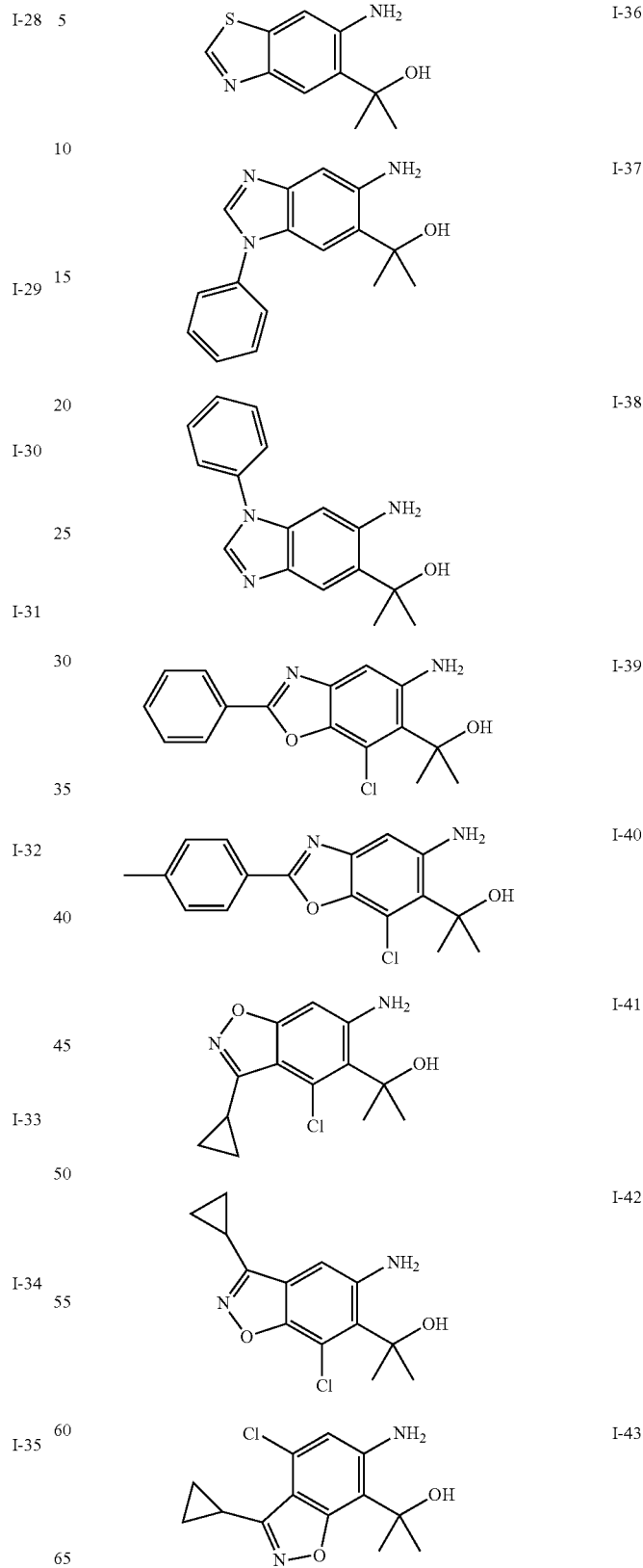

TABLE 1a-continued
Exemplary Compounds of Formula I
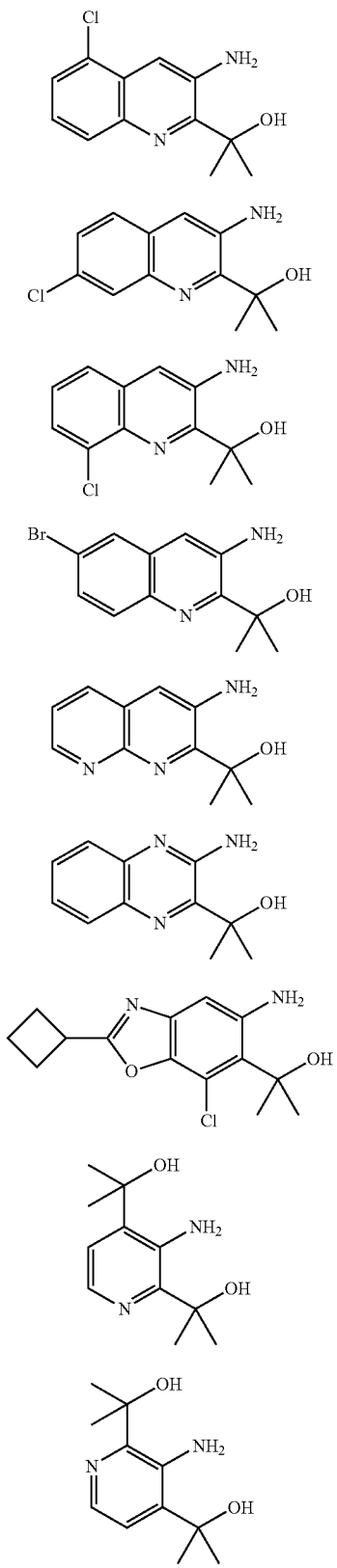
In some embodiments, the compound is selected from
In another aspect, the present invention provides a compound selected from these depicted in Table 1b, below.
TABLE 1b
Representative Compounds of Formula IV
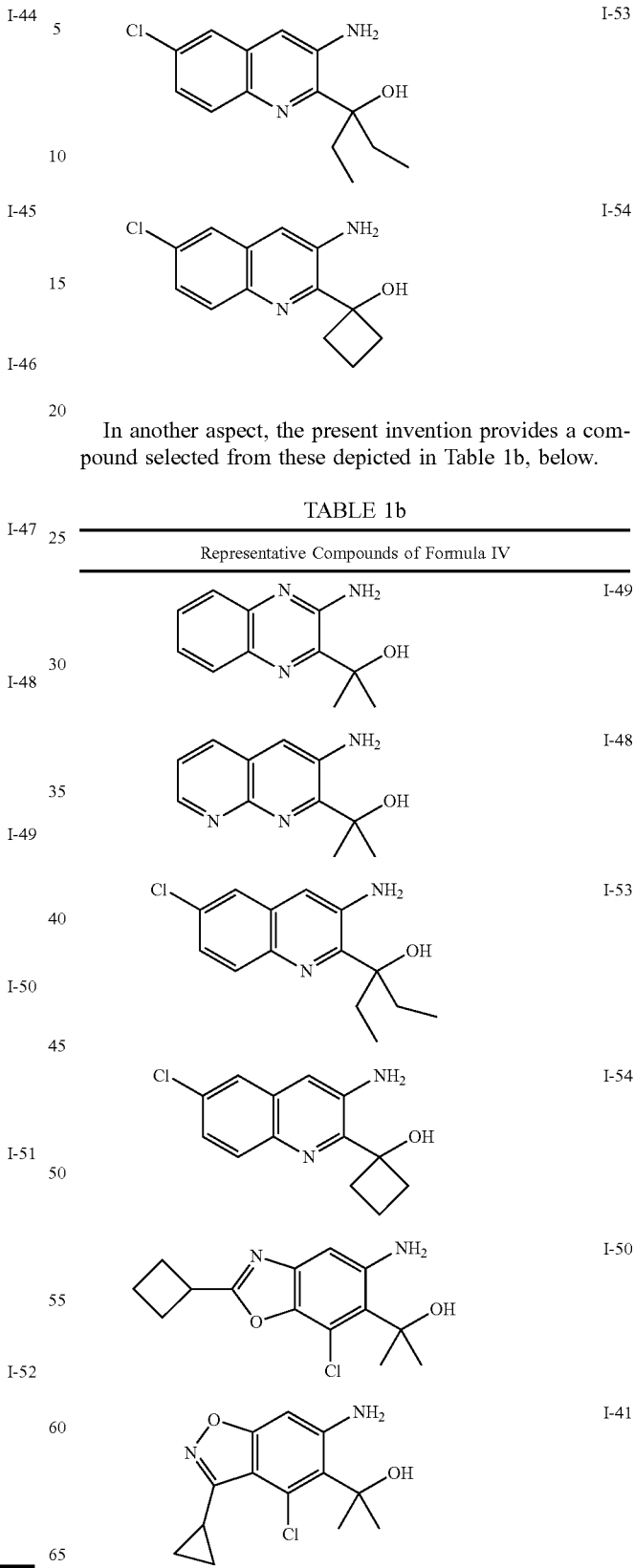

TABLE 1b-continued

Representative Compounds of Formula IV

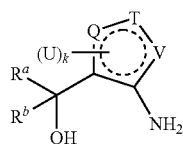

or a pharmaceutically acceptable salt thereof.

In some embodiments, compound for use in the method is a compound of formula VIII:

VIII

or a pharmaceutically acceptable salt thereof, wherein:
each Q, T, and V is independently selected from N or NH, S, O, CU, and CH;

represents two double bonds within the ring, which comply with the valency requirements of the atoms and heteroatoms present in the ring;
k is 0, 1, 2, 3, or 4;

$R^a$ is $C_{1-4}$ aliphatic optionally substituted with 1, 2, or 3 deuterium or halogen atoms;
$R^b$ is $C_{1-4}$ aliphatic optionally substituted with 1, 2, or 3 deuterium or halogen atoms; or
$R^a$ and $R^b$, taken together with the carbon atom to which they are attached, form a 3- to 8-membered cycloalkyl or heterocyclyl ring containing 1-2 heteroatoms selected from nitrogen, oxygen, and sulfur;
each U is independently selected from halogen, cyano, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;
two occurrences of U on adjacent carbon atoms can form an optionally substituted fused ring, selected from a fused phenyl ring; a fused 5- to 6-membered saturated or partially unsaturated heterocyclic ring containing 1-3 heteroatoms independently selected from nitrogen, oxygen, and sulfur; and a fused 5- to 6-membered heteroaryl ring containing 1-3 heteroatoms independently selected from nitrogen, oxygen, and sulfur; and
each R is independently selected from hydrogen, deuterium, or an optionally substituted group selected from $C_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, or sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; or a 7- to 10-membered bicyclic heteroaryl ring having 1-5 heteroatoms independently selected from nitrogen, oxygen, and sulfur.

Each k, U, and R is as defined and described above.

As defined above and described herein, Q is selected from N or NH, S, O, CU, and CH. In some embodiments, Q is selected from N or NH, S, O, CU, and CH. In some embodiments, Q is N or NH. In some embodiments, Q is S. In some embodiments, Q is O. In some embodiments, Q is CU. In some embodiments, Q is CH.

As defined above and described herein, T is selected from N or NH, S, O, CU, and CH. In some embodiments, T is selected from N or NH, S, O, CU, and CH. In some embodiments, T is N or NH. In some embodiments, T is S. In some embodiments, T is O. In some embodiments, T is CU. In some embodiments, T is CH.

As defined above and described herein, V is selected from N or NH, S, O, CU, and CH. In some embodiments, V is selected from N or NH, S, O, CU, and CH. In some embodiments, V is N or NH. In some embodiments, V is S. In some embodiments, V is O. In some embodiments, V is CU. In some embodiments, V is CH.

As defined above and described herein, k is 0, 1, 2, 3, or 4. In some embodiments k is 0. In some embodiments, k is 1. In some embodiments, k is 2. In some embodiments, k is 3. In some embodiments, k is 4.

As defined above and described herein, represents two double bonds within the ring, which comply with the valency requirements of the atoms and heteroatoms present in the ring. In some embodiments, the ring formed is thiophene. In some embodiments, the ring formed is oxazole. In some embodiments, the ring formed is isothiazole.

In some embodiments, one or more of Q and V are CH; T is S;

is arranged to form a thiophene; and k is 0. In some embodiments, one or more of Q is CH; T is N or NH; V is O;

is arranged to form an isoxazole; and k is 0. In some embodiments, one or more of Q is S; T and V are CH;

is arranged to form a thiophene; k is 1; and U is —S(O)$_2$R. In some embodiments, one or more of Q is S; T and V are CH;

is arranged to form a thiophene; k is 1; and U is —S(O)$_2$CH$_3$. In some embodiments, one or more of Q is CH; T is N or NH; V is S;

is arranged to form an isothiazole; and k is 0.

In some embodiments, the compound of formula VIII is selected from those depicted in Table 2, below:

TABLE 2

Exemplary Compounds of Formula VIII

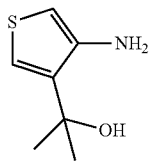

VIII-1

TABLE 2-continued

Exemplary Compounds of Formula VIII

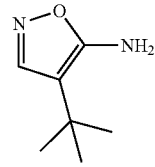

VIII-2

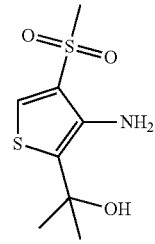

VIII-3

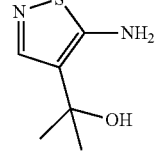

VIII-4

In some embodiments, the compound for use in the method is a compound of formula IX-A or IX-B:

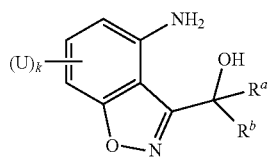

IX-A

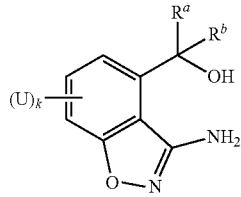

IX-B or a pharmaceutically acceptable salt thereof, wherein:
k is 0, 1, 2, 3, or 4;
$R^a$ is $C_{1-4}$ aliphatic optionally substituted with 1, 2, or 3 deuterium or halogen atoms;
$R^b$ is $C_{1-4}$ aliphatic optionally substituted with 1, 2, or 3 deuterium or halogen atoms; or
$R^a$ and $R^b$, taken together with the carbon atom to which they are attached, form a 3- to 8-membered cycloalkyl or heterocyclyl ring containing 1-2 heteroatoms selected from nitrogen, oxygen, and sulfur;
each U is independently selected from halogen, cyano, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;
two occurrences of U on adjacent carbon atoms can form an optionally substituted fused ring, selected from a fused phenyl ring; a fused 5- to 6-membered saturated or partially unsaturated heterocyclic ring containing 1-3 heteroatoms independently selected from nitrogen, oxygen, and sulfur; or a fused 5- to 6-membered heteroaryl ring containing 1-3 heteroatoms independently selected from nitrogen, oxygen, and sulfur; and each R is independently selected from hydrogen, deuterium, and an optionally substituted group selected from $C_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, and sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur.

Each of k, U, and R is as defined and described above.

In some embodiments, the compound for use in the method is a compound of formulae IX-A or IX-B selected from those depicted in Table 3, below:

TABLE 3

Exemplary Compounds of Formula IX

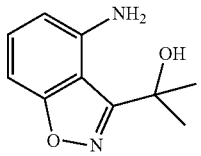

IX-1

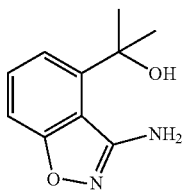

IX-2

1.3. Deuterated Compounds

In some embodiments, the compound is a deuterated form of a compound above or a pharmaceutically acceptable salt thereof.

In some embodiments, the compound for use in the method is a compound of formula X:

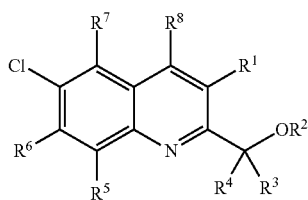

X or a pharmaceutically acceptable salt thereof, wherein:
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and $R^5$, $R^6$, $R^7$, and $R^8$ are each independently selected from hydrogen or deuterium; provided that at least one of $R^1$, $R^2$, $R^3$, $R^4$, $R^5$, $R^6$, $R^7$, or $R^8$ is or contains deuterium.

In some embodiments, the compound for use in the method is a compound of formula X-A:

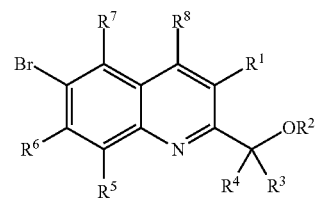

X-A or a pharmaceutically acceptable salt thereof, wherein:
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and $R^5$, $R^6$, $R^7$, and $R^8$ are each independently selected from hydrogen or deuterium; provided that at least one of $R^1$, $R^2$, $R^3$, $R^4$, $R^5$, $R^6$, $R^7$, or $R^8$ is or contains deuterium.

In some embodiments, the compound for use in the method is a compound of formulae XI-A or XI-B:

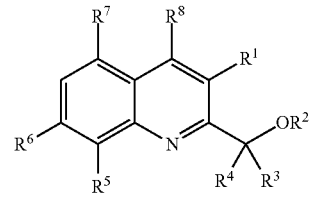

XI-A

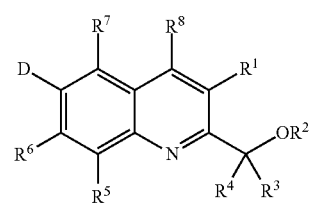

XI-B pharmaceutically acceptable salt thereof, wherein:
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and $R^5$, $R^6$, $R^7$, and $R^8$ are each independently selected from hydrogen or deuterium; provided that at least one of $R^1$, $R^2$, $R^3$, $R^4$, $R^5$, $R^6$, $R^7$, or $R^8$ in formula XI-A is or contains deuterium.

In some embodiments, the compound for use in the method is a compound of formulae XII-A, XII-B, or XII-C:

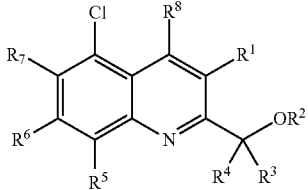

XII-A

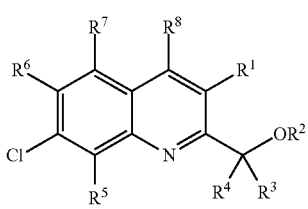

XII-B

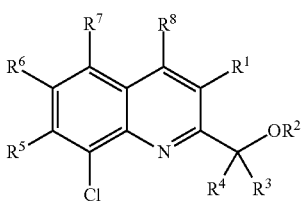

XII-C or a pharmaceutically acceptable salt thereof, wherein:

$R^1$ is selected from —$NH_2$, —NHD, or —$ND_2$;

$R^2$ is selected from hydrogen or deuterium;

$R^3$ and $R^4$ are independently selected from —$CH_3$, —$CH_2D$, —$CHD_2$, or —$CD_3$; and $R^5$, $R^6$, $R^7$, and $R^8$ are each independently selected from hydrogen or deuterium; provided that at least one of $R^1$, $R^2$, $R^3$, $R^4$, $R^5$, $R^6$, $R^7$, or $R^8$ is or contains deuterium.

In some embodiments, the compound for use in the method is a compound of formula XIII:

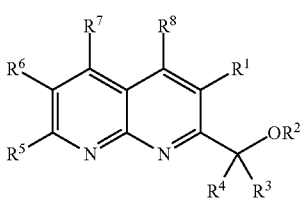

XIII or a pharmaceutically acceptable salt thereof, wherein:

$R^1$ is selected from —$NH_2$, —NHD, or —$ND_2$;

$R^2$ is selected from hydrogen or deuterium;

$R^3$ and $R^4$ are independently selected from —$CH_3$, —$CH_2D$, —$CHD_2$, or —$CD_3$; and $R^5$, $R^6$, $R^7$, and $R^8$ are each independently selected from hydrogen or deuterium; provided that at least one of $R^1$, $R^2$, $R^3$, $R^4$, $R^5$, $R^6$, $R^7$, or $R^8$ is or contains deuterium.

In some embodiments, the compound for use in the method is a compound of formula XIV:

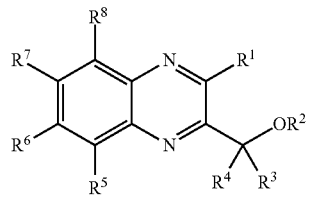

XIV or a pharmaceutically acceptable salt thereof, wherein:

$R^1$ is selected from —$NH_2$, —NHD, or —$ND_2$;

$R^2$ is selected from hydrogen or deuterium;

$R^3$ and $R^4$ are independently selected from —$CH_3$, —$CH_2D$, —$CHD_2$, or —$CD_3$; and $R^5$, $R^6$, $R^7$, and $R^8$ are each independently selected from hydrogen or deuterium; provided that at least one of $R^1$, $R^2$, $R^3$, $R^4$, $R^5$, $R^6$, $R^7$, or $R^8$ is or contains deuterium.

In some embodiments, the compound for use in the method is a compound of formulae XV-A or XV-B:

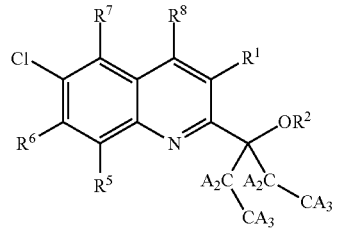

XV-A

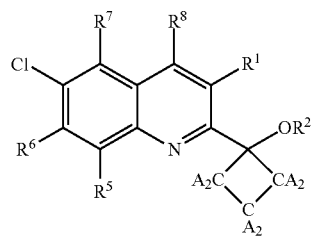

XV-B or a pharmaceutically acceptable salt thereof, wherein:

each A is independently hydrogen or deuterium;

$R^1$ is selected from —$NH_2$, —NHD, or —$ND_2$;

$R^2$ is selected from hydrogen or deuterium; and $R^5$, $R^6$, $R^7$, and $R^8$ are each independently selected from hydrogen or deuterium; provided that at least one of A, $R^1$, $R^2$, $R^5$, $R^6$, $R^7$, or $R^8$ is or contains deuterium.

In some embodiments, the compound for use in the method is a compound of formulae XVI-A or XVI-B:

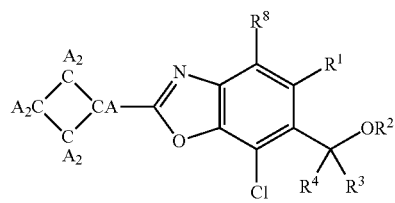

XVI-A

-continued

XVI-B

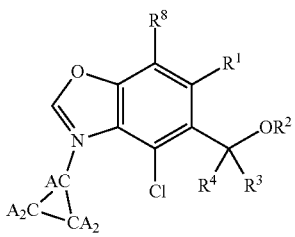

or a pharmaceutically acceptable salt thereof, wherein:
each A is independently hydrogen or deuterium;
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^8$ is selected from hydrogen or deuterium;

In some embodiments, the compound for use in the method is a compound of formulae XVII-A or XVII-B:

XVII-A

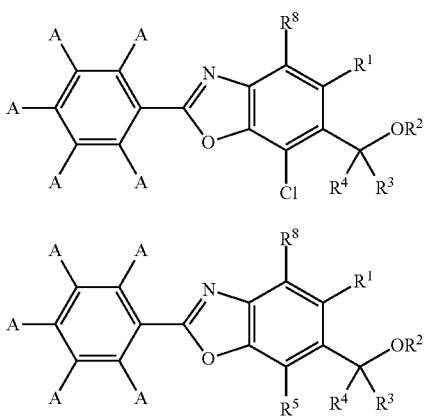

XVII-B or a pharmaceutically acceptable salt thereof, wherein:
each A is independently hydrogen or deuterium;
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^5$ and $R^8$ are each independently selected from hydrogen or deuterium; provided that at least one of A, $R^1$, $R^2$, $R^3$, $R^4$, $R^5$, or $R^8$ is or contains deuterium.

In some embodiments, the compound for use in the method is a compound of formula XVIII-A or XVIII-B:

XVIII-A

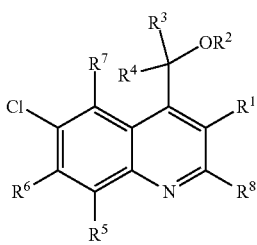

XVIII-B

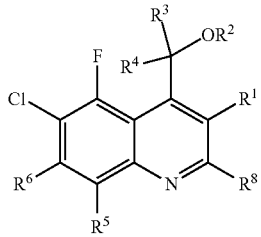

or a pharmaceutically acceptable salt thereof, wherein:
$R^1$ is selected from $NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^5$, $R^6$, $R^7$, and $R^8$ are each independently selected from hydrogen or deuterium; provided that at least one of $R^1$, $R^2$, $R^3$, $R^4$, $R^5$, $R^6$, $R^7$, or $R^8$ is or contains deuterium.

In some embodiments, the compound for use in the method is a compound of formula XIX:

XIX

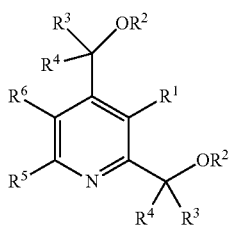

or a pharmaceutically acceptable salt thereof, wherein:
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^5$ and $R^6$ are each independently selected from hydrogen or deuterium; provided that at least one of $R^1$, $R^2$, $R^3$, $R^4$, $R^5$, or $R^6$ is or contains deuterium.

The following embodiments are applicable to each of the preceding formulae X-XIX.

As defined above and described herein, $R^1$ is selected from —$NH_2$, —NHD, or —$ND_2$.

In some embodiments, $R^1$ is —$NH_2$. In some embodiments, $R^1$ is —$NH_2$ and at least one of $R^2$, $R^3$, $R^4$, $R^5$, $R^6$, $R^7$, or $R^8$ is or contains deuterium.

In some embodiments, $R^1$ is —NHD. In some embodiments, $R^1$ is —NHD and at least one of $R^2$, $R^3$, $R^4$, $R^5$, $R^6$, $R^7$, or $R^8$ is or contains deuterium.

In some embodiments, $R^1$ is —$ND_2$. In some embodiments, $R^1$ is —$ND_2$ and at least one of $R^2$, $R^3$, $R^4$, $R^5$, $R^6$, $R^7$, or $R^8$ is or contains deuterium.

As defined above and described herein, A is selected from hydrogen or deuterium.

In some embodiments, A is hydrogen. In some embodiments, A is hydrogen and at least one of $R^1$, $R^3$, $R^4$, $R^5$, $R^6$, $R^7$, or $R^8$ is or contains deuterium. In some embodiments, A is deuterium. In some embodiments, A is deuterium and at least one of $R^1$, $R^3$, $R^4$, $R^5$, $R^6$, $R^7$, or $R^8$ is or contains deuterium.

As defined above and described herein, $R^2$ is selected from hydrogen or deuterium.

In some embodiments, $R^2$ is hydrogen. In some embodiments, $R^2$ is hydrogen and at least one of $R^1$, $R^3$, $R^4$, $R^5$, $R^6$, $R^7$, or $R^8$ is or contains deuterium. In some embodiments, $R^2$ is deuterium. In some embodiments, $R^2$ is deuterium and at least one of $R^1$, $R^3$, $R^4$, $R^5$, $R^6$, $R^7$, or $R^8$ is or contains deuterium.

As defined above and described herein, $R^3$ is selected from —CH$_3$, —CH$_2$D, —CHD$_2$, or —CD$_3$.

In some embodiments, $R^3$ is —CH$_3$. In some embodiments, $R^3$ is —CH$_3$ and at least one of $R^1$, $R^2$, $R^4$, $R^5$, $R^6$, $R^7$, or $R^8$ is or contains deuterium.

In some embodiments, $R^3$ is —CH$_2$D. In some embodiments, $R^3$ is —CH$_2$D and at least one of $R^1$, $R^2$, $R^4$, $R^5$, $R^6$, $R^7$, or $R^8$ is or contains deuterium.

In some embodiments, $R^3$ is —CHD$_2$. In some embodiments, $R^3$ is —CHD$_2$ and at least one of $R^1$, $R^2$, $R^4$, $R^5$, $R^6$, $R^7$, or $R^8$ is or contains deuterium.

In some embodiments, $R^3$ is —CD$_3$. In some embodiments, $R^3$ is —CD$_3$ and at least one of $R^1$, $R^2$, $R^4$, $R^5$, $R^6$, $R^7$, or $R^8$ is or contains deuterium.

As defined above and described herein, $R^4$ is selected from —CH$_3$, —CH$_2$D, —CHD$_2$, or —CD$_3$.

In some embodiments, $R^4$ is —CH$_3$. In some embodiments, $R^4$ is —CH$_3$ and at least one of $R^1$, $R^2$, $R^3$, $R^5$, $R^6$, $R^7$, or $R^8$ is or contains deuterium.

In some embodiments, $R^4$ is —CH$_2$D. In some embodiments, $R^4$ is —CH$_2$D and at least one of $R^1$, $R^2$, $R^3$, $R^5$, $R^6$, $R^7$, or $R^8$ is or contains deuterium.

In some embodiments, $R^4$ is —CHD$_2$. In some embodiments, $R^4$ is —CHD$_2$ and at least one of $R^1$, $R^2$, $R^3$, $R^5$, $R^6$, $R^7$, or $R^8$ is or contains deuterium.

In some embodiments, $R^4$ is —CD$_3$. In some embodiments, $R^4$ is —CD$_3$ and at least one of $R^1$, $R^2$, $R^3$, $R^5$, $R^7$, or $R^8$ is or contains deuterium.

As defined above and described herein, $R^5$ is selected from hydrogen or deuterium.

In some embodiments, $R^5$ is hydrogen. In some embodiments, $R^5$ is hydrogen and at least one of $R^1$, $R^2$, $R^3$, $R^4$, $R^6$, $R^7$, or $R^8$ is or contains deuterium. In some embodiments, $R^5$ is deuterium. In some embodiments, $R^5$ is deuterium and at least one of $R^1$, $R^2$, $R^3$, $R^4$, $R^6$, $R_7$, or $R^8$ is or contains deuterium.

As defined above and described herein, $R^6$ is selected from hydrogen or deuterium.

In some embodiments, $R^6$ is hydrogen. In some embodiments, $R^6$ is hydrogen and at least one of $R^1$, $R^2$, $R^3$, $R^4$, $R^5$, $R^7$, or $R^8$ is or contains deuterium. In some embodiments, $R^6$ is deuterium. In some embodiments, $R^6$ is deuterium and at least one of $R^1$, $R_2$, $R^3$, $R^4$, $R^5$, $R^7$, or $R^8$ is or contains deuterium.

As defined above and described herein, $R^7$ is selected from hydrogen or deuterium.

In some embodiments, $R^7$ is hydrogen. In some embodiments, $R^7$ is hydrogen and at least one of $R^1$, $R^2$, $R^3$, $R^4$, $R^5$, $R^6$, or $R^8$ is or contains deuterium. In some embodiments, $R^7$ is deuterium. In some embodiments, $R^7$ is deuterium and at least one of $R^1$, $R^2$, $R^3$, $R^4$, $R^5$, $R^6$, or $R^8$ is or contains deuterium.

As defined above and described herein, $R^8$ is selected from hydrogen or deuterium.

In some embodiments, $R^8$ is hydrogen. In some embodiments, $R^8$ is hydrogen and at least one of $R^1$, $R^2$, $R^3$, $R^4$, $R^5$, $R^6$, or $R^7$ is or contains deuterium. In some embodiments, $R^8$ is deuterium. In some embodiments, $R^8$ is deuterium and at least one of $R^1$, $R^2$, $R^3$, $R^4$, $R^5$, $R^6$, or $R^7$ is or contains deuterium.

In some embodiments, the compound for use in the method is a compound of formulae X, X-A, XI-A, XI-B, XII-A, XII-B, XII-C, XIII, or XIV, or a pharmaceutically acceptable salt thereof, wherein each of $R^3$, $R_4$, $R^5$, $R^6$, $R^7$, and $R^8$ is as defined above and described herein, and wherein each of $R^1$ and $R^2$ is as defined in an entry set forth in Table 4a, below.

TABLE 4a

Exemplary Compounds of Formulae X, X-A, XI-A, XI-B, XII-A, XII-B, XII-C, XIII, or XIV

| Entry | $R^1$ | $R^2$ |
|---|---|---|
| i | —NH$_2$ | H |
| ii | —NH$_2$ | D |
| iii | —NHD | H |
| iv | —NHD | D |
| v | —ND$_2$ | H |
| vi | —ND$_2$ | D |

In some embodiments, the compound for use in the method is a compound of formulae X, X-A, XI-A, XI-B, XII-A, XII-B, XII-C, XIII, or XIV, or a pharmaceutically acceptable salt thereof, wherein each of $R^1$, $R^2$, $R^5$, $R^6$, $R^7$, and $R^8$ is as defined above and described herein, and wherein each of $R^3$ and $R^4$ is as defined in an entry set forth in Table 4b, below.

TABLE 4b

Exemplary Compounds of Formulae X, X-A, XI-A, XI-B, XII-A, XII-B, XII-C, XIII or XIV

| Entry | $R^3$ | $R^4$ |
|---|---|---|
| i | —CH$_3$ | —CH3 |
| ii | —CH$_3$ | —CH$_2$D |
| iii | —CH$_3$ | —CHD$_2$ |
| iv | —CH$_3$ | —CD$_3$ |
| v | —CH$_2$D | —CH$_3$ |
| vi | —CH$_2$D | —CH$_2$D |
| vii | —CH$_2$D | —CHD$_2$ |
| viii | —CH$_2$D | —CD$_3$ |
| ix | —CHD$_2$ | —CH$_3$ |
| x | —CHD$_2$ | —CH$_2$D |
| xi | —CHD$_2$ | —CHD$_2$ |
| xii | —CHD$_2$ | —CD$_3$ |
| xiii | —CH$_3$ | —CH$_3$ |
| xiv | —CH$_3$ | —CH$_2$D |
| xv | —CH$_3$ | —CHD$_2$ |
| xvi | —CH$_3$ | —CD$_3$ |

In some embodiments, the compound for use in the method is a compound of formulae X, X-A, XI-A, XI-B, XII-A, XII-B, XII-C, XIII, or XIV, or a pharmaceutically acceptable salt thereof, wherein each of $R^1$, $R^2$, $R^3$, and $R^4$ is as defined above and described herein, and wherein each of $R^5$, $R^6$, $R^7$, and $R^8$ is as defined in an entry set forth in Table 4c, below.

TABLE 4c

Exemplary Compounds of Formulae X, X-A, XI-A, XI-B, XII-A, XII-B, XII-C, XIII or XIV

| Entry | $R^5$ | $R^6$ | $R^7$ | $R^8$ |
|---|---|---|---|---|
| i | H | H | H | H |
| ii | H | H | H | D |
| iii | H | H | D | H |
| iv | H | D | H | H |
| v | D | H | H | H |

TABLE 4c-continued

Exemplary Compounds of Formulae X, X-A, XI-A, XI-B, XII-A, XII-B, XII-C, XIII or XIV

| Entry | $R^5$ | $R^6$ | $R^7$ | $R^8$ |
|---|---|---|---|---|
| vi | H | H | D | D |
| vii | H | D | H | D |
| viii | D | H | H | D |
| ix | H | D | D | H |
| x | D | H | D | H |
| xi | D | D | H | H |
| xii | H | D | D | D |
| xiii | D | H | D | D |
| xiv | D | D | H | D |
| xv | D | D | D | H |
| xvi | D | D | D | D |

In some embodiments, the compound for use in the method is a compound of formulae X, X-A, XI-A, XI-B, XII-A, XII-B, XII-C, XIII, or XIV, or a pharmaceutically acceptable salt thereof, wherein each of $R^1$ and $R^2$ is as defined in an entry set forth in Table 4a, above, each of $R^3$ and $R^4$ is as defined in an entry set forth in Table 4b, above, and each of $R^5$, $R^6$, $R^7$, and $R^8$, is as defined in an entry set forth in Table 4c, above.

In some embodiments, the compound for use in the method is a compound selected from those recited in any of Table 4a, Table 4b, or Table 4c, or a pharmaceutically acceptable salt thereof.

In some embodiments, the compound for use in the method is a compound of formula X selected from these depicted in Table 5, below.

TABLE 5

Representative Compounds of Formula X

X-1

X-2

X-3

X-4

TABLE 5-continued

Representative Compounds of Formula X

X-5

X-6

X-7

X-8

X-9

X-10

X-11

TABLE 5-continued
Representative Compounds of Formula X
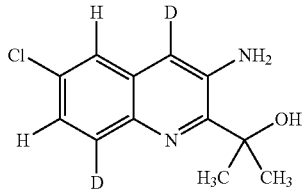
X-12
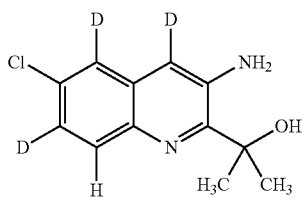 [SMILES: [2H]c1cc2nc(C(C)(C)O)c(N)c([2H])c2cc1Cl]
X-13
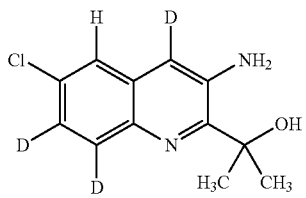 [SMILES: [2H]c1c(Cl)cc2c([2H])c(N)c(C(C)(C)O)nc2c1[2H]]
X-14
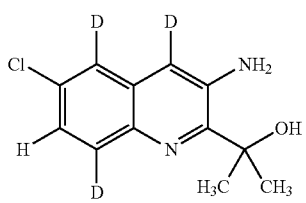
X-15
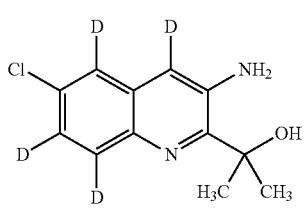
X-16
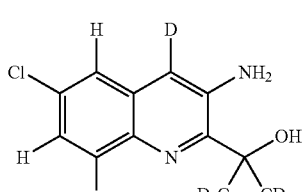
X-17
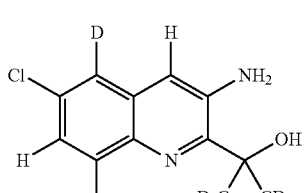
X-18
TABLE 5-continued
Representative Compounds of Formula X
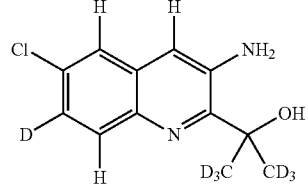
X-19
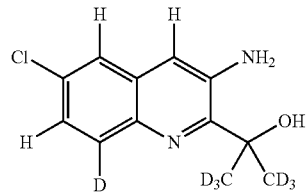
X-20
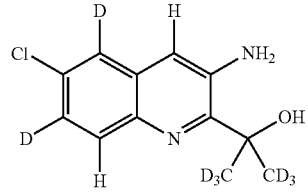
X-21
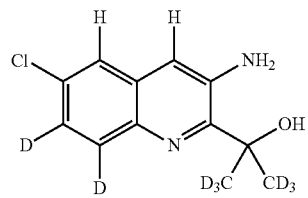
X-22
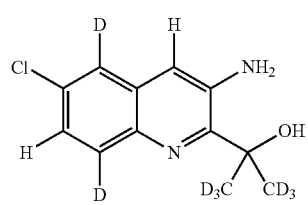 [SMILES: [2H]c1c(Cl)c([2H])c2c([2H])c(N)c(C(O)(C([2H])([2H])[2H])C([2H])([2H])[2H])nc2c1[2H]]
X-23
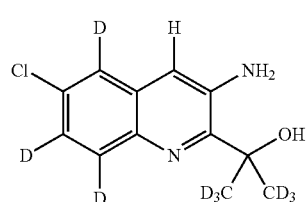
X-24
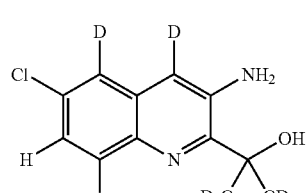
X-25

TABLE 5-continued

Representative Compounds of Formula X

| Structure | ID |
|---|---|
| (chloroquinoline with D at positions 4, 7; H at 5, 8; NH2; C(OH)(CD3)(CD3)) | X-26 |
| (chloroquinoline with D at 4, 8; H at 5, 7; NH2; C(OH)(CD3)(CD3)) | X-27 |
| (chloroquinoline with D at 4, 5, 7; H at 8; NH2; C(OH)(CD3)(CD3)) | X-28 |
| (chloroquinoline with D at 4, 7, 8; H at 5; NH2; C(OH)(CD3)(CD3)) | X-29 |
| (chloroquinoline with D at 4, 5, 8; H at 7; NH2; C(OH)(CD3)(CD3)) | X-30 |
| (chloroquinoline with D at 4, 5, 7, 8; NH2; C(OH)(CD3)(CD3)) | X-31 |

In some embodiments, the compound for use in the method is a compound depicted in Table 5, above, or a pharmaceutically acceptable salt thereof.

In some embodiments, the present invention provides a deuterium-enriched analogue of a compound depicted in Table 6, below, or a pharmaceutically acceptable salt thereof, in which deuterium is enriched at any available hydrogen.

TABLE 6

Representative Compounds of Formula X

| Structure | ID |
|---|---|
| quinoline-3-amine-2-C(OH)(CH3)2 | X-32 |
| 5-chloroquinoline-3-amine-2-C(OH)(CH3)2 | X-33 |
| 7-chloroquinoline-3-amine-2-C(OH)(CH3)2 | X-34 |
| 8-chloroquinoline-3-amine-2-C(OH)(CH3)2 | X-35 |
| 6-bromoquinoline-3-amine-2-C(OH)(CH3)2 | X-36 |
| quinoxaline-3-amine-2-C(OH)(CH3)2 | X-37 |
| 1,8-naphthyridine-3-amine-2-C(OH)(CH3)2 | X-38 |
| 6-chloroquinoline-3-amine-2-C(OH)(Et)(Et) | X-39 |
| 6-chloroquinoline-3-amine-2-(1-hydroxycyclobutyl) | X-40 |

TABLE 6-continued

Representative Compounds of Formula X

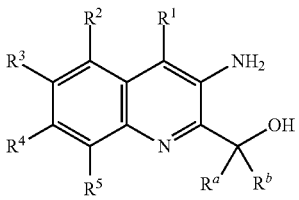

In some embodiments, the compound for use in the method is any compound described herein comprising one, two, three, four, five, six, seven, eight, nine, ten, eleven, twelve, or thirteen deuterium atoms.

In some embodiments, the compound for use in the method is any compound described above and herein in isolated form. As used herein, the term "isolated" means that a compound is provide in a form that is separated from other compounds that might be present in the usual environment of that compound. In some embodiments, an isolated compound is in solid form. In some embodiments, provided compounds comprise deuterium in an amount of about 5%, about 10%, about 15%, about 20%, about 25%, about 30%, about 35%, about 40%, about 45%, about 50%, about 55%, about 60%, about 65%, about 70%, about 75, about 80%, about 85%, about 90%, about 95%, or about 100%. As used herein in the context of deuterium enrichment, the term "about" means±2%.

1.4. Other Compounds

In some embodiments, the compound for use in the method is a compound of formula XX:

$$XX$$

[Structure of formula XX showing quinoline with $R^1$, $R^2$, $R^3$, $R^4$, $R^5$ substituents, $NH_2$ group, and $C(OH)(R^a)(R^b)$ group]

or a pharmaceutically acceptable salt thereof, wherein:
$R^1$ is H, D, or halogen;
$R^2$ is H, D, or halogen;
$R^3$ is H, D, Br, or I;
$R^4$ is H, D, or halogen;
$R^5$ is H, D, or halogen;
$R^a$ is $C_{1-4}$ aliphatic optionally substituted with 1, 2, or 3 deuterium or halogen atoms; and
$R^b$ is $C_{1-4}$ aliphatic optionally substituted with 1, 2, or 3 deuterium or halogen atoms.

As defined generally above, $R^1$ is H, D, or halogen.
In some embodiments, $R^1$ is H. In some embodiments, $R^1$ is D. In some embodiments, $R^1$ is halogen. In some embodiments, $R^1$ is Cl. In some embodiments, $R^1$ is Br.

As defined generally above, $R^2$ is H, D, or halogen.
In some embodiments, $R^2$ is H. In some embodiments, $R^2$ is D. In some embodiments, $R^2$ is halogen. In some embodiments, $R^2$ is Cl. In some embodiments, $R^2$ is Br.

As defined generally above, $R^3$ is H, D, Br, or I.
In some embodiments, $R^3$ is H. In some embodiments, $R^3$ is D. In some embodiments, $R^3$ is Br. In some embodiments, $R^3$ is I.

As defined generally above, $R^4$ is H, D, or halogen.
In some embodiments, $R^4$ is H. In some embodiments, $R^4$ is D. In some embodiments, $R^4$ is halogen. In some embodiments, $R^4$ is Cl. In some embodiments, $R^4$ is Br.

As defined generally above, $R^5$ is H, D, or halogen.
In some embodiments, $R^5$ is H. In some embodiments, $R^5$ is D. In some embodiments, $R^5$ is halogen. In some embodiments, $R^5$ is Cl. In some embodiments, $R^5$ is Br.

As defined generally above, $R^6$ is $C_{1-4}$ aliphatic optionally substituted with 1, 2, or 3 deuterium or halogen atoms.
In some embodiments, $R^a$ is $C_{1-4}$ aliphatic substituted with 1, 2, or 3 deuterium or halogen atoms. In some embodiments, $R^a$ is $C_{1-4}$ aliphatic. In some embodiments, $R^a$ is $C_{1-4}$ alkyl. In some embodiments, $R^a$ is methyl, ethyl, n-propyl, or isopropyl. In some embodiments, $R^a$ is methyl.

As defined generally above, $R^b$ is $C_{1-4}$ aliphatic optionally substituted with 1, 2, or 3 deuterium or halogen atoms.
In some embodiments, $R^7$ is $C_{1-4}$ aliphatic substituted with 1, 2, or 3 deuterium or halogen atoms. In some embodiments, $R^b$ is $C_{1-4}$ aliphatic. In some embodiments, $R^b$ is $C_{1-4}$ alkyl. In some embodiments, $R^b$ is $C_{1-4}$ ablkyl optionally substituted with 1, 2, or 3 fluorine atoms. In some embodiments, $R^b$ is methyl, ethyl, n-propyl, or isopropyl. In some embodiments, $R^b$ is methyl.

In some embodiments, $R^a$ and $R^b$ are methyl or ethyl. In some embodiments, $R^a$ and $R^b$ are methyl.

In some embodiments, the compound for use in the method is a compound of formula XX-a:

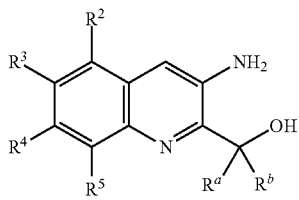

XX-a or a pharmaceutically acceptable salt thereof, wherein:
each of $R^2$, $R^3$, $R^4$, $R^5$, $R^a$, and $R^b$ is as defined is as defined above and described in embodiments herein, both singly and in combination.

In some embodiments, the compound for use in the method is a compound of formula XX-b:

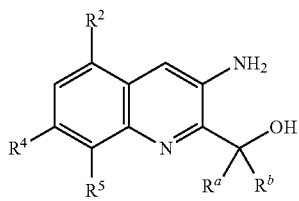

XX-b or a pharmaceutically acceptable salt thereof, wherein:
each of $R^2$, $R^4$, $R^5$, $R^a$, and $R^b$ is as defined is as defined above and described in embodiments herein, both singly and in combination.

In some embodiments, the compound for use in the method is a compound of formulae XX-c, XX-d, XX-e, or XX-f:

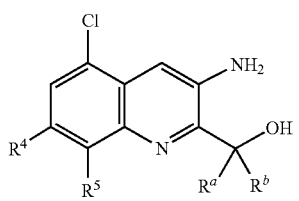

XX-c

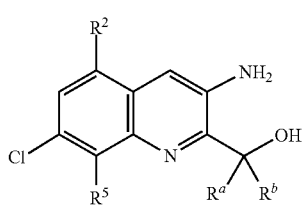

XX-d

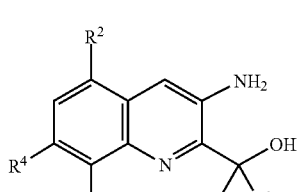

XX-e

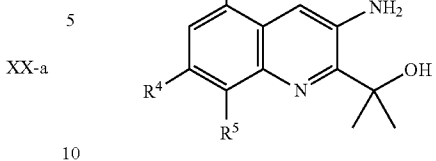

XX-f or a pharmaceutically acceptable salt thereof, wherein:
each of $R^2$, $R^4$, $R^5$, $R^a$, and $R^b$ is as defined is as defined above and described in embodiments herein, both singly and in combination.

In some embodiments, the compound for use in the method is a compound of formulae XX-g, XX-h, XX-i, or XX-j:

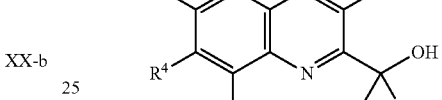

XX-g

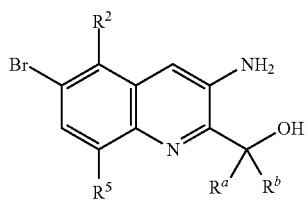

XX-h

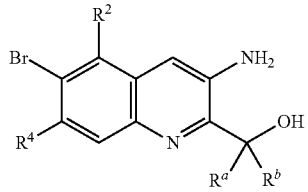

XX-i

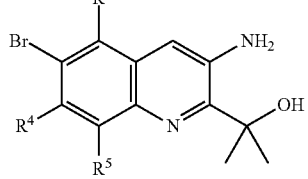

XX-j or a pharmaceutically acceptable salt thereof, wherein:
each of $R^2$, $R^4$, $R^5$, $R^a$, and $R^b$ is as defined is as defined above and described in embodiments herein, both singly and in combination.

In some embodiments, the compound for use in the method is a compound of formulae XX-k or XX-l:

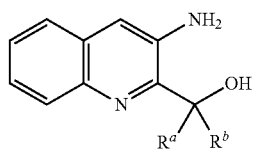

XX-k

-continued

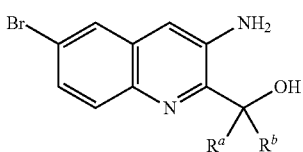
XX-1 or a pharmaceutically acceptable salt thereof, wherein:
each of $R^a$ and $R^b$ is as defined is as defined above and described in embodiments herein, both singly and in combination.

In some embodiments, the compound for use in the method is a compound of formula I-5:

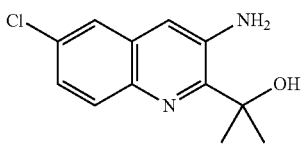
I-5 or a pharmaceutically acceptable salt thereof, in combination with at least one compound of formula XX:

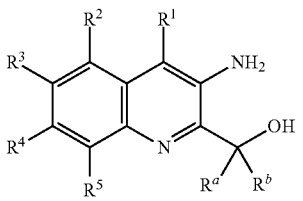
XX or a pharmaceutically acceptable salt thereof, wherein:
$R^1$ is H, D, or halogen;
$R^2$ is H, D, or halogen;
$R^3$ is H, D, Br, or I;
$R^4$ is H, D, or halogen;
$R^5$ is H, D, or halogen;
$R^a$ is $C_{1-4}$ aliphatic optionally substituted with 1, 2, or 3 deuterium or halogen atoms; and
$R^b$ is $C_{1-4}$ aliphatic optionally substituted with 1, 2, or 3 deuterium or halogen atoms.

In some embodiments, the composition for use in the method comprises a compound of formula I-5, or a pharmaceutically acceptable salt thereof, and at least one compound according to formulae XX-a, XX-b, XX-c, XX-d, XX-e, XX-f, XX-g, XX-h, XX-i, XX-j, XX-k, or XX-l; or a pharmaceutically acceptable salt thereof.

In some embodiments, the composition for use in the method comprises a compound of formula I-5:

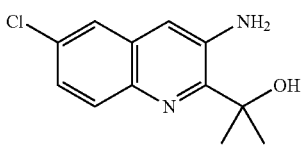
I-5 or a pharmaceutically acceptable salt thereof, and a compound selected from the following, or a pharmaceutically acceptable salt thereof:

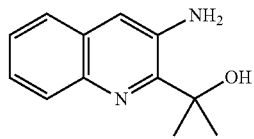
XX-1

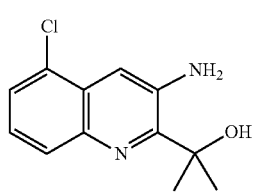
XX-2

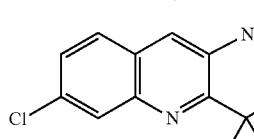
XX-3

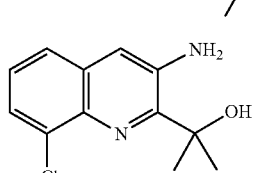
XX-4

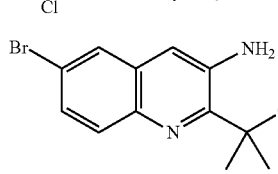
XX-5

In some embodiments, the composition for use in the method comprises a compound of formula I-5, or a pharmaceutically acceptable salt thereof, and one additional compound selected from XX-1, XX-2, XX-3, XX-4, or XX-5; or a pharmaceutically acceptable salt thereof.

In some embodiments, the composition for use in the method comprises a compound of formula I-5, or a pharmaceutically acceptable salt thereof, and two additional compounds selected from XX-1, XX-2, XX-3, XX-4, or XX-5; or a pharmaceutically acceptable salt thereof.

In some embodiments, the composition for use in the method comprises a compound of formula I-5, or a pharmaceutically acceptable salt thereof, and three additional compounds selected from XX-1, XX-2, XX-3, XX-4, or XX-5; or a pharmaceutically acceptable salt thereof.

In some embodiments, the composition for use in the method comprises a compound of formula I-5, or a pharmaceutically acceptable salt thereof, and four additional compounds selected from XX-1, XX-2, XX-3, XX-4, or XX-5; or a pharmaceutically acceptable salt thereof.

In some embodiments, the composition for use in the method comprises a compound of formula I-5, or a pharmaceutically acceptable salt thereof, and one additional compound selected from XX-2, XX-3, or XX-4; or a pharmaceutically acceptable salt thereof.

In some embodiments, the composition for use in the method comprises a compound of formula I-5, or a pharmaceutically acceptable salt thereof, and two additional compounds selected from XX-2, XX-3, or XX-4; or a pharmaceutically acceptable salt thereof. In some embodiments, the composition comprises XX-2, XX-3, and XX-4; or a pharmaceutically acceptable salt thereof.

In some embodiments, the composition for use in the method comprises a compound of formula I-5, or a pharmaceutically acceptable salt thereof, and XX-1; or a pharmaceutically acceptable salt thereof.

In some embodiments, the composition for use in the method comprises a compound of formula I-5, or a pharmaceutically acceptable salt thereof, and XX-2; or a pharmaceutically acceptable salt thereof.

In some embodiments, the composition for use in the method comprises a compound of formula I-5, or a pharmaceutically acceptable salt thereof, and XX-3; or a pharmaceutically acceptable salt thereof.

In some embodiments, the composition for use in the method comprises a compound of formula I-5, or a pharmaceutically acceptable salt thereof, and XX-4; or a pharmaceutically acceptable salt thereof.

In some embodiments, the composition for use in the method comprises a compound of formula I-5, or a pharmaceutically acceptable salt thereof, and XX-5; or a pharmaceutically acceptable salt thereof.

In some embodiments, the compound for use in the method is a compound of formula XX selected from those depicted in Table 7, below.

TABLE 7

Representative Compounds of Formula XX

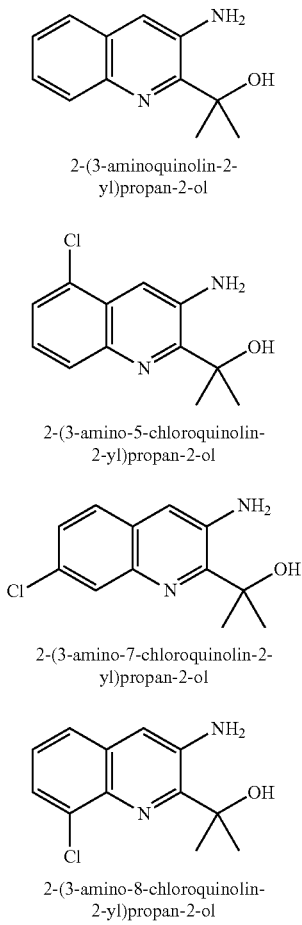

| | |
|---|---|
| 2-(3-aminoquinolin-2-yl)propan-2-ol | XX-1 |
| 2-(3-amino-5-chloroquinolin-2-yl)propan-2-ol | XX-2 |
| 2-(3-amino-7-chloroquinolin-2-yl)propan-2-ol | XX-3 |
| 2-(3-amino-8-chloroquinolin-2-yl)propan-2-ol | XX-4 |

TABLE 7-continued

Representative Compounds of Formula XX

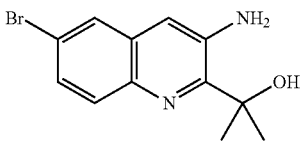

| | |
|---|---|
| 2-(3-amino-6-bromoquinolin-2-yl)propan-2-ol | XX-5 |

In some embodiments, the compound for use in the method is a compound depicted in Table 7, above, or a pharmaceutically acceptable salt thereof.

In some embodiments, the compound for use in the method is any compound described above and herein in isolated form. As used herein, the term "isolated" means that a compound is provided in a form that is separated from other components that might be present in the usual environment of that compound. In certain embodiments, an isolated compound is in solid form. In some embodiments, an isolated compound is at least about 50% pure as determined by a suitable HPLC method. In certain embodiments, an isolated compound is at least about 60%, 70%, 80%, 90%, 95%, 98%, 99%, 99.5%, 99.6%, 99.7%, 99.8%, 99.9%, 99.95%, 99.99%, or 99.999% as determined by a suitable HPLC method. Methods of preparation applicable to certain compounds of the invention are disclosed in US 2013/0190500, published Jul. 25, 2013, which is hereby incorporated by reference.

In certain embodiments, the compound for use in the method is any compound described above and herein, or a pharmaceutically acceptable salt thereof.

In other embodiments, the composition for use in the method contains a compound of any one of formulae XX, XX-a, XX-b, XX-c, XX-d, XX-e, XX-f, XX-g, XX-h, XX-i, XX-j, XX-k, or XX-l, or a pharmaceutically acceptable salt thereof, in an amount of at least about 97, 97.5, 98, 98.5, 99.0, 99.5, 99.8, 99.9, 99.95, or 99.999 weight percent where the percentages are based on the free base of said compound and the total weight of the composition. In other embodiments, the composition contains no more than about 2.0 area percent HPLC of total organic impurities or, in other embodiments, no more than about 1.5, 1.25, 1, 0.75, 0.5, 0.25, 0.2, 0.1, 0.01, 0.005, or 0.001 area percent HPLC total organic impurities relative to the total area of the HPLC chromatogram.

In other embodiments, a composition for use in the method comprises a compound of formula I-5 or a pharmaceutically acceptable salt thereof, at least one compound of formulae XX, XX-a, XX-b, XX-c, XX-d, XX-e, XX-f, XX-g, XX-h, XX-i, XX-j, XX-k, or XX-l, or a pharmaceutically acceptable salt thereof, and at least one pharmaceutically acceptable carrier. In some embodiments, the composition contains the compound of formula I-5 or pharmaceutically acceptable salt thereof in an amount of about 1 weight percent to about 99 weight percent, where the percentages are based on the free base of said compound and on the total weight of the composition. In other embodiments, the composition contains no more than about 2.0 area percent HPLC of total organic impurities or, in other embodiments, no more than about 1.5, 1.25, 1, 0.75, 0.5, 0.25, 0.2, 0.1, 0.01, 0.005, or 0.001 area percent HPLC total organic impurities relative to the total area of the HPLC chromatogram.

In some embodiments, the composition for use in the method comprises a compound of formula I-5 or pharmaceutically acceptable salt thereof and a compound of formulae XX, XX-a, XX-b, XX-c, XX-d, XX-e, XX-f, XX-g, XX-h, XX-i, XX-j, XX-k, or XX-l, or pharmaceutically acceptable salt thereof, wherein the compound of formula I-5 or pharmaceutically acceptable salt thereof comprises about 98% and the compound of formulae XX, XX-a, XX-b, XX-c, XX-d, XX-e, XX-f, XX-g, XX-h, XX-i, XX-j, XX-k, or XX-l, or pharmaceutically acceptable salt thereof comprises about 2% of the total weight of the compounds or pharmaceutically acceptable salts thereof taken together or of the total HPLC peak area of the compounds or pharmaceutically acceptable salts thereof taken together. In some embodiments, the composition for use in the method comprises a compound of formula I-5 or pharmaceutically acceptable salt thereof and a compound of formulae XX, XX-a, XX-b, XX-c, XX-d, XX-e, XX-f, XX-g, XX-h, XX-i, XX-j, XX-k, or XX-l, or pharmaceutically acceptable salt thereof, wherein the compound of formula I-5 or pharmaceutically acceptable salt thereof comprises about 99%, 99.5%, 99.6%, 99.7%, 99.8%, 99.9%, 99.95%, 99.99%, or 99.999%, and the compound of formulae XX, XX-a, XX-b, XX-c, XX-d, XX-e, XX-f, XX-g, XX-h, XX-i, XX-j, XX-k, or XX-l, or pharmaceutically acceptable salt thereof comprises about 1%, 0.5%, 0.4%, 0.3%, 0.2%, 0.1%, 0.05%, 0.01%, or 0.001%, of the total weight of the compounds or pharmaceutically acceptable salts thereof taken together or of the total HPLC peak area of the compounds or pharmaceutically acceptable salts thereof taken together. In some embodiments, the compound of formulae XX, XX-a, XX-b, XX-c, XX-d, XX-e, XX-f, XX-g, XX-h, XX-i, XX-j, XX-k, or XX-l, or pharmaceutically acceptable salt thereof comprises about 100 ppm, 50 ppm, 10 ppm, 1 ppm, 500 ppb, 100 ppb, or 10 ppb of the total weight of the compounds or pharmaceutically acceptable salts thereof taken together.

In some embodiments, the composition for use in the method comprises a compound of formula I-5 or pharmaceutically acceptable salt thereof and a compound of formulae XX, XX-a, XX-b, XX-c, XX-d, XX-e, XX-f, XX-g, XX-h, XX-i, XX-j, XX-k, or XX-l, or pharmaceutically acceptable salt thereof, wherein the compound of formula I-5 or pharmaceutically acceptable salt thereof comprises about 99%-99.9999%, 99.5-99.9999%, 99.6-99.9999%, 99.7-99.9999%, 99.8-99.9999%, 99.9-99.9999%, 99.95-99.9999%, 99.99-99.9999%, or 99.999-99.9999%, and the compound of formulae XX, XX-a, XX-b, XX-c, XX-d, XX-e, XX-f, XX-g, XX-h, XX-i, XX-j, XX-k, or XX-l, or pharmaceutically acceptable salt thereof comprises about 10 ppm to 2%, 100 ppm to 1%, 0.0001-0.5%, 0.0001-0.4%, 0.0001-0.3%, 0.0001-0.2%, 0.0001-0.1%, 0.0001-0.05%, 0.0001-0.01%, or 0.0001-0.001% of the total weight of the compounds or pharmaceutically acceptable salts thereof taken together.

In some embodiments, the compound of formula I-5 or pharmaceutically acceptable salt thereof and the compound of formula XX, XX-a, XX-b, XX-c, XX-d, XX-e, XX-f, XX-g, XX-h, XX-i, XX-j, XX-k, or XX-l, or pharmaceutically acceptable salt thereof, are present in a ratio of about 98:2, 99:1, 99.5:0.5, 99.6:0.4, 99.7:0.3, 99.8:0.2, 99.9:0.1, 99.95:0.05, 99.99:0.01, or 99.999:0.001.

In some embodiments, the compound of any of formulae XX, XX-a, XX-b, XX-c, XX-d, XX-e, XX-f, XX-g, XX-h, XX-i, XX-j, XX-k, or XX-l, or pharmaceutically acceptable salt thereof, comprises about 0.01-0.20 area percent of the HPLC chromatogram relative to the compound of formula I-5 or pharmaceutically acceptable salt thereof. In some embodiments, the compound of formulae XX, XX-a, XX-b, XX-c, XX-d, XX-e, XX-f, XX-g, XX-h, XX-i, XX-j, XX-k, or XX-l, or pharmaceutically acceptable salt thereof, comprises about 0.02-0.18, 0.03-0.16, 0.05-0.15, 0.075-0.13, 0.09-0.1, 0.1-0.2, or 0.15-0.2 area percent of the HPLC chromatogram relative to the compound of formula I-5 or pharmaceutically acceptable salt thereof. In some embodiments, the foregoing area percentages of the HPLC chromatogram are measured relative to the total area of the HPLC chromatogram.

In some embodiments, the present invention provides any compound described above and herein in isolated form. As used herein, the term "isolated" means that a compound is provided in a form that is separated from other components that might be present in that compound's usual environment. In certain embodiments, an isolated compound is in solid form. In some embodiments, an isolated compound is at least about 50% pure as determined by a suitable HPLC method. In certain embodiments, an isolated compound is at least about 60%, 70%, 80%, 90%, 95%, 98%, 99%, 99.5%, 99.6%, 99.7%, 99.8%, 99.9%, 99.95%, 99.99%, or 99.999% as determined by a suitable HPLC method. Methods of preparation applicable to certain compounds of the invention are disclosed in US 2013/0190500, published Jul. 25, 2013, which is hereby incorporated by reference.

1.5. Diseases and Indications

As discussed above, the compounds of the disclosure are used to treat inflammatory disorders. In some embodiments, the compound is administered in a therapeutically effective amount to a subject to treat a systemic inflammatory disorder. In some embodiments, the systemic inflammatory disorder is non-alcoholic fatty liver disease (NAFLD), non-alcoholic steatohepatitis (NASH), inflammatory bowel disease (IBD), Crohn's disease, ulcerative colitis (UC), psoriasis, IBS (irritable bowel syndrome or spastic colon), ankylosing spondylitis, osteoporosis, rheumatoid arthritis (RA), psoriatic arthritis, chronic obstructive pulmonary disease (COPD), atherosclerosis, pulmonary arterial hypertension, pyridoxine-dependent epilepsy, atopic dermatitis, rosacea, multiple sclerosis (MS), systemic lupus erythematosus (SLE), lupus nephritis, sepsis, eosinophilic esophagitis, chronic kidney disease (CKD), fibrotic renal disease, chronic eosinophilic pneumonia, extrinsic allergic alveolitis, pre-eclampsia, endometriosis, polycystic ovary syndrome (PCOS), reduced female fertility, reduced sperm viability and motility, or cyclophosphamide-induced hemorrhagic cystitis.

In some embodiments, a compound of the disclosure, or a pharmaceutically acceptable salt thereof, is used to treat a systemic disease, disorder, or condition. In some embodiments, the systemic disease, disorder, or condition is light chain deposition disease, IgA nephropathy, end-stage renal disease, gout, pseudogout, diabetic nephropathy, diabetic neuropathy, traumatic brain injury, noise-induced hearing loss, Alzheimer's Disease, Parkinson's Disease, Huntington Dieseaese, amyotrophic lateral sclerosis, primary biliary cirrhosis, primary sclerosing cholangitis, uterine leiomyoma, sarcoidosis, or chronic kidney disease.

In some embodiments, a compound of the disclosure, or a pharmaceutically acceptable salt thereof, is administered in an effective amount to treat non-alcoholic fatty liver disease (NAFLD).

In some embodiments, a compound of the disclosure, or a pharmaceutically acceptable salt thereof, is administered in an effective amount to treat non-alcoholic steatohepatitis (NASH).

In some embodiments, a compound of the disclosure, or a pharmaceutically acceptable salt thereof, is administered in an effective amount to treat inflammatory bowel disease (IBD).

In some embodiments, a compound of the disclosure, or a pharmaceutically acceptable salt thereof, is administered in an effective amount to treat Crohn's disease.

In some embodiments, a compound of the disclosure, or a pharmaceutically acceptable salt thereof, is administered in an effective amount to treat ulcerative colitis (UC).

In some embodiments, a compound of the disclosure, or a pharmaceutically acceptable salt thereof, is administered in an effective amount to treat psoriasis.

In some embodiments, a compound of the disclosure, or a pharmaceutically acceptable salt thereof, is administered in an effective amount to treat IBS (irritable bowel syndrome) or spastic colon.

In some embodiments, a compound of the disclosure, or a pharmaceutically acceptable salt thereof, is administered in an effective amount to treat ankylosing spondylitis.

In some embodiments, a compound of the disclosure, or a pharmaceutically acceptable salt thereof, is administered in an effective amount to treat osteoporosis.

In some embodiments, a compound of the disclosure, or a pharmaceutically acceptable salt thereof, is administered in an effective amount to treat rheumatoid arthritis (RA).

In some embodiments, a compound of the disclosure, or a pharmaceutically acceptable salt thereof, is administered in an effective amount to treat psoriatic arthritis.

In some embodiments, a compound of the disclosure, or a pharmaceutically acceptable salt thereof, is administered in an effective amount to treat chronic obstructive pulmonary disease (COPD).

In some embodiments, a compound of the disclosure, or a pharmaceutically acceptable salt thereof, is administered in an effective amount to treat atherosclerosis.

In some embodiments, a compound of the disclosure, or a pharmaceutically acceptable salt thereof, is administered in an effective amount to treat pulmonary arterial hypertension.

In some embodiments, a compound of the disclosure, or a pharmaceutically acceptable salt thereof, is administered in an effective amount to treat pyridoxine-dependent epilepsy.

In some embodiments, a compound of the disclosure, or a pharmaceutically acceptable salt thereof, is administered in an effective amount to treat atopic dermatitis.

In some embodiments, a compound of the disclosure, or a pharmaceutically acceptable salt thereof, is administered in an effective amount to treat rosacea.

In some embodiments, a compound of the disclosure, or a pharmaceutically acceptable salt thereof, is administered in an effective amount to treat multiple sclerosis (MS).

In some embodiments, a compound of the disclosure, or a pharmaceutically acceptable salt thereof, is administered in an effective amount to treat systemic lupus erythematosus (SLE).

In some embodiments, a compound of the disclosure, or a pharmaceutically acceptable salt thereof, is administered in an effective amount to treat lupus nephritis.

In some embodiments, a compound of the disclosure, or a pharmaceutically acceptable salt thereof, is administered in an effective amount to treat sepsis.

In some embodiments, a compound of the disclosure, or a pharmaceutically acceptable salt thereof, is administered in an effective amount to treat eosinophilic esophagitis.

In some embodiments, a compound of the disclosure, or a pharmaceutically acceptable salt thereof, is administered in an effective amount to treat chronic kidney disease (CKD).

In some embodiments, a compound of the disclosure, or a pharmaceutically acceptable salt thereof, is administered in an effective amount to treat fibrotic renal disease.

In some embodiments, a compound of the disclosure, or a pharmaceutically acceptable salt thereof, is administered in an effective amount to treat chronic eosinophilic pneumonia.

In some embodiments, a compound of the disclosure, or a pharmaceutically acceptable salt thereof, is administered in an effective amount to treat extrinsic allergic alveolitis.

In some embodiments, a compound of the disclosure, or a pharmaceutically acceptable salt thereof, is administered in an effective amount to treat pre-eclampsia.

In some embodiments, a compound of the disclosure, or a pharmaceutically acceptable salt thereof, is administered in an effective amount to treat endometriosis.

In some embodiments, a compound of the disclosure, or a pharmaceutically acceptable salt thereof, is administered in an effective amount to treat polycystic ovary syndrome (PCOS).

In some embodiments, a compound of the disclosure, or a pharmaceutically acceptable salt thereof, is administered in an effective amount to treat reduced female fertility.

In some embodiments, a compound of the disclosure, or a pharmaceutically acceptable salt thereof, is administered in an effective amount to treat reduced sperm viability and motility.

In some embodiments, a compound of the disclosure, or a pharmaceutically acceptable salt thereof, is administered in an effective amount to treat cyclophosphamide-induced hemorrhagic cystitis.

In some embodiments, a compound of the disclosure, or a pharmaceutically acceptable salt thereof, is administered in an effective amount for treatment and/or prevention of light chain deposition disease.

In some embodiments, a compound of the disclosure, or a pharmaceutically acceptable salt thereof, is administered in an effective amount for treatment and/or prevention of IgA nephropathy.

In some embodiments, a compound of the disclosure, or a pharmaceutically acceptable salt thereof, is administered in an effective amount for treatment and/or prevention of end-stage renal disease.

In some embodiments, a compound of the disclosure, or a pharmaceutically acceptable salt thereof, is administered in an effective amount for treatment and/or prevention of gout.

In some embodiments, a compound of the disclosure, or a pharmaceutically acceptable salt thereof, is administered in an effective amount for treatment and/or prevention of pseudogout.

In some embodiments, a compound of the disclosure, or a pharmaceutically acceptable salt thereof, is administered in an effective amount for treatment and/or prevention of diabetic nephrophathy.

In some embodiments, a compound of the disclosure, or a pharmaceutically acceptable salt thereof, is administered in an effective amount for treatment and/or prevention of diabetic neurophathy.

In some embodiments, a compound of the disclosure, or a pharmaceutically acceptable salt thereof, is administered in an effective amount for treatment and/or prevention of traumatic brain injury.

In some embodiments, a compound of the disclosure, or a pharmaceutically acceptable salt thereof, is administered in an effective amount for treatment and/or prevention of noise-induced hearing loss.

In some embodiments, a compound of the disclosure, or a pharmaceutically acceptable salt thereof, is administered in an effective amount for treatment and/or prevention of Alzheimer's disease.

In some embodiments, a compound of the disclosure, or a pharmaceutically acceptable salt thereof, is administered in an effective amount for treatment and/or prevention of Parkinson's disease.

In some embodiments, a compound of the disclosure, or a pharmaceutically acceptable salt thereof, is administered in an effective amount for treatment and/or prevention of Huntington's disease.

In some embodiments, a compound of the disclosure, or a pharmaceutically acceptable salt thereof, is administered in an effective amount for treatment and/or prevention of amyotrophic lateral sclerosis.

In some embodiments, a compound of the disclosure, or a pharmaceutically acceptable salt thereof, is administered in an effective amount for treatment and/or prevention of primary biliary cirrhosis.

In some embodiments, a compound of the disclosure, or a pharmaceutically acceptable salt thereof, is administered in an effective amount for treatment and/or prevention of primary sclerosing cholangitis.

In some embodiments, a compound of the disclosure, or a pharmaceutically acceptable salt thereof, is administered in an effective amount for treatment and/or prevention of uterine leiomyoma.

In some embodiments, a compound of the disclosure, or a pharmaceutically acceptable salt thereof, is administered in an effective amount for treatment and/or prevention of sarcoidosis.

In some embodiments, a compound of the disclosure, or a pharmaceutically acceptable salt thereof, is administered in an effective amount for treatment and/or prevention of chronic kidney disease.

In some embodiments, the inflammatory disorder is an ocular inflammatory disorder. In some embodiments, the ocular inflammatory disorder is diabetic macular edema (DME), atopic keratoconjunctivitis (AKC), vernal keratoconjunctivitis (VKC), age-related macular degeneration (AMD), dry eye disease (DED), allergic conjunctivitis (AC), dry eye disease with allergic conjunctivitis, noninfectious anterior uveitis, posterior uveitis, pan-uveitis, post-surgical ocular pain and inflammation.

In some embodiments, the compound of the disclosure, or a pharmaceutically acceptable salt thereof, is administered in an effective amount for the prevention of corneal fibrosis after radial keratotomy, prevention of corneal fibrosis after trauma, or prevention of corneal fibrosis after infection.

In some embodiments, a compound of the disclosure, or a pharmaceutically acceptable salt thereof, is administered in an effective amount to treat diabetic macular edema (DME). In some embodiments, the diabetic macular edema for treatment is non-clinically significant macular edema (Non-CSME). In some embodiments, the diabetic macular edema for treatment is clinically significant macular edema (CSME).

In some embodiments, a compound of the disclosure, or a pharmaceutically acceptable salt thereof, is administered in an effective amount to treat uveitis, including pan-uveitis, anterior uveitis, posterior uveitis, and non-infectious uveitis, which are ocular disorders that can be secondary to a primary underlying disorder. Some of the disorders with which uveitis is sometimes associated are Behcet's syndrome, ankylosing spondylitis, Lyme disease, sarcoidosis, and psoriasis. Uveitis is an inflammation of the iris, ciliary body, and choroid. It is associated with blurred vision; seeing dark, floating spots ("floaters"); eye pain; redness of the eye; and sensitivity to light (photophobia). A standard course of therapy for uveitis is a topical corticosteroid, and in some instances, a dilator such a cyclopentolate, or an immunomodulatory agent.

In some embodiments, a compound of the disclosure, or a pharmaceutically acceptable salt thereof, is administered in an effective amount to treat atopic keratoconjunctivitis (AKC) or vernal keratoconjunctivitis (VKC).

In some embodiments, a compound of the disclosure, or a pharmaceutically acceptable salt thereof, is administered in an effective amount to treat age-related macular degeneration (AMD).

In some embodiments, a compound of the disclosure, or a pharmaceutically acceptable salt thereof, is administered in an effective amount to treat dry eye disease (DED).

In some embodiments, a compound of the disclosure, or a pharmaceutically acceptable salt thereof, is administered in an effective amount to treat allergic conjunctivitis (AC).

In some embodiments, a compound of the disclosure, or a pharmaceutically acceptable salt thereof, is administered in an effective amount to treat DED with AC.

In some embodiments, a compound of the disclosure, or a pharmaceutically acceptable salt thereof, is administered in an effective amount to treat post-surgical ocular pain and inflammation.

In some embodiments, a compound of the disclosure, or a pharmaceutically acceptable salt thereof, is administered in an effective amount for prevention of corneal fibrosis after radial keratotomy.

In some embodiments, a compound of the disclosure, or a pharmaceutically acceptable salt thereof, is administered in an effective amount for prevention of corneal fibrosis after trauma.

In some embodiments, a compound of the disclosure, or a pharmaceutically acceptable salt thereof, is administered in an effective amount for prevention of corneal fibrosis after infection.

In some embodiments, the compound for treating each of the inflammatory diseases or conditions above is a compound of formulae I to XX or subformulae thereof as described above, including any one of the exemplary compounds of Table 1a, Table 1b, Table 2, Table 3, Table 4, Table 5, Table 6, Table 7, or the other tables above. In some embodiments, a method of the inflammatory disorder comprises administering to a subject in need thereof a therapeutically effective amount of compound I-22, I-5 or I-6 of Table 1a or Table 1b, such as compound I-22.

1.6. Combination Treatments

In some embodiments, the compound above is used in combination with a second therapeutic agent. In some embodiments, the compounds of the disclosure can be administered with one or more of a second therapeutic agent, sequentially or concurrently, either by the same route or by different routes of administration. When administered sequentially, the time between administrations is selected to benefit, among others, the therapeutic efficacy and/or safety of the combination treatment. In some embodiments, the compound of the disclosure can be administered first followed by a second therapeutic agent, or alternatively, the second therapeutic agent administered first followed by the compound of the disclosure. In some embodiments, the compound of the disclosure can be administered for the same duration as the second therapeutic agent, or alternatively, for a longer or shorter duration as the second therapeutic compound.

When administered concurrently, the compounds of the disclosure can be administered separately at the same time as the second therapeutic agent, by the same or different routes, or administered in a single composition by the same route. In some embodiments, the compound of the disclosure is prepared as a first pharmaceutical composition, and the second therapeutic agent prepared as a second pharmaceutical composition, where the first pharmaceutical composition and the second pharmaceutical composition are administered simultaneously, sequentially, or separately. In some embodiments, the amount and frequency of administration of the second therapeutic agent can used standard dosages and standard administration frequencies used for the particular therapeutic agent. See, e.g., Physicians' Desk Reference, 70th Ed., PDR Network, 2015; incorporated herein by reference.

In some embodiments, the second therapeutic agent is a leukotriene inhibitor, non-steroidal anti-inflammatory drug (NSAID), steroid, tyrosine kinase inhibitor, receptor kinase inhibitor, modulator of nuclear receptor family of transcription factor, HSP90 inhibitor, adenosine receptor ($A_{2A}$) agonist, disease modifying antirheumatic drugs (DMARDS), phosphodiesterase (PDE) inhibitor, neutrophil elastase inhibitor, modulator of Axl kinase, or combinations thereof.

In some embodiments, the second therapeutic agent is a leukotriene inhibitor. In some embodiments, the leukotriene inhibitor is montelukast, zafirlukast, pranlukast, zileuton, or combinations thereof.

In some embodiments, the second therapeutic agent is a an NSAID. In some embodiments, the NSAID is acetylsalicylic acid, diflunisal, salsalate, ibuprofen, dexibuprofen, naioxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, phenylbutazone, mefenamic acid, meclofenamic acid, flufenamic acid, tolfenamic acid, celecoxib or combinations thereof.

In some embodiments, the second therapeutic agent is a steroid. In some embodiments, the steroid is prednisone, prednisolone, methylprednisone, triacmcinolone, betamethasone, dexamethasone, and prodrugs thereof.

In some embodiments, the second therapeutic agent is a tyrosine kinase inhibitor. In some embodiments, the tyrosine kinase inhibitor is an inhibitor of the following kinases, including, among others, JAK, Syk, JNK/SAPK, MAPK, PI-3K, or Ripk2. In some embodiments, the tyrosine kinase inhibitor is ruxolitinib, tofacitinib, oclactinib, filgotinib, ganotinib, lestaurtinib, momelotinib, pacritinib, upadacitinib, peficitinib, fedratinib, bentamapimod, D-JNKI-1 (XG-102, AM-111), ponatinib, WEHI-345, OD36, GSK583, idelalisib, copanlisib, taselisib, duvelisib, alpelisib, umbralisib, dactolisib, CUDC-907, entospletinib, fostamatinib, or combinations thereof.

In some embodiments, the second therapeutic agent is a receptor kinase inhibitor, including among others, and inhibitor of EGFR or HER2. In some embodiments, the receptor kinase inhibitor is gefitinib, erlotinib, neratinib, lapatinib, cetuximab, panitumumab, vandetanib, necitumumab, osimertinib, trastuzumab, neratinib, lapatinib, pertuzumab, or combinations thereof.

In some embodiments, the second therapeutic agent is a modulator of nuclear receptor family of transcription factors, including, among others, and inhibitor of PPAR, RXR, FXR, or LXR. In some embodiments, the inhibitor is pioglitazone, bexarotene, obeticholic acid, ursodeoxycholic acid, fexaramine, hypocholamide, or combinations thereof.

In some embodiments, the second therapeutic agent is an HSP90 inhibitor. In some embodiments, the HSP90 inhibitor is ganetespib, 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010, or combinations thereof.

In some embodiments, the second therapeutic agent is an adenosine receptor 2A ($A_{2A}$) agonist. In some embodiments, the adenosine receptor agonist is, among others, disclosed in U.S. Pat. No. 9,067,963, which is incorporated herein by reference. In some embodiments, the adenosine receptor agonist is LNC-3050, LNC-3015, LNC-3047, LNC-3052, or combinations thereof.

In some embodiments, the second therapeutic agent is selected from disease modifying antirheumatic drugs (DMARDS). In some embodiments, the DMARDS is, among others, tocilizumab, certolizumab, etanercept, adalimumab, anakinra, abatacept, infliximab, rituximab, golimumab, uteskinumab, or combinations thereof.

In some embodiments, the second therapeutic agent is a phosphodiesterase (PDE) inhibitor. In some embodiments, the phosphodiesterase inhibitor is apremilast, crisaborole, piclimilast, drotaverine, ibudulast, roflumilast, sildenafil, tadalafil, vardenafil, or combinations thereof.

In some embodiments, the second therapeutic agent is a neutrophil elastase inhibitor. In some embodiments, the neutrophil elastase inhibitor is, among others, sivelestat.

In some embodiments, the second therapeutic agent is a modulator of Axl kinase. In some embodiments, the modulator of Axl kinase is bemcentinib (BGB324 or R428), TP-0903, LY2801653, amuvatinib (MP-470), bosutinib (SKI-606), MGCD 265, ASP2215, cabozantinib (XL184), foretinib (GSK1363089/XL880), and SGI-7079. In some embodiments, the modulator of Axl kinase is a monoclonal antibody targeting AXL (e.g., YW327.6S2) or an AXL decoy receptor (e.g., GL2I.T), or glesatinib, merestinib, or a dual Flt3-Axl inhibitor such as gilteritinib.

1.7. Pharmaceutically Acceptable Compositions

The compounds and compositions, according to the method of the present disclosure, are administered using any amount and any route of administration and any duration of treatment effective for treating or lessening the severity of a disorder provided above. The exact amount required will vary from subject to subject, depending on the species, age, and general condition of the subject, the severity of the disorder, the particular agent, its mode of administration, and the like. The compounds are preferably formulated in dosage unit form for ease of administration and uniformity of dosage. The expression "dosage unit form" or "unit dosage form" as used herein refers to a physically discrete unit of agent appropriate for the patient to be treated. It will be understood, however, that the total daily usage of the compounds and compositions described herein can be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of the compounds can be administered to humans and other animals orally, rectally, intrathecally, subcutaneously, intravenously, intranasally, parenterally, intracisternally, intravaginally, intraperitoneally, intravitreally, topically (as by powders, ointments, or drops), buccally, as an oral or nasal spray, or the like, depending on the severity of the condition being treated. In certain embodiments, the compounds described herein are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. In some embodiments, the compounds are administered systemically, such as by oral or parenteral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulate matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues. Subcutaneous depot formulations are also prepared with hyaluronidase.

Compositions for rectal or vaginal administration are preferably suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the present disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the embodiments herein contemplate the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the present disclosure can also be administered topically, such as directly to the eye, e.g., as an eye-drop or ophthalmic ointment. Eye drops typically comprise an effective amount of at least one compound described herein and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104 (Pt 4):402-9; Ashton et al., 1991, J Pharmacol Exp Ther. 259(2):719-24; Green et al., 1971, Am J Ophthalmol. 72(5):897-905). The most commonly used penetration enhancer is benzalkonium chloride (Tang et al., 1994, J Pharm Sci. 83(1):85-90; Burstein et al, 1980, Invest Ophthalmol Vis Sci. 19(3):308-13), which also works as preservative against microbial contamination. It is typically added to a final concentration of 0.01-0.05%.

In some embodiments, the compounds for use in the method can be formulated with a cyclodextrin, for example as described in U.S. patent publication no. US 2012/0302601, incorporated herein by reference. In some embodiments, the cyclodextrin for use in the pharmaceutical compositions can be selected from α-cyclodextrin, β-cyclodextrin, γ-cyclodextrin, derivatives thereof, and combinations thereof. In particular, the cyclodextrin for use in the methods is selected from β-cyclodextrin, γ-cyclodextrin, derivatives thereof, and combinations thereof.

In some embodiments, the compounds can be formulated with a cyclodextrin or derivative thereof selected from carboxyalkyl cyclodextrin, hydroxyalkyl cyclodextrin, sulfoalkylether cyclodextrin, and an alkyl cyclodextrin. In various embodiments, the alkyl group in the cyclodextrin is methyl, ethyl, propyl, butyl, or pentyl.

In some embodiments, the cyclodextrin is α-cyclodextrin or a derivative thereof. In some embodiments, the α-cyclodextrin or derivative thereof is selected from carboxyalkyl-α-cyclodextrin, hydroxyalkyl-α-cyclodextrin, sulfoalkylether-α-cyclodextrin, alkyl-α-cyclodextrin, and combinations thereof. In some embodiments, the alkyl group in the α-cyclodextrin derivative is methyl, ethyl, propyl, butyl, or pentyl.

In some embodiments, the cyclodextrin is β-cyclodextrin or a derivative thereof. In some embodiments, the β-cyclodextrin or derivative thereof is selected from carboxyalkyl-β-cyclodextrin, hydroxyalkyl-β-cyclodextrin, sulfoalkylether-β-cyclodextrin, alkyl-β-cyclodextrin, and combinations thereof. In some embodiments, the alkyl group in the β-cyclodextrin derivative is methyl, ethyl, propyl, butyl, or pentyl.

In some embodiments, the β-cyclodextrin or a derivative thereof is hydroxyalkyl-β-cyclodextrin or sulfoalkylether-β-cyclodextrin. In some embodiments, the hydroxyalkyl-β-cyclodextrin is hydroxypropyl-β-cyclodextrin. In some embodiments, the sulfoalkylether-β-cyclodextrin is sulfobutylether-β-cyclodextrin. In some embodiments, β-cyclodextrin or a derivative thereof is alkyl-β-cyclodextrin, in particular methyl-β-cyclodextrin. In some embodiments using methyl-β-cyclodextrin, the β-cyclodextrin is randomly methylated β-cyclodextrin.

In some embodiments, the cyclodextrin is γ-cyclodextrin or a derivative thereof. In some embodiments, the γ-cyclodextrin or derivative thereof is selected from carboxyalkyl-γ-cyclodextrin, hydroxyalkyl-γ-cyclodextrin, sulfoalkylether-γ-cyclodextrin, and alkyl-γ-cyclodextrin. In some embodiments, the alkyl group in the γ-cyclodextrin derivative is methyl, ethyl, propyl, butyl, or pentyl. In some embodiments, the γ-cyclodextrin or derivative thereof is hydroxyalkyl-γ-cyclodextrin or sulfoalkylether-γ-cyclodextrin. In some embodiments, the hydroxyalkyl-γ-cyclodextrin is hydroxypropyl-γ-cyclodextrin.

When used in a formulation with the compound, the cyclodextrin can be present at about 0.1 w/v to about 30% w/v, about 0.1 w/v to about 20% w/v, about 0.5% w/v to about 10% w/v, or about 1% w/v to about 5% w/v. In some embodiments, the cyclodextrin is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v or more.

In some embodiments, such as for topical or intravitreal administration, the compound can be present at a concentration of about 0.05% w/v to about 10% w/v, about 0.1% w/v to about 5% w/v, about 0.2% w/v to about 4% w/v, about 0.3% to about 3% w/v, about 0.4% w/v to about 2% w/v, or about 0.5% w/v to about 1.5% w/v. In some embodiments, the compound can be present at a concentration at about least about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 1.5% w/v, about 2% w/v, about 3% w/v, about 4% w/v, about 5% w/v, about 6% w/v, about 7% w/v, about 8% w/v, about 9% w/v, or about 10% w/v. In some embodiments, the concentrations are for a formulation with a cyclodextrin, such as β-cyclodextrin. In some embodiments, the amount administered topically can be about 20 to about 100 μL per dose, about 30 to 80 μL per dose or about 40 to 60 μL per dose of a defined concentration of the compound effective for treating the disorder. In some embodiments, compound I-22, I-5 or 1-6 of Table 1a or Table 1b is formulated with a β-cyclodextrin, such as hydroxypropyl-β-cyclodextrin or sulfobutylether-β-cyclodextrin.

In some embodiments, the compound is formulated as an ophthalmic solution such as those described in U.S. provisional patent application Ser. No. 62/736,417, the entire contents of which are hereby incorporated by reference. In some embodiments, the compound is I-5.

In order that the invention described herein may be more fully understood, the following examples are set forth. It should be understood that these examples are for illustrative purposes only and are not to be construed as limiting this invention in any manner.

EXAMPLES

As depicted in the Examples below, the following general methods, and other methods known to one of ordinary skill in the art, can be applied to all compounds and subclasses and species of each of these compounds, as described herein.

Example 1: Treatment of Animal Model of Diabetic Macular Edema

Diabetic macular edema (DME) is a common cause of vision loss. Hyperglycemia leads to carbonyl stress in the retina, resulting in accumulation of toxic aldehydes such as methylglyoxal, 4-hydroxy-trans-2-nonenal, and malondialdehyde, which induce inflammatory changes in the eye, including the development of DME.

To assess the effect of Compound I-22 in a rat model of diabetic macular edema (DME), Type 1 diabetes was induced in male brown Norway rats by intraperitoneal administration of streptozotocin (STZ; 55 mg/kg). Forty days after STZ administration, animals were assessed for the presence of diabetes by testing blood glucose levels.

Compound I-22 was supplied as a preformulated sterile solution at 5 mg/mL. The vehicle was 25% hydroxypropyl-β-cyclodextrin solution (333 mOsm/kg) in a sodium phosphate buffer, pH 7.2. Animals with diabetes were assigned to groups of ten, to receive either vehicle (HPβCD) or compound I-22.

The study consisted of three groups of male brown Norway rats. Diabetes and diabetic retinopathy were induced in Groups 2 and 3 by intraperitoneal injection of streptozotocin (STZ) on Day 0; Group 1 animals served as non-STZ (non-diabetic) untreated controls. Six and eight weeks after STZ injection, Vehicle (3.5 µL) and Compound I-22 (17.5 µg per eye; 3.5 µL) were administered intravitreally to both eyes of rats in Group 2 and Group 3, respectively. Clinical observations (daily), body weights (weekly), qualitative food consumption, and blood glucose levels (weekly) were assessed. To evaluate retinopathy, electroretinography (ERG) was conducted at Weeks 8, 9 and 10; and optical coherence tomography (OCT) and fundus fluorescein angiography (FFA) were performed pre-dose at Week 6, and at Weeks 8, 9, and 10. Animals were euthanized at 10 weeks post-STZ administration and eyes were collected for histopathological evaluation.

Induction of Diabetic Retinopathy by Streptozotocin

Type 1 diabetes was induced by intraperitoneal administration of 55 mg/kg STZ after an overnight fast. The STZ dosing solution (27.5 mg/mL) was prepared immediately prior to injection by dissolving STZ (Sigma-Aldrich Corp, St. Louis, Mo., Catalog S0130) in a citrate solution (see below) followed by filtration of the STZ solution using a 0.2 µm syringe filter (Pall Life Sciences, Ann Arbor, Mich., Catalog PN4192). The STZ dosing solution was used for injection within approximately 30 minutes after reconstitution.

The citrate solution (0.01 M) used for reconstitution of STZ was made by mixing 1.9 g citric acid (Sigma-Aldrich Corp, St. Louis, Mo., Catalog C0759) with 1 L 0.9% Sodium Chloride for Injection (Hospira NDC0409-7983-02, Lot 62-034-JT), adjusting the pH to 4.5 with sodium hydroxide (Sigma-Aldrich Corp, St. Louis, Mo., Catalog S2770 for 1 N NaOH) followed by filtration of the STZ solution using a 0.2 µm syringe filter. This citrate solution was stored at room temperature and used for reconstituting STZ within two weeks of preparation.

Clinical Observations

Clinical observations, including morbidity, mortality, and overt signs of toxic or pharmacologic effect(s) were recorded for individual animals once daily throughout the in-life phase (acclimation and treatment period). All signs of clinical abnormality were recorded.

Body Weights

The rats were weighed prior to dosing, weekly thereafter, and prior to necropsy.

Food Consumption

Food consumption was qualitatively assessed weekly.

Blood Glucose Determination

Non-fasting blood glucose levels were determined prior to STZ administration, weekly thereafter and at necropsy, by a glucometer (AlphaTrak Blood Glucose Monitoring System, Abbott Laboratories, North Chicago, Ill.).

OCT, FFA and ERG

Electroretinography (ERG) was performed on Days 55, 62 and 69. After an overnight dark adaption, both eyes were dilated with 1% tropicamide. Animals were anesthetized by isoflurane prior to the procedure. ERG responses to light stimuli (8.0 cd·s/m$^2$) were recorded by RETevet (LKC Technologies, Inc.). Implicit times and amplitudes of a-waves and b-waves were reported. There was a deviation from the protocol in which ERG was not performed prior to Test Article administration (~Day 40). The deviation had no impact on the conclusion of the study. Baseline ERG measurements are not required to determine efficacy of the Test Article. A Day −62 ERG assessment was added to the study.

Optical coherence tomography (OCT) and fundus fluorescein angiography (FFA) were performed on Day 41 (pre-dose) and Days 56, 63 and 70 (post-dose initiation). Both eyes were dilated with 1% tropicamide. Animals were anesthetized (by ketamine/xylazine intramuscular injection) prior to the procedures.

Retinas of both eyes in each animal were scanned by OCT (Envisu R-Class, Leica/Bioptogen). Thickness of retinal mid-layers, approximately including the outer plexiform layer (OPL), the outer nuclear layer (ONL) and the photoreceptor inner segment (IS), were measured using Bioptigen InVivoVue Reader software. For each eye, four (4) digital calipers were placed randomly on a cross-section image between OPL and IS, away from optic nerve; and measurements were exported to Microsoft Excel files. An average thickness of each retina was calculated from the four (4) measurements, using Microsoft Excel.

For FFA, ~1.5 mL/kg fluorescein (AK-FLUOR® fluorescein injection, USP, 10%, NDC 17478253-10) was injected intraperitoneally to visualize the retinal vasculature. Retinal angiograms were obtained from both eyes of each animal (Micron VR, Phoenix Phoenix Research Labs) and the images were manually scored for retinal vasculature leakage on a scale of 0 to 4 (0-normal, 1-slight, 2-mild, 3-moderate, 4-severe).

Necropsy

Animals were euthanized on Day 71. Both eyes of each animal were enucleated and fixed in modified Davidson's solution overnight before being transferred to 10% neutral buffered formalin for histopathological processing and evaluation at the Testing Facility. The carcasses were disposed of without further analysis.

Histopathology

Fixed eyes were dehydrated and embedded in paraffin. Sections of 3- to 5-μm thickness were cut and stained with hematoxylin and eosin. The slides were evaluated via light microscopy by a board-certified veterinary pathologist. Abnormalities, such as inflammation (increase in leukocytes) and neovascularization were described and semi-quantitatively scored as normal (0), slight (1), mild (2), moderate (3), and severe (4). Six step sections per eye were evaluated.

Statistical Analysis

Means and standard deviations were calculated using Microsoft Excel. Statistical analysis was performed using GraphPad Prism 5 (GraphPad Software, San Diego, Calif.). Homogeneity of variance was assumed due to small group size. Continuous normal data was analyzed by one-way analysis of variance (ANOVA) followed by Dunnett's test. Nonparametric data was analyzed by Kruskal-Wallis test followed by Dunn's test. Group 1 and Group 3 were individually compared to Group 2 in the post tests. P values<0.05 were considered statistically significant.

Results

As expected, STZ injected rats showed elevated blood glucose levels and reduced body weight (and body weight gain) from one week post-STZ administration until the end of study, compared to the non-diabetic control rats (Group 1). Compared to Group 1, rats in the vehicle-treated diabetic group (Group 2) exhibited delayed ERG a-waves and b-waves, and thickened retinal mid-layers by OCT at 8, 9 and 10 weeks post-STZ injection. Increased vascular leakage (FFA) was observed at 8 and 9 weeks post-STZ injection in Group 2 as well. No statistically significant differences were observed between the Test Article-treated Group 3 and the Vehicle-treated Group 2 for these parameters (body weights, glucose levels, ERG, OCT or FFA).

Histopathological evaluation performed on ocular tissues collected ten weeks after the STZ injection showed increased retinal thickness, vascularity, and neutrophil infiltration in the Vehicle-treated Group 2 compared to the non-diabetic Group 1. The severities of the retinal lesions were significantly diminished in the Compound I-22-treated Group 3 compared to the Vehicle-treated Group 2.

Increases in retinal thickness, vascularity, and neutrophil infiltration were observed in the diabetic rats (Group 2) compared to the non-diabetic rats (Group 1). There were reductions in the severity of each of the retinal lesions in I-22-treated diabetic rats (Group 3) compared to vehicle-treated diabetic rats (Group 2), with the reductions in retinal layer thickness and neutrophil infiltration being statistically significant. The retinal thickness and vascular leakage slightly increased in the STZ-induced rat model at Week 8. Mean vascular scores were 3.0 for the control group and 2.47 (p<0.05) in the compound I-22-treated group. At Week 9, OCT showed a mean retinal thickness of 82.3 μm in the compound I-22-treated group, and 83.3 μm in the vehicle-treated group. Retinal thickness in the compound I-22-treated group was reduced at Weeks 9 and 10, however it was not statistically significant from the vehicle treated group.

A further analysis of the change in retinal thickness based on scoring of microscopically visible changes also showed a reduction in retinal thickness in diabetic rats treated with compound I-22 compared to the vehicle treated rats. The scoring used the following: 0=normal, 1=minimal microscopically visible changes; 2=mild microscopically visible changes; 3=moderate microscopically visible changes. **p<0.01 Statistical analysis was performed by a non-parametric Dunn's multiple comparison followed by the Kruskal-Wallis test. Treatment with compound I-22 resulted in a statically significant decrease in retinal thickness.

Histopathology assessments at Week 10 showed significantly reduced retinal thickness (p<0.0001) in the compound I-22-treated group. This decrease in retinal inflammation was accompanied by a significant reduction in neutrophil infiltration compared to vehicle based on assessment of microscopic sections of the retinas. Scoring was based on the following: 0=normal, 1=minimal microscopically visible changes, 2=mild microscopically visible changes, 3=moderate microscopically visible changes. **p<0.01 Statistical analysis was performed by a non-parametric Dunn's multiple comparison followed by the Kruskal-Wallis test.

Microscopic sections of the retinas were also assessed for vascular leakage. Treatment with compound I-22 inhibited diabetes-induced retinal vascular changes, as indicated by a decrease in retinal vascularity score by 36% (p<0.05) in the compound I-22-treated group compared to vehicle. However, the reduction in retinal vascularity compared to vehicle was not statistically significant. Retinal vascularity was based on the following scoring: 0=normal, 1=minimal microscopically visible changes, 2=mild microscopically visible changes, 3=moderate microscopically visible changes. STZ did not induce ERG changes, nor were there any ERG changes in the compound I-22- or vehicle-treated groups relative to the non-diabetic control group.

A decrease in vascular leakage was observed between the diabetic compound I-22-treated group and the vehicle-treated group, but the decrease did not reach statistical significance. In addition, although significant histopathological improvements were observed following treatment with compound I-22, ERG, OCT, or FFA did not show statistically significant effects following treatment with compound I-22.

Discussion and Conclusions

Diabetic retinopathy was successfully induced in rats in this 10-week study. Histopathologic scoring showed statistically significant reductions in severities of retinopathy lesions in Compound I-22-treated diabetic rats compared to vehicle-treated diabetic rats. Interestingly, clinical evaluations (ERG, OCT or FFA) did not show any statistically significant Test Article effects.

In conclusion, the data suggest that sequestration of aldehydes represents a novel therapeutic approach for the treatment of the ophthalmic inflammatory sequelae of diabetes. Compound I-22 decreased retinal inflammation, blocked neutrophil infiltration and blocked retinal vascular changes in this model of DME. Compound I-22 was also well tolerated in the retina.

Example 2: Treatment of Animal Model of Uveitis

An in vivo study was conducted to assess the efficacy of intravitreal administration of compound I-22 in a rat model of endotoxin induced uveitis, one of the most appropriate models for the study of NIU (Smith et al., 1998) (Toxikon Study 16-04078-N1). Ocular inflammation was induced in female Lewis rats (n=10/group) by a single foot pad injection of LPS (100 μL) (Herbort et al., 1988, Graefe's Arch Clin Exp Ophthalmol. 226:553-558). Compound I-22 (5 mg/mL) was administered intravitreally into each eye (25 μg/eye), or topically to both eyes at 1, 3, 7, 10, and 17 hours post-LPS injection, within one hour of LPS administration. Balanced salt solution (BSS) served as a vehicle control.

Retinal exams were performed prior to study start and six and 24 hours following LPS administration and scored using a Combined Draize and McDonald Shadduck scoring system, based on assessments of: retinal vasculopathy and retinal hemorrhage, exudate, and detachment.

Parameters evaluated during the study included changes in the anterior and posterior segments of the eye.

Endotoxin-induced uveitis was created by a single injection of lipopolysaccharide (LPS; 100 µL) into one hind footpad. Ten (10) female Lewis rats per group received control (balanced salt solution, BSS) or test article (compound I-22) topically to both eyes at 1, 3, 7, 10, and 17 hours post-LPS injection. At each dosing time point, two drops (5 µL each, separated by approximately two minutes, for a total of 10 µL/eye/dose) were instilled into each eye of the animals. Ten female Lewis rats per group received control (BSS) or compound I-22 by a single intravitreal injection (IVT) in each eye at one hour post-LPS injection. Each eye received 5 µL of vehicle or test article.

Animals were anesthetized with isoflurane 1-3.5% for ophthalmic examinations. Both eyes of each animal were evaluated pre-dose using slit-lamp biomicroscopy, and an indirect ophthalmoscope or a surgical microscope, according to the Combined Draize and McDonald-Shadduck Scoring System, and the Ocular Posterior Segment Scoring Scale. All pupils were dilated with 1% tropicamide ophthalmic solution before ocular examination. Only rats showing no signs of eye irritation, ocular defects or preexisting corneal injury were used in the study.

Post-Dose Procedure:

Ophthalmic Examinations:

Ophthalmic examinations were performed on both eyes of each animal approximately six and 24 hours following LPS administration, using slit-lamp biomicroscopy and a surgical microscope or via indirect ophthalmoscopy. Pupils were dilated with 1% Tropicamide Ophthalmic Solution before ophthalmic examinations.

Statistical Analysis:

Quantitative, continuous data from this study were analyzed using one-way ANOVA. Alternative or additional statistical methods were used as necessary. Differences between control and treated animals were considered statistically significant only if the probability of the differences being due to chance were equal to or less than 5% ($p<0.05$). Statistically significant differences in the parameters were further assessed for biological significance.

Results

Overall scores from ophthalmic examinations were assessed approximately six and 24 hours after LPS administration. Overall score is the sum of scores from the criteria for evaluation.

Approximately six hours post LPS administration, rats that had received Compound I-22 topical) had a significantly lower ($p<0.05$) overall ophthalmic examination score than rats that had received control topically. Approximately 24 hours post LPS administration, the overall scores for rat that had received Compound I-22 topical were significantly lower ($p<0.05$) than rats that had received control topically.

Following IVT administration of test articles, ophthalmic examination scores for rats that had received Compound I-22 IVT were significantly lower ($p<0.05$) than for rats that had received control IVT, at approximately six and 24 hours post LPS administration.

Analysis of ophthalmic examination scores for topically dosed groups showed statistically lower scores for rats dosed with compound I-22 topically, relative to rats dosed with control topically, approximately six hours post-LPS administration. Rats that received compound I-22 topically had significantly lower ophthalmic examination scores than the topical control group at approximately 24 hours post LPS administration. When dosed with compound I-22 IVT, rats showed significantly lower scores relative to rats dosed IVT with control, at approximately six and 24 hours post LPS administration.

Figure 2:
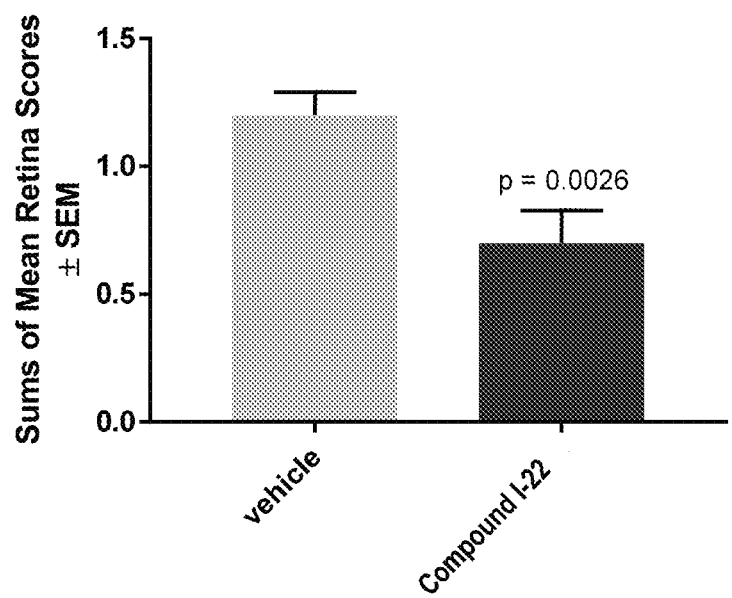
FIG. 2 shows results of administering compound I-22 in a rat model of endotoxin-induced uveitis. Retinas of test animals were scored for retinal vasculopathy, and retinal hemorrhage, exudate and detachment.
Figure 3:
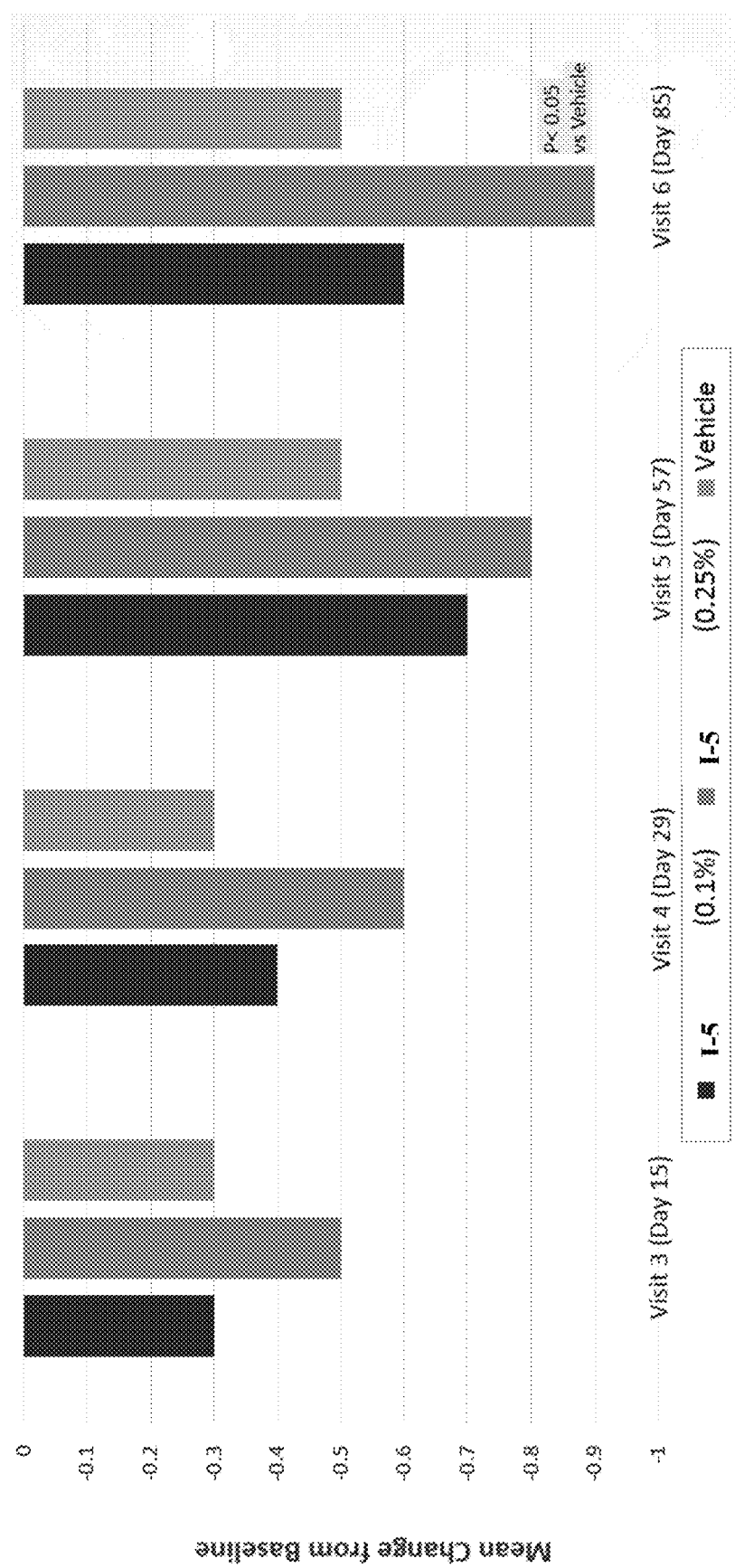
FIG. 3 depicts ocular discomfort & 4-Symptom Questionnaire: Dryness [Intent-To-Treat (ITT) Population with Observed Data Only] for a dry eye disease (DED) clinical trial.
Figure 4:
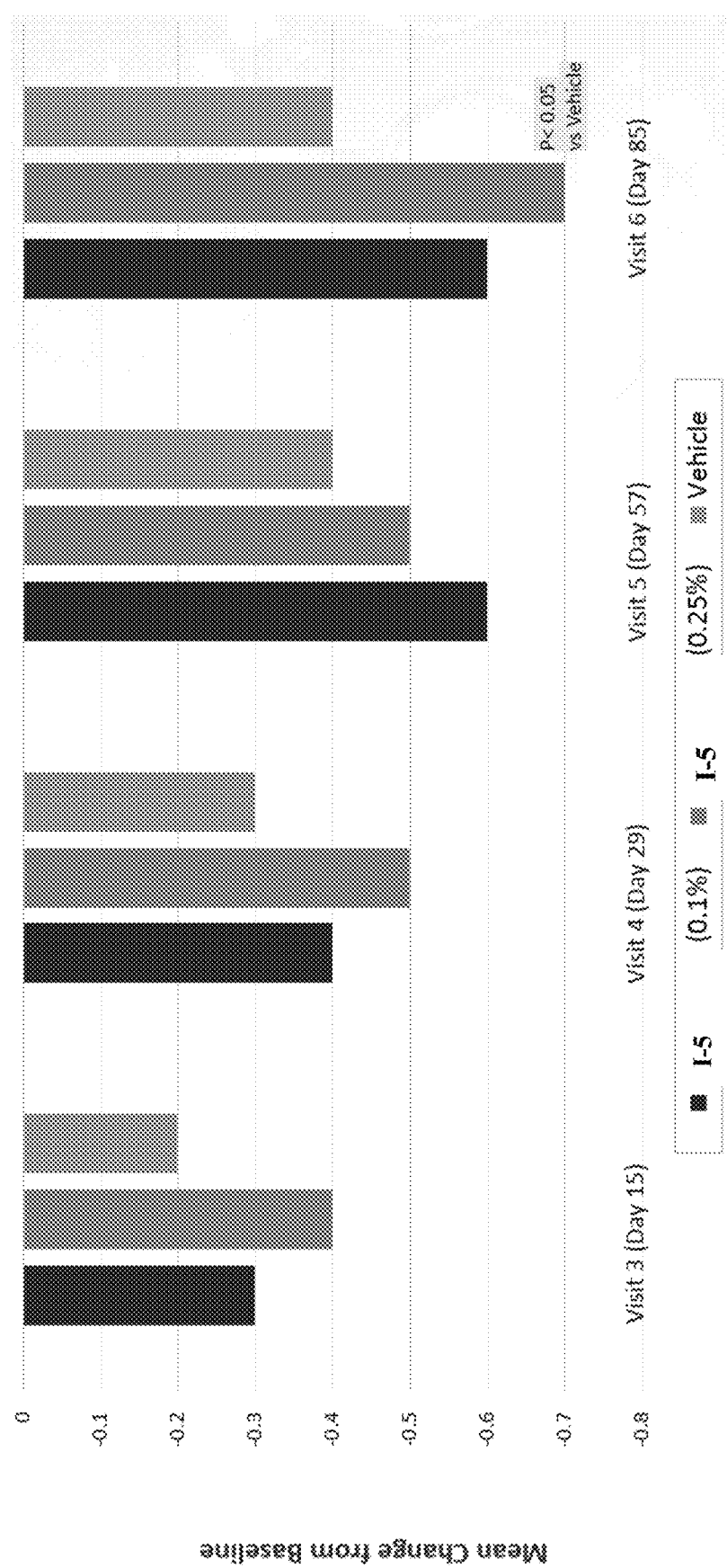
FIG. 4 depicts ocular discomfort & 4-Symptom Questionnaire: Overall Ocular Discomfort (ITT Population with Observed Data Only) for a DED clinical trial.
Figure 5:
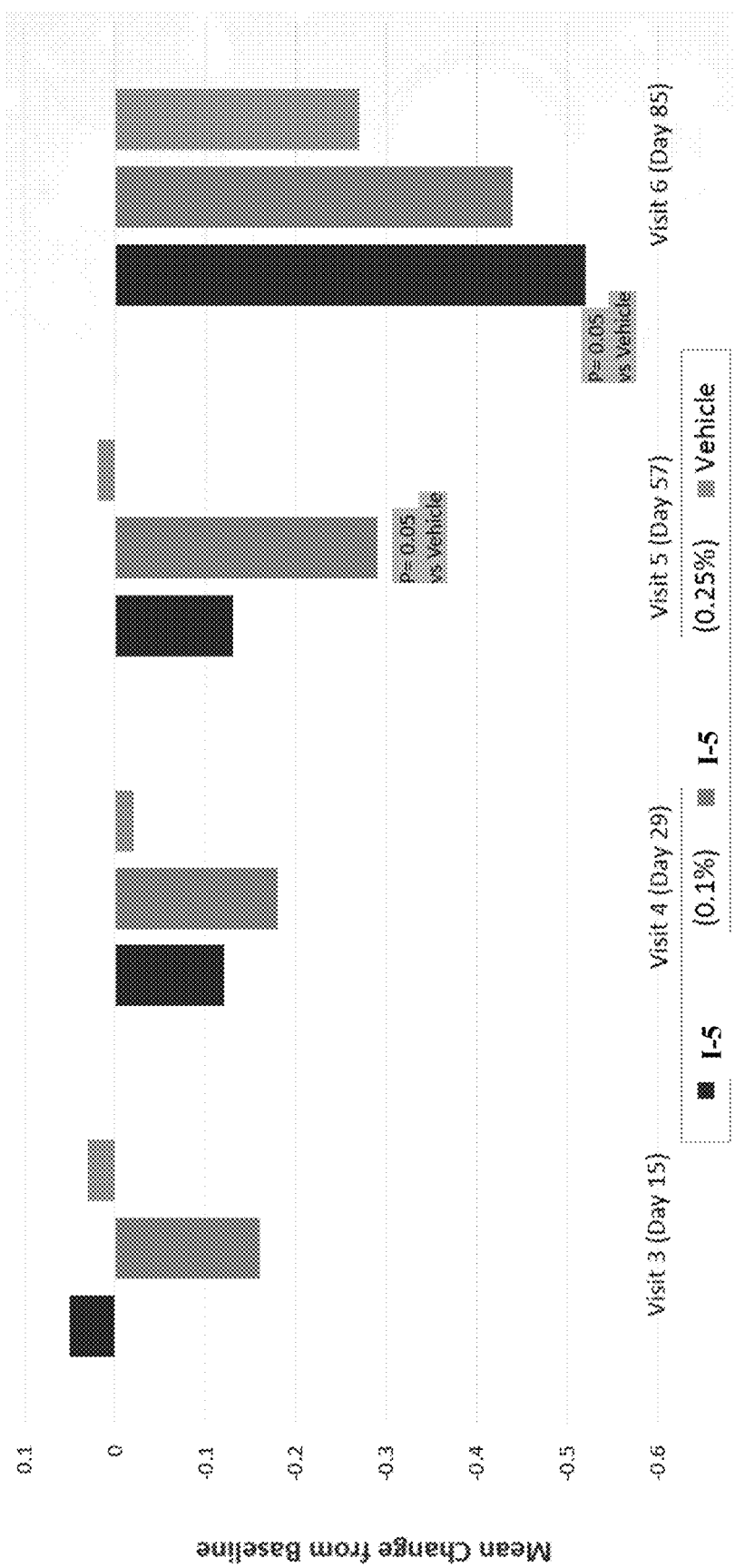
FIG. 5 depicts Fluorescein Staining: Conjunctival Sum Score (Nasal and Temporal) (ITT Population with Observed Data Only) for a DED clinical trial.
Figure 6:
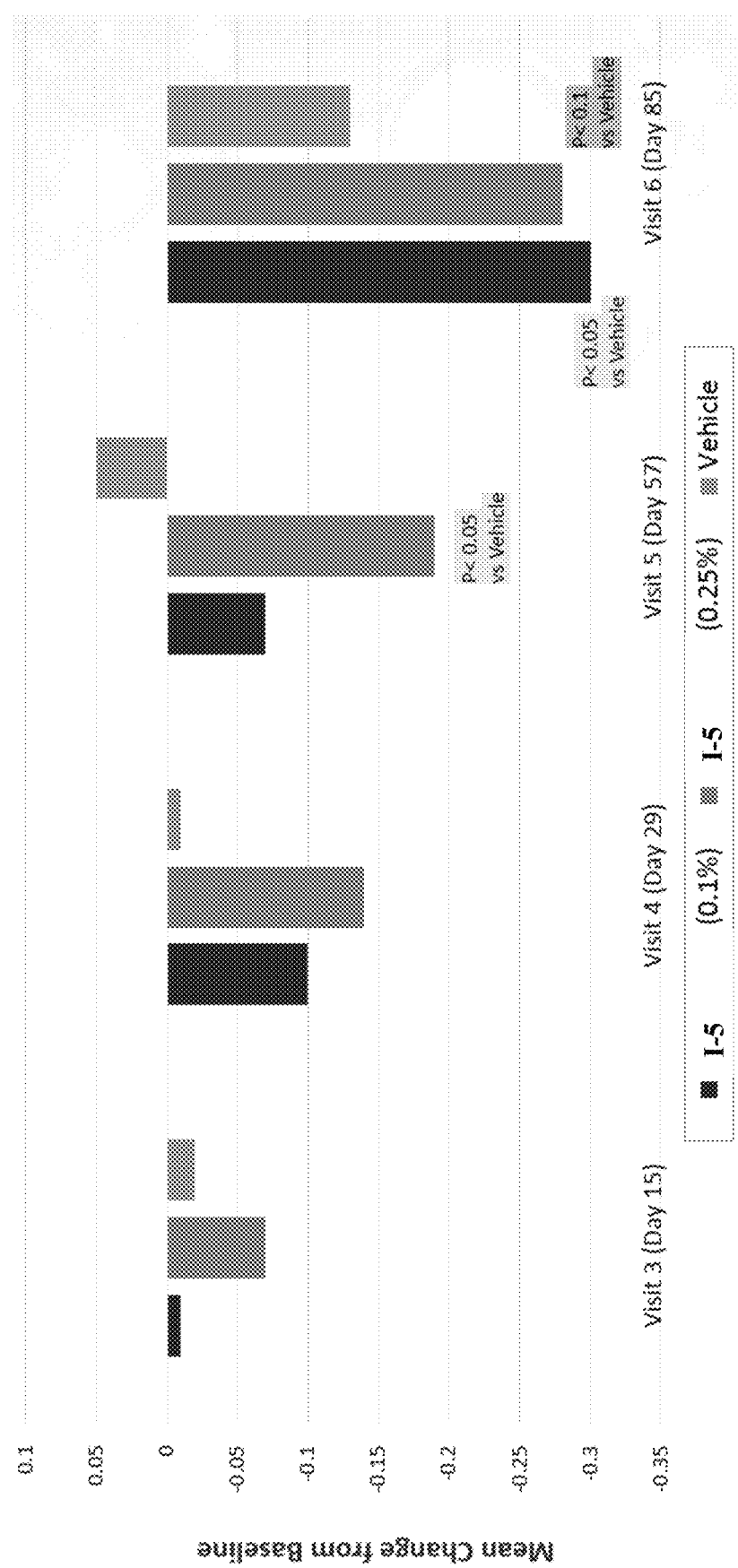
FIG. 6 depicts Fluorescein Staining: Nasal (ITT Population with Observed Data Only) for a DED clinical trial.
Figure 7:
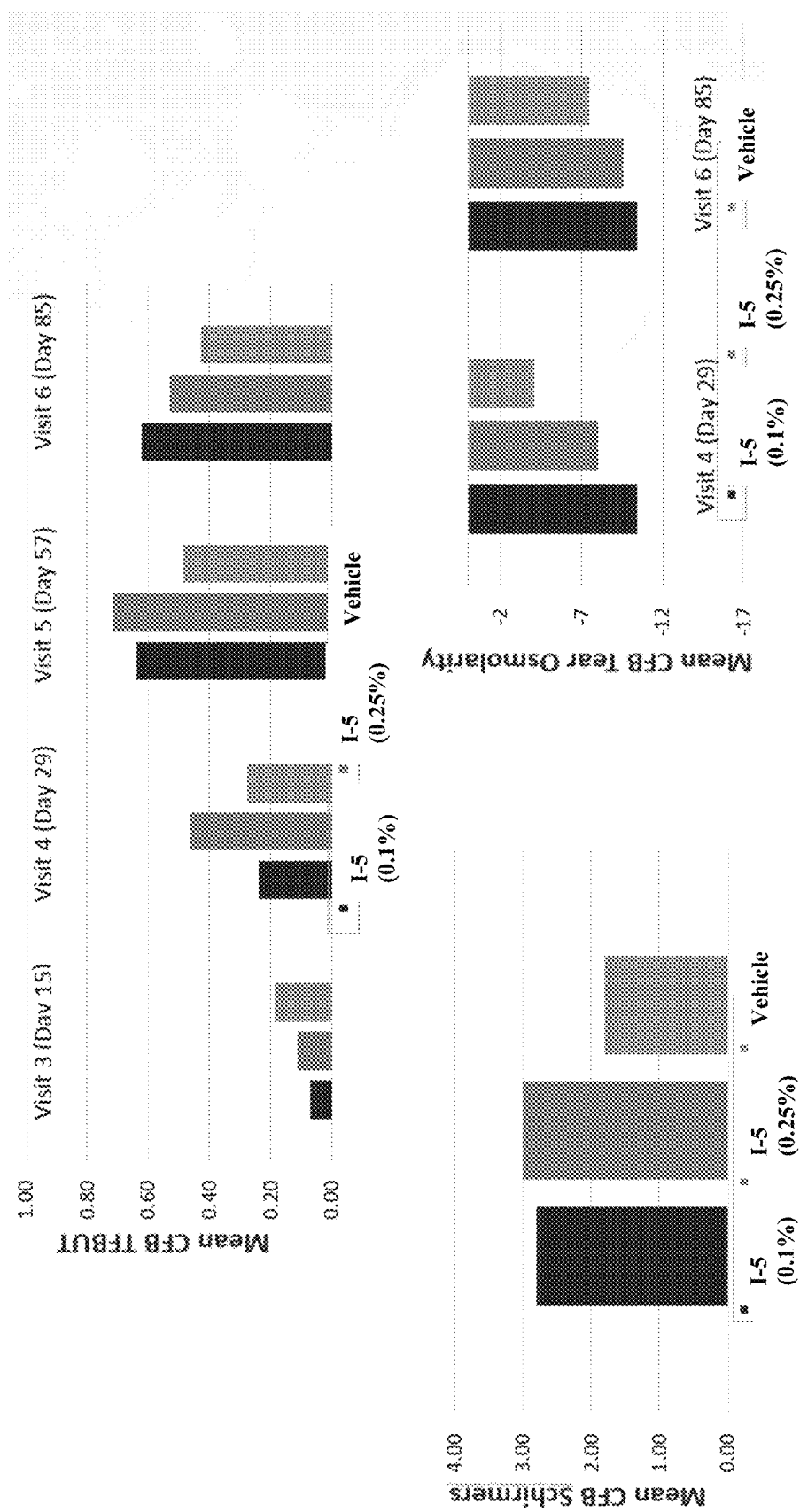
FIG. 7 depicts Tear Quantity and Quality Improved: Tear Film Break-Up Time (TFBUT), Schirmer's Test and Tear Osmolarity Supports Broad Activity Profile (Endpoint-Specific Worst Eye: ITT Population with Observed Data Only) for a DED clinical trial. CFB=change from baseline.
Figure 8:
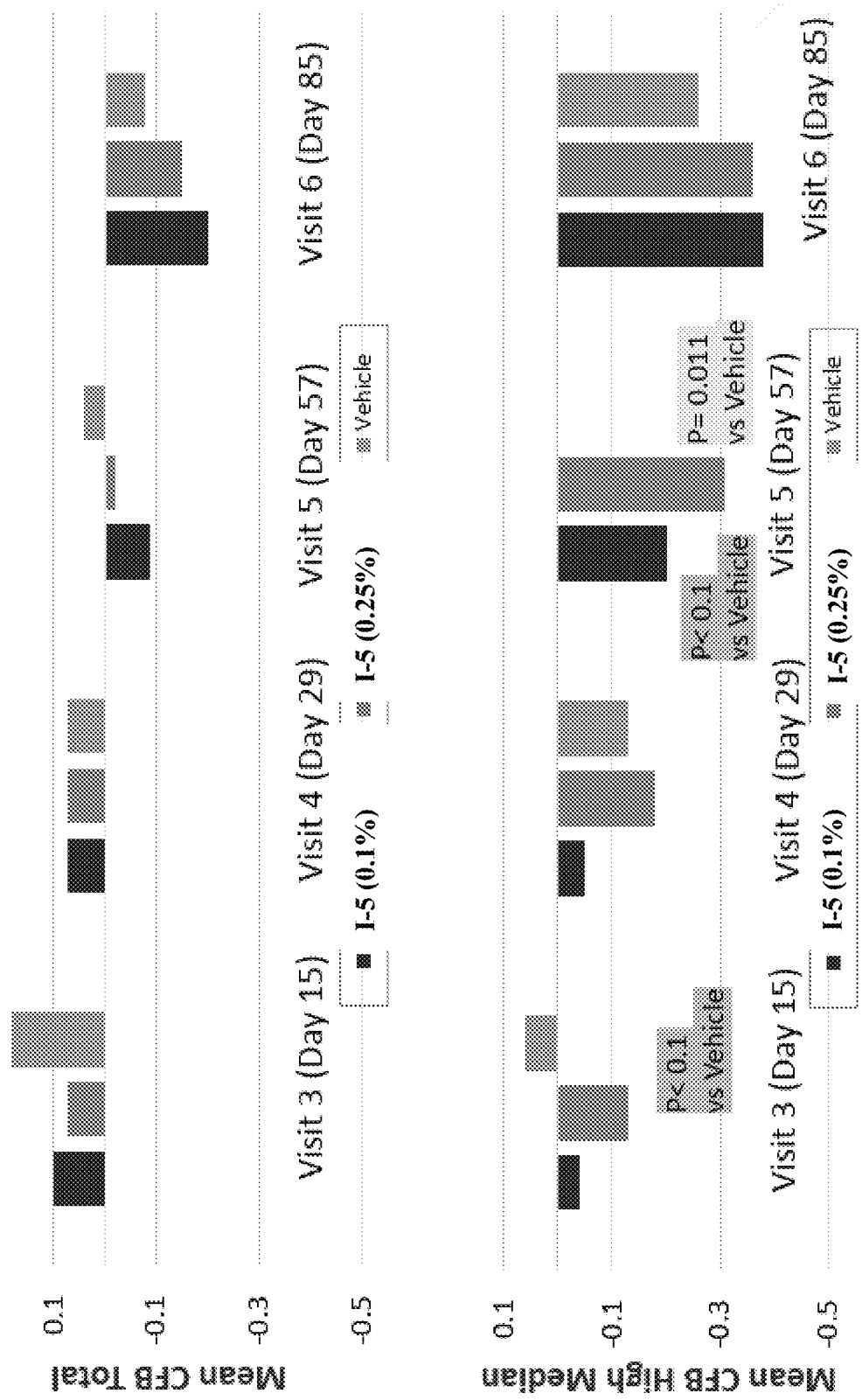
FIG. 8 depicts Fluorescein Staining: Inferior Total Population (N=100/100/100) vs High Median Subgroup (N=68/69/66) (ITT Population with Observed Data Only) for a DED clinical trial. CFB=change from baseline.
Figure 9:
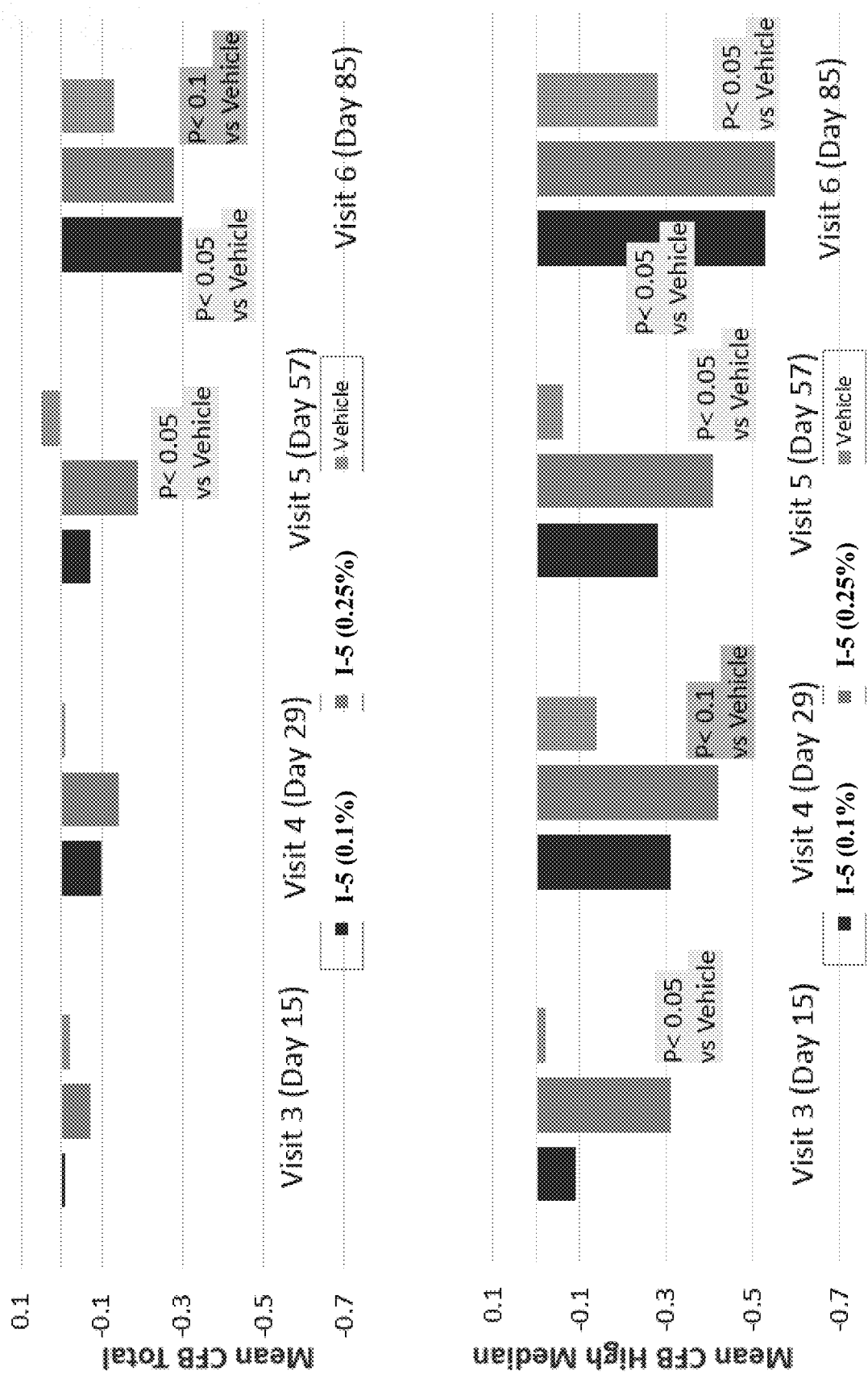
FIG. 9 depicts Fluorescein Staining: Nasal Total Population (N=100/100/100) vs High Median Subgroup (N=59/56/62) (ITT Population with Observed Data Only) for a DED clinical trial. CFB=change from baseline.
Figure 10:
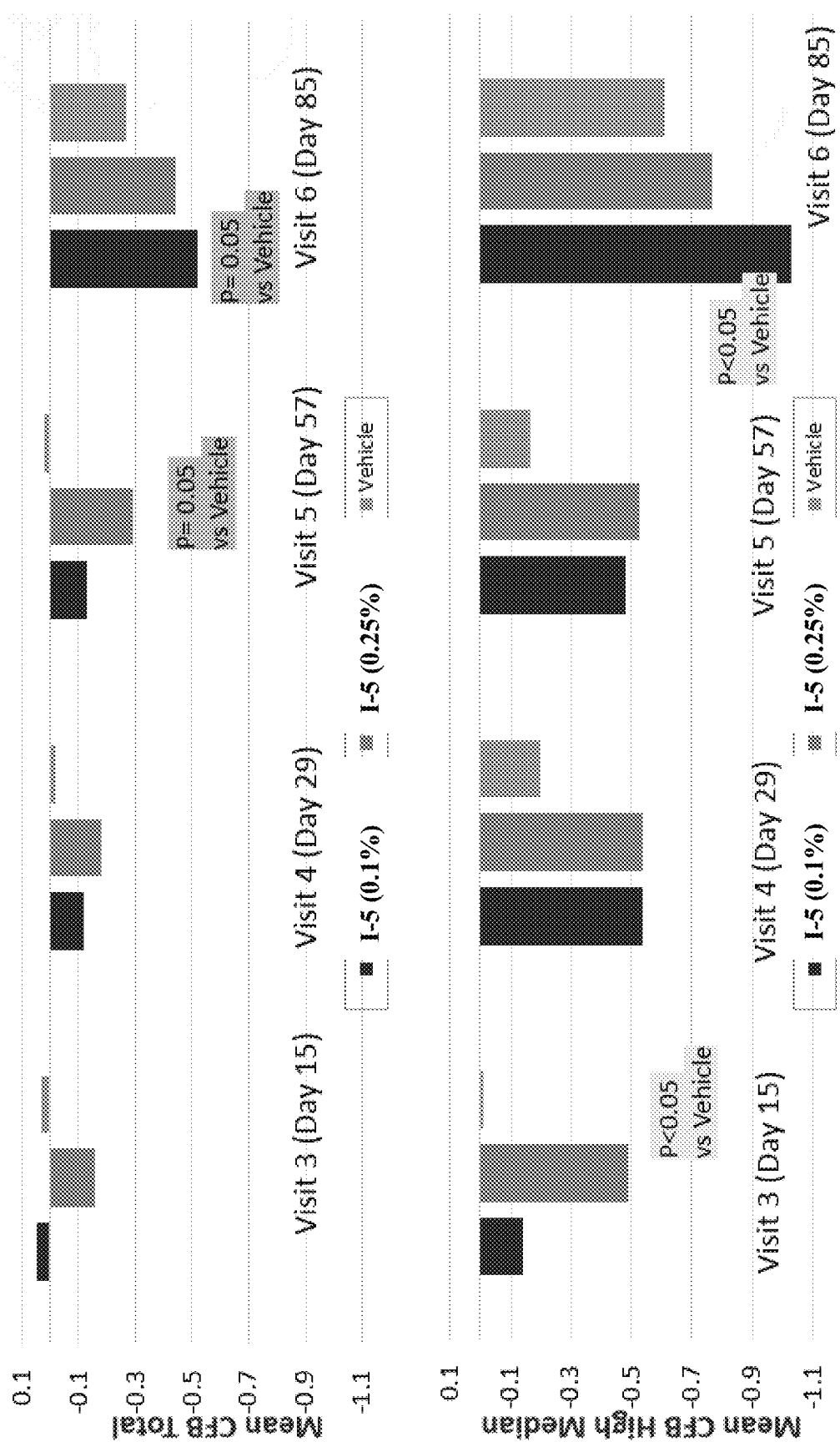
FIG. 10 depicts Fluorescein Staining: Conjunctival Sum Score (Nasal and Temporal) Total Population (N=100/100/100) vs High Median Subgroup (N=55/56/60) (ITT Population with Observed Data Only) for a DED clinical trial. CFB=change from baseline.

The sums of the mean retinal examination scores for compound I-22-treated (IVT) animals were significantly reduced relative to vehicle controls, as illustrated in FIG. 2.

In the same study, the efficacy of compound 1-5 was compared to that of compound 1-22. Compound 1-5 was topically administered topically to the eye at hours 1, 3, 7, 10, and 17, after LPS induction, or by a single intravitreal (IVT) injection one hour after LPS induction (n=10 per group), as was compound I-22. Ocular exams were performed 6 and 24 hours after LPS injection. Anterior segments were scored using a combined Draize and McDonald-Shadduck scoring system, and posterior segments were scored using 0 to 1 (vitreous, optic disc, retinal vasculature) and 0 to 4 (retinal and choroidal hemorrhage, exudation, and detachment) scales. Statistical significance from vehicle control was determined by ANOVA, followed by Tukey's post hoc test.

Ocular exam scores were significantly improved, compared to vehicle, at 6 hours and 24 hours after topical (TO) administration of Compound I-5 or Compound I-22. Total ocular inflammation, anterior chamber inflammation and retina-choroid inflammation scores were all lower in the Compound I-5- or Compound I-22-treated groups. After IVT administration of Compound I-5 or Compound I-22, ocular exam scores were also significantly improved vs. vehicle. Total ocular inflammation, anterior chamber inflammation, and retina-choroid inflammation for intravitreal administration were all lower in the Compound I-5- and Compound I-22-treated groups compared to vehicles.

Overall, Compound I-5 and Compound I-22 reduced the signs of inflammation in the rat EIU model. Intravitreal administration of the test articles yielded results of greater statistical significance compared to topical administration. Both Compound I-5 and Compound I-22 showed positive response in the EIU model, with Compound I-22 showing a slightly more positive response than Compound I-5.

Example 3: A Multi-Center, Phase 2b, Randomized, Double-Masked, Parallel-Group, Vehicle-Controlled, Clinical Study to Assess the Safety and Efficacy of 1-5 Ophthalmic Solution (0.25% and 0.1%) Compared to Vehicle in Subjects with Dry Eye Disease Abbreviations CAE: controlled adverse environment
GMP: Good Manufacturing Practice
ICH: International Council for Harmonization of Technical Requirements for Pharmaceuticals for Human Use
OD: right eye
OS: left eye
OU: both eyes
PRN: as needed
QD: once daily
QID: Four times daily
QS: as much as will suffice Objectives:

To evaluate the efficacy of I-5 Ophthalmic Solutions (0.25% and 0.1%) on baseline to weeks 2, 4, 8, and 12 change scores for sign and symptom endpoints of dry eye disease.

To evaluate effect sizes for efficacy endpoints of I-5 Ophthalmic Solutions (0.25% and 0.1%) vs vehicle for the treatment of the signs and symptoms of dry eye disease to confirm the endpoint selection and sample size for Phase 3 studies.

To evaluate the safety and tolerability of I-5 Ophthalmic Solutions (0.25% and 0.1%) to vehicle for the treatment of the signs and symptoms of dry eye disease.

Investigational Product:
1) I-5 Ophthalmic Solution (0.25%)
2) I-5 Ophthalmic Solution (0.1%)
3) Vehicle Ophthalmic Solution In the Phase 2b study, I-5 was formulated as an ophthalmic solution as described in the specification.

Duration: A subject's participation was estimated to be approximately 14 weeks (98 days).

Dosage/Dose Regimen/Instillation/Application/Use:

Screening: Between Visits 1 and 2, all subjects received 14 consecutive days (±2) of Run-in (vehicle) ocular drops self-administered QID in both eyes.

Treatment: During the 12-week (84±3 days) treatment period, I-5 Ophthalmic Solution at concentrations of 0.1%, 0.25%, or vehicle ophthalmic solution was administered QID by bilateral topical ocular dosing. Subjects were randomized to one of three treatment groups (1:1:1) to receive study drug after the Post-CAE® assessments at Visit 2.

Summary of Visit Schedule: Six visits over the course of approximately 14 weeks
 Visit 1=Day −14±2, CAE® Screening
 Visit 2=Day 1, CAE® Confirmation/Baseline
 Visit 3=Day 15±2, 2-Week Follow-Up
 Visit 4=Day 29±2, 4-Week Follow-Up
 Visit 5=Day 57±3, 8-Week Follow-Up
 Visit 6=Day 85±3, 12-Week CAE® Follow-Up & Study Exit Condition/Disease: Dry Eye Disease (DED)

Inclusion Criteria: Subjects for treatment were based on the following criteria:
1 Been at least 18 years of age of either gender and any race;
2 Provide written informed consent and sign the Health Information Portability and Accountability Act (HIPAA) form;
3 Had a reported history of dry eye for at least six months prior to Visit 1;
4 Had a history of use or desire to use eye drops for dry eye symptoms within six months of Visit 1;
5 Reported a score of ≥2 on the Ora Calibra® Ocular Discomfort & 4-Symptom Questionnaire in at least one symptom at Visit 1 and Visit 2 Pre-CAE®;
6 Had a Schirmer's Test score of ≤10 mm and ≥1 mm at Visit 1 and Visit 2;
7 Had a tear film break-up time (TFBUT)≥5 seconds at Visit 1 and Visit 2 Pre-CAE®;
8 Had a corneal fluorescein staining score of ≥2 in at least one region (e.g., inferior, superior, or central) at Visit 1 and Visit 2 Pre-CAE®;
9 Have a sum corneal fluorescein staining score of ≥4, based on the sum of the inferior, superior, and central regions, at Visit 1 and Visit 2 Pre-CAE®,
10 Had a total Lissamine green conjunctival score of ≥2, based on the sum of the temporal and nasal regions at Visit 1 and Visit 2 Pre-CAE®,
11 Demonstrated a response to the CAE® at Visits 1 and 2 as defined by:
 A. Having at least a ≥1 point increase in fluorescein staining in the inferior region in at least one eye following CAE® exposure;
 B. Reporting an Ocular Discomfort score ≥3 at two or more consecutive time points in at least one eye during CAE® exposure (if a subject had an Ocular Discomfort rating of 3 at time=0 for an eye, s/he must have reported an Ocular Discomfort rating of 4 for two consecutive measurements for that eye). Note: a subject could not have an Ocular Discomfort score of 4 at time=0);
12 Had at least one eye, the same eye, satisfy all criteria for 6, 7, 8, 9, 10, and 11 above.

Exclusion Criteria: Subject were excluded based on the following criteria:
1 Had any clinically significant slit lamp findings at Visit 1 that may have included active blepharitis, meibomian gland dysfunction (MGD), lid margin inflammation, or active ocular allergies that require therapeutic treatment, and/or in the opinion of the investigator, might have interfered with study parameters;
2 Been diagnosed with an ongoing ocular infection (bacterial, viral, or fungal), or active ocular inflammation at Visit 1;
3 Worn contact lenses within seven days of Visit 1 or anticipate using contact lenses during the study;
4 Used any eye drops within 2 hours of Visit 1;
5 Had laser-assisted in situ keratomileusis (LASIK) surgery within the last 12 months;
6 Used cyclosporine 0.05% or lifitigrast 5.0% ophthalmic solution within 90 days of Visit 1;
7 Had any planned ocular and/or lid surgeries over the study period or any ocular surgery within 6 months of Visit 1;
8 Been using or anticipated using temporary punctal plugs during the study that had not been stable within 30 days of Visit 1;
9 Been currently taking any topical ophthalmic prescription (including medications for glaucoma) or over-the-counter (OTC) solutions, artificial tears, gels or scrubs, and cannot discontinue these medications for the duration of the trial (excluding medications allowed for the conduct of the study);
10 Had corrected visual acuity greater than or equal to logarithm of the minimum angle of resolution (log MAR)+0.7 as assessed by Early Treatment of Diabetic Retinopathy Study (ETDRS) scale in both eyes at Visit 1;
11 Been a woman who is pregnant, nursing, or planning a pregnancy;
12 Been unwilling to submit a urine pregnancy test at Visit 1 and Visit 6 (or early termination visit) if of childbearing potential. Non-childbearing potential was defined as a woman who is permanently sterilized (e.g., has had a hysterectomy or tubal ligation), or was postmenopausal (without menses for 12 consecutive months);
13 Been a man or woman of childbearing potential who was not using an acceptable means of birth control; acceptable methods of contraception include: hormonal—oral, implantable, injectable, or transdermal contraceptives; mechanical—spermicide in conjunction with a barrier such as a diaphragm or condom; intrauterine device (IUD); or surgical sterilization of partner. For non-sexually active males or females, abstinence may have been regarded as an adequate method of birth control; however, if the subject became sexually active during the study, he/she must have agreed to use adequate birth control as defined above for the remainder of the study;
14 Had a known allergy and/or sensitivity to the test article or its components;
15 Had a condition or be in a situation which the investigator feels may have put the subject at significant risk, confounded the study results, or interfered significantly with the subject's participation in the study;
16 Been currently enrolled in an investigational drug or device study or have used an investigational drug or device within 30 days of Visit 1;
17 Previously used 1-5 ophthalmic solution;
18 Been currently using any medication known to cause ocular drying that was not used on a stable dosing regimen for at least 30 days prior to Visit 1;
19 Been unable or unwilling to follow instructions, including participation in all study assessments and visits.

The following efficacy measures and endpoints were used in the study:

Lissamine green staining (Ora Calibra® scale); regions: inferior, superior, central, temporal, nasal, corneal sum, conjunctival sum, and total eye score)
Fluorescein staining (Ora Calibra® scale); regions: central, superior, inferior, temporal, nasal, corneal sum, conjunctival sum, and total eye score)
Tear film break-up time
Unanesthetized Schirmer's Test
Ora Calibra® Ocular Discomfort Scale
Ora Calibra® Ocular Discomfort & 4-Symptom Questionnaire
Ocular Surface Disease Index (OSDI)©
SANDE questionnaire
Tear Osmolarity Safety Measures:
Visual acuity
Slit-lamp evaluation
Adverse event query
Intraocular Pressure (IOP)
Dilated fundoscopy
General Statistical Methods and Types of Analyses
Sample Size The study sample size of 100 per group was selected based on prior Phase 2 and 3 clinical trial results using the DED Hybrid CAE study design with other development programs and the effect size seen in Phase 2a with I-5 on change from baseline after four weeks of treatment. This sample size was deemed sufficient to assess the effect size on the DED sign and symptom endpoints with I-5 vs vehicle, to confirm the endpoint selection and sample size needed for Phase 3 studies with I-5. A sample size of 100 per group provided 90% power at $\alpha=0.05$ to detect an effect size of 0.26 for inferior lissamine green staining (Ora Calibra® scale), assuming a common standard deviation of 0.56 and an effect size of 0.44 for ocular discomfort assessed with the Ora Calibra® Ocular Discomfort Scale assuming a common standard deviation of 0.97.

Efficacy Analysis

Evaluated baseline to weeks 2, 4, 8 and 12 change scores with I-5 on DED sign and symptom endpoints (both pre-CAE and CAE endpoints). Each endpoint was analyzed at a two-sided alpha level of 0.05, and the overall type I error was not controlled for in this investigative study.

Evaluated effect size of baseline to weeks 2, 4, 8 and 12 change scores of I-5 vs vehicle on DED sign and symptom endpoints (both pre-CAE and CAE endpoints) to confirm the endpoint selection for primary outcome parameters and sample size for Phase 3 studies with I-5.

Sub-group analyses on effect size of baseline to weeks 2, 4, 8 and 12 change scores of I-5 vs vehicle on DED sign and symptom endpoints (both pre-CAE and CAE endpoints) [Subgroups were prospectively detailed in the Statistical Analysis Plan (SAP)].

TABLE A

| | Summary of Subject Disposition | | | |
|---|---|---|---|---|
| | 1-5 (0.1%) N = 100 | 1-5 (0.25%) N = 100 | Vehicle N = 100 | All Subjects N = 300 |
| Intent-to-Treat Population | 100 (100.0%) | 100 (100.0%) | 100 (100.0%) | 300 (100.0%) |
| Per Protocol Population | 97 (97.0%) | 86 (86.0%) | 98 (98.0%) | 281 (93.7%) |
| Safety Population | 100 (100.0%) | 100 (100.0%) | 100 (100.0%) | 300 (100.0%) |
| Study Completion | | | | |
| Completed | 97 (97.0%) | 88 (88.0%) | 99 (99.0%) | 284 (94.7%) |
| Discontinued | 3 (3.0%) | 12 (12.0%) | 1 (1.0%) | 16 (5.3%) |
| Reason for Study Withdrawal | | | | |
| Adverse Events | 2 (2.0%) | 10 (10.0%) | 0 | 12 (4.0%) |
| Administrative Reasons | 1 (1.0%) | 0 | 0 | 1 (0.3%) |
| Withdrawal by Subject | 0 | 1 (1.0%) | 1 (1.0%) | 2 (0.7%) |
| Other | 0 | 1 (1.0%) | 0 | 1 (0.3%) |

The phase 2b data are shown in FIGS. 1 through 8 and Table above.

Key Observations from Phase 2b Clinical Trial

1. Early Onset of Effect from Phase 2b Evidenced Across Multiple Signs and Symptoms
Majority (>50-100%) of effect vs vehicle seen at the first study endpoint (Week 2 or 4) in 0.25% group:
Positive early onset for 3 out of 4 symptom endpoints:
ODS, OD4SQ, OSDI
Negative for SANDE
Positive early onset for 3 out of 4 sign endpoints:
Lissamine green total score, fluorescein total score, tear osmolarity
Negative for TFBUT® (met definition at week 4)
Schirmer's Test only assessed at week 12

2. Dose Response was Demonstrated Between 0.1% and 0.25% Dose Strengths
3. 0.1% 1-5 Matched Higher Dose Effects at Later Time Points
Clearest effect with signs, especially ocular staining
Compliance poorest in 0.25% group (8% non-compliant vs 3% in the 0.1% group and 1% in the vehicle group)
4. Vehicle effect increased with study duration
Clearest effect was observed with signs, especially ocular staining
Normal pattern in DED with plateau around two to three months
QID vehicle in Phase 2b was expected to have increased this effect

TABLE B

Phase 2b Clinical Trial Results Heat Map: Broad Phase 2a Activity Reproduced

| Reproxalap Phase 2b DED Results Heat Map Intent-to-Treat (ITT) Population with Observed Data Only Non-CAE and Pre-CAE Endpoint-Specific Worst Eye (where applicable) | p-value Key $p < 0.05 = A$ $p < 0.10 = B$ $p < 0.15 = C$ wrong signal = N/A | Drug Trend? | Dose Trend? | Reproxalap 0.1% Effect Size >0.5 | vs. Vehicle: p-value, ANCOVA V3 | | V4 | V5 | V6 | Reproxalap 0.25% Effect Size >0.5 | vs. Vehicle: p-value, ANCOVA V3 | | V4 | V5 | V6 |
|---|---|---|---|---|---|---|---|---|---|---|---|---|---|---|---|
| | | | | Symptom Measures | | | | | | | | | | | |
| Ocular Discomfort Scale | | ✓ | ✓ | ✓ | | | | | | ✓ | | | | | |
| OD & 4-Symptom Questionnaire: Overall Ocular Discomfort | (0-4) (0-5) | ✓ | ✓ | ✓ | | | | | C | ✓ | | | | | A |
| Burning | (0-5) | ✓ | | | N/A | | B | | | N/A | | | | | |
| Dryness | (0-5) | ✓ | ✓ | ✓ | | | | | | ✓ | C | | | | A |
| Grittiness | (0-5) | ✓ | ✓ | | | | | | | ✓ | | | | | C |
| Stinging | (0-5) | ✓ | ✓ | | | | | B | C | | C | | | | A |
| Ocular Surface Disease Index (OSDI) | (0-100) | ✓ | ✓ | | N/A | | | | | | | | | | |
| SANDE Questionnaire Severity | (0-100 mm) | ✓ | ✓ | | | | N/A | | | ✓ | | | | | B |
| Frequency | (0-100 mm) | ✓ | | ✓ | | | | | | ✓ | | | | | |
| | | | | Sign Measures | | | | | | | | | | | |
| Lissamine Green Staining: Total Score (all five regions) | (0-20; Σ 5×) | ✓ | ✓ | ✓ | | | | | | ✓ | | | | | |
| Corneal Sum Score (Inferior, Superior, and Central) | (0-12; Σ 3×) | ✓ | ✓ | ✓ | | | | | | ✓ | C | | | | |
| Conjunctival Sum Score (Nasal and Temporal) | (0-8; Σ 2×) | ✓ | ✓ | | | | | | | ✓ | | | | | C |
| Inferior | (0-4) | ✓ | ✓ | | | | | | | | | | | | |
| Superior | (0-4) | ✓ | ✓ | ✓ | | | N/A | | | | A | | N/A | N/A | |
| Central | (0-4) | ✓ | ✓ | | N/A | | N/A | | | ✓ | N/A | | | | |
| Temporal | (0-4) | ✓ | ✓ | | | | | | | ✓ | | | B | | |
| Nasal | (0-4) | ✓ | ✓ | ✓ | N/A | | N/A | B | | ✓ | | | | | C |
| Fluorescein Staining: Total Score (all five regions) | (0-20; Σ 5×) | ✓ | | ✓ | | | | | | ✓ | B | | | | |
| Corneal Sum Score (Inferior, Superior, and Central) | (0-12; Σ 3×) | ✓ | | ✓ | | | | | | ✓ | A | | | | N/A |
| Conjunctival Sum Score (Nasal and Temporal) | (0-8; Σ 2×) | ✓ | ✓ | | N/A | | | B | | | B | | | | |
| Inferior | (0-4) | ✓ | | | | | | | C | | | | | | |
| Superior | (0-4) | | ✓ | | | | N/A | | | ✓ | | | N/A | N/A | |
| Central | (0-4) | ✓ | ✓ | ✓ | N/A | | N/A | | | ✓ | | | | | N/A |
| Temporal | (0-4) | ✓ | ✓ | | N/A | N/A | | | | | B | | B | | |
| Nasal | (0-4) | ✓ | ✓ | | N/A | | | A | | | | C | A | | B |
| Tear Film Break-up Time | (sec) | | ✓ | ✓ | N/A | N/A | | | | ✓ | N/A | | | | N/A |
| Schirmer's Test | (mm) | ✓ | ✓ | ✓ | | | | | | ✓ | | | | | |
| Osmolarity | (mOsm/L) | ✓ | | ✓ | | | | | | | | | | | |

^wrong signal defined as an effect less than vehicle, or a worsening vs. baseline.

Example 4: 7-Day DSS-Induced Acute Ulcerative Colitis Model

A study was conducted to evaluate the effects of test compounds on female Swiss Webster mice in a model of dextran sulfate sodium (DSS)-induced acute ulcerative colitis (UC).

Introduction

Mice have been shown to develop acute colitis with signs of diarrhea, gross rectal bleeding, and body weight loss within six to ten days after ingesting 3% to 10% DSS (Okayasu, 1990). Gross and histopathologic changes resulting from this treatment resemble those occurring in human ulcerative colitis, a subset of inflammatory bowel disease (Okayasu, 1990; MacDermott, 1992; Cooper, 1993). Compounds that are effective in the treatment of human IBD have activity in this model and it is being used to investigate potential new therapies (Axelsson, 1998; Egger, 1999; Miceli, 1999).

through 11 were started on 3% DSS in drinking water. On Study Day 5, DSS water was replaced with normal drinking water for the remainder of the study. On Study Days 0 through 6, mice in Groups 3, 5, 6, and 7 were dosed PO, BID with PO vehicle (MC), Compound I-5 (200 mg/kg), I-22 (200 mg/kg), or I-6 (200 mg/kg), respectively, and mice in Groups 2 and 11 were dosed QD by the intraperitoneal (IP) route with IP vehicle [SBECD (Captisol®)] or I-6 (100 mg/kg), respectively. Positive control mice were dosed PO, QD on Days 0 through 6 with cyclosporine A (CsA, 75 mg/kg). Group 1 animals served as naive controls. On Study Day 7, the mice were euthanized for necropsy and tissue collection. Efficacy was evaluated based on animal body weight measurements, colon lengths and weights, colon weight-length ratio, colon content scores, disease activity index (DAI) scores (percent body weight loss, stool consistency, occult/gross blood, and summed scores), and histopathology of colons (full, proximal, and distal). All animals in the main study survived to the scheduled termination.

TABLE C

Group and Treatment Information

| Group | N | DSS | Treatment | Dose Level (mg/kg) | Dose Route | Regimen[1] | Dosing Days | Dose Vol. (mL/kg)[2] |
|---|---|---|---|---|---|---|---|---|
| 1 | 5 | N | Naive | N/A | N/A | N/A | N/A | N/A |
| 2 | 10 | 3% | Vehicle (SBECD) | N/A | IP | QD | D0 through D6 | 10 |
| 3 | 10 | 3% | Vehicle (MC) | N/A | PO | BED | D0 through D6 | 10 |
| 4 | 10 | 3% | CsA | 75 | PO | QD | D0 through D6 | 10 |
| 5 | 10 | 3% | Compound I-5 | 200 | PO | BID | D0 through D6 | 10 |
| 6 | 10 | 3% | Compound I-22 | 200 | PO | BID | D0 through D6 | 10 |
| 7 | 10 | 3% | Compound I-6 | 200 | PO | BID | D0 through D6 | 10 |
| 8 | 10 | 3% | Compound I-5 | 200 | PO | BID | D(-3) through D6 | 10 |
| 9 | 10 | 3% | Compound I-22 | 200 | PO | BID | D(-3) through D6 | 10 |
| 10 | 10 | 3% | Compound I-6 | 200 | PO | BID | D(-3) through D6 | 10 |
| 11 | 10 | 3% | Compound I-6 | 100 | IP | QD | D0 through D6 | 10 |

[1]BID dosing occurred at 10- to 12-hour intervals; QD dosing occurred at approximately 24-hour intervals.
[2]The doses of test articles were calculated daily in mg/kg based on the latest animal body weight.

Summary

Female Swiss Webster mice, aged six to eight weeks, were used in the study. The mice weighed approximately 20 to 27 grams (mean 23 g) at enrollment on Study Day −3.

Dextran sulfate sodium (DSS; Spectrum, Cat #DE136, Lot #2DC0020) was stored at room temperature until added to appropriate volume of sterile filtered water (VetOne, Lot #B1712033) to prepare a 3% DSS solution.

The test articles were: Compound I-5, Compound I-22, and Compound I-6.

Test articles for oral (PO) dosing were supplied for the main study were prepared in methylcellulose vehicle (MC: Sigma, Lot #SLBM2910V) at 10 mL/kg.

Compound I-6 for IP dosing at 10 mL/kg was prepared in sulfobutylether-β-cyclodextrin (SBECD) vehicle (Captisol®) by dissolving 20% w/v Captisol® into a solution of sterile saline with sodium phosphate, dibasic, anhydrous and sodium phosphate, monobasic, monohydrate. NaOH was added to adjust the pH to 7.3.

Cyclosporine A (CsA: Teva) was prepared in Kolliphor EL (Sigma)/1% carboxymethylcellulose for PO dosing at 10 mL/kg.

Doses and treatment groups are shown in Table C. On Study Days −3 through 6, mice in Groups 8, 9, and 10 were dosed BID by the oral (PO) route with Compound I-5 (200 mg/kg), Compound I-22 (200 mg/kg), or Compound I-6 (200 mg/kg), respectively. On Study Day 0, Groups 2

Disease Activity Index (DAI)

Disease activity was scored on Study Days 0, 2, 4, and 6 according to the following criteria:

| Score | Weight Loss (%) | Stool Consistency | Occult Blood or Gross Bleeding |
|---|---|---|---|
| 0 | <2% | Normal Stool (well formed) | Normal (no blood in stool) |
| 1 | 3-8% | Semi-Solid Stool | Positive blood result in stool |
| 2 | 9-15 | Loose to pasty stool (does not adhere to anus) | Gross blood observed in stool |
| 3 | >15 | Diarrhea (liquid stool that adheres to anus) | Rectal Bleeding |

The three scores were added at each point to obtain a summed score. The area under the curve (AUC) was calculated for each of the three parameters and the summed score for Days 0 through 6.

The three scores were added at each time point to obtain a summed score. The area under the curve (AUC) was calculated for each of the three parameters and the summed score for Days 0 through 6.

Necropsy Specimens

At necropsy on Study Day 7, animals from each group were bled to exsanguination and euthanized by cervical dislocation for tissue collection. Whole blood was collected via cardiac blood draw and processed for plasma (K$_2$EDTA, >150 μL/mouse), which was stored at −80° C. The entire colon from each animal was harvested, inspected visually, and measured for length, and weighed. The colon contents were assessed for clinical evidence of blood or blood-tinged fluid, and scored using the following criteria:
0=Normal, no blood observed
1=Semi-solid stool, may be slightly blood tinged
2=Semi-solid to fluid stool with definite evidence of blood
3=Bloody fluid or no content (animals with no observable distal content included in this category)

Morphologic Pathology Methods

Preserved proximal and distal tissues are submitted individually for histopathology. For each region, pieces were cut and embedded in paraffin. Sections were cut and stained with hematoxylin & eosin (H&E). Each piece was evaluated individually, and values were averaged separately for the various regions.

Edema—Submucosal edema was quantitated by measuring the distance from the muscularis mucosa to the internal border of the outer muscle layer in a non-tangential area thought to most represent the severity of this change.

Inflammation Score—The extent of macrophage, lymphocyte and polymorphonuclear leukocyte cell (PMN) infiltrate was assigned severity scores according to the following criteria:
0=Normal
0.5=Very Minimal, one or two small foci, mononuclear inflammatory cells (MNIC), affects less than 1% of the mucosa
1=Minimal, larger focal area with MNIC and neutrophils affecting 1 to 10% of the mucosa or minimal diffuse, may be mostly in areas of submucosal edema or mesentery
2=Mild, diffuse mild, or multifocal affecting 11 to 25% of mucosa with minor focal or multifocal gland separation, no separation in most areas
3=Moderate, 26 to 50% of mucosa affected with minimal to mild focal or multifocal separation of glands by inflammatory cell infiltrate, milder in remaining areas of mucosa with some areas having no gland separation by inflammation
4=Marked, 51 to 75% of mucosa affected with mild to moderate separation of glands by inflammatory cell infiltrate, minimal to mild in remaining areas of mucosa but all glands have some separation by infiltrate
5=Severe, 76 to 100% of mucosa affected with moderate to marked areas of gland separation by inflammatory cell infiltrate, mild to moderate in remaining areas of mucosa Gland Loss Score—Crypt epithelial and remaining gland epithelial loss was scored based on the approximate percent of the mucosa that was affected, as follows:
0=None
0.5=Very Minimal, one or two small focal areas of gland loss affecting less than 1% of the mucosa
1=Minimal, 1 to 10% of the mucosa affected
2=Mild, 11 to 25% of the mucosa affected
3=Moderate, 26 to 50% of the mucosa affected
4=Marked, 51 to 75% of the mucosa affected
5=Severe, 76 to 100% of the mucosa affected Erosion Score—The loss of surface epithelium was scored based on the approximate percent of the mucosa that was affected as follows. This may have been associated with mucosal hemorrhage (reflective of the bleeding seen clinically and at necropsy):
0=None
0.5=Very Minimal, one or two small focal areas of mucosal erosion affecting less than 1% of the mucosa
1=Minimal, 1 to 10% of the mucosa affected
2=Mild, 11 to 25% of the mucosa affected
3=Moderate, 26 to 50% of the mucosa affected
4=Marked, 51 to 75% of the mucosa affected
5=Severe, 76 to 100% of the mucosa affected Mucosal Thickness and Hyperplasia Score—Mucosal thickness was measured in a non-tangential area of the section that best represents the overall mucosal thickness. This parameter was indicative of gland elongation and mucosal hyperplasia. A hyperplasia score was derived from the measurement as follows:
0=Normal, ≤200 μm
0.5=Very Minimal, 201 to 250 μm
1=Minimal, 251 to 350 μm
2=Mild, 351 to 450 μm
3=Moderate, 451 to 550 μm
4=Marked, 551 to 650 μm
5=Severe, >650 μm Histopathology Sum—A sum of inflammation, gland loss, erosion, and hyperplasia scores was calculated.

PMN Percent and Neutrophil Score—Inflammatory cell infiltrates in the colonic mucosa were evaluated for approximate percent of neutrophils in the total infiltrate, rounded to 0, 10, 25, 50, or 75 percent. This value was then multiplied by the inflammation score to determine the neutrophil score.

Lymphoid Aggregate Count and Diameter—The number of definite mucosal lymphoid aggregates (GALT, Peyer's patches) were recorded. Measurements were made by optical micrometer, and comments about the general size range are included.

Statistical Analysis

Clinical data were entered into Microsoft Excel, and arithmetic means and standard errors were calculated. Groups were compared to vehicle controls using a one-way analysis of variance (ANOVA) with a Dunnett's post-hoc analysis or a Student's two-tailed t-test for measured data (parametric) or a Kruskal-Wallis test with a Dunn's post hoc analysis or Mann-Whitney U test for scored data (non-parametric). Naïve animals were compared to vehicle controls using a Student's two-tailed t-test for model validation. Statistical analysis was performed using Prism 7.0d software (GraphPad). Unless indicated statistical analyses were performed on raw (untransformed) data only. Statistical tests make certain assumptions regarding normality and homogeneity of variance, and further analysis may be required if testing resulted in violations of these assumptions. P values were rounded to three decimal places. Significance for all tests was set at $p<0.050$.

Percent inhibition was calculated using the following formula:

$$\% \text{ Change} = B/A \times 100$$

$$A = \text{Mean Normal} - \text{Mean Disease Control}$$

$$B = \text{Mean Treated} - \text{Mean Disease Control}$$

Results

Figure 11:
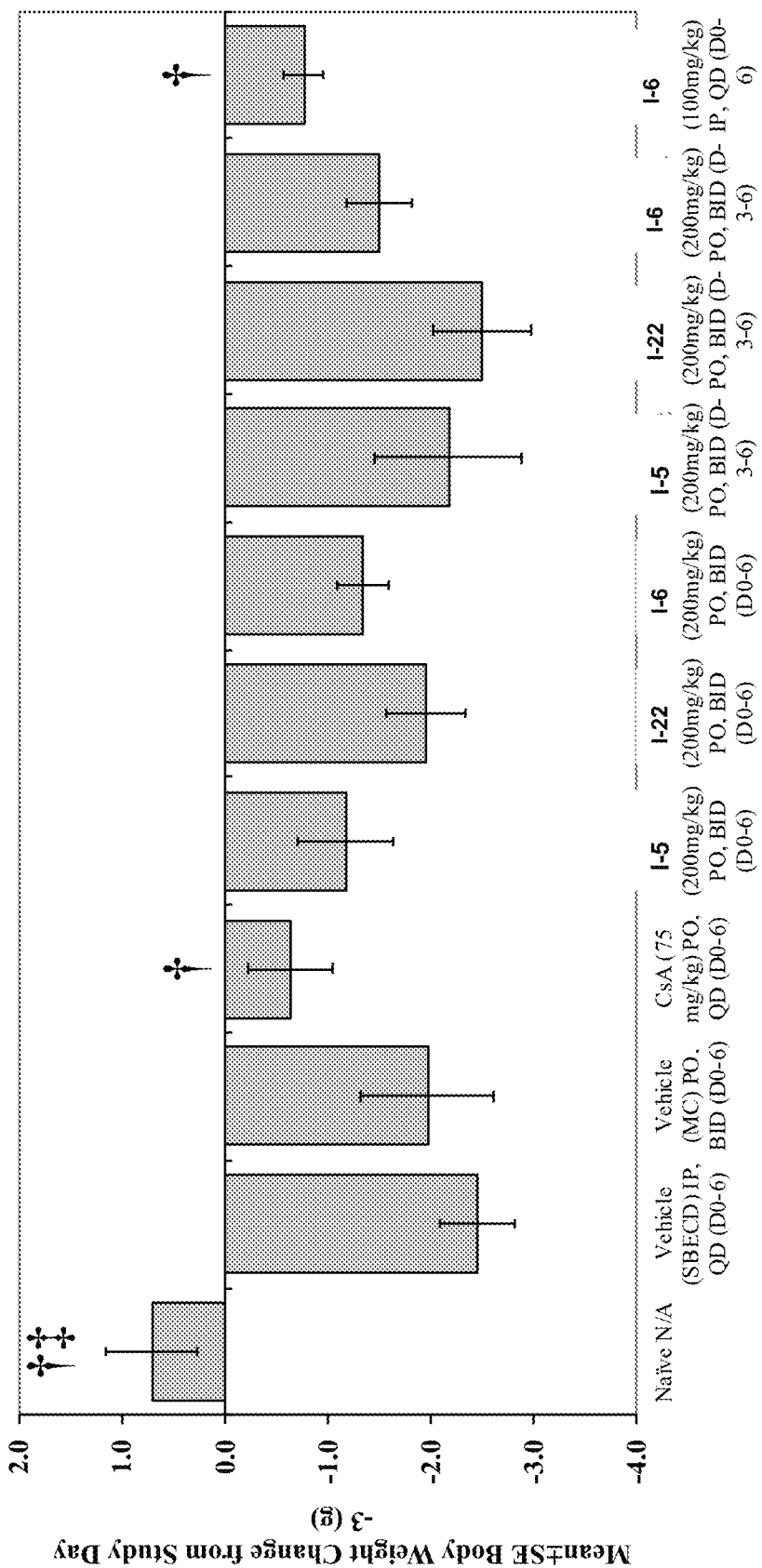
FIG. 11 shows body weight change from Study Day −3 (g) in female Swiss Webster mice in a model of dextran sulfate sodium (DSS)-induced acute ulcerative colitis (UC). n=five naive Controls; n=10/treatment group; †$p<0.05$ Student's t-test vs. Vehicle (IP); ‡$p<0.05$ Student's t-test vs. Vehicle PO; *$p<0.05$ ANOVA (Dunnett's post-hoc) vs. Vehicle (PO).
Figure 12:
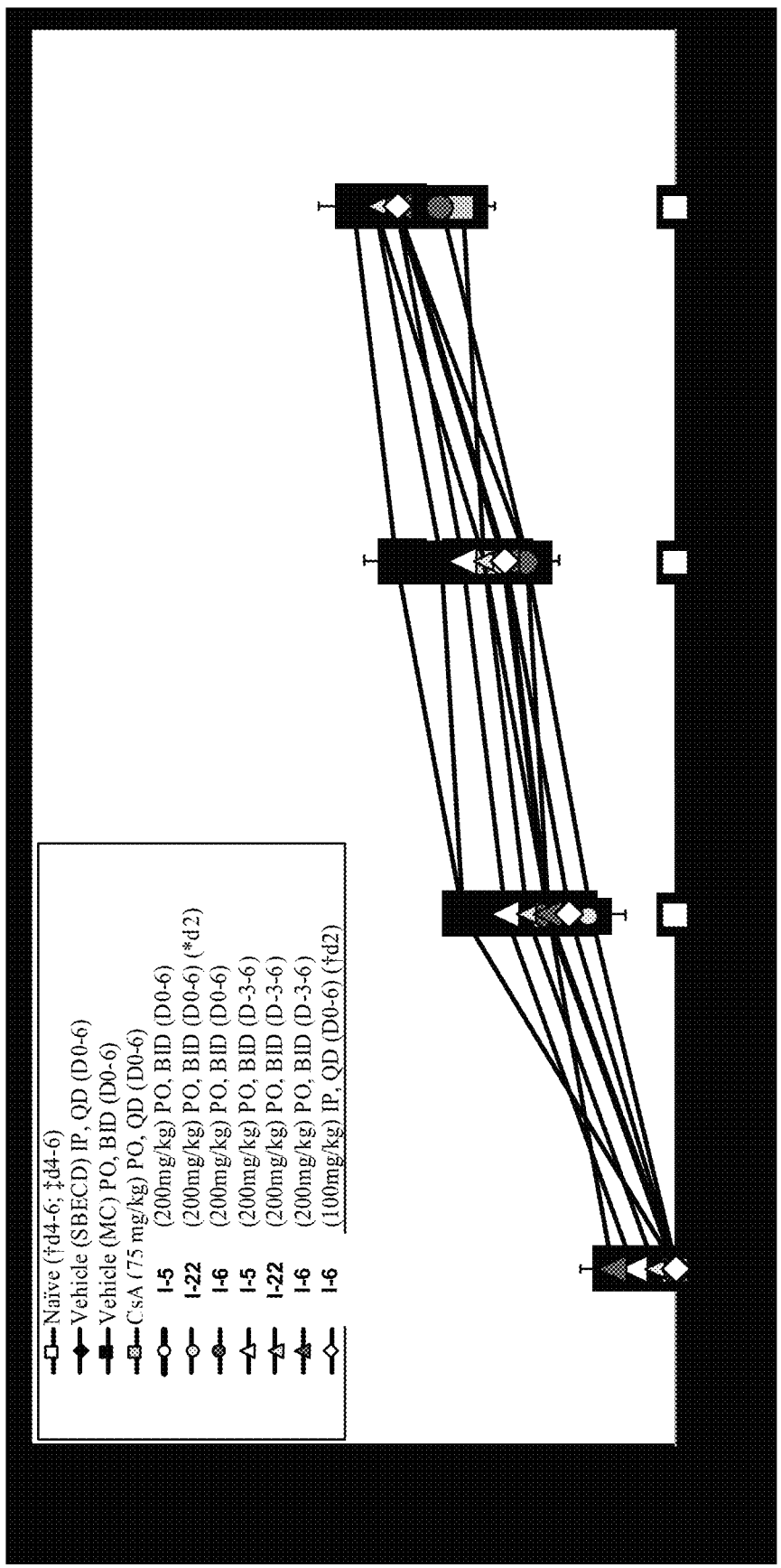
FIG. 12 shows Disease Activity Index Stool Consistency Score data in female Swiss Webster mice in a model of DSS-induced acute UC. *$p<0.05$ Kruskal-Wallis test (Dunn's post hoc) vs. Vehicle (PO); †$p<0.05$ Student's t-test/Mann-Whitney test vs. Vehicle (IP)
Figure 13:
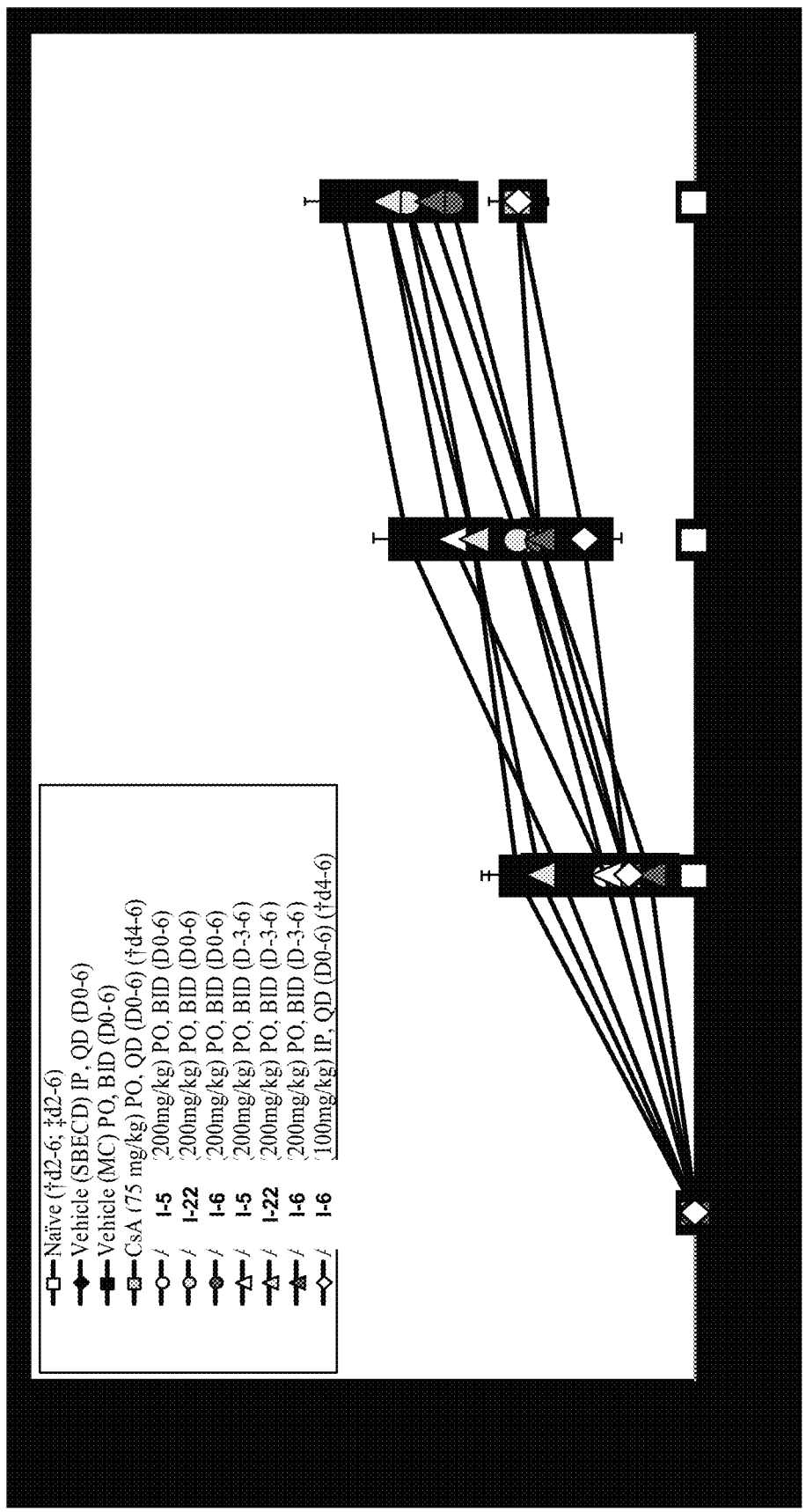
FIG. 13 shows Disease Activity Index Occult/Gross Blood Score data in female Swiss Webster mice in a model of DSS-induced acute UC. †$p<0.05$ Student's t-test/Mann-Whitney test vs. Vehicle (IP)
Figure 14:
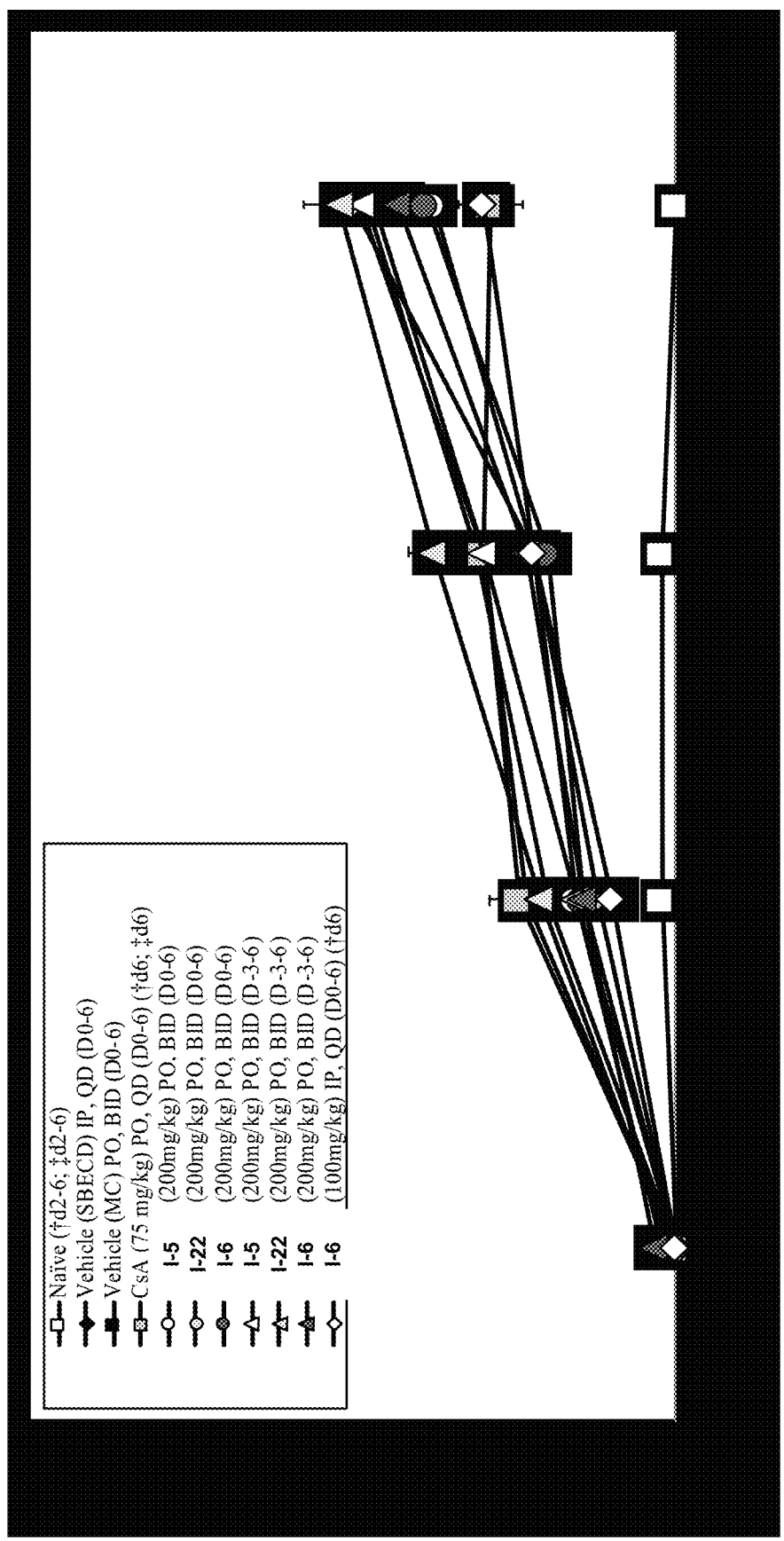
FIG. 14 shows Disease Activity Index Summed Score data in female Swiss Webster mice in a model of DSS-induced acute UC. †$p<0.05$ Student's t-test/Mann-Whitney test vs. Vehicle (IP); ‡$p<0.05$ Student's t-test vs. Vehicle (PO)
Figure 15:
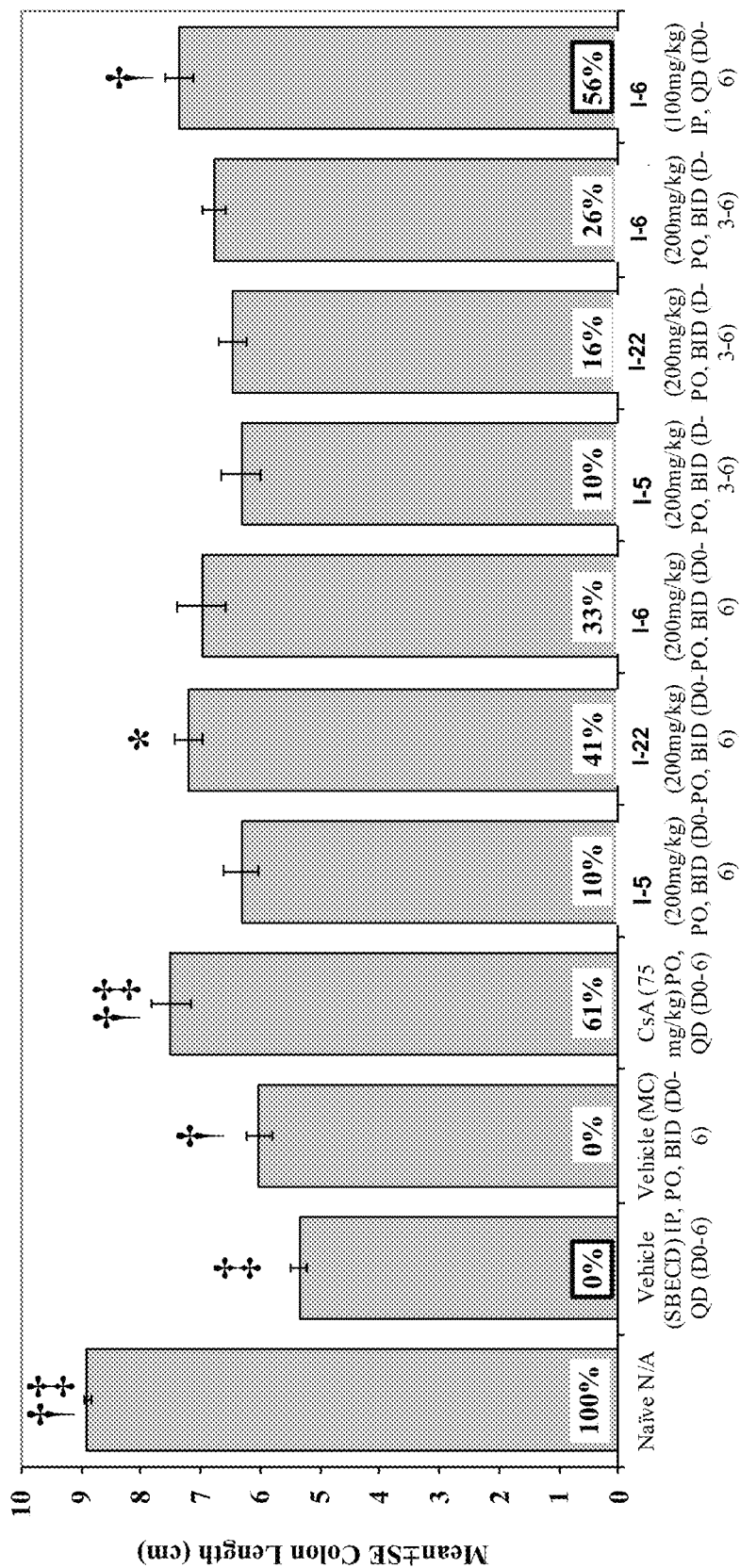
FIG. 15 shows Colon Length in cm for mice treated with I-5, I-22, or I-6 in a model of DSS-induced acute UC. n=5/Naive Controls, n=10/treatment group; †$p<0.05$ Student's t-test vs. Vehicle (SBECD) IP; ‡$p<0.05$ Student's t-test vs. Vehicle (MC) PO; *$p<0.05$ ANOVA (Dunnett's post-hoc) vs. Vehicle (MC) PO.
Figure 16:
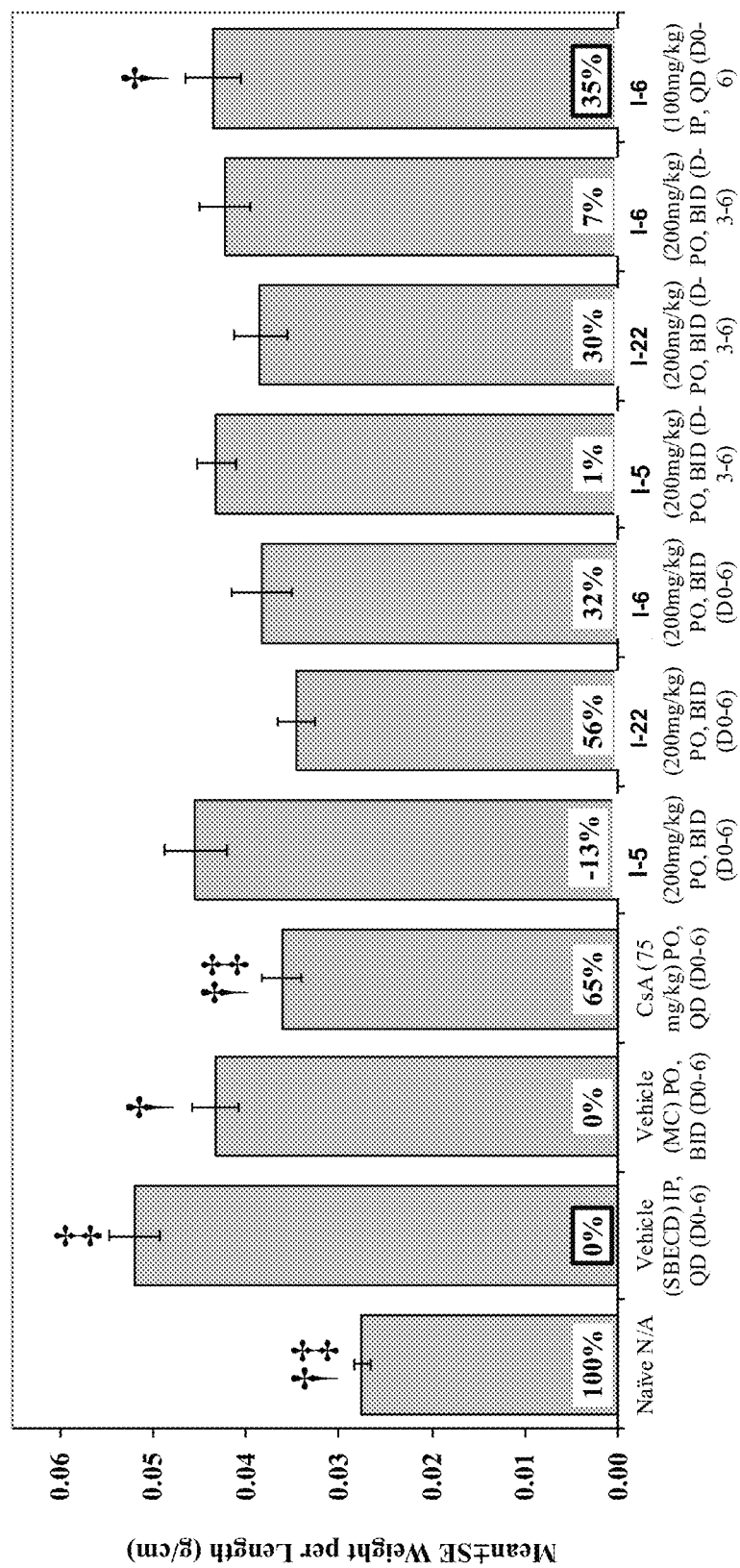
FIG. 16 shows Colon Weight per length (g/cm) for mice treated with I-5, I-22, or I-6 in a model of DSS-induced acute UC. †$p<0.05$ Student's t-test vs. Vehicle (IP); ‡$p<0.05$ Student's t-test vs. Vehicle PO.
Figure 17:
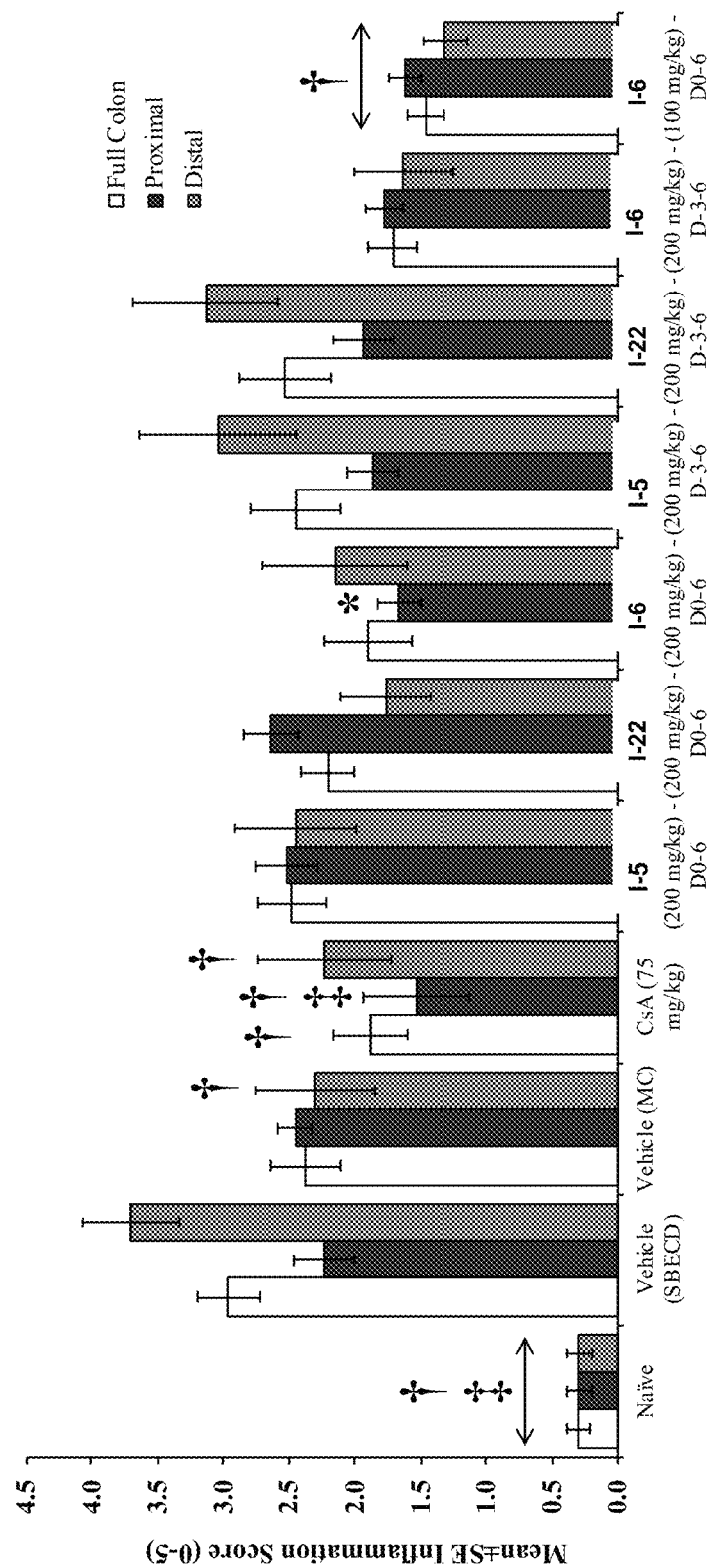
FIG. 17 shows Mean Inflammation Score (0-5) for mice treated with I-5, I-22, or I-6 in a model of DSS-induced acute UC. †$p<0.05$ Student's t-test vs. Vehicle (IP); ‡$p<0.05$ Student's t-test vs. Vehicle PO.
Figure 18:
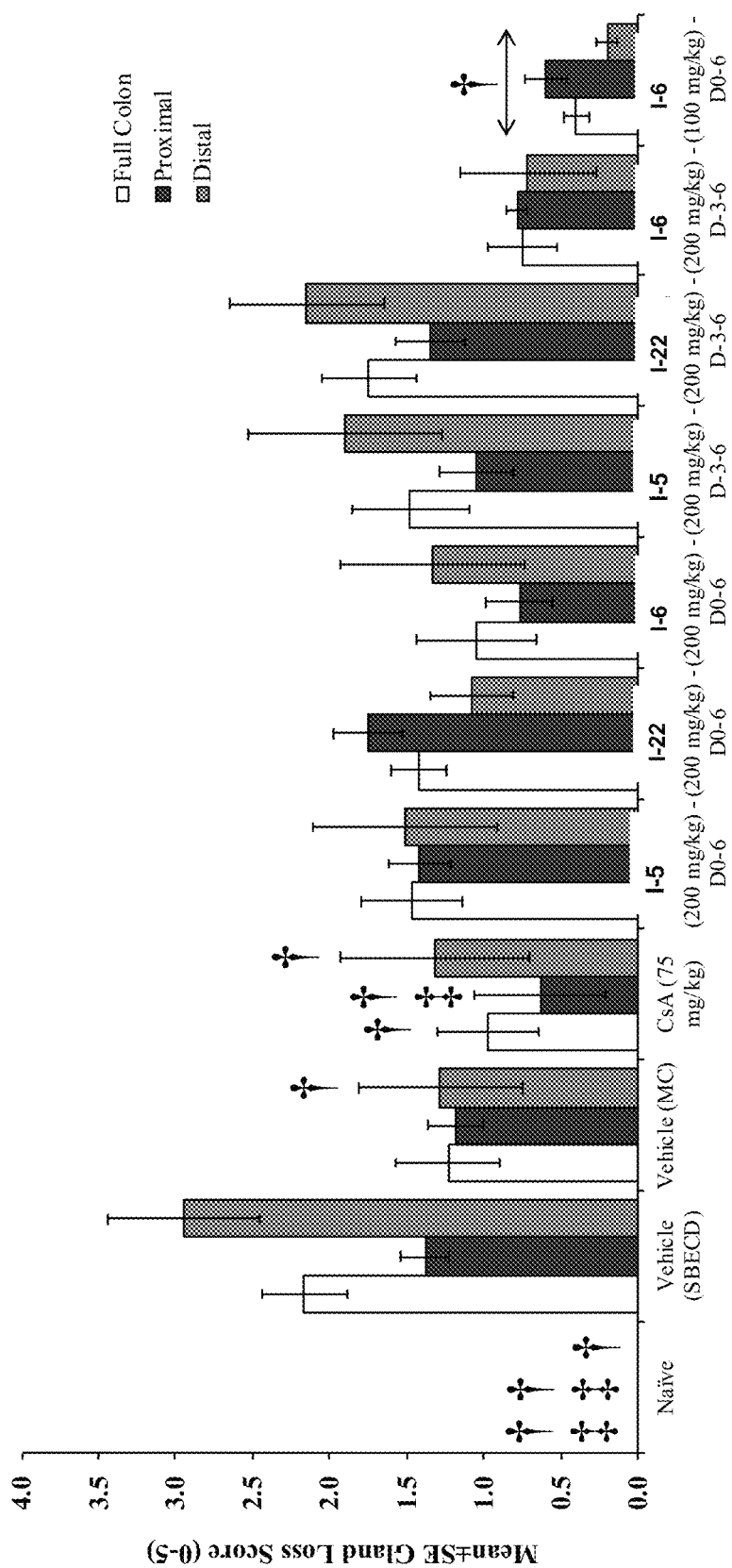
FIG. 18 shows Mean Gland Loss Score (0-5) for mice treated with I-5, I-22, or I-6 in a model of DSS-induced acute UC. †$p<0.05$ Student's t-test vs. Vehicle (IP); ‡$p<0.05$ Student's t-test vs. Vehicle PO.
Figure 19:
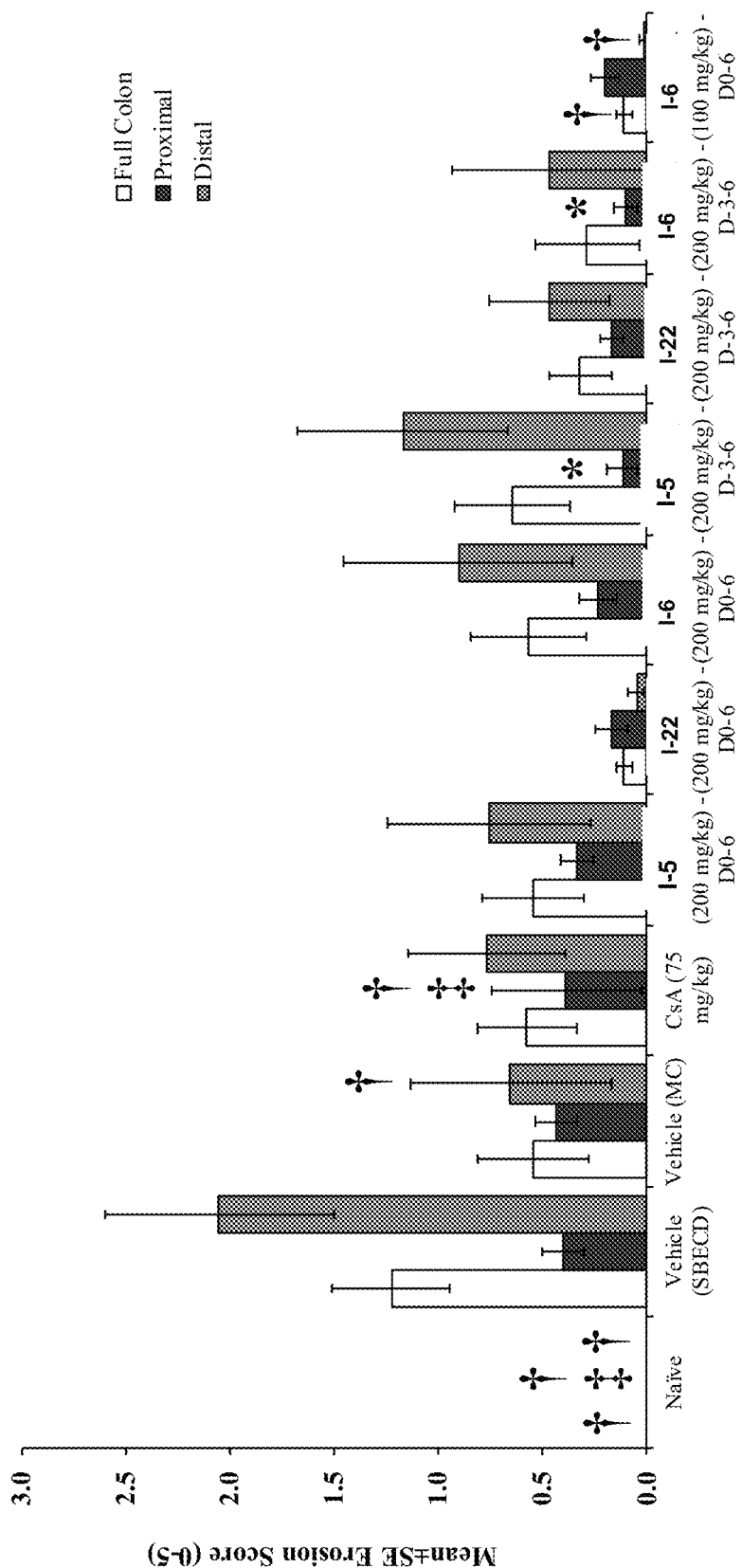
FIG. 19 shows Erosion Score (0-5) for mice treated with I-5, I-22, or I-6 in a model of DSS-induced acute UC. †$p<0.05$ Student's t-test vs. Vehicle (IP); ‡$p<0.05$ Student's t-test vs. Vehicle PO; *$p<0.05$ ANOVA (Dunnett's post-hoc) vs. Vehicle (PO).
Figure 20:
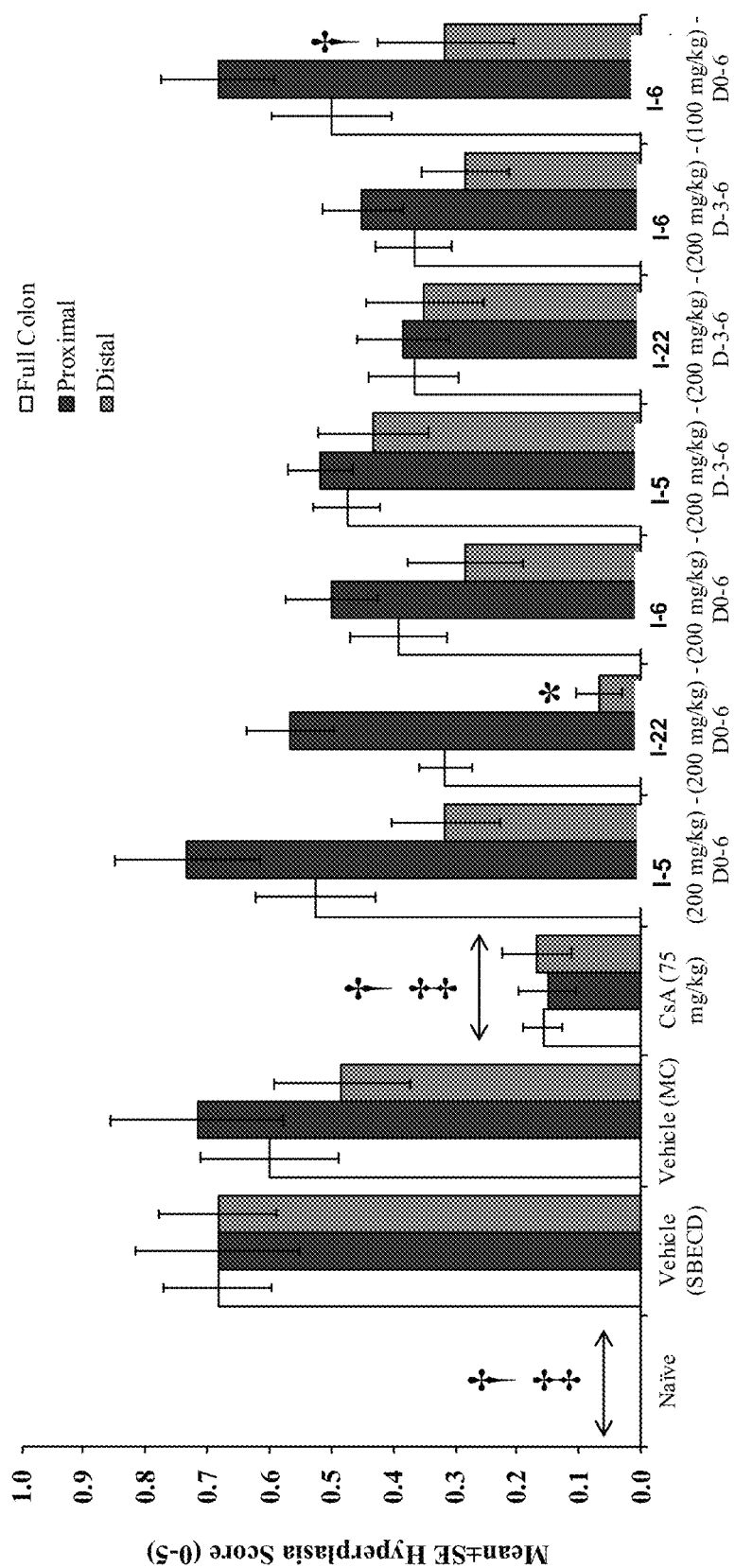
FIG. 20 shows Mean Hyperplasia Score (0-5) for mice treated with I-5, I-22, or I-6 in a model of DSS-induced acute UC. †$p<0.05$ Student's t-test vs. Vehicle (IP); ‡$p<0.05$ Student's t-test vs. Vehicle PO; *$p<0.05$ ANOVA (Dunnett's post-hoc) vs. Vehicle (PO).
Figure 21:
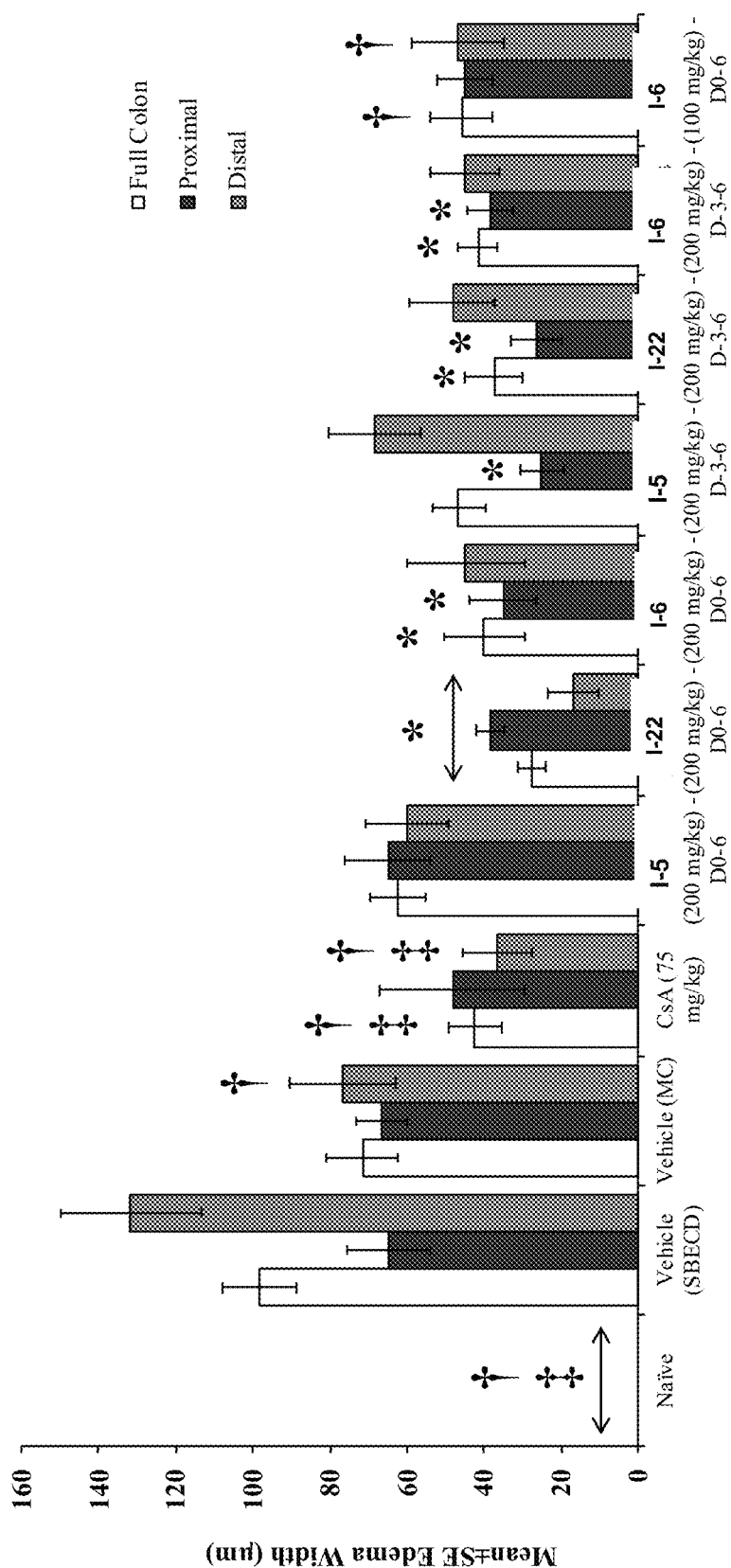
FIG. 21 shows Edema Width (μm) for mice treated with I-5, I-22, or I-6 in a model of DSS-induced acute UC. †p<0.05 Student's t-test vs. Vehicle (IP); ‡p<0.05 Student's t-test vs. Vehicle PO; *p<0.05 ANOVA (Dunnett's post-hoc) vs. Vehicle (P0).
Figure 22:
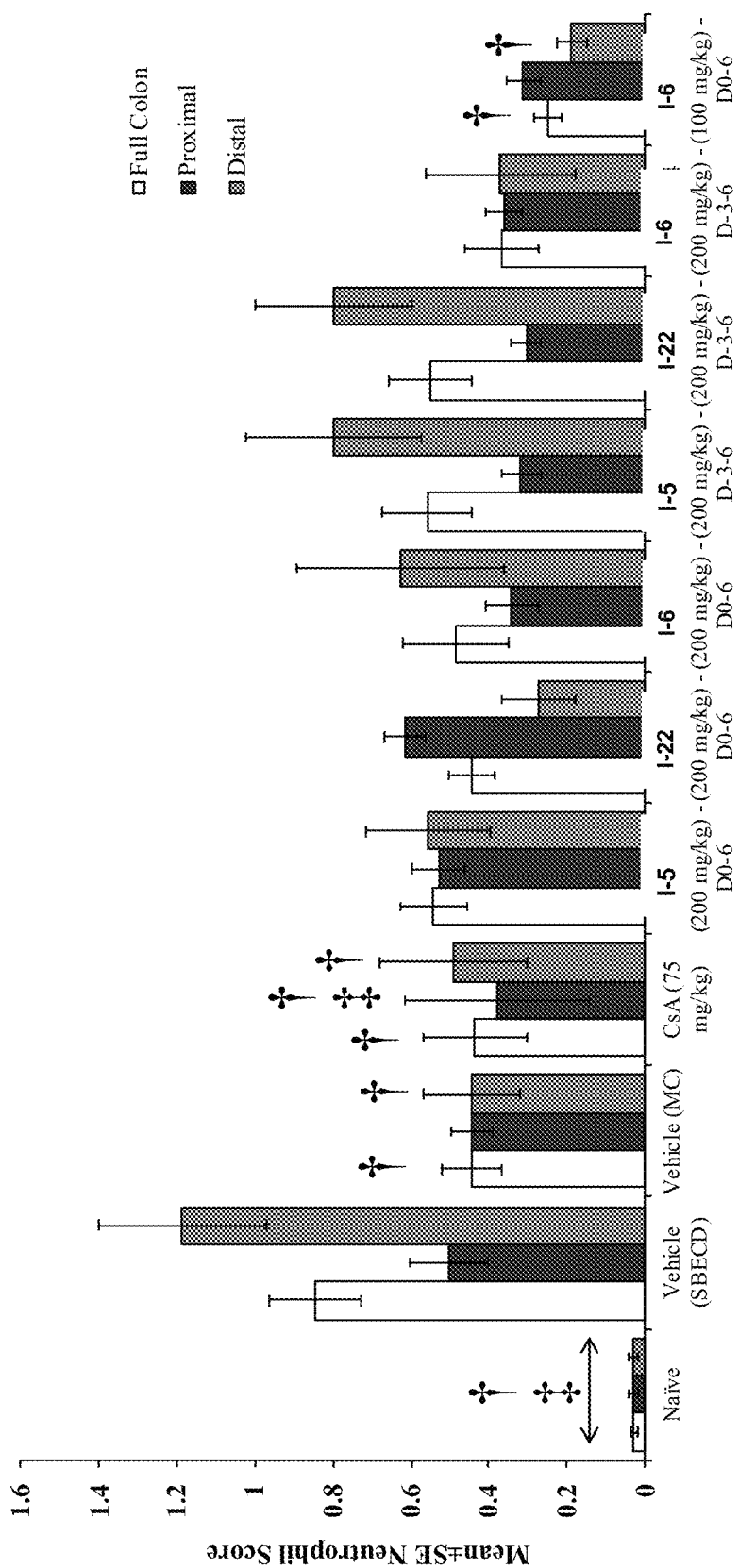
FIG. 22 shows Neutrophil score for mice treated with I-5, I-22, or I-6 in a model of DSS-induced acute UC. †p<0.05 Student's t-test vs. Vehicle (IP); ‡p<0.05 Student's t-test vs. Vehicle PO.
Figure 23:
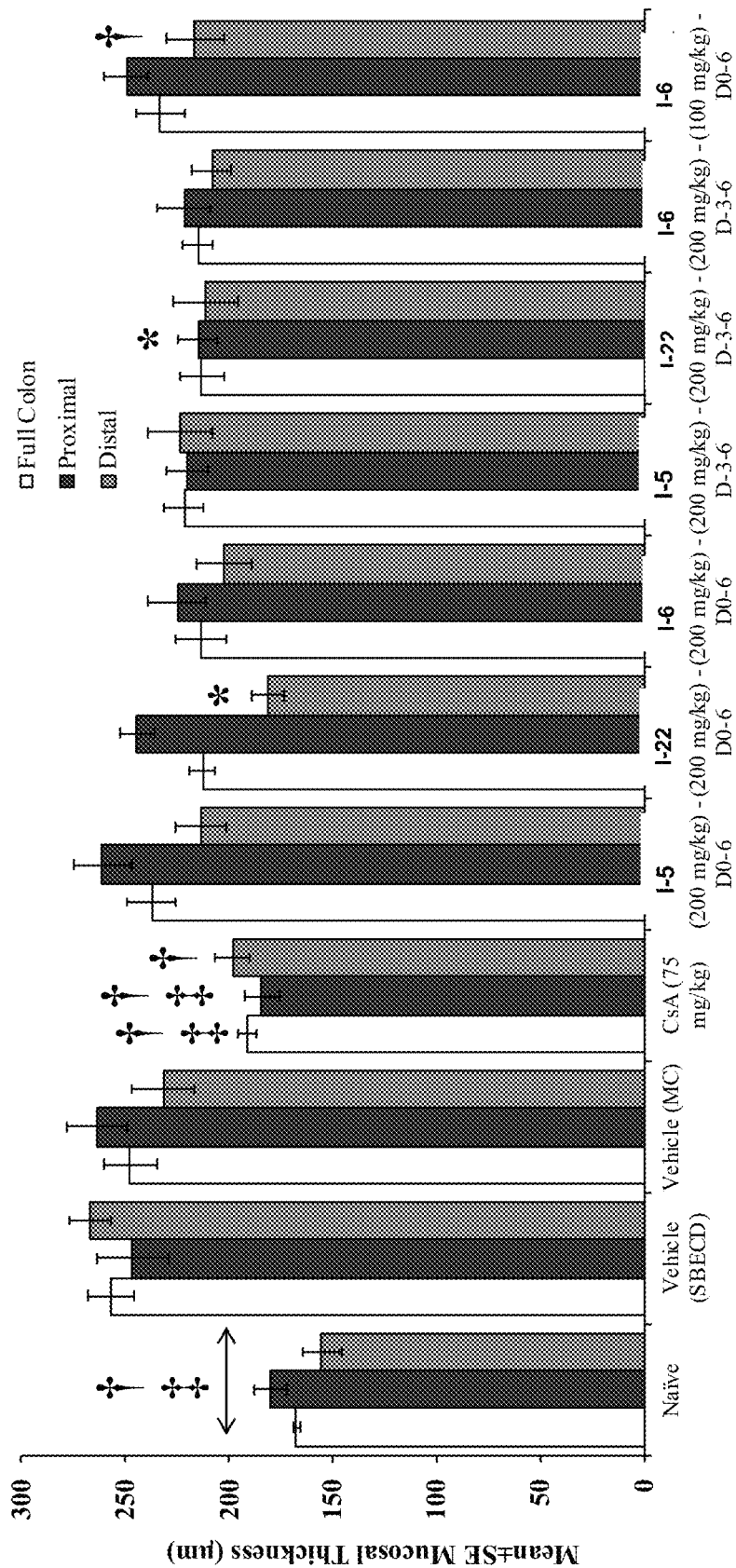
FIG. 23 shows Mucosal Thickness (μm) for mice treated with I-5, I-22, or I-6 in a model of DSS-induced acute UC. †p<0.05 Student's t-test vs. Vehicle (IP); ‡p<0.05 Student's t-test vs. Vehicle PO; *p<0.05 ANOVA (Dunnett's post-hoc) vs. Vehicle (PO).
Figure 24:
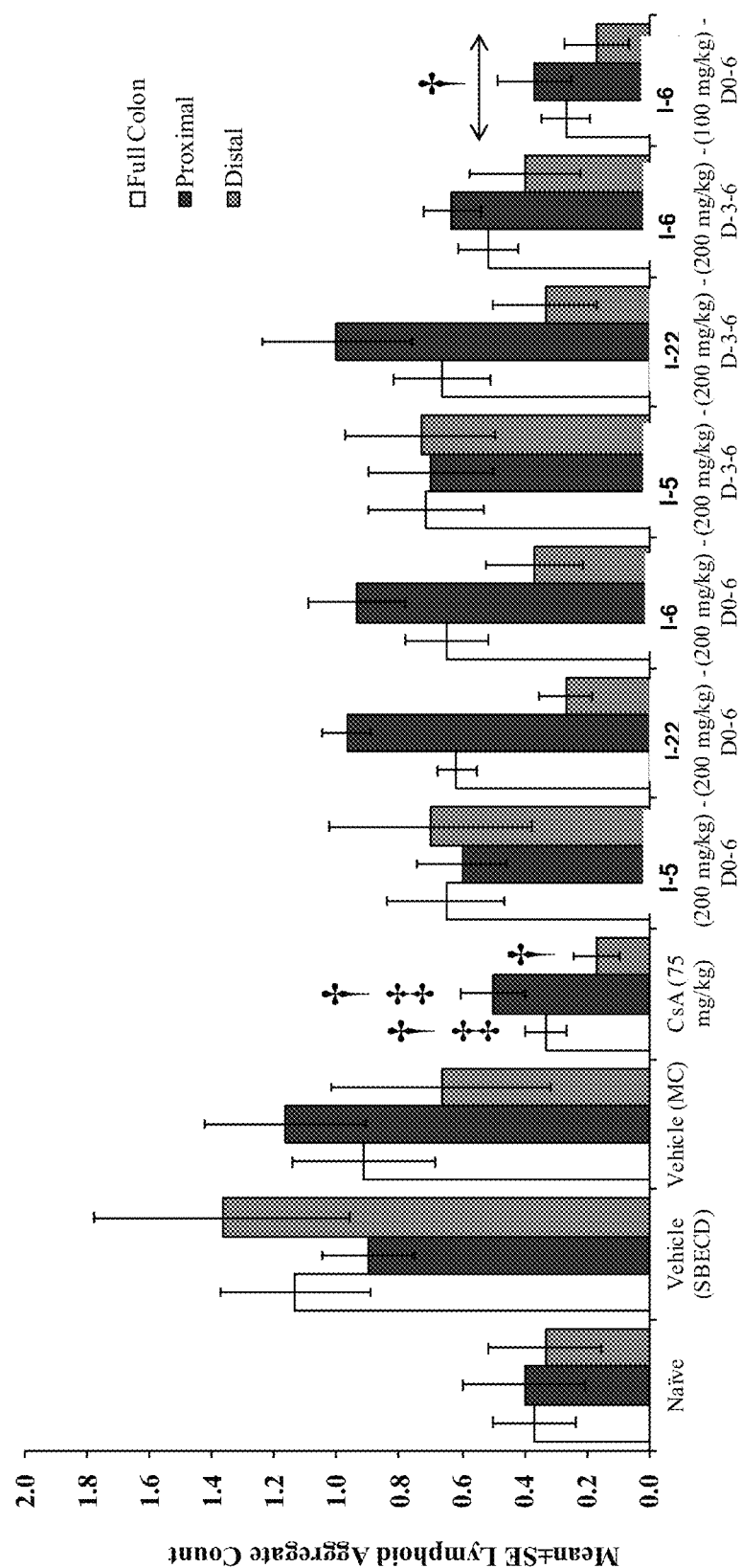
FIG. 24 shows Lymphoid Aggregate Count for mice treated with I-5, I-22, or I-6 in a model of DSS-induced acute UC. †p<0.05 Student's t-test vs. Vehicle (IP); ‡p<0.05 Student's t-test vs. Vehicle PO.

Oral vehicle control mice (Group 3) had disease-induced body weight loss, with a maximum decrease of 9.1% on Day 7 (mean decrease of 1.97 g). IP vehicle control mice (Group 2) had disease-induced body weight loss, with a maximum decrease of 11.8% on Day 7 (mean decrease of 2.46 g). Body weight loss was significantly inhibited in mice treated IP with 100 mg/kg Compound I-6 (Group 11; Days 0 through 6) compared to IP vehicle (SBECD) control mice (Group 2). Body weights of mice treated PO with Compound 1-5, Compound 1-22, or Compound 1-6 (Groups 5, 6, 7, 8, 9, and 10) did not differ significantly from PO vehicle control animals. Body weight loss in mice treated PO with CsA (Group 4) was significantly less than in IP vehicle (SBECD) control mice (FIG. 11).

Disease activity index (DAI) scores of body weight loss, stool consistency, occult/gross blood in stool, and summed scores peaked on Day 6 in PO and IP vehicle control mice. DAI scores between Vehicle (IP) control mice (Group 2) and Vehicle (PO) control mice (Group 3) did not differ significantly. Mice treated IP with 100 mg/kg Compound I-6 (Group 11; Days 0 through 6) had significantly reduced stool consistency scores on Day 2, significantly reduced occult/gross blood in stool scores on Days 4 and 6, and significantly reduced summed scores on Day 6, compared to IP vehicle control mice (Group 2). DAI scores of stool consistency, occult/gross blood in stool and summed scores expressed as area under the curve (AUC) were significantly lower following IP treatment with Compound I-6 (Group 11), compared to IP vehicle control mice (Group 2). Mice treated PO with 200 mg/kg Compound I-22 (Group 6; Days 0 through 6) had significantly reduced stool consistency scores on Day 2, compared to PO vehicle control mice (Group 3). Body weight loss in CsA-treated mice (Group 4) was significantly less than in IP vehicle control mice (Group 2) on Days 2 and 4 and in PO vehicle control mice (Group 3) on Day 2. Occult/gross blood in stool scores were significantly lower on Days 4 and 6 in CsA-treated mice (Group 4) compared to IP vehicle control animals (Group 2), and summed scores in CsA-treated mice were significantly lower on Day 6 than in either the PO or IP vehicle controls. DAI scores AUC for stool consistency and occult/gross blood in stool were significantly lower following treatment with CsA (Group 4) compared to PO and IP vehicle controls (Groups 3 and 2, respectively), and DAI scores AUC for body weight loss in CsA-treated mice were significantly increased as compared to IP vehicle controls.

PO vehicle control mice (Group 3) had colon lengths that ranged from 5.25 cm to 7.25 cm (mean=6.03 cm). IP vehicle control mice (Group 2) had colon lengths that ranged from 4.75 cm to 6.25 cm (mean=5.35 cm). Mean colon lengths were significantly increased in PO vehicle control mice (Group 3) compared to IP vehicle control mice (Group 2). Colon lengths were significantly (41%) increased, in the direction of normal, in mice treated PO with 200 mg/kg Compound I-22 (Group 6; Days 0 through 6) compared to PO vehicle control mice (Group 3). Colon lengths were significantly (56%) increased, in the direction of normal, in mice treated IP with 100 mg/kg Compound I-6 (Group 11; Days 0 through 6) compared to IP vehicle control mice (Group 2). Mice treated with CsA had significantly increased colon lengths compared to IP vehicle control mice (61%) and PO vehicle control mice (51%).

PO vehicle control mice (Group 3) had colon weights that ranged from 0.215 g to 0.303 g (mean=0.257 g). IP vehicle control mice (Group 2) had colon weights that ranged from 0.201 g to 0.325 g (mean=0.276 g). Mean colon weights in treated animals did not differ significantly from their respective vehicle controls.

PO vehicle control mice (Group 3) had colon weight-to-length ratios that ranged from 0.030 g/cm to 0.051 g/cm (mean=0.043 g/cm). IP vehicle control mice (Group 2) had colon weight-to-length ratios that ranged from 0.035 g/cm to 0.062 g/cm (mean=0.052 g/cm). Mean colon weight-to-length ratios were significantly increased in IP vehicle control mice (Group 2) as compared to PO vehicle control mice (Group 3). Colon weight-to-length ratios were significantly (35%) reduced, in the direction of normal, in mice treated IP with 100 mg/kg Compound I-6 (Group 11); Days 0 through 6) compared to IP vehicle control mice (Group 2). Mice treated with CsA (Group 4) had significantly reduced colon weight-to-length ratios compared to IP vehicle control mice (65%) and PO vehicle control mice (45%).

At necropsy, all PO and IP vehicle control mice (Groups 2 and 3) had semi-solid to fluid, blood-tinged, or bloody stool. Colon content scores were significantly (37%) reduced, in the direction of normal, in mice treated with CsA (Group 4) as compared to IP vehicle control mice, but not PO vehicle mice (Group 3).

Morphologic Pathology

All PO vehicle control mice (Group 3) had very minimal-to-severe colon inflammation with none-to-severe gland loss and erosion, and none-to-mild hyperplasia. Disease severity was similar in the distal colon (mean summed score=4.7) and the proximal colon (mean score=4.8). Colon mucosa had approximately 17% polymorphonuclear leukocyte cell (PMN) infiltrates, contributing to a mean neutrophil score of 0.4 in the full colon. Mean colon edema was 71.7 µm. Mean mucosal thickness was 247.5 µm. Lymphoid aggregates were seen in nine of ten PO vehicle mice and had a maximum size range of 50 to 250 µm. All full colon parameters except erosion and lymphoid aggregate counts were significantly increased in PO vehicle controls compared to naïve mice (FIGS. 17 through 24).

All IP vehicle control mice (Group 2) had very minimal-to-severe colon inflammation (one of ten animals had no inflammation in one proximal colon section) with none-to-severe gland loss and erosion, and none-to-mild hyperplasia. Disease severity was increased in the distal colon (mean summed score=9.4) as compared to the proximal colon (mean score=4.7). Colon mucosa had approximately 24% PMN infiltrates, contributing to a mean neutrophil score of 0.8 in the full colon. Mean colon edema was 98.3 µm. Mean mucosal thickness was 256.7 µm. Lymphoid aggregates were seen in all IP vehicle mice and had a maximum size range of 50 to 250 µm. All full colon parameters, except lymphoid aggregate counts, were significantly increased in IP vehicle controls as compared to naïve mice. IP vehicle control mice had significantly increased distal colon edema, inflammation, gland loss, erosion, summed scores, PMN percentages, and neutrophil scores, and significantly increased full colon PMN percentages and neutrophil scores compared to PO vehicle control mice (FIGS. 17 through 24).

Mice treated PO with 200 mg/kg Compound I-22 (Group 6; Days 0 through 6) had significantly reduced full colon edema (62% reduction), proximal colon edema (43%), distal colon edema (78%), distal colon hyperplasia (86%), and distal colon mucosal thickness (66%) compared to PO vehicle control mice (Group 3). PMN percentages in the proximal colon were significantly increased in mice treated PO with 200 mg/kg Compound I-22 (Days 0 through 6) as compared to PO vehicle control mice (FIGS. 17 through 24).

Mice treated PO with 200 mg/kg Compound I-6 (Group 7; Days 0 through 6) had significantly reduced full colon edema (44% reduction), proximal colon edema (48%), and proximal colon inflammation (36%) compared to PO vehicle control mice (FIGS. 17 through 24).

Mice treated PO with 200 mg/kg Compound I-5 (Group 8; Days −3 through 6) had significantly reduced proximal colon edema (63% reduction) and proximal colon erosion (73%) compared to PO vehicle control mice (FIGS. 17 through 24).

Mice treated PO with 200 mg/kg Compound I-22 (Group 9; Days −3 through 6) had significantly reduced full colon edema (48% reduction), proximal colon edema (60%), and proximal colon mucosal thickness (58%) compared to PO vehicle control mice (FIGS. 17 through 24).

Mice treated PO with 200 mg/kg Compound I-6 (Group 10; Days −3 through 6) had significantly reduced full colon edema (58% reduction), proximal colon edema (41%), and proximal colon erosion (75%) compared to PO vehicle control mice (FIGS. 17 through 24).

Mice treated IP with 100 mg/kg Compound I-6 (Group 11; Days 0 through 6) had significantly reduced edema (53%), inflammation (56%), gland loss (82%), erosion (91%), summed scores (68%) PMN percentages (53%), neutrophil scores (73%), and lymphoid aggregate counts (113%) in the full colon compared to IP vehicle control mice. In the proximal colon, inflammation (32%), gland loss (57%), summed scores (36%), and lymphoid aggregate counts (107%) were significantly reduced by IP treatment with 100 mg/kg Compound I-6 (Days 0 through 6). In the distal colon, all histopathology parameters were significantly reduced (45 to 116%) by IP treatment with 100 mg/kg Compound I-6 (Days 0 through 6) compared to IP vehicle control mice (FIGS. 17 through 24).

Mice treated with CsA (Group 4) had significantly reduced edema (57%), inflammation (41%), gland loss (55%), hyperplasia (77%), summed scores (51%) PMN percentages (48%), neutrophil scores (50%), mucosal thickness (73%), and lymphoid aggregate counts (104%) in the full colon compared to IP vehicle control mice. Full colon edema (41%), hyperplasia (74%), mucosal thickness (70%), and lymphoid aggregate counts (106%) were significantly reduced by CsA treatment compared to PO vehicle controls. In the proximal colon, all histopathology parameters except edema and PMN percentages were significantly (4 to 95%) reduced by CsA treatment compared to PO and IP control mice. In the distal colon, CsA treatment resulted in significantly reduced edema (72%), inflammation (43%), gland loss (55%), hyperplasia (76%), summed scores (54%) PMN percentages (58%), neutrophil scores (60%), mucosal thickness (61%), and lymphoid aggregate counts (116%) compared to IP vehicle controls and significantly reduced edema (52%) and hyperplasia (66%) compared to PO vehicle controls (FIGS. 17 through 24).

Discussion and Conclusion

Results of treatment with CsA were as expected, in that treatment resulted in significant improvement to DAI scores, colon lengths, colon weight-length ratios, colon content scores, and colon histopathology.

Daily, intraperitoneal treatment with 100 mg/kg Compound I-6 dosed on Days 0 through 6 showed significant beneficial effect on DSS-induced acute UC in female Swiss Webster mice as determined by evaluation of body weight loss, disease activity scores, colon lengths and weight-length ratios, and colon histopathology. Twice daily, oral treatment with 200 mg/kg Compound I-22 dosed on Days 0 through 6 showed significant beneficial effects on daily stool consistency scores, colon lengths, and colon histopathology. Twice daily, oral treatment with 200 mg/kg Compound I-6 dosed on Days 0 through 6 and twice daily, oral treatment with 200 mg/kg Compound 1-5, 200 mg/kg Compound 1-22, or 200 mg/kg Compound I-6 resulted in significant beneficial effects on colon histopathology. All main study animals survived to the scheduled termination.

All publications, patents, patent applications and other documents cited in this application are hereby incorporated by reference in their entireties for all purposes to the same extent as if each individual publication, patent, patent application or other document were individually indicated to be incorporated by reference for all purposes.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of treating a disease, disorder, or condition, comprising administering to a subject in need thereof an effective amount of the following compound:

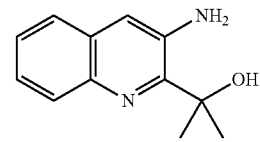

I-6 or a pharmaceutically acceptable salt thereof;
wherein the disease, disorder, or condition is non-alcoholic fatty liver disease (NAFLD).

2. The method according to claim 1, wherein the compound or pharmaceutically acceptable salt thereof is administered systemically to the subject.

3. The method according to claim 1, wherein the compound or pharmaceutically acceptable salt thereof is administered orally to the subject.

4. A method of treating a disease, disorder, or condition, comprising administering to a subject in need thereof an effective amount of the following compound:

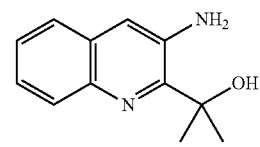

I-6 or a pharmaceutically acceptable salt thereof;
wherein the disease, disorder, or condition is non-alcoholic steatohepatitis (NASH).

5. The method according to claim 4, wherein the compound or pharmaceutically acceptable salt thereof is administered systemically to the subject.

6. The method according to claim 4, wherein the compound or pharmaceutically acceptable salt thereof is administered orally to the subject.

* * * * *